United States Patent [19]

Hershey et al.

[11] Patent Number: 5,608,143

[45] Date of Patent: Mar. 4, 1997

[54] EXTERNAL REGULATION OF GENE EXPRESSION

[75] Inventors: Howard P. Hershey, West Chester, Pa.; Carol D. Katayama, Encinitas; Edward J. Ralston, Pleasant Hill, both of Calif.; Timothy D. Stoner, New Freedom, Pa.; James F. Wong, Newark, Del.

[73] Assignee: E. I. Du Pont de Nemours and Company, Wilmington, Del.

[21] Appl. No.: 280,041

[22] Filed: Jul. 25, 1994

Related U.S. Application Data

[60] Division of Ser. No. 730,853, Jul. 31, 1991, Pat. No. 5,364,780, which is a continuation-in-part of Ser. No. 327,205, Mar. 17, 1989, abandoned.

[51] Int. Cl.$^6$ .............................. A01H 4/00; C12N 15/82; C12N 15/11
[52] U.S. Cl. ....................... 800/205; 800/250; 435/320.1; 536/24.1
[58] Field of Search ........................... 536/24.1; 800/205, 800/250; 435/172.3, 320.1

[56] References Cited

PUBLICATIONS

Sargent in Guide to Molecular Cloning Techniques, Methods in Enzymology 152 (Berger, et al, eds.) Academic Press, NY, 1987, pp. 423–432.
Marcotte, et al. (1988) Nature 335: 454–457.
Cornellissen, et al (1986) The EMBO J. 5: 37–40.
van Loon (1983) Neth J. Pl. Path. 89:265, Table 1.
Steppuhn, et al (1987) Mol. Gen. Genet. 210: 171–177.
Boswell, et al. in Computational Molecular Biology (Lesk, ed.) Oxford University Press, Oxford, 1988, pp. 170–171.

*Primary Examiner*—Che S. Chereskin

[57] ABSTRACT

The preparation and use of nucleic acid promoter fragments derived from several genes from corn, petunia and tobacco which are highly responsive to a number of substituted benzenesulfonamides and related compounds are described. These promoter fragments are useful in creating recombinant DNA constructions comprising nucleic acid sequences encoding any desired gene product operably linked to such promoter fragments which can be utilized to transform plants and bring the expression of the gene product under external chemical control in various tissues of monocotyledonous and dicotyledonous plants.

12 Claims, 39 Drawing Sheets

FIG. 1

1. GROW CORN SEEDLINGS HYDROPONICALLY

2. ADD N-(AMINOCARBONYL)-2-CHLOROBENZENESULFONAMIDE TO HYDROPONIC MEDIUM OF HALF OF THE PLANTS AND GROW FOR SIX HOURS

3. ISOLATE mRNA FROM ROOTS OF TREATED AND UNTREATED PLANTS

4. CREATE cDNA LIBRARY FROM mRNA FROM TREATED PLANTS AND REPARE REPLICA COPIES OF LIBRARY

5. SCREEN COPIES OF cDNA LIBRARY WITH $^{32}$P-DNA PROBES MADE FROM EITHER TREATED OR UNTREATED ROOT mRNA TO ISOLATE CLONE CONTAINING SEQUENCES INDUCED BY N-(AMINOCARBONYL)-2-CHLOROBENZENESULFONAMIDE

6. PREPARE CORN GENOMIC LIBRARY

7. USE cDNA CLONE TO ISOLATE CORRESPONDING CHEMICALLY INDUCED GENE(S)

8. DETERMINE SEQUENCES OF cDNA CLONE AND GENE. IDENTIFY PROMOTER AND 3' DOWNSTREAM REGIONS OF GENE TO BE REMOVED FROM STRUCTURAL PORTION OF GENE

9. ADD CONEVIENENT RESTRICTION SITES FOR CLONING (IF NEEDED) AND CREATE RECOMBINANT GENE BY OPERABLY LINK B-GLUCURONIDASE CODING REGION TO PROMOTER AND 3' DOWNSTREAM REGION OF INDUCIBLE GENE

10. TRANSFORM RECOMBINANT GENE INTO PLANTS

11. TEST PLANTS FOR N-(AMINOCARBONYL)-2-CHLOROBENZENESULFONAMIDE INDUCIBLE EXPRESSION OF RECOMBINANT GENE

FIG.2

```
  1  CTACCTTCAT GAGACGTAAC TGCAGAAGAT GTGCTTTCCA ACTTCGGTTA
 51  TGTTACCTTT AATCCCAAGC CTTCAGCGCT GCTGATGTAT GGCTTAACTT
101  CTTATTGAAG CCAAGATATC TGTTAGCAAA TAGCATGCAA AGATATACGA
                                  V
151  GAGAAAATAG CACGCTATGG GCCTTTCTAA TAAGAGATCC TTGTAGACAT
201  GACTTCAGCA GTTTAGGTCA TAGATGACGA CGACGAGTAA GCACCTGCAA
251  TGGGGCCAAC ACGAATTGTT CGTGCGTCAC AACGAGGCGA AGATGACACA
301  ATCGATTACG TCATCAGTCG TTTAACTCAA GTGCAACACT ATGAGGTCCT
351  GACAGGTGGG GCGCCACCGC AATTTATTAG CAGCCAGCGA GCGAGCGGCG
401  ACAGAGACGT GGTGGGCCTG TGGGGTCTG GCAACCCAAA CGTGGAAAAG
451  TCATGCATGC ACTGCGCTAA AGTCTAAGCC ATCACTAAAA CACCACGCGT
501  ATAAATACCC GGACCAATCA GCCATGCCGG CAGCCGGGTC GCGTTTCCAA
551  CAGGCCAGTC CCCTCCCACT CCCAGTCCCA TCTCGACGAC ATGGC
```

FIG. 4

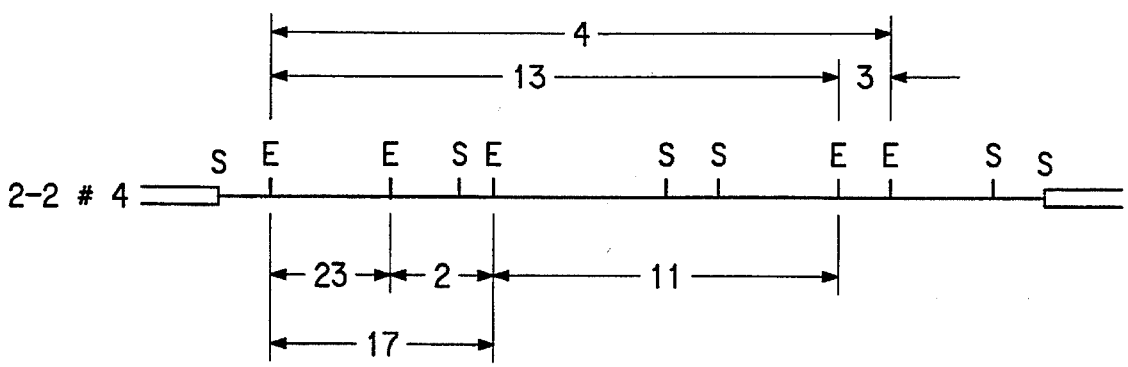

E = EcoRI
S = SalI

```
  1  AGGAATTCCT CTCCATGGAT CCCCTCTATT TACCTGGCCA CCAAACATCC
 51  CTAATCATCC CCAAATTTTA TAGGAACTAC TAATTTCTCT AACTTAAAAA
101  AAATCTAAAA TAGTATACTT TAGCAGCCTC TCAATCTGAT TTGTTCCCCA
151  AATTTGAATC CTGGCTTCGC TCTGTCACCT GTTGTACTCT ACATGGTGCG
201  CAGGGGGAGA GCCTAATCTT TCACGACTTT GTTTGTAACT GTTAGCCAGA
251  CCGGCGTATT TGTCAATGTA TAAACACGTA ATAAAATTTA CGTACCATAT
301  AGTAAGACTT TGTATATAAG ACGTCACCTC TTACGTGCAT GGTTATATGC
351  GACATGTGCA GTGACGTTAT CAGATATAGC TCACCCTATA TATATAGCTC
401  TGTCCGGTGT CAGTGACAAT CACCATTCAT CAGCACCCCG GCAGTGCCAC
451  CCCGACTCCC TGCACCTGCC ATGG
```

FIG. 5

```
  1  GCGGTCACAA TTACCCTATA TATCTACTAT ATACCAACTA CCATTTATTA
 51  TATCATATTT TTACCATACT CTATACCAAC TCCATCACAC GGCTGCTGTA
101  CTGCTTCCTT CTACTGCTAC TGTACTGGTT CTCTAGGCCC ACCTCGTCTG
151  CTGGGAGAGA GCAGTGGCAG AGCGCTACAT TTGGCGTAGA AGAGGCGGAG
201  AGAGAGCGTA GAGTGAGATA TAGAGTGCAC CGTTGCAGAT CTTGTCTACT
251  GTAAAANTTT AGCGTAGCTT TTCCAGCTGA CCACTGCGGC TAGCCTAAAA
301  CGGATTGGGG GTACTCAGTG GNNNNGCCGT GGGCGGTACG TCGCCCCAAA
351  TAATTAAACG GTGCTCGATG TACCTCTACG GGACCTTTTT CAGCCTTTTT
401  TCTTTATTTT ATTATTATTA TTTTGGTACT ACACAAGGGA CCTTTTGACG
451  CTGAGATGAT GCCCAAAAAC AAAAGGACGC TCATCATCAG TGACGCCCAG
501  TCGTCGCCAA GCAGCTAGCT AGCATGCCAA TAATTTTTTT CTTGTTAATG
551  TTGTCGCAGC TGGTACTATA CTACTACTAC TACGCCGTAT ATGAATGCGC
601  GTTTTGTCTG ATGCTCAGGC TGATTCCATC CAATTGTCTT TCTTCTCTCC
651  TCTCCACCCA TGCCCCGTCC GTCGCAGCAG GGGTTATATA GTGCCCGCGA
701  ACGGACGCAG GCGCCACGAA GCCGAGATCG AGCAGCTACC TCTCCGATCC
751  GAGGCCTGAG CGAGCGAGCT GAGGACTGCA GCCTATATAA TATCTAGACT
801  AGAGTACACC ACAACGACGA GGCACATATA TATACACGCG GCGGCGGCCA
851  GATCCATCTT GGTATACACG TAATATATAT ACACGCACGA TGG
```

FIG.7A

```
   1 GAATTCGTTT ATAAAAATAT ATCGTTCCGC AGGCGTTGAG CCTTTTTCTA
  51 CTAGTGATGT CTTCACAACG TTTCGAGCTT TTCCCTAATT GGCGGGTGAT
 101 TAAGGCTTGT ACACGGAGTC TTTCTCCTAC TCTACCCCTG TTAGAAGGCG
 151 TAACCCCTTT TTATAAGCCC GAACACCTGA TGACCAAACC AGGCCAAAGG
 201 GTATAACGAT TGTTGCCCCC CTAATCAGCG CAATAATGCG CGTGGGCCTA
 251 ACGCTGTTAA GACTCGATCC TATTGACCCG TCCGAGATCA ACCTAACAAA
 301 GTTCTAGCCA TGTGCCATTT CGTAATGAAA ATGAGGGCCA AGGTGTCACC
 351 TTGCTGGTCT AAAAAATGTG CCTCGATCCA AGGGACTGTT CATTTTTAA
 401 AATGACCATA TGACAGACAT CAGGCTAATG GACATGGTTG AGTTTGGATT
 451 GGCTCAACTC GGTTCGTTAA CAAACCAATC CAAAAGTCA GCTCGCTATT
 501 TACGAGCTCG AACAATTATT ATCATTAATC AATTTGCTTG TTAGTTACAA
 551 ATTCAGTTTT ACTTAACAGA AAAATAGTTA ATTTATTCTT CATAATTTCA
 601 CAGACCATTA TAAATTAAAC ACTAAATTAA TATAGAATCA ATCACAGACA
 651 TAATTTATCA TCATCAGTTT GAATCCACGA GCTACATAAG CCGCACATAC
 701 AATGTAGCAT ATTCACCGAT TCTAGATGAA ATATACTGCA TATAGTTTTA
 751 TTTTTTGAAN GTGATAGGTC GTTTGACATC ACGAACTGGC TCGTTAACAA
 801 ACAAGCTAGG ATGTTAGCTT ATGCTTTGCT ATTAGTTAGG ATATGGTTCT
 851 GGGTGATCAA AAGGAAGAAA AAACACGAAA AATTTAATGA GGTTCTTGGA
 901 TGACCGGAGT CAACCAACTT GGTTGGAGCG TTCTTCTTCC CTGATCGTTC
 951 GTAGTCGGCA CTCTCCCCTC ACGGCTGACG TCCTCACCTC TCCTCGTCCA
1001 CGCGAACCAG ACGTACGGTA GCTGTTTCAC ATTTCTAATT TACTATACGT
1051 AGTGAACTCG CTGTGGTGTT ACCACCTCTC GCATTGCTAA TTTACTGGAT
1101 ACGCTCTTAG CTTGGACACA AATTGGACCT GCAACGGACT GATGAATTGC
1151 AAAGTTTATT TTTCCATTTG GAAGGTAAAG CTGAAACGAG TTCCTCCGTC
1201 AGACATTCTT ATATTTTGAA CCGCGAGAGT TCAAATCCCC AGCCAAGCTG
1251 AAAGGTCAGA GCCTGAAATT TCGTGCTGG GATGACGTTC GCCCTTACGT
1301 CGCGCGCTGC AAACTGAAAC GAGTTCCCAT GCCCAAATAA ACTTGAGAAA
```

FIG. 7B

```
1351  AGTGCTGTCT TGTTCAGCTA TGCCCGCATT ATAGATCGAT ATGGTGAGGT

1401  CACTGCTTAT GCCAGGCACA TGACTCAATA TAGCTCCATA TCTTAGGCGA

1451  ATTAATCACA TCTCTCTGAC CGATCTTGGG CTCTCCTATA AATATATAGG

1501  AACGTACGTA AAGTTTCTCC AAGCAGATAG CAGCAAGCTA AGCAAGTGCC

1551  AACCAACGAG TAGCAGGAAA CATG
```

FIG. 8

```
  1  ACTGAAGAAT GATGAGTGAC TCACAAAATG GTTTCCCATT GTGGATCAAG
 51  AATGGGATTT TCTTGTGAAT TGGGTTCATT TGTAGGAGCA GAGGACTTTT
101  GATCCTCAAG TCCTCCTTCC TTGTATTCAT AATGAATTCC TTTTTCAGCC
151  AGGGCAATCC TGACCCTCAT CCCAAACATA CTGTAAGTAT CTAGTAGGAC
201  AATTTCATCT GCCTTTTTTT TTAAAATGAA ATTAAGGAT AGTATAATGG
251  AATTCCAACA AATATAAAAC TAGAATCAGT TATTATTCAA CATAAACCCA
301  TGAAGTACCA AATTTGTGGG GGTAGAGAGA AGATTTGGAT CGACTAAAAT
351  TTTGACTAGT AAGTTAAAAA AATTAAGGAA CAGAAGAAAG TGGAGCCTTC
401  TTGCTTAACG TTTACTACTA TAAGACCCCG TGACGAATGT GATGACATAA
451  GTAGGTCGGC CACACAAAAA AATCTGGAAA CTCCCGGACC ACAACACCGC
501  TTGTACCCAT AATAAAAATG TTTAAAAATG AAGACATCTA AGTTTCTACT
551  GGTCTATATA TAGAACTTGA ACTATATACG AAGCATATCA GTTCTAAGCA
601  TTTGTGCAAA TTCTATAAAT TCTTCTTACT TGCCTTTCAT AATTCATAAG
651  CATAACAATG
```

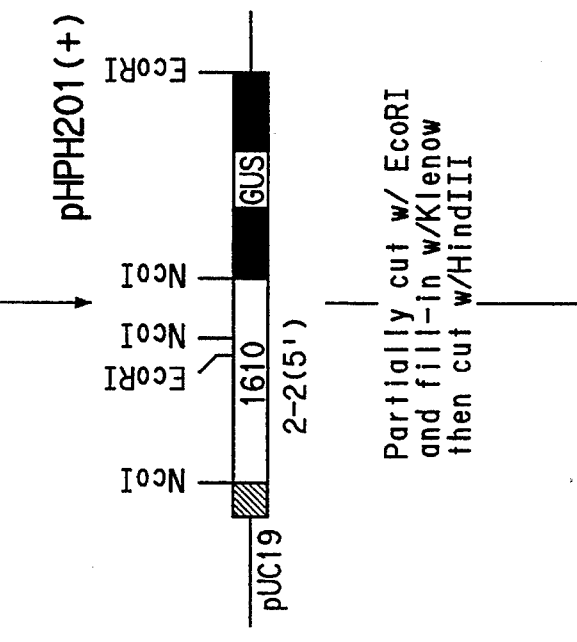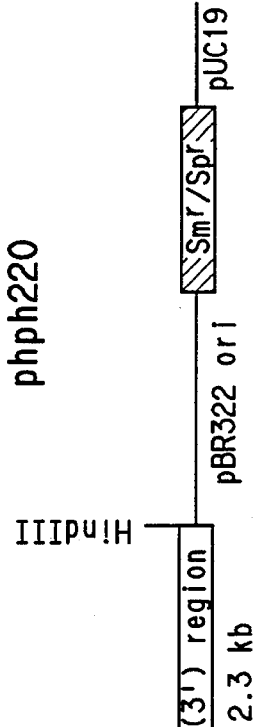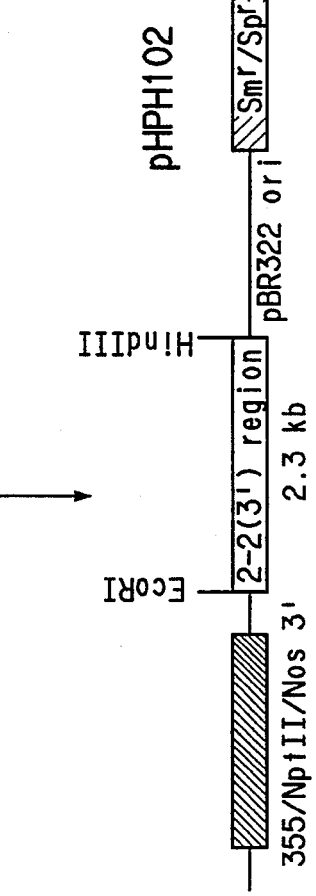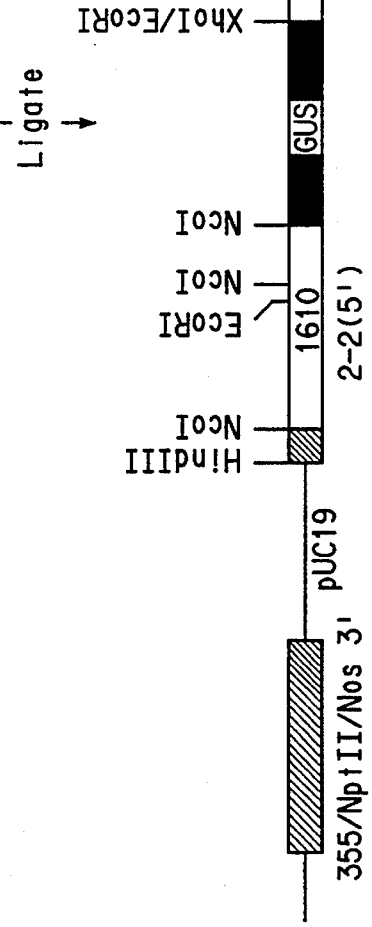
FIG. 12B

FIG. 13B
CONTINUED FROM FIG 13A
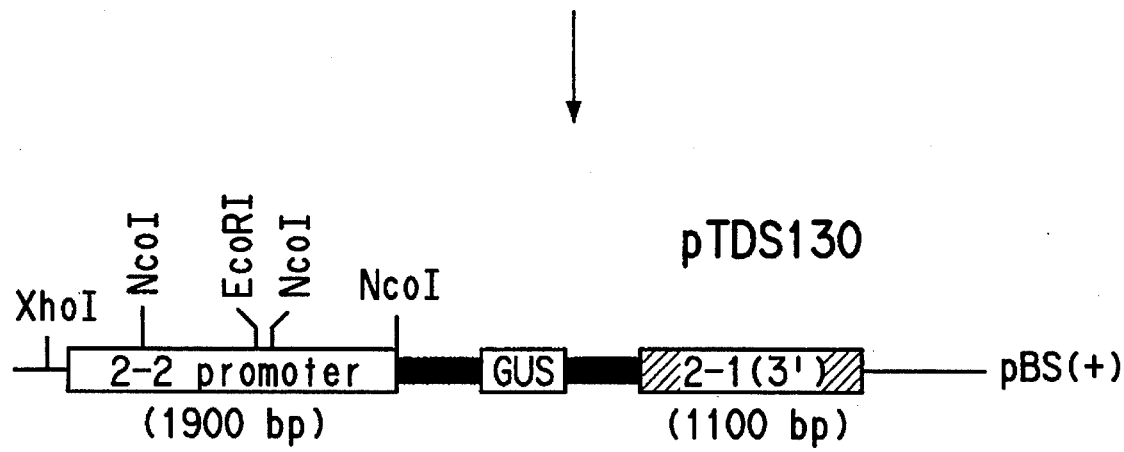
Cut w/ EcoRI and XhoI
then blunt with Klenow
and close with Ligase
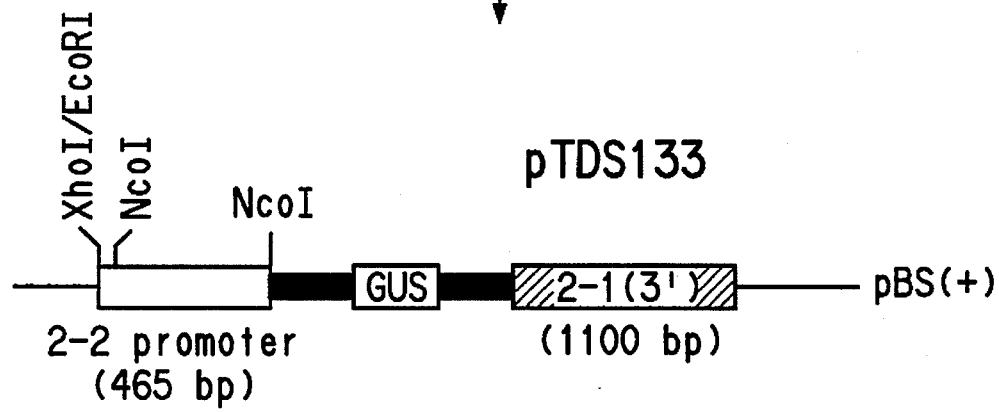

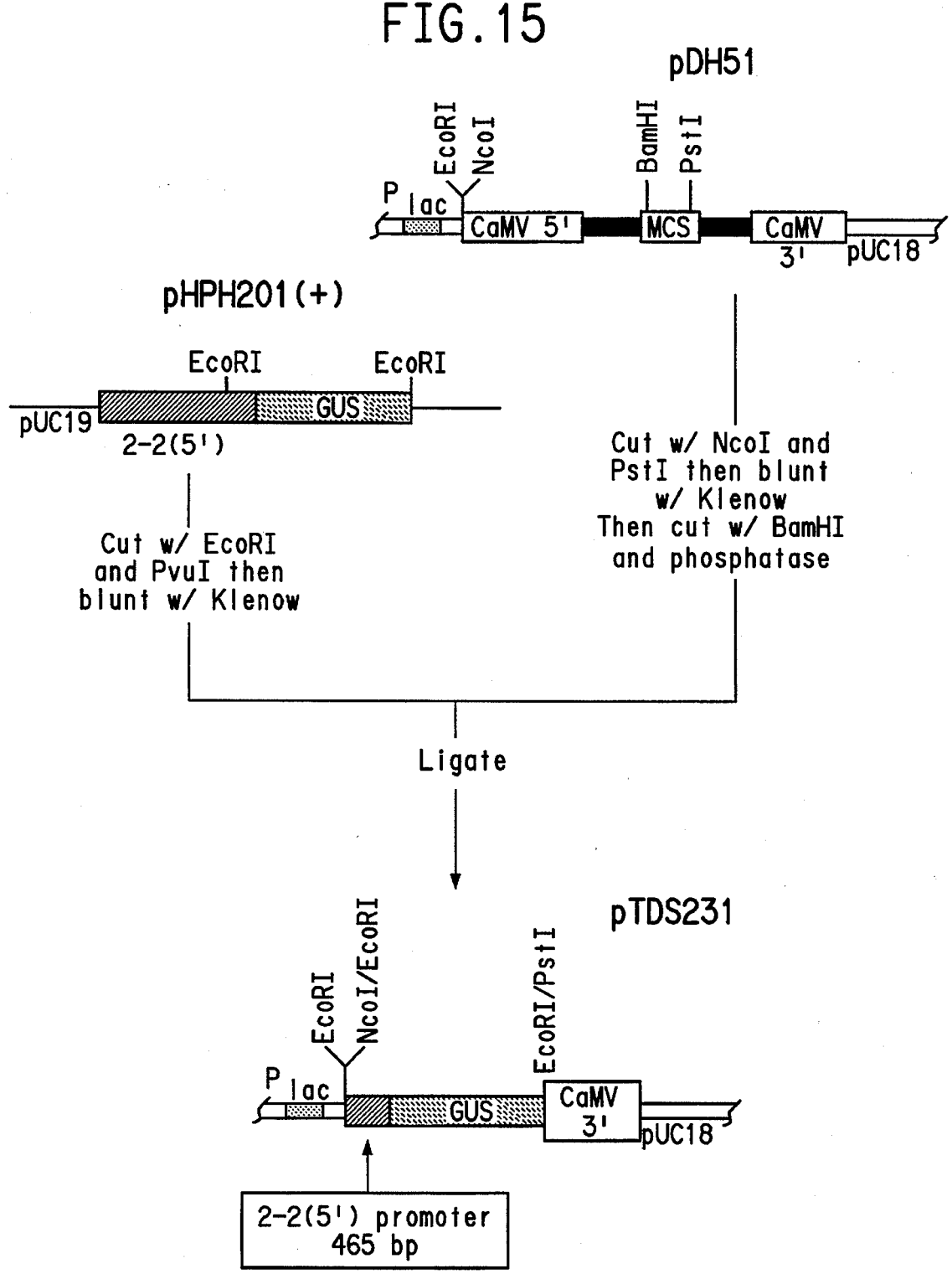

FIG. 16

```
                   ▽ pTDS133 (-468)    ▽ pTDS134 (-454)
  1   AGGAATTCCT   CTCCATGGAT   CCCCTCTATT   TACCTGGCCA   CCAAACATCC

51   CTAATCATCC   CCAAATTTTA   TAGGAACTAC   TAATTTCTCT   AACTTAAAAA

101   AAATCTAAAA   TAGTATACTT   TAGCAGCCTC   TCAATCTGAT   TTGTTCCCCA

151   AATTTGAATC   CTGGCTTCGC   TCTGTCACCT   GTTGTACTCT   ACATGGTGCG
                                ▽ pDuPM17 (-249)
201   CAGGGGGAGA   GCCTAATCTT   TCACGACTTT   GTTTGTAACT   GTTAGCCAGA
                         ▽ pDuPN27 (-207)
251   CCGGCGTATT   TGTCAATGTA   TAAACACGTA   ATAAAATTTA   CGTACCATAT
                                   ▽ pDuPN4 (-149)        ▽ pDuPN7 (-130)
301   AGTAAGACTT   TGTATATAAG   ACGTCACCTC   TTACGTGCAT   GGTTATATGC

351   GACATGTGCA   GTGACGTTAT   CAGATATAGC   TCACCCTATA   TATATAGCTC

401   TGTCCGGTGT   CAGTGACAAT   CACCATTCAT   CAGCACCCCG   GCAGTGCCAC

451   CCCGACTCCC   TGCACCTGCC   ATGG
```

CONTINUED ON FIG 18B

FIG. 18B
CONTINUED FROM FIG 18A
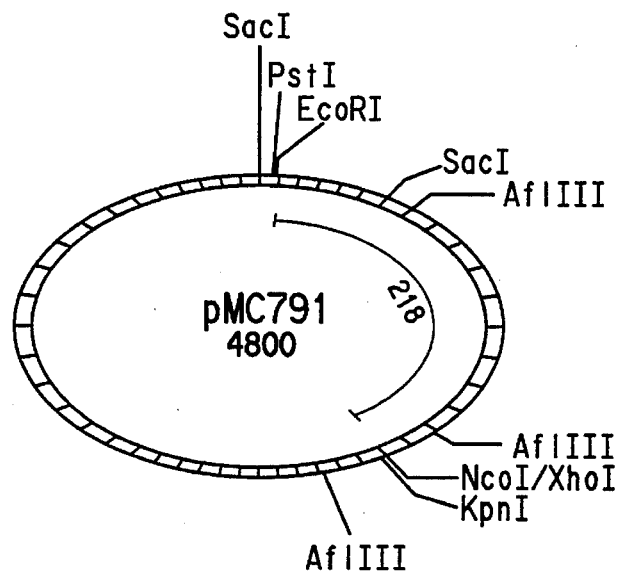
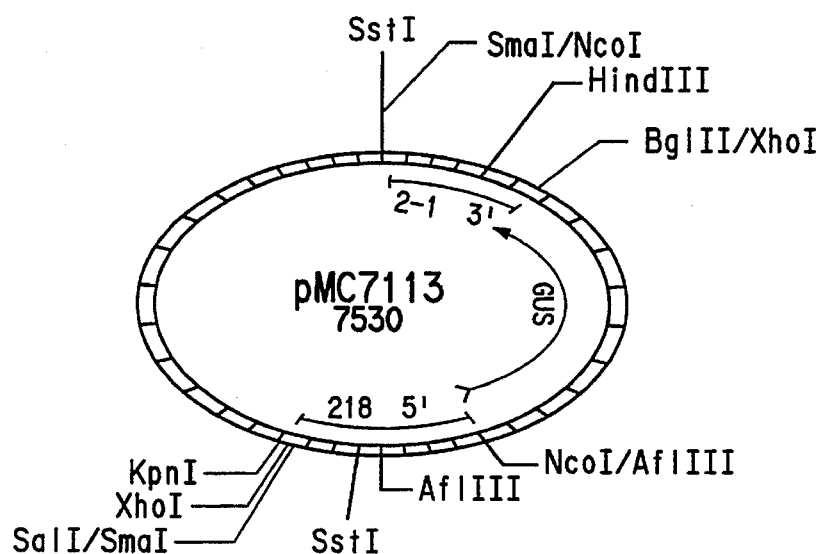

FIG. 19B
CONTINUED FROM FIG 19A
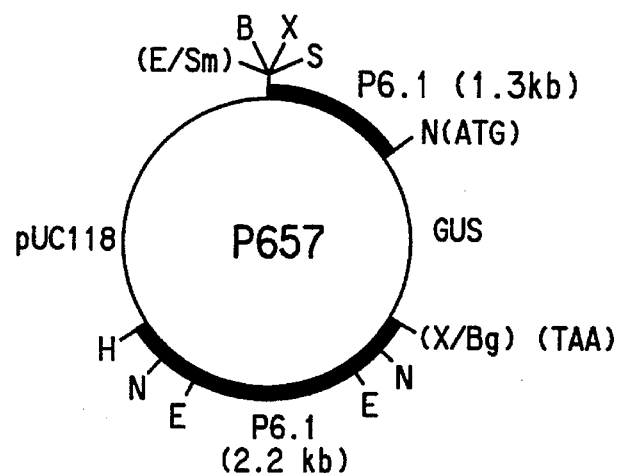
E  EcoRI
N  NcoI
S  SalI
X  XbaI
B  BamHI
H  HindIII
Sm SmaI
Bg BglII
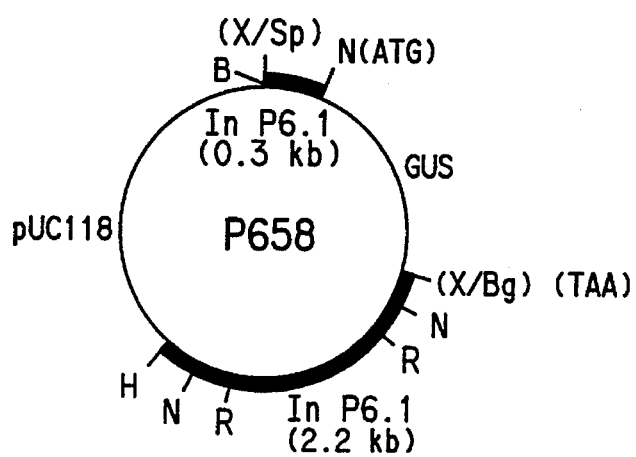

CONTINUED ON FIG 20B

FIG.20B
CONTINUED FROM FIG 20A
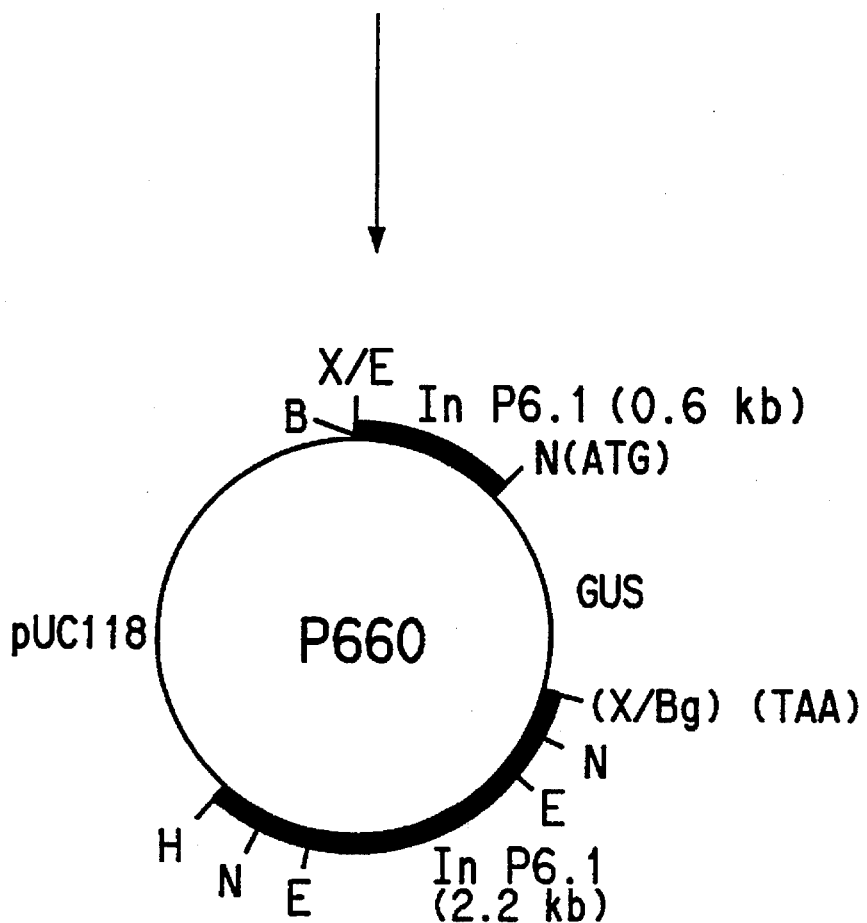

FIG.21

```
  1  GAATTCTACG TACCATATAG TAAGACTTTG TATATAAGAC GTCACCTCTT
 51  ACGTGCATGG TTATATGCGA CATGTGCAGT GACGTTAACC GCACCCTCCT
101  TCCCGTCGTT TCCCATCTCT TCCTCCTTTA GAGCTACCAC TATATAAATC
151  AGGGCTCATT TTCTCGCTCC TCACAGGCTC ATCAGCACCC CGGCAGTGCC
201  ACCCCGACTC CCTGCACCTG CCATGGCTGT GGCTCGAGGT ACC
```

FIG.22

```
  1  CTGCAGTACG TACCATATAG TAAGACTTTG TATATAAGAC GTCACCTCTT
 51  ACGTGCATGG TTATATGCGA CATGTGCAGT GACGTTATCA GATATAGCTC
101  ACCCTATATA TATAGCTCTG TCCGGTGTCA GTGACAATCA CCATTCATCT
151  CGCTTTGGAT CGATTGGTTT CGTAACTGGT GAAGGACTGA GGGTCTCGGA
201  GTGGATGATT TGGGATTCTG TTCGAAGATT TGCGGAGGGG GGCCATGGCG
251  ACGGTACC
```

FIG. 23

```
  1  GGATCCCCCG TACCATATGT AAGACTTTGT ATATAAGACG TCACCTCTTA
 51  CGTGCATGGT TATATGCGAC ATGTGCAGTG ACGTTAACAA GGATCGGCGC
101  GCCACGCCGA GCTCGCCGCT ATATTTATAT TTGCTCAATG GACAGGCATG
151  GGGCTATCTC GCTTTGGATC GATTGGTTTC GTAACTGGTG AAGGACTGAG
201  GGTCTCGGAG TGGATGATTT GGGATTCTGT TCGAAGATTT GCGGAGGGGG
251  GCCATGGCGA CGGTACC
```

FIG.24

```
  1  GAATTCTACG TACCATATAG TAAGACTTTG TATATAAGAC GTCACCTCTT
 51  ACGTGCATGG TTATATGCGA CATGTGCAGT GACGTTAACC GCACCCTCCT
101  TCCCGTCGTT TCCCATCTCT TCCTCCTTTA GAGCTACCAC TATATAAATC
151  AGGGCTCATT TTCTCGCTCC TCACAGGCTC ATCTCGCTTT GGATCGATTG
201  GTTTCGTAAC TGGTGAAGGA CTGAGGGTCT CGGAGTGGAT GATTTGGGAT
251  TCTGTTCGAA GATTTGCGGA GGGGGGCCAT GGCGACGGTA CC
```

- LB — TDNA left border
- RB — TDNA right border

- LB — TDNA left border
- RB — TDNA right border

- LB - TDNA left border
- RB - TDNA right border

- LB – TDNA left border
- RB – TDNA right border

FIG. 28B
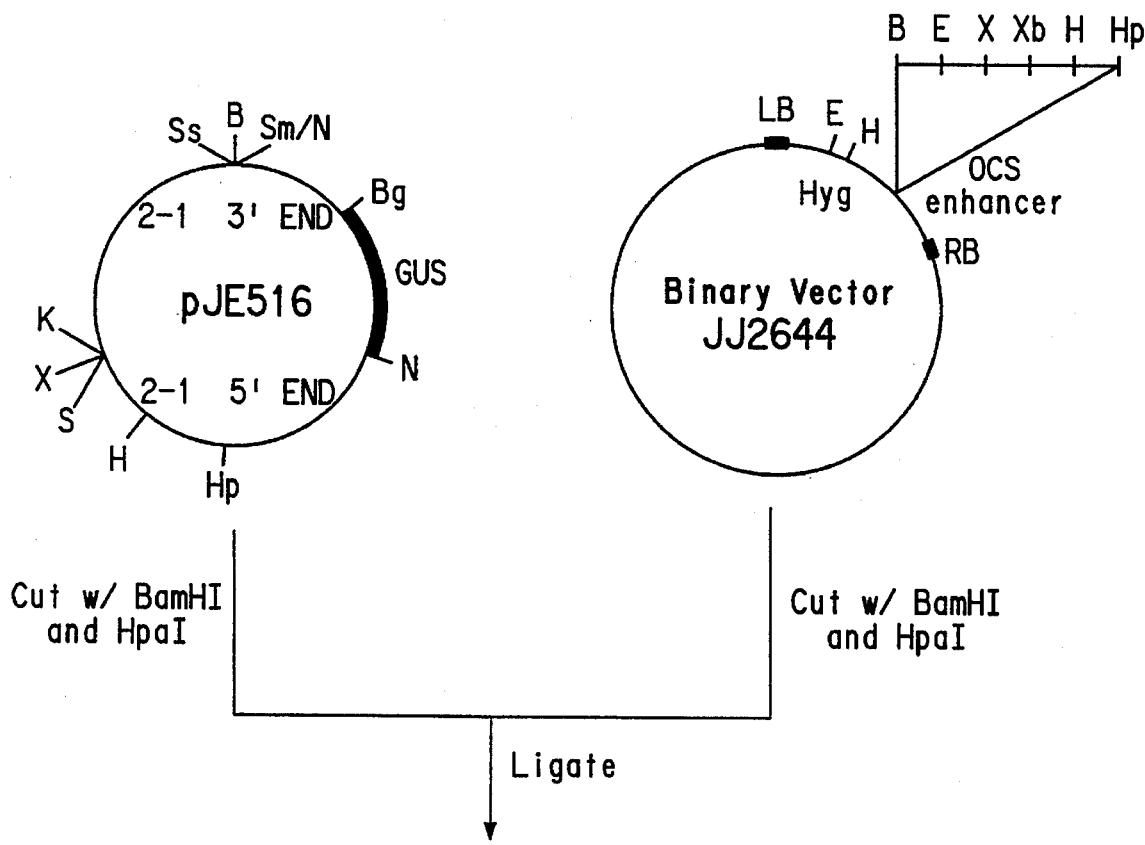
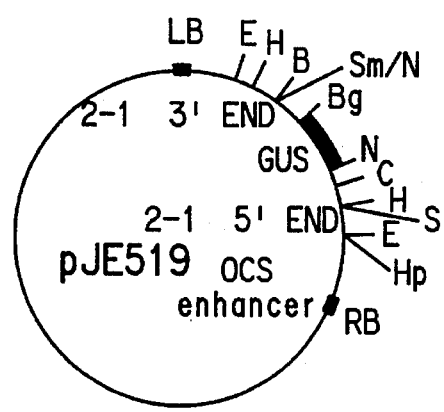

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 595 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( x i ) SEQUENCE DESCRIPTION: SEQ ID NO:1:

```
CTACCTTCAT   GAGACGTAAC   TGCAGAAGAT   GTGCTTTCCA   ACTTCGGTTA   TGTTACCTTT      60

AATCCCAAGC   CTTCAGCGCT   GCTGATGTAT   GGCTTAACTT   CTTATTGAAG   CCAAGATATC     120

TGTTAGCAAA   TAGCATGCAA   AGATATACGA   GAGAAAATAG   CACGCTATGG   GCCTTTCTAA     180

TAAGAGATCC   TTGTAGACAT   GACTTCAGCA   GTTTAGGTCA   TAGATGACGA   CGACGAGTAA     240

GCACCTGCAA   TGGGGCCAAC   ACGAATTGTT   CGTGCGTCAC   AACGAGGCGA   AGATGACACA     300

ATCGATTACG   TCATCAGTCG   TTTAACTCAA   GTGCAACACT   ATGAGGTCCT   GACAGGTGGG     360

GCGCCACCGC   AATTTATTAG   CAGCCAGCGA   GCGAGCGGCG   ACAGAGACGT   GGTGGGCCTG     420

TGGGGGTCTG   GCAACCCAAA   CGTGGAAAAG   TCATGCATGC   ACTGCGCTAA   AGTCTAAGCC     480

ATCACTAAAA   CACCACGCGT   ATAAATACCC   GGACCAATCA   GCCATGCCGG   CAGCCGGGTC     540

GCGTTTCCAA   CAGGCCAGTC   CCCTCCCACT   CCCAGTCCCA   TCTCGACGAC   ATGGC          595
```

( 2 ) INFORMATION FOR SEQ ID NO:2:

( i ) SEQUENCE CHARACTERISTICS:
        ( A ) LENGTH: 474 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | | |
|---|---|---|---|---|---|---|
| AGGAATTCCT | CTCCATGGAT | CCCCTCTATT | TACCTGGCCA | CCAAACATCC | CTAATCATCC | 60 |
| CCAAATTTTA | TAGGAACTAC | TAATTTCTCT | AACTTAAAAA | AAATCTAAAA | TAGTATACTT | 120 |
| TAGCAGCCTC | TCAATCTGAT | TTGTTCCCCA | AATTTGAATC | CTGGCTTCGC | TCTGTCACCT | 180 |
| GTTGTACTCT | ACATGGTGCG | CAGGGGGAGA | GCCTAATCTT | TCACGACTTT | GTTTGTAACT | 240 |
| GTTAGCCAGA | CCGGCGTATT | TGTCAATGTA | TAAACACGTA | ATAAAATTTA | CGTACCATAT | 300 |
| AGTAAGACTT | TGTATATAAG | ACGTCACCTC | TTACGTGCAT | GGTTATATGC | GACATGTGCA | 360 |
| GTGACGTTAT | CAGATATAGC | TCACCCTATA | TATATAGCTC | TGTCCGGTGT | CAGTGACAAT | 420 |
| CACCATTCAT | CAGCACCCCG | GCAGTGCCAC | CCCGACTCCC | TGCACCTGCC | ATGG | 474 |

( 2 ) INFORMATION FOR SEQ ID NO:3:

( i ) SEQUENCE CHARACTERISTICS:
        ( A ) LENGTH: 896 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| | | | | | | |
|---|---|---|---|---|---|---|
| GCGGTCACAA | TTACCCTATA | TATCTACTAT | ATACCAACTA | CCATTTATTA | TATCATATTT | 60 |
| TTACCATACT | CTATACCAAC | TCCATCACAC | GGCTGCTGTA | CTGCTTCCTT | CTACTGCTAC | 120 |
| TGTACTGGTT | CTCTAGGCCC | ACCTCGTCTG | CTGGGAGAGA | GCAGTGGCAG | AGCGCTACAT | 180 |
| TTGGCGTAGA | AGAGGCGGAG | AGAGAGCGTA | GAGTGAGATA | TAGAGTGCAC | CGTTGCAGAT | 240 |
| CTTGTCTACT | GTAAAANTTT | AGCGTAGCTT | TTCCAGCTGA | CCACTGCGGC | TAGCCTAAAA | 300 |
| CGGATTGGGG | GTACTCAGTG | GNNNNGCCGT | GGGCGGTACG | TCGCCCCAAA | TAATTAAACG | 360 |
| GTGCTCGATG | TACCTCTACG | GGACCTTTTT | CAGCCTTTTT | TCTTTATTTT | ATTATTATTA | 420 |
| TTTTGGTACT | ACACAAGGGA | CCTTTTGACG | CTGAGATGAT | GCCCAAAAAC | AAAAGGACGC | 480 |
| TCATCATCAG | TGACGCCCAG | TCGTCGCCAA | GCAGCTAGCT | AGCATGCCAA | TAATTTTTTT | 540 |
| CTTGTTAATG | TTGTCGCAGC | TGGTACTATA | CTACTACTAC | TACGCCGTAT | ATGAATGCGC | 600 |
| GTTTTGTCTG | ATGCTCAGGC | TGATTCCATC | CAATTGTCTT | TCTTCTCTCC | TCTCCACCCA | 660 |
| TGCCCCGTCC | GTCGCAGCAG | GGGTTATATA | GTGCCCGCGA | ACGGACGCAG | GCGCCACGAA | 720 |
| GCCGAGATCG | AGCAGCTACC | TCTCCGATCC | GAGGCCTGAG | CGAGCGAGCT | GAGGACTGCA | 780 |
| GCCTATATAA | TATCTAGACT | AGAGTACACC | ACAACGACGA | GGCACATATA | TATACACGCG | 840 |
| GCGGCGGCCA | GATCCATCTT | GGTATACACG | TAATATATAT | ACACGCACGA | TGGGCA | 896 |

( 2 ) INFORMATION FOR SEQ ID NO:4:

( i ) SEQUENCE CHARACTERISTICS:
        ( A ) LENGTH: 1574 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

| | | | | | |
|---|---|---|---|---|---|
| GAATTCGTTT | ATAAAAATAT | ATCGTTCCGC | AGGCGTTGAG | CCTTTTTCTA | CTAGTGATGT | 60 |
| CTTCACAACG | TTTCGAGCTT | TTCCCTAATT | GGCGGGTGAT | TAAGGCTTGT | ACACGGAGTC | 120 |
| TTTCTCCTAC | TCTACCCCTG | TTAGAAGGCG | TAACCCCTTT | TTATAAGCCC | GAACACCTGA | 180 |
| TGACCAAACC | AGGCCAAAGG | GTATAACGAT | TGTTGCCCCC | CTAATCAGCG | CAATAATGCG | 240 |
| CGTGGGCCTA | ACGCTGTTAA | GACTCGATCC | TATTGACCCG | TCCGAGATCA | ACCTAACAAA | 300 |
| GTTCTAGCCA | TGTGCCATTT | CGTAATGAAA | ATGAGGGCCA | AGGTGTCACC | TTGCTGGTCT | 360 |
| AAAAAATGTG | CCTCGATCCA | AGGGACTGTT | CATTTTTAA | AATGACCATA | TGACAGACAT | 420 |
| CAGGCTAATG | GACATGGTTG | AGTTTGGATT | GGCTCAACTC | GGTTCGTTAA | CAAACCAATC | 480 |
| CAAAAAGTCA | GCTCGCTATT | TACGAGCTCG | AACAATTATT | ATCATTAATC | AATTTGCTTG | 540 |
| TTAGTTACAA | ATTCAGTTTT | ACTTAACAGA | AAAATAGTTA | ATTTATTCTT | CATAATTTCA | 600 |
| CAGACCATTA | TAAATTAAAC | ACTAAATTAA | TATAGAATCA | ATCACAGACA | TAATTTATCA | 660 |
| TCATCAGTTT | GAATCCACGA | GCTACATAAG | CCGCACATAC | AATGTAGCAT | ATTCACCGAT | 720 |
| TCTAGATGAA | ATATACTGCA | TATAGTTTTA | TTTTTTGAAN | GTGATAGGTC | GTTTGACATC | 780 |
| ACGAACTGGC | TCGTTAACAA | ACAAGCTAGG | ATGTTAGCTT | ATGCTTTGCT | ATTAGTTAGG | 840 |
| ATATGGTTCT | GGGTGATCAA | AAGGAAGAAA | AAACACGAAA | AATTTAATGA | GGTTCTTGGA | 900 |
| TGACCGGAGT | CAACCAACTT | GGTTGGAGCG | TTCTTCTTCC | CTGATCGTTC | GTAGTCGGCA | 960 |
| CTCTCCCCTC | ACGGCTGACG | TCCTCACCTC | TCCTCGTCCA | CGCGAACCAG | ACGTACGGTA | 1020 |
| GCTGTTTCAC | ATTTCTAATT | TACTATACGT | AGTGAACTCG | CTGTGGTGTT | ACCACCTCTC | 1080 |
| GCATTGCTAA | TTTACTGGAT | ACGCTCTTAG | CTTGGACACA | AATTGGACCT | GCAACGGACT | 1140 |
| GATGAATTGC | AAAGTTTATT | TTTCCATTTG | GAAGGTAAAG | CTGAAACGAG | TTCCTCCGTC | 1200 |
| AGACATTCTT | ATATTTGAA | CCGCGAGAGT | TCAAATCCCC | AGCCAAGCTG | AAAGGTCAGA | 1260 |
| GCCTGAAATT | TTCGTGCTGG | GATGACGTTC | GCCCTTACGT | CGCGCGCTGC | AAACTGAAAC | 1320 |
| GAGTTCCCAT | GCCCAAATAA | ACTTGAGAAA | AGTGCTGTCT | TGTTCAGCTA | TGCCCGCATT | 1380 |
| ATAGATCGAT | ATGGTGAGGT | CACTGCTTAT | GCCAGGCACA | TGACTCAATA | TAGCTCCATA | 1440 |
| TCTTAGGCGA | ATTAATCACA | TCTCTCTGAC | CGATCTTGGG | CTCTCCTATA | AATATATAGG | 1500 |
| AACGTACGTA | AAGTTCTCC | AAGCAGATAG | CAGCAAGCTA | AGCAAGTGCC | AACCAACGAG | 1560 |
| TAGCAGGAAA | CATG | | | | | 1574 |

( 2 ) INFORMATION FOR SEQ ID NO:5:

( i ) SEQUENCE CHARACTERISTICS:
        ( A ) LENGTH: 660 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

| | | | | | |
|---|---|---|---|---|---|
| ACTGAAGAAT | GATGAGTGAC | TCACAAAATG | GTTTCCCATT | GTGGATCAAG | AATGGGATTT | 60 |
| TCTTGTGAAT | TGGGTTCATT | TGTAGGAGCA | GAGGACTTTT | GATCCTCAAG | TCCTCCTTCC | 120 |

```
TTGTATTCAT  AATGAATTCC  TTTTTCAGCC  AGGGCAATCC  TGACCCTCAT  CCCAAACATA      180

CTGTAAGTAT  CTAGTAGGAC  AATTTCATCT  GCCTTTTTTT  TTAAAATGAA  ATTTAAGGAT      240

AGTATAATGG  AATTCCAACA  AATATAAAAC  TAGAATCAGT  TATTATTCAA  CATAAACCCA      300

TGAAGTACCA  AATTTGTGGG  GGTAGAGAGA  AGATTTGGAT  CGACTAAAAT  TTTGACTAGT      360

AAGTTAAAAA  AATTAAGGAA  CAGAAGAAAG  TGGAGCCTTC  TTGCTTAACG  TTTACTACTA      420

TAAGACCCCG  TGACGAATGT  GATGACATAA  GTAGGTCGGC  CACACAAAAA  AATCTGGAAA      480

CTCCCGGACC  ACAACACCGC  TTGTACCCAT  AATAAAAATG  TTTAAAAATG  AAGACATCTA      540

AGTTTCTACT  GGTCTATATA  TAGAACTTGA  ACTATATACG  AAGCATATCA  GTTCTAAGCA      600

TTTGTGCAAA  TTCTATAAAT  TCTTCTTACT  TGCCTTTCAT  AATTCATAAG  CATAACAATG      660
```

( 2 ) INFORMATION FOR SEQ ID NO:6:

( i ) SEQUENCE CHARACTERISTICS:
    ( A ) LENGTH: 243 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

```
GAATTCTACG  TACCATATAG  TAAGACTTTG  TATATAAGAC  GTCACCTCTT  ACGTGCATGG       60

TTATATGCGA  CGTGTGCAGT  GACGTTAACC  GCACCCTCCT  TCCCGTCGTT  TCCCATCTCT      120

TCCTCCTTTA  GAGCTACCAC  TATATAAATC  AGGGCTCATT  TTCTCGCTCC  TCACAGGCTC      180

ATCAGCACCC  CGGCAGTGCC  ACCCCGACTC  CCTGCACCTG  CCATGGCTGT  GGCTCGAGGT      240

ACC                                                                        243
```

( 2 ) INFORMATION FOR SEQ ID NO:7:

( i ) SEQUENCE CHARACTERISTICS:
    ( A ) LENGTH: 258 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

```
CTGCAGTACG  TACCATATAG  TAAGACTTTG  TATATAAGAC  GTCACCTCTT  ACGTGCATGG       60

TTATATGCGA  CATGTGCAGT  GACGTTATCA  GATATAGCTC  ACCCTATATA  TAGCTCTG       120

TCCGGTGTCA  GTGACAATCA  CCATTCATCT  CGCTTTGGAT  CGATTGGTTT  CGTAACTGGT      180

GAAGGACTGA  GGGTCTCGGA  GTGGATGATT  TGGGATTCTG  TTCGAAGATT  TGCGGAGGGG      240

GGCCATGGCG  ACGGTACC                                                       258
```

( 2 ) INFORMATION FOR SEQ ID NO:8:

( i ) SEQUENCE CHARACTERISTICS:
    ( A ) LENGTH: 267 base pairs
    ( B ) TYPE: nucleic acid
    ( C ) STRANDEDNESS: double
    ( D ) TOPOLOGY: linear (ii) MOLECULE TYPE: DNA (genomic)

(iii) HYPOTHETICAL: NO (xi) SEQUENCE DESCRIPTION: SEQ ID NO:8:

```
GGATCCCCCG TACCATATGT AAGACTTTGT ATATAAGACG TCACCTCTTA CGTGCATGGT      60
TATATGCGAC ATGTGCAGTG ACGTTAACAA GGATCGGCGC GCCACGCCGA GCTCGCCGCT     120
ATATTTATAT TTGCTCAATG GACAGGCATG GGGCTATCTC GCTTTGGATC GATTGGTTTC     180
GTAACTGGTG AAGGACTGAG GGTCTCGGAG TGGATGATTT GGGATTCTGT TCGAAGATTT     240
GCGGAGGGGG GCCATGGCGA CGGTACC                                         267
```

(2) INFORMATION FOR SEQ ID NO:9:

(i) SEQUENCE CHARACTERISTICS:
  (A) LENGTH: 292 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
GAATTCTACG TACCATATAG TAAGACTTTG TATATAAGAC GTCACCTCTT ACGTGCATGG      60
TTATATGCGA CATGTGCAGT GACGTTAACC GCACCCTCCT TCCCGTCGTT TCCCATCTCT     120
TCCTCCTTTA GAGCTACCAC TATATAAATC AGGGCTCATT TTCTCGCTCC TCACAGGCTC     180
ATCTCGCTTT GGATCGATTG GTTTCGTAAC TGGTGAAGGA CTGAGGGTCT CGGAGTGGAT     240
GATTTGGGAT TCTGTTCGAA GATTTGCGGA GGGGGGCCAT GGCGACGGTA CC             292
```

EXTERNAL REGULATION OF GENE EXPRESSION

This is a divisional of Ser. No. 07/730,853, filed Jul. 31, 1991, now U.S. Pat. No. 5,364,780, which is a continuation-in-part of U.S. Ser. No. 07/327,205, filed Mar. 17, 1989, now abandoned.

FIELD OF THE INVENTION

This invention relates to the preparation and use of nucleic acid promoter fragments derived from several genes from corn, petunia and tobacco which are highly responsive to a number of substituted benzenesulfonamides and related compounds. Chimetic genes consisting of nucleic acid sequences encoding a desired gene product operably linked to one of these promoter fragments in recombinant DNA constructions may be made. Transformation of plants with such constructions will result in new plants in which the expression of the product encoded by such chimeric genes can be controlled by the application of a suitable inducing chemical.

BACKGROUND OF THE INVENTION

The ability to externally control the expression of selected genes and thereby their gene products in field-grown plants by the application of appropriate chemical substances in the field can provide important agronomic and foodstuff benefits. This control is especially desirable for the regulation of genes that might be placed into transgenic plants and has many applications including (1) prolonging or extending the accumulation of desirable nutritional food reserve in seeds, roots, or tubers, (2) producing and accumulating products in plant tissues at a defined time in the developmental cycle such that these products are convenient for harvest and/or isolation, and (3) initiating the expression of a pest-specific toxin at the site of pathogen attack. The latter example may provide a means of avoiding contamination of the ultimate food product with the toxic agent as well as minimizing the development of resistance in the pest population by selective, tissue specific, rather than constitutive expression of the toxic agent. These and other benefits have been unattainable to date since a practical means to bring known plant genes under external control in the field has not been available.

In eukaryotic systems, the expression of genes is directed by a region of DNA called the promoter. In general, the promoter is considered to be that portion of DNA in a gene upstream from the coding region that contains the site for the initiation of transcription. The premoter region also comprises other elements that act to regulate gene expression. These include the "TATA box" at approximately 30 bp (−30) 5' relative to the transcription start site and often a "CAAT box" at −75 bp. Other regulatory elements that may be present in the promoter are those that affect gene expression in response to environmental stimuli, such as light, nutrient availability, heat, anaerobioisis, the presence of heavy metals, and so forth. Other DNA sequences contained within the promoter may affect the developmental timing or tissue specificity of gene expression. In additien, enhancer-like sequences that act to increase overall expression of nearby genes in a manner that is independent of position or orientation have been described in a number of eukaryotic systems. Homologs of these enhancer-like sequences have been described for plants as well. The vast diversity of promoter function in eukaryotic systems therefore provisos the opportunity to isolate promoters with relatively stringent requirements for their transcriptional activation which may be useful in regulating the timely expression of gene products in transgenic plants.

While current technology exists to transform plants with the genes encoding selected products, the expression of these genes is either continuous throughout the life cycle (controlled by a constitutive promoter), or regulated by the developmentally timed program of maturation inherent in each organ/tissue/cell (stage or tissue specific promoters) in which the gene product is destined to be expressed. Continuous expression precludes controlled production of a gene product at particular stages of the life cycle, in specific tissues or in response to environmentally unpredictable events. In addition, such constitutive expression could place a major penalty on yield, due to greatly increased energy demands accompanying prolonged high level synthesis of a single gene product. Tissue or stage specific expression, although valuable for the temporal and spatial accumulation of products, is under the variable timing of the developmental program of each plant. The practical use of promoters from these types of genes would therefore necessitate the isolation of a multitude of stage- and tissue-specific promoters for all crop species of interest.

Ideally, one would prefer to externally control the expression of a gene product in transgenic plants by application of an inducing signal that stimulates expression of the desired gene in any tissue(s) at any time in the plant's life cycle. This regulation would be accomplished by controlling the expression of a structural gene encoding the desired product with a promoter that is highly responsive to application of the inducing signal. The proposed inducer/promoter combination should be functional in a wide variety of plant species, with the inducer having no effect on the normal plant growth, development or morphology. Chemicals that fit the above criteria for regulating gene expression in plants would be of great utility in the field, as their use would be compatible with current agricultural practices. For instance, application of a chemical inducer could be easily accomplished using equipment currently in use by most plant growers. Ideally, a chemical/chemically responsive promoter combination could be made functional at any stage or in any tissue of a transformable plant to control the expression of any desired gene product.

There are inducer/promoter combinations that have been shown to regulate the expression of foreign genes in both bacterial and animal systems. Many of the inducible bacterial systems are based on the use of promoters that respond to metabolites or metabolite analogs that normally regulate bacterial growth. Addition of an appropriate metabolite to the media of active growing bacterial cultures transformed with genes driven by promoters that are responsive to these metabolites results in expression of the desired product. Examples of such inducer/promoter combinations include 3-β-indoylacrylic acid/Trp promoter, IPTG/lac promoter, phosphate/phosphate starvation inducible promoter, and L-arabinose/ara B promoter combinations. Similarly, heavy metal/metallothionine promoter, and heat/heat shock promoter combinations have been used in animal cell culture systems to control the expression of foreign genes.

There are a number of inducer/promoter combinations derived from plant genes that are known. Activation of many of these promoters is regulated by environmental factors such as light, heat shock and anaerobiosia. The promoters of these inducible genes have been extensively analyzed [c.f., Kuhlemeier et al., Ann. Rev. Plant Physiol., 38:221–257 (1987)]. However, the use of environmental inducers for regulating foreign genes is impractical since the inducing signal (i.e., light, temperature and $O_2$ levels) are not easily or practically controllable under conditions of normal agronomic practices. Other plant genes have been described that are induced by oligosaccharides, such as those generated during pathogen infection and/or wounding. Examples include the induction of phenylalanine ammonia lyase and chalcone synthase by glucan elicitors in soybean [Ebel, J., et al., Arch. Biochem. Biophys. 232, 240–248 1984] and induction of a wound-inducible inhibitor gene in potato [Cleveland, T. E. et al., Plant Mol. Biol. 8, 199–208 1987]. Again, the promoters of these inducible genes lack utility in regulating the expression of foreign genes in transformed plants due to either lack of a practical method of induction (wounding) or the deleterious effects that result from diverting metabolic energy from plant growth to large scale synthesis of products designed to combat pathogen attack (oliogsaccharide inducers).

A large number of chemicals, both natural products and synthetic compounds, have potential use in controlling gene expression in plants. However, any chemical that may be useful as an inducer of gene expression in the field must minimally be environmentally safe, have little or no effect on the normal growth, morphology and development of plants, and be easily used under conditions of normal agronomic practice.

A number of natural products are known that affect gene expression. These are mainly naturally occurring plant growth regulators such as the auxins, cytokinins, gibberellic acid, ethylene and abscisic acid [c.f., Davies, P. (Ed.) Plant Hormones and Their Roles In Plant Growth and Development, Martinus Nijhoff Publ. 1987], while other chemicals have equally dramatic effects such as salicylic acid [Hooft Vanhuijsduijnen et al., J. Gen. Virol., 67:235–2143 1986]. When the growth regulators described above are applied to various plants or plant derived cells/tissues/organs, a change in the metabolism is observed that has been shown to be due, at least in part, to new gene expression. Some products of these genes as well as the genes themselves have been isolated and characterized. However, since the chemicals that induce these genes normally function in regulating the growth and development of plants, they cannot be candidates for inducers of recombinant, chemically inducible genes in transgenic plants. This lack of utility is a direct result of undesirable pleiotropic effects that would arise from the undesired co-activation of the plant's endogenous hormone sensitive developmental programs along with the desired recombinant gene. For example, activation of a foreign gene by abscisic acid in developing plaDtS would induce many undesirable hormone effects including negative effects on plant metabolism [Milborrow, B. V. An Rev. Plant Physiol. 25, 259–207 1974], a sharp decline in growth rate, an induction of stomatal closure, and premature abscission of young leaves and fruits. Other phytohormones have similar negative effects on plant growth and development that preclude their use in regulating the expression of foreign genes in transformed plants. A more general review of phytohormone effects on vegetative plants including ABA, ethylene, cytokinins, and auxins, is presented in Phytohormones and Related Compounds: A Comprehensive Treatise Vols I and II, Letham, D. S., Goodwin, P. S., and Higgins, T. G. V. eds. Elsevier/North Holland (1978).

Among the potentially attractive chemical candidates that may have utility in regulating gene expression in transgenic plants is the group of compounds collectively called herbicide antidotes or safeners. Safeners are functionally defined as chemicals that have the ability to increase the tolerance of a crop plant to the toxic effects of herbicides when the plant is treated with the safener. It now appears that the safening action of these compounds is related to their ability to increase the metabolism of the herbicide in safener-treated plants [Sweetser, P. B., Proceedings of the 1985 British Crop Protection Society Conference-Weeds. 3:1147–1153 1985]. For example, treatment of maize and other cereal crops with safenets such as the dichloroacetamides increases their tolerance toward several groups of herbicides [Lay, M. M., and Casida, J. E. Pest. Biochem. Physiol. 6:442–456 1976, Parker, C. Pesticide Science 14:533–536 1983]. More specifically, N,N-diallyl-2,2-dichloroacetamide safening is correlated with an increased level of glutathione-S-transferases (GSTs), a family of enzymes knOwD tO detoxify several major classes of pre-emergent, selective herbicides by conjugating them with glutathione [Mozer et al., Biochemistry 22:1068–1072 1983]. This increase in GST activity is correlated with an increased steady-state level of GST mRNA in treated plants, as shown by the work of Wiegand et al [Wiegand, R. et al., Plant Mol. Biol., 7:235–243 1986]. Thus safener treatment of selected plants can increase the steady state level of a gene product without having significant effects on growth and morphology.

It has been shown that changes in the rate of metabolic detoxification of sulfonylurea herbicides in corn plants are induced by treatment with a variety of safeners [Sweetser, P. B., Proceedings of the 1985 British Crop PrOtection society conference, weeds 3:1147–1153 1985]. The result of this accelerated metabolic detoxification is increased herbicide tolerance in safener-treated plants. For example, 2 to 5 fold increases in the metabolism rates of chlorsulfuron and metsulfuron methyl have been observed in wheat and corn following application of the antidotes napthalic anhydride, N,N-diallyl-2,2-dichloroacetamide, or cyometrinil. This observed increase in sulfonylurea herbicide metabolism occurs within hours following antidote treatment. In addition, the safening activity of the chemicals is not seen if plants are treated with the protein synthesis inhibitor cycloheximide prior to safener treatment, indicating that the increase in herbicide metabolism is dependant on de novo protein synthesis. This requirement for new protein synthesis indicates that safener treatment may activate the transcription of specific nuclear genes, and that a safener/safener-induced gene promoter combination may exist that will have utility in regulating the expression of foreign genes introduced into transgenic plants. To date, however, there has been no reported example of an inducible expression system for transgenic plants based on activation of safeherresponsive promoter/structural gene recombinant DNA construction by the external application of a safener or safener like compound. Indeed, no system with real utility for externally regulating the expression of a desired gene in transgenic plants that is compatible with current agronomic practices is known.

The instant invention focuses on DNA promoter fragments derived from several plant species which are inducible by herbicide safenets of cereal crops. These promoters have been used to develop a safener/safener inducible gene system for controlling the expression of foreign genes in transformed plants. This system has utility for externally regulating the expression of desired genes in transgenic plants in a grower's field. Its advantages include the high level of activity shown by several of these promoters in response to application of an appropriate inducing chemical, the apparent expression of these promoters in all plant tissues tested to date, and the absence of pleiotropic effects generated by treatment of plants with these chemicals.

Ebert et al., [Ebert et al., Proc. Natl. Acad. Sci. (U.S.A.) 84:5745–5749 1987], discloses studies of the active fragment of DNA containing the nopaline synthase promoter. This promoter is constitutive rather than inducible, and while of bacterial origin, operates in a wide range of plant tissues. A construction was made so that the promoter controlled the expression of the reporter gene chloramphenicol acetyl transferase (CAT). The authors reported that a fragment of 33 bp (−97 to −130) of DNA was sufficient to promote expression of the CAT gene. They reported further that the presence of two copies of the fragment tripled the expression of the CAT gene. These results from stably transformed tobacco tissue were repeatable in a transient assay using tobacco protoplasts. Comparison of the level of CAT activity obtained when gene expression was controlled by the 33 bp fragment in both the transient expression and stably transformed tobacco protoplasts and tissues resulted in some differences. The authors nevertheless indicated their belief that such transient assays are valuable for studies of promoter sequences in stable transformation systems. Operable linkage of the nopaline synthase promoter to a structural gene, however results in constituitive expression of the gene product in transformed plants precluding its use in externally controlling gene expression.

Studies of the anaerobic induction of the maize alcohol dehydrogenase (Adh I) gene by electroporating gene fragments of Adhl into maize protoplasts from suspension culture cells nave been performed [Howard, et al., Planta, 170:535–450 (1987]. Transformed protoplasts were subjected to reduced oxygen levels and assayed for Adhl expression 20 hours later. To facilitate measurement of anaerobiosis-induced Adhl gene expression, the 5' promoter or regulatory fragment of the native Adhl gene (1096 base pairs) was functionally linked to a CAT gene. Their results demonstrated the normal anaerobic regulation of the inducible Adhl promoter/CAT gene from a monocot maize gene (i.e., Adhl) in protoplasts derived from a homologous cell culture system. They also showed that the Adhl promoter fragment, without the coding and 3' regions of the Adhl gene, is sufficient for anaerobic induction of a foreign coding region in maize protoplasts.

Other researchers [Lee et al., Plant Physiology 85:327–330 1987], have further defined the size of the DNA fragment responsible for anaerobic induction of the maize Adhl gene. These researchers transformed maize protoplasms with a recombinant gene consisting of a CAT coding region under the control of the Adhl promoter and measured the production of CAT 24 hours later. By modifying the length of the promoter fragment used in the construction, Lee et al. determined that 146 bp 5' to the transcription start site were sufficient to place the expression of CAT under anaerobic induction. However, the expression of CAT was increased 5× or 8× by the addition of 266 or 955 bp, respectively, of contiguous 5' promoter sequences.

Walker et al., [Walker et al., Proc. Natl. Acad. Sci. (U.S.A.) 84:6624–6628 1987], continued the studies of the DNA sequences in the promoter region of the maize Adhl gene required for aneorbically induced gene expression in a transient assay. They determined that control of anaerobic induction of gene expression resided in two sequences from the promoter: those being the sequence between −133 and −124 bp and the sequence between −113 and −99 by (5' to the transcription start site). Both sequences are necessary for induction. Attachment of the full 40 bp element to an unrelated viral promoter conferred anaerobic regulation to the chimeric promoter.

Others have shown that extremely low levels of CAT gene expression could be observed under appropriate anaerobic conditions when the DNA fragment between base pairs −1094 and +106 bp of the maize Adhl gene was used to regulate CAT gene expression in stably transformed tobacco cells, [Ellis et al., EMBO Journal 6:11–16 1987]. In fact, only CAT messenger RNA was detected. However, promoter elements from the octopine synthase gene of bacteria, or those from the Cauliflower Mosaic Virus (CaMV) linked 5' to the Adhl promoter, stimulated the expression of the CAT gene and permitted detection of CAT after anaerobic induction. The fragment of DNA consisting of 247 bp obtained adjacent and 5' to the transcription start site of the structural gene for Adhl, was sufficient to put the expression of the CAT gene under anaerobic control. Therefore, anaerobic control by the 247 bp fragment of DNA was maintained even when the octopine synthase and CaMV 35S promoters, which are constitutive promoters, were present. The region of the Adhl promoter responsible for anaerobic induction demonstrated in transient assays by Howard et al., Lee et al., and Walker et al. were similar and identical to the region showing anaerobic induction in stably transformed plants by Ellis et al.

Patents have been issued to animal and microbial systems in which the expression of selected gene sequences have been induced by chemicals that interact with certain regulatory sequences. U.S. Pat. No. 4,579,821 issued ho Palmiter and Brinster discloses the isolation of promoter/regulator sequences of the mouse metallothionein-I gene and its use to control the expression of selected DNA sequences operably linked to the promoter by exposure to heavy metal ions or steroid hormones. The expression of thymidine kinase fused to the metallothionein-I promoter was obtained in differentiated cells of adult mice upon administration of cadmium or dexamethasone. U.S. Pat. No. 4,703,005 issued to Nakata and Shinagaua discloses the isolation ef a gene for phosphate-binding protein (phoS) to which was fused a foreign gene 3' to phoS. The foreign gene is controlled by phosphate in the culture medium. None of these inventions, though has any potential utility for use with plants in the field. The heavy metal ions that activate the metallothionein promoter are both toxic to plants and would pose an extreme environmental hazard in the field. Similarly, promoters responsive to nutrients such as phosphate lack utility due to the requirement of plants for constant levels of these nutrients for normal growth in the field.

Several reports of attempts to regulate the expression of genes in transgenic plants have been reported. European patent application number 85302593.0 discloses the isolation of four heat shock gene promoters from soybean and claims their use for driving the expression of foreign genes in transgenic plants. In the applications, the authors claim the use of these promoters in temporarily activating expression of foreign genes such as a crystalline toxic protein structural gene of *Bacillus thuringensis* or an herbicide resistance gene in response to heat stress in vivo. However, this leaves the expression of a gene linked to one of these heat shock promoters to chance changes of the daily temperature in the field.

Marcotte and Quatrano [J. Cellular Biochem. Supplement 12C, 1988; Marcotte, W. R., Bayley, C. C., and Quatrano, R. S., Nature 335, 454–457 (1988)] have reported initial results of studies of the inducibility of a chimeric gene whose transcription is driven by promoter fragments derived from two abscisic acid (ABA)-inducible genes (Em and a 7S globulin) from wheat. The products of these genes were shown to be induced in whole plants by addition of ABA. The induction was shown to be, at least in part, at the level of transcription. Promoter fragments of varying lengths from the 5' region an Em genomic clone were translationally fused to a bacterial β-glucuronidase (GUS) coding region that was linked to polyadenylation signals from the CaMV 35S transcript. The ABA inducibility of GUS activity using these different length promoter fragments was analyzed in transient expression assays using both monocot (rice) and dicot (tobacco) protoplasts. They demonstrated that regions upstream of the Em coding region (650 bp) and the 7S globulin coding region (1800 bp) contain sequences that are sufficient for ABA-regulated expression of GUS activity in rice protoplasts transient assays. The Em promoter failed to show any responsiveness in the dicot transient expression assay, indicating that the promoter may not function in dicot plant species. However, as discussed in detail in an earlier section of this work, the induction of undesirable pleiotropic effects resulting from application of phytohormones (including ABA) to whole plants in the field precludes the use of these compounds in regulating gene expression in transformed plants.

A patent was issued in Europe to De Danske Sukkerfab A/B [CC87-106623] that claims a method to improve the nitrogen fixing system of leguminous plants by controlling the expression of genes of interest with a promoter from a root/nodule specific gene. Specifically, the inventors demonstrated that a chloramphenicol acetyltransferase (CAT) gene driven by the promoter derived from a soybean leghemoglobin gene was inducible in the roots of transformed plants in a fashion similar to other root specific genes that are affected by nodulation. The method is severely limited in that induction of genes is limited to simulation by nodulation and the induction is root specific. It cannot provide a true means to externally control the expression of genes at any time in all tissues of field grown transformed plants.

To date, there are no reports of practical means to externally regulate the expression of foreign genes in transgenic plants using a method compatible with those used in normal agronomic practices. While reports of plant promoter sequences stimulated by light, heat, anaerobic stress, and phytohormones have appeared, no disclosures of specific inducible promoters that are responsive to chemical substances that might constitute the basis for a practical method to control gene expression in plants by application of the chemical in the field have appeared. At this time, a clear need exists for such promoter sequences to be used in recombinant DNA constructions that would enable one to externally control the expression of genes that can confer agronomic advantages if expressed at the proper time. Further, this specificity of expression should be amenable to external control through exposure of plants to chemical substances which can be readily applied by a variety of application methods and which only induce the expression of the desired target gene.

SUMMARY OF THE INVENTION

A practical means to control the expression of selected genes in transformed plants and plant tissues by the application of a chemical substance has been discovered. The present invention provides nucleic acid promoter fragments and downstream sequences derived from corn, tobacco and petunia genes whose expression are responsive to a number of substituted benzenesulfonamides, and other compounds. These nucleic acid promoter fragments have been incorporated into recombinant DNA constructs containing a structural gene of non-plant origin. Transformation of plants with such constructions demonstrate that the expression level of the structural gene is regulated by chemical treatment. Specifically, one aspect of the present invention is a nucleic acid promoter fragment inducible by a compound of Formula I–IX:

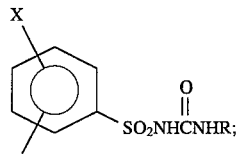
I

II

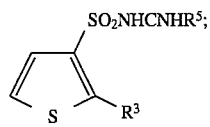
III

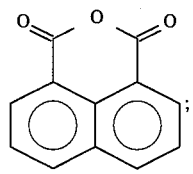
IV

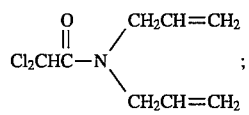
V

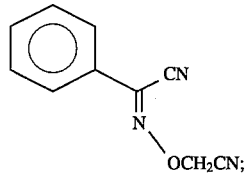
VI

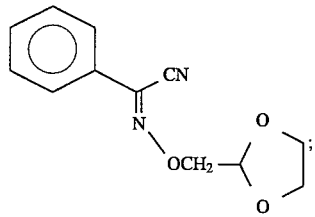
VII

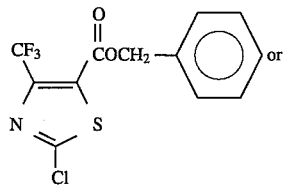
VIII

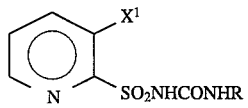
IX wherein
X is H, F, Cl, Br $CF_3$, or $C_1$–$C_2$ alkyl;
$X^1$ is H, F, Cl, $C_1$–$C_2$ alkyl, $SO_2NR^1R^2$ or $CO_2R^1$;
Y is H, Cl or $SO_2NR^1R^2$, $CO_2R^1$, $NO_2$, $P(O)(OR^1)_2$;
R is H, $C_1$–$C_6$ alkyl, $C_3$–$C_6$ cycloalkyl, benzyl or $C_2$–$C_4$ haloalkyl or $C_2$–$C_4$ substituted with $C_1$–$C_2$ alkoxy or $C_1$–$C_2$ alkylthio;
$R^1$ is $C_1$–$C_3$ alkyl;
$R^2$ is $C_1$–$C_3$ alkyl;

$R^3$ is $CO_2R_2$;

$R^4$ is $C_1$–$C_6$ alkyl or $C_3$–$C_6$ cycloalkyl;

$R^5$ is $C_1$–$C_3$ alkoxy or $NR^6R^7$;

$R^6$ is H, $OCH_3$, $C_1$–$C_4$ alkyl, $C_3$–$C_6$ cycloalkyl, $C_1$–$C_4$ alkyl substituted with $C_1$–$C_2$ alkoxy or ethoxyethoxy; and $R^7$ is H or $C_1$–$C_2$ alkyl;

and agriculturally suitable salts thereof such that exposure of plants transformed with said promoter fragment to a compound of Formula I–IX causes increased expression of a DNA sequence coding for a selected gene product operably linked to said promoter fragment.

Preferred nucleic acid promoter fragments are obtained from plants, while more preferred nucleic acid promoter fragments are obtained from monocotyledenous plants including corn, oats, millet, wheat, straw, barley, sorghum, amaranth, onion, asparagus and sugar cane; and from dicotyledonous plant selected from the group consisting of alfalfa, soybean, petunia, cotton, sugarbeet, sunflower, carrot, celery, cabbage, cucumber, pepper, canola, tomato, potato, lentil, flax, broccoli, tobacco, bean, lettuce, oilseed rape, cauliflower, spinach, brussel sprout, artichoke, pea, okra, squash, kale, collard greens, tea and coffee. Most preferred are nucleic acid promoter fragments obtained from corn, specifically those homologous to cDNA clones 2-1, 2-2, and 5-2.

Preferred compounds by virtue of activity or ease of synthesis are compounds of Formula I wherein:

X is H or 2-Cl;

Y is 3-Cl or $SO_2N(CH_3)_2$;

R is H, $C_1$–$C_6$ alkyl or $C_5$–$C_6$ cycloalkyl; and compounds of Formula II wherein:

R is $C_1$–$C_4$ alkyl or $C_5$–$C_6$ cycloalkyl;

$R_4$ is $C_1$–$C_4$ alkyl; and compounds of Formula III wherein:

$R_5$ is $OCH_3$ or $NR_6R_7$;

$R_6$ is H or $C_1$–$C_4$ alkyl; and $R_7$ is H.

More preferred for use with recombinant DNA constructions whose expression is regulated by a 2-1 promoter are the compounds N-(aminocarbonyl)-2-chlorobenzenesulfonamide, 2-chloro-N-(methylaminocarbonyl)benzenesulfonamide, 1-(n-butyl)-3-methylsulfonylurea, 1-cyclohexyl-3-(methylsunfonyl)urea, diethyl [[2-(butylaminocarbonyl)aminosulfonyl]phenyl]]phosphonate, methyl 1-[(aminocarbonyl)aminosulfonyl]benzoate, 2,3-dichloro-N-[(cyclopentylamino)carbonyl]benzenesulfonamide, and N-(aminocarbonyl)-2,3-dichlorobenzenesulfonamide. Most preferred is N-(aminocarbonyl)-2-chlorobenzenesulfonamide.

More preferred for use with recombinant DNA constructions whose expression is regulated by a 2-2 promoter are the compounds diethyl [[2-(butylaminocarbonyl)aminosulfonyl]phenyl]phosphonate, N'-[2-(n-butylaminocarbonyl)]-6-chloro-N,N-dimethyl-1,2-benzenedisulfonamide, N-isopropylcarbamoylbenzenesulfonamide, 2-chloro-N-(methylaminocarbonyl)benzenesulfonamide, 2,5-dichloroacetanilide, N-(aminocarbonyl)-2-chlorobenzenesulfonamide, and 1-cyclohexyl-3-(methylsulfonylurea. Most preferred is diethyl [[2-[(butylaminocarbonyl)aminosulfonyl]phenyl]]phosphate.

More preferred for use with recombinant DNA constructions whose expression is regulated by a 5-2 promoter are the compounds 2-chloro-N-(methylaminocarbonyl)benzenesulfonamide, 1-(n-butyl)-3-methylsulfonylurea, methyl 2-[(aminocarbonyl)aminosulfonyl]benzoate, N-isopropylcarbamoylbenzenesulfonamide, N-(aminocarbonyl)-2-chlorobenzenesulfonamide and N'-[2-(n-butylaminocarbonyl)]-6-chloro-N,N-dimethyl-1,2-benzenedisulfonamide. Most preferred is 2-chloro-N-(methylaminocarbonyl)benzenesulfonamide.

Another aspect of this invention involves a nucleic acid promoter fragment comprising a nucleotide sequence from the 5' flanking promoter regions of genes substantially homologous to specific cDNA clones, such that exposure of plants transformed with said promoter fragment to a compound of Formula I–IX causes increased expression of DNA sequence coding for selected gene products operably linked on the 3' end to said promoter fragment. Preferred genes are those from corn homologous to cDNA clones 2-1, 2-2, 218 or 5-2; those from petunia homologous to cDNA clone P6.1; and those from tobacco homologous to cDNA clone T2.1. Most preferred as a nucleic acid promoter fragment for the regulation of expression of DNA sequences for selected gene products upon exposure to a compound of Formula I–IX are those derived from the corn 2-2 gene.

Another aspect of the instant invention involves a recombinant DNA construct, capable of transforming a plant, comprising a nucleic acid promoter fragment of the invention, a DNA sequence coding for a selected gene product operably linked to said promoter fragment, and a suitable 3' downstream region such that exposure of said transformed plant to a compound of Formula I–IX causes increased expression of said DNA sequence for a selected gene product. Preferred DNA sequences for selected gene products are those encoding for β-glucuronidase, genes encoding herbicide resistance such as mutant acetolactate synthase and 5-enolpyruvylskikimate-3-phosphate synthase, genes encoding insect resistance, genes encoding protease inhibitors, genes encoding *Bacillus thuringiensis* insecticidal endotoxins, genes encoding phytohormone biosynthetic enzymes, genes encoding ethylene biosynthetic enzymes, genes encoding auxin biosynthetic enzymes, genes encoding cytokinin biosynthetic enzymes, genes encoding giberellin biosynthetic enzymes, genes encoding chitinases, genes encoding biosynthetic enzymes for oil production, genes encoding restriction endonucleases, genes encoding starch biosynthesis and/or degradation enzymes, genes encoding male sterility/fertility phenotype and genes encoding transposors and/or transposessors.

Yet another aspect of the invention involves plants transformed with a recombinant DNA construct of the invention such that exposure of said transgenic plant to a compound of Formula I–IX causes increased expression of a DNA sequence coding for a selected gene product operably linked 3' to said promoter fragment. The seeds of such transgenic plants are also envisioned as embodiments of the invention.

A final aspect of the invention involves a method of causing increased expression of a selected gene product in a plant comprising the steps of (a) transforming said plant with a recombinant DNA construct described abeve, (b) exposing the transgenic plant to a compound of Formula I–IX, and (c) causing said transgenic plant to increase expression of said selected gene product at a desired time.

BRIEF DESCRIPTION OF THE DRAWINGS

FIG. 1 shows the major steps used in one preferred embodiment of the invention.

FIG. 2 shows the nucleotide sequence of the 2-1 gene promoter from the gene designated as 21.14.

FIG. 4 shows subcloning of the 2-2 gene designated 2-2 #4 and the nucleotide sequence of the promoter from the 2-2 #4 gene.

FIG. 5 shows the nucleotide sequence of the 5-2 gene promoter from the gene designated as 52.411.

FIG. 7 shows the nucleotide sequence of the 218 gene promoter.

FIG. 8 shows the nucleotide sequence and transcription start site of the petunia P6 gene 1 promoter from the genesdesignated as P6.1.

FIG. 15 depicts the creation of plasmid pTDS231.

FIG. 16 shows the nucleotide sequence of the 21.14 gene promoter indicating the positions of deletions made in the promoter.

FIG. 21 shows the nucleotide sequence of the 443 promoter.

FIG. 22 shows the nucleotide sequence of the 463 promoter.

FIG. 23 shows the nucleotide sequence of the 478 promoter.

FIG. 24 shows the nucleotide sequence of the 420 promoter.

BRIEF DESCRIPTION OF SEQUENCE ID NUMBERS

Figure 3:
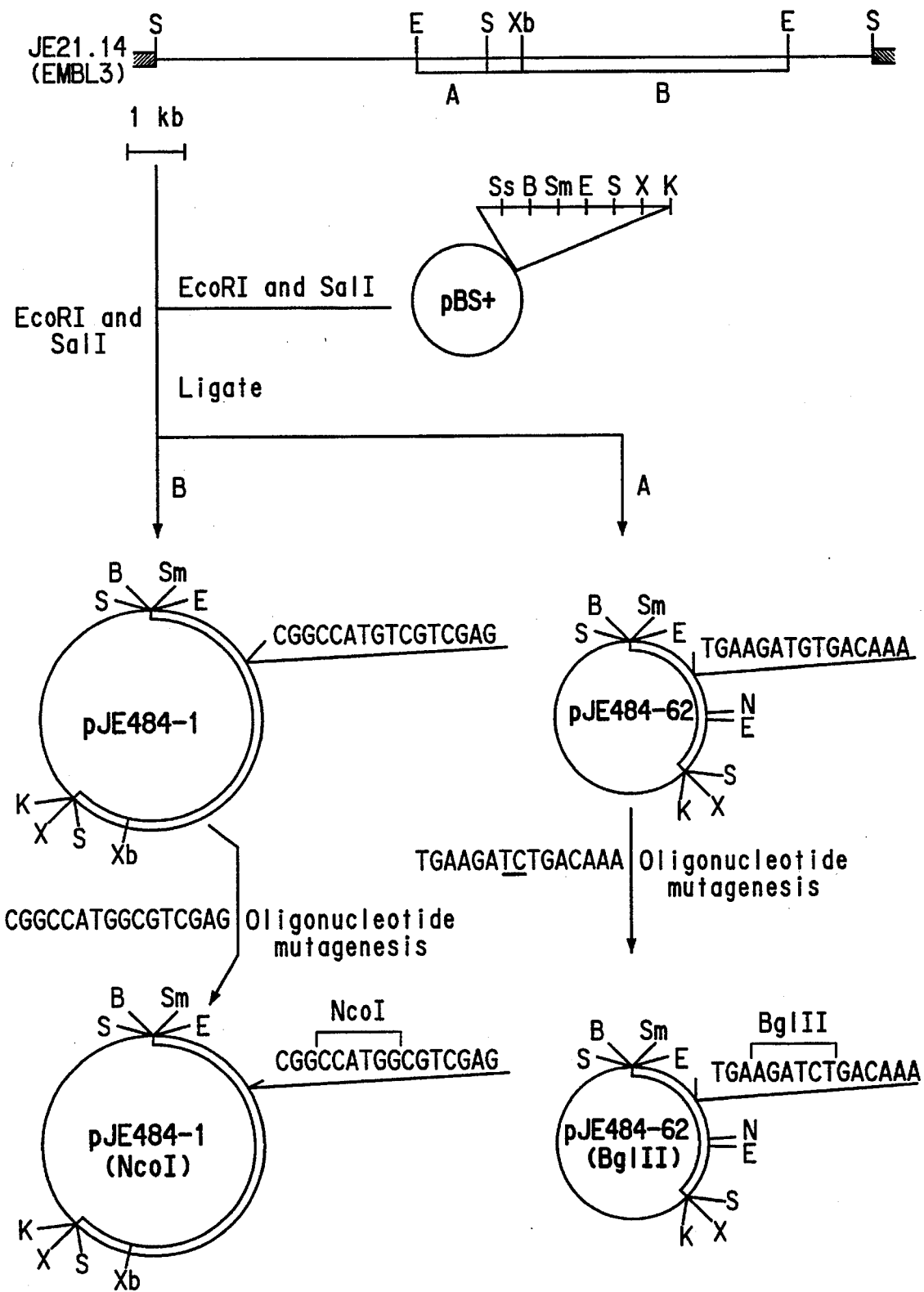
FIG. 3 depicts the creation of plasmids pJE481-1(Nco I) and pJE484-62(Xba I) from the 21.14 corn gene.

SEQ ID NO: 1 shows the nucleotide sequence of the 2-1 gene promoter from the gene designated as 21.14.

SEQ ID NO: 2 shows the nucleotide sequence of the promoter from the 2-2 #4 gene.

SEQ ID NO: 3 shows the nucleotide sequence of the 5-2 gene promoter from the gene designated as 52.411.

SEQ ID NO: 4 shows the nucleotide sequence of the 218 gene promoter.

SEQ ID NO: 5 shows the nucleotide sequence of the petunia P6 gene 1 promoter from the gene designate P6.1.

SEQ ID NO: 6 shows the nucleotide sequence of the 443 promoter.

SEQ ID NO: 7 shows the nucleotide sequence of the 463 promoter.

SEQ ID NO: 8 shows the nucleotide sequence of the 478 promoter.

SEQ ID NO: 9 shows the nucleotide sequence of the 420 promoter.

DETAILED DESCRIPTION OF THE INVENTION

The present invention provides DNA promoter fragments that are useful in bringing the expression of DNA sequence coding for selected gene products under the control of externally applied chemicals in transgenic plants. The promoter fragments described in this invention are derived from genes of corn, tobacco, and petunia that were found to be strongly inducible by a number of substituted benzenesulfonamides and weakly by several commercial herbicide antidotes. Expression of the gene product is obtained by treatment of the transgenic plant with a suitable inducing compound.

To accomplish the invention, cDNA libraries were made using RNA from the roots of plants treated hydroponically with the chemical N-(aminocarbonyl)2-chlorobenzenesulfonamide, a compound of formula I wherein X is H, Y is Cl, and R is H. Libraries were differentially screened using a strategy designed to identify clones representing mRNA species whose steady-state levels rise following treatment with this compound. These cDNAs were then characterized and used as hybridization probes to isolate the gene(s) encoding the induced RNAs from appropriate libraries of plant genomic DNA. Comparison of the nucleotide sequences derived for the cDNAs and their corresponding genomic clones permitted identification of putative promoter, structural gene, and 3' downstream regions for each gene. The DNA fragments comprising the promoter regions from these genes were isolated and operably linked to foreign coding regions to create novel chemically inducible genes. Suitable 3' downstream regions containing polyadenylation signals. were added to the promoter/coding regionsfusions to complete the construction of chemically inducible recombinant genes. These genes were then transformed into both plants and plant-derived tissues. Assays of N-(aminocarbonyl)-2-chlorobenzenesulfonamide-treated plants and plant tissues transformed with these DNA constructions demonstrate that these promoters are functional in transgenic plants and that they retain their responsiveness to external chemical stimulation.

As genes from three divergent plant species have been found to have promoters that are inducible by a number of compounds of formulae I–IX, it is likely that any number of plant species will possess promoters responsive to selected members of these classes of chemistry. Therefore, it is expected that the invention can also be accomplished using promoters unrelated to those disclosed here that are derived from other plant species as long as the expression of the promoter is responsive to scope of chemistry defined in this invention. Indeed, it is expected that the invention may well be accomplished by using promoters derived from genes inducible by compounds of formulae I–IX that are isolated from any prokaryotic or eukaryotic species.

The promoters disclosed in this work may be further modified if desired to alter their expression characteristics. It is expected that a small DNA fragment can be derived from a chemically-inducible promoter that is responsible for the chemical responsiveness of that promoter. This fragment may be combined with suitable regions from other promoters to create recombinant promoters whose expression level can be increased in transformed plants by treatment with compounds of Formulae I–IX. For example, the 77 bp fragment corresponding to bases 264 and 340 of FIG. 4 that appears to be necessary for chemical responsiveness in the 2-2 promoter may be incorporated into seed-specific promoters such as the β-conglycinin or phaseolin promoters to create chimeric promoters that are chemically inducible and active only in developing seeds. Similarly, any number of chimetic promoters can be created by ligating a DNA fragment sufficient to confer chemical inducibility from any of the promoter claimed here to constitute promoters or promotes with other specificities such as tissue-specific promoters, developmentally-regulated promoters, light-regulated promoters, stress-responsive promoters, hormone-responsive promoters and so on. This should result in the creation of chimeric promoters capable of inducing expression of gene products in any plant tissues or combination of tissues at any specific time in the plant's life cycle in response to chemical treatment.

Chemically-inducible promoters disclosed herein include possible variations of said promoters such as those derived from deletion, rearrangement, random or controlled mutagenesis of the promoters, promoters driven by ligation with foreign operator regions, promoters ligated to enhancer or enhancer-like elements (transcription activators) from any source such as the enhancer-like element from the 35S cauliflower mosaic virus transcripts, etc.

It is believed that any 3' downstream region capable of providing a polyadenylation signal and other regulatory sequences that may be required for the proper expression and processing of a mRNA may be operably linked to the 3' end of a structural gene to accomplish the invention. This would include the native 3' end of the homologous gene from which the chemically-inducible promoter itself was derived, the 3' end from a heterologous gene encoding the same protein in another species, the 3' end from viral genes such as the 3' end of the 35S or the 19S cauliflower mosaic virus transcripts, the 3' end of the opine synthesis genes of *Agrobacterium tumefaciens*, the 3' ends of RUBISCO or CAB genes, or the 3' end sequences from any source such that the sequence employed provides the necessary regulatory information within its nucleic acid sequence to result in the proper expression of the promoter/coding region combination to which it is operably linked.

Since the transcription start site for each of the various genes diclosed in this work has yet to be determined for all promoters the numbers for nucleotide positions in the various promoter fragments used in constructions are based upon either the assignment of the A residue of the ATG codon that initiates translation of the protein encoded by that gene as nucleotide 1 of the promoter fragment or assignment of the actual transcription start site as nucleotide 1. Nucleotides 5' to number 1 residue are numbered sequentially starting with −1. It is understood and expected that the DNA sequence between the transcription start site in each of these promoter fragments and, the translation start site, i.e. the region comprising the 5' untranslated leaders of the mRNAs encoded by these genes, can be replaced by other 5' untranslated leaders from other genes without affecting the chemical-inducibility of the resulting DNA constructions.

In the context of this disclosure, a number of terms shall be utilized. As used herein, the terms "promoter" and "promoter region" refer to a sequence of DNA, usually upstream (5') to the coding sequence of a structural gene, which controls the expression of the coding region by providing the recognition for RNA polymerase and/or other factors required for transcription to start at the correct site. Promoter sequences are necessary but not always sufficient to drive the expression of the gene. A "promoter fragment" constitutes a fraction of the DNA sequence of the promoter region. "Nucleic acid" refers to a large molecule which can be single stranded or double stranded, composed of monomers (nucleotides) containing a sugar, phosphate and either a purine or pyrimidine. In higher Flanks, deoxyribonucleic acid (DNA) is the genetic material while ribonucleic acid (RNA) is involved in the translation of the information from DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. As used herein, "DNA sequence for a selected gene product" refers to a DNA sequence that codes for a specific RNA transcript. "Suitable regulatory sequence", as used herein, refers to a nucleotide sequence located upstream (5'), within, and/or downstream (3') to a DNA sequence for a selected gene product whose transcription and expression is controlled by the regulatory sequence, potentially in conjunction with the protein biosynthetic apparatus of the cell. "RNA transcript" refers to the product resulting from the RNA polymerase catalyzed transcription of a DNA sequence. The RNA transcript may be a perfect complementary copy of the DNA sequence and is referred to as the primary transcript or it may be an RNA sequence derived from posttranscriptional processing of the primary transcript and is referred to as the mature RNA. "Regulation" and "regulate" refer to the modulation of gene expression induced by DNA sequence elements located primarily, but not exclusively upstream of (5' to) the transcription start of agene. Regulation may result in an all or none response to a stimulation, or it may result in variations in the level of gene expression. "Responsive" and "response", as used herein, refer to the change in the expression level of a regulated promoter or gene following the application of an environmental stimulus. The term "structural" gene refers to that portion of a gene encoding a protein, polypeptide, or a portion thereof, and excluding the regulatory sequences which drive the initiation of transcription. A structural gene may be one normally found in the cell or it may be one not normally found in a cellular location wherein it is introduced, in which case it is termed a heterologous gene. A heterologous gene may be derived in whole or in part from any source known to the art, including a bacterial genome or episome, eukaryotic nuclear or plasmid DNA, cDNA, or chemically synthesized DNA. The structural gene may constitute an uninterrupted coding region or it may include one or more introns bounded by appropriate splice junctions. The structural gene may be a composite of segments derived from different sources, naturally occurring or synthetic. A "3' downstream region" (or "3' end") refers to that portion of agene comprising a DNA segment, excluding the 5' sequence which drives the initiation of transcription and the structural portion of the gene, that contain a polyadenylation signal and any other regulatory signals capable of affecting mRNA processing or gene expression. The polyadenylation signal is usually characterized by affecting the addition of polyadenylic acid tracts to the 3' end of the mRNA precursor. Polyadenylation signals are commonly recognized by the presence of homology to the canonical form 5'-AATAAA-3', although variations are not uncommon. The term "recombinant DNA construct" refers to a plasmid, virus, autonomously replication sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a plant cell. As used herein, "plant" refers to whole plants and plant-derived tissues. "Plant-derived tissues" refers to differentiated and undifferentiated tissues of plants, including, but not limited to roots, shoots, leaves, pollen, ovules, seeds, tumor tissue, and various forms of cells in culture such as intact cells, protoplasts, embryos and callus tissue. Plant-derived tissues may be in planta or in organ, tissue or cell culture. A "monocotyledonous plant" refers to a plant whose seeds have only one cotyledon, or organ of the embryo that stores and absorbs food. A "dicotyledonous plant" refers to a plant whose seeds have two cotyledons. A "protoplast" refers to a plant cell without a cell wall or extracellular matrix. As used herein, "transformation" means processes by which cell/tissue/plant acquire properties encoded on a nucleic acid molecule that has been transferred to the cell/tissue/plant. "Transferring" refers to methods to transfer DNA into cells including microinjection, or permeabilizing the cell membrane with various physical (e.g., electroporation) or chemical (e.g., polyethylene glycol, PEG) treatments. As used herein, "exposure of" a protoplast or a plant to a chemical substance refers to treating, incubating, contacting said protoplast or plant with the substance. The term, "operably linked" refers to the chemical fusion of two fragments of DNA in a proper orientation and reading frame to be transcribed into functional RNA. As used herein, the term "homologous to" refers to the similarity between the nucleotide sequences of two nucleic acid molecules or between the amino acid sequences of two protein molecules. Estimates of such homology are provided by the use of either DNA-DNA or DNA-RNA hybridization under conditions of stringency as is well understood to those skilled in the art [as described in Hames and Higgins (eds.) Nucleic Acid Hybridization, IKL Press, Oxford, UK]; or by the comparison of the sequence similarity between two nucleic acids or proteins. As used herein, "substantially homologous" refers to nucleic acid molecules which require less stringent conditions for hybridization than conditions required for such molecules to be homologous to each other; as well as to DNA protein coding sequences which may involve base changes that do not cause a change in the encoded amino acid, or which involve base changes which may alter an amino acid but not affect the functional properties of the prorein encoded by the DNA sequence, or this may refer to DNA sequences involved in regulating transcription of a gene. Thus, the nucleic acid promoter fragments described herein include molecules which comprise possible variations of the nucleotide bases derived from deletion, rearrangement, and random or controlled mutagenesis of the promoter fragment so long as the DNA sequences of the promoter fragments are substantially homologous. "Effective sequence" of a DNA sequence coding, for a protein refers to a truncated version of the DNA sequence which encodes a peptide which is at least partially functional with respect to the utility of the original protein. The term "expression" as used herein is intended to mean the transcription and/or translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein. Expression, which is constitutive and further enhanced by an externally controlled promoter fragment thereby producing multiple copies of messenger RNA and large quantities of the selected gene preduct, is referred to as "over-production". The "translation start codon" refers to a unit of three nucleotides (codon) in a nucleic acid that specifies the initiation protein synthesis.

The techniques of DNA recombination used throughout this invention are known to those skilled in the art and are generally described in Maniatis et al., *Molecular Cloning: A Laboratory Manual,* Cold Spring Harbor Laboratory, Cold Spring Harbor, N.Y., 1982).

Enzymatic Treatments of DNA

Restriction Enzyme Digestions

The restriction enzyme digestion buffers and digestion conditions used were those supplied by the manufacturer of each particular enzyme. Enzyme was added to give 5–10 units per microgram of DNA and the reaction mixture was adjusted to the appropriate final volume with water (usually 10–20 µl). The restriction enzyme reaction mixtures used routinely contained 0.7–10 µg of plasmid DNA. The reaction mixtures were mixed and then generally incubated at the appropriate temperature for up to 2 hours. Digestion of DNA with multiple enzymes was done concomitantly when the optimal salt and temperature conditions of the separate enzymes are compatible. When these conditions were sufficiently different, digestions were done sequentially beginning with the enzyme requiring the lowest salt concentration. Subsequent reactions were supplemented to the appropriate buffer conditions for the enzyme used.

Gel Electrophoresis of DNA

For polyacrylamide gel electrophoresis of DNA, the Tris-Borate-EDTA (TBE) buffer described by Bethesda Research Laboratories, Gaithersburg, Md. 20877 which consists of 89 mM Tris and 89 mM borate (pH 8.3), 2.5 mM $Na_2EDTA$ was used. The gels used consisted of 5% acrylamide and 0.2% bis-acrylamide dissolved in 100 ml 1×TBE. To this solution, 0.225 ml of an aqueous 25% ammonium persulfate solution was added.

After adding 55 µl of N,N,N',N'-tetramethyl ethylenediamine (TEMED), the solution was pipetted into a gel mold. One mm comb and spacers were commonly used and approximately 0.5 to 2 µg of DNA was loaded per well. Electrophoresis was carried out at 150–250 volts in 1 × TBE. After electrophoresis, the gel was stained in an aqueous solution of ethidium bromide (1 µg/ml) and the DNA was visualized on an ultraviolet transilluminator. The gel was photographed using a Polaroid camera and Polaroid 667 film (Polaroid Tech. Photo, Cambridge, Mass. 02139).

DNA was recovered from polyacrylamide gels as follows: The desired band, visualized by ethidium bromide (EtBr) staining, was cut from the gel, placed in an Eppendorf tube and minced with a teflon pestle. An equal volume of a 0.5M ammonium acetate, 1 mM EDTA solution was added and the tube was incubated at 37° C. overnight with vigorous shaking. The following day, the tube was centrifuged at 14,000 x g in a microfuge for 10 minutes at room temperature, the supernatant was removed, ½ volume of elution buffer was added to the minced polyacrylamide and the contents were mixed and vortexed. The tube was centrifuged again as above, and the supernatant was removed and pooled with the original sample. The pooled supernatants were passed over a small glass wool column to remove any residual polyacrylamide gel pieces and the DNA in the sample was precipitated by addition of 2 volumes of ethanol and incubation in dry ice-ethanol. The DNA was collected by centrifugation of the sample in a microfuge, as above, for 15 minutes at 4° C. The pellet was then rinsed with 70% ethanol, dried under vacuum and resuspended in the buffer of choice depending on the nature of the next manipulation.

Agarose gel electrophoresis of DNA was performed in 0.7% agarose gels using the buffer described above for polyacrylamide gels. Electrophoresis was conducted at a voltage of 50 to 150 volts depending on the amount of DNA per lane and the desired timing of the run. After electrophoresis, the gel was stained with 1 μg/ml of EtBr and the DNA is visualized on an ultraviolet transilluminator and photographed as described above.

DNA was often recovered from agarose gels using low gelling temperature agarose, Sea Plaque Agarose from FMC Corporation, Marine Colloids Division, Rockland, ME 04841. The electrophoresis procedure was stated above. After visualization of the DNA of interest, the band was cut out and placed into a microcentrifuge tube. The tube was then frozen at −80° C. for 30 minutes and then thawed. The agarose was then smashed with a pestle and the sample was centrifuged in a Beckman TL-100 table-top ultracentrifuge at 25,000 rpm for 30 minutes. The supernatant was removed from the tube without disturbing the agarose pellet at the bottom of the tube. The sample was precipitated with the addition of 1/10 volume of 3M sodium acetate pH 6.0 and 2 volumes of ethanol followed by a 15–30 minute incubation at −80° C. The DNA was recovered by centrifugation in a microfuge for 15 minutes at 4° C. The DNA pellet was then washed with 70% ethanol, dried under vacuum and resuspended in TE buffer.

Plasmid Isolation and Purification

A 25 ml overnight culture (or exponentially growing culture) of the bacteria containing the desired plasmid was prepared. Two ml of the overnight culture was diluted into 1 liter of M9CA or L broth (as described in Molecular Cloning: A Laboratory Manual, Maniatis T. et al., Cold Spring Harbor Laboratory, Cold Spring Harbor, N.Y.) and incubated for 16 hours [overnight] at 37° C. with vigorous shaking using appropriate antibiotic selection. The bacteria were collected by centrifugation at 4000xg [5500 rpm] in a GSA rotor] for 5 min at 4° C. The pellets were drained well and resuspend in a total volume of 36 ml of GTE buffer (50 mM glucose, 25 mM TRIS-HCl, pH 8 and 10 mM EDTA). Four ml of 40 mg/ml lysozyme were added to the bacterial suspension and the mixture was incubated at room temperature for ten minutes. The cell suspension was cooled on ice and 80 ml of freshly made [0.2 N NaOH and 1% SDS] were added with gentle swirling to lyse bacteria. The lysate was incubated the on ice for 10 minutes 40 ml of 3M potassium acetate in 2M acetic acid were added. The mixture was then incubated on ice for 15 minutes. The precipitate was removed by centrifugation at 24,000 g [12 K rpm] for 15 minutes and the supernatant was filtered through 4–5 layers of cheesecloth. Nucleic acids were precipitated by addition of 0.6 volumes of isopropanol. The resulting precipitate was collected by centrifugation at 12,000 rpm for 10 minutes at 15° C. in a GSA rotor. The pellet was washed with 70% ethanol (in TE buffer) and the DNA was re-centrifuged as before. The nucleic acid pellet was dissolved in 3.85 ml of TE, pH 8. After the DNA has dissolved, 4.4 g of CsCl were added to the solution. After dissolution of CsCl, 0.32 ml of ethidium bromide (EtBr) was added to the solution from a 10 mg/ml stock (final concentration of 600 ug/ml). The plasmid DNA was banded by centrifugation at 65,000 rpm for at least 15 hr in a Beckman 70.1 Ti rotor. The gradient generally contained three bands. The lowest band absorbed no ethidium bromide, while the two upper bands did absorb the dye. The less dense top band which corresponds to chromosomal DNA often was barely visible. The plasmid band, which was the lower of the two EtBr absorbing bands was removed from the gradient by puncturing the side of the tube below the band with a 20 gauge needle and drawing the DNA out of the tube. The EtBr was removed by repeated extraction of the DNA with NaCl saturated 2-propanol. This was made by adding 10 ml of 50 mM TRIS-HCl, pH 8.0, 1 mM EDTA and 10 ml of 5M NaCl to 80 ml of 2-propanol. The extracted plasmid DNA was diluted 3 fold with TE pH 8.0 and precipitated with 2 volumes of ethanol at −20° C. The DNA was recovered by centrifugation at 10,000 g for 30 minutes, resuspend in TE buffer and re-precipitated with sodium acetate and ethanol. The DNA was resuspend in TE buffer and stored at −20° C.

Biological Material Deposits

The following cell lines and plasmids, as described herein, have been deposited with the American Type Culture Collection, 12301 Parklawn Drive, Rockville, Md. 20852, and have been given the following ATCC accession designations:

| ITEM | DATE | ATCC ACCESSION |
|---|---|---|
| plasmid pIn2-2-3 in E. coli strain HB101 | 9/27/88 | 67803 |
| plasmid pIn5-2.32 in E. coli strain HB101 | 9/27/88 | 67804 |
| plasmid pIn2-1.12A in E. coli strain HB101 | 9/27/88 | 67805 |
| plasmid pMSP$^r$K in E. coli strain HB101 | 6/08/88 | 67723 |
| plasmid T2.1 in E. coli JM83 | 10/11/88 | 67822 |
| plasmid P6.1 in E. coli JM83 | 10/11/88 | 67823 |
| plasmid pJJ3431 in E. coli JM83 | 2/03/89 | 67884 |

The present invention is further defined in the following EXAMPLES, in which all parts and percentages are by weight and degrees are Celsius, unless otherwise stated. It should be understood that these EXAMPLES, while indicating preferred embodiments of the invention, are given by way of illustration only. From the above discussion and these EXAMPLES, one skilled in the art can ascertain the essential characteristics of this invention, and without departing from the spirit and scope thereof, can make various changes and modifications of the invention to adapt it to various usages and conditions. Further, the present invention is not to be limited in scope by the biological materials deposited, since the deposited materials are intended to provide illustrations of starting materials from which many embodiments cf the invention may be derived. All such modifications are intended to fall within the scope of the appended claims.

EXAMPLE 1

Identification, Isolation and Modification of the Promoter and 3' Downstream Regions of the 21.14 Corn 2-1 gene

Growth and Chemical Treatment of Plants

Missouri 17 corn seeds were surface sterilized by soaking them in a solution of 10% commercial bleach and 0.1% sodium dodecylsulfate (SDS) for 30 minutes. Seeds were then rinsed thoroughly in a buchner funnel with sterile distilled water and prepared for germination by placing them onto 5–6 layers of moist sterile paper towels in a 8"×10" glass baking tray. The tray was covered with aluminum foil and placed in the dark in a 30° C. incubator for 48–72 hours to allow the seeds to germinate. After germination, seedlings were grown hydroponically in an apparatus consisting of a sheet of 8 mesh stainless steel wire gauze suspended over the top of a 2 liter glass beaker filled with sterile half strength Hoagland's solution (referred to 0.5× Hoagland's) so that the roots extended through the mesh and into the media. The hydroponic apparatus was aerated by introducing humidified air into the bottom of the beaker with a gas diffusing stone commonly used in tropical fish aquariums. The apparatus was covered with a loose-fitting sheet of aluminum foil and placed in a reach-in growth chamber illuminated by both fluorescent and incandescent lamps at an intensity of 4400 lux. Seedlings were grown at 28° C., 75% relative humidity using a 16 hour day/8 hour night cycle. After two days, the foil was removed and plants were grown for an additional 5–6 days. Any 0.5× Hoagland's lost to evaporation was replenished every 2–3 days. On the tenth day, plants were transferred into either fresh 0.5× Hoagland's for untreated plants, 0.5× Hoagland's containing 0.2 g/liter of 2-chlorobenzenesulfonamide for chemically treated control plants, of 0.5× Hoagland's containing 0.2 g/liter of N-(aminocarbonyl)-2-chlorobenzenesulfonamide for chemically treated plants. Plants were then allowed to grow for six additional hours prior to harvest.

Roots were harvested from hydroponically grown plants by removing the wire mesh from the beakers with the corn plants still intact. The roots were cut from the plants just below where they were immersed in growth media and 10–15 g portions of root tissue were wrapped in aluminum foil and immersed in liquid nitrogen. Frozen tissue was transferred from liquid $N_2$ to a −80° C. freezer where it was stored for up to one year before use.

Isolation of Total Cellular RNA From Root Tissue

Guanidine thiocyanate reagent was prepared by dissolving the contents of a 100 g bottle of guanidine thiocyanate (Kodak Laboratory and Specialty Chemicals, CAT #705) in 80 ml of water and adding 10.6 ml 1M Tris-HCl, pH 7.6 and 10.6 ml 200 mM $Na_2EDTA$, pH 7.6. The solution was stirred until the contents of the bottle were dissolved and 4.24 g of sodium lauryl sarcosinate and 2.1 ml β-mercaptoethanol were added. The volume of the solution was adjusted to 212 ml with sterile $H_2O$ and it was filtered twice through disposable 0.2 μm sterile filtration units. The guanidine thiocyanate reagent was stored at 4° C. in the dark until used.

Frozen root tissue samples were removed from the −80° C. freezer and transferred to liquid nitrogen. Once cooled to liquid $N_2$ temperature, 10–15 g of tissue was transferred to a mortar and pestle that had been pre-cooled with liquid nitrogen and the tissue was ground to a fine powder. The powdered tissue was then transferred to a 150 ml Corex® centrifuge bottle containing five volumes (v/w) of ice cold guanidine thiocyanate reagent, 0.5 ml of $CHCl_3$, 0.2 ml n-octanol, 1 drop pourire (American Scientific Products, McGaw Park, Ill. 60085, CAT #B 1162-1), and 2.5 ml vanadyl ribonucleoside complex (Bethesda Research Laboratories, Gaithersburg, Md. 20877, CAT #5522SA). The tissue was then ground further by vigorous homogenization with a PT-10/35 polytron (Brinkmann Instruments) for one minute at maximum speed. The crude tissue extract was then centrifuged at 27,000 g for 10 minutes at 4° C. The supernatant was decanted into a graduated cylinder and 1 g of CsCl was added for each 2.5 ml of supernatant. The solution was then centrifuged at 36,000 g for 10 minutes at 4° C. and the resulting supernatant was layered over 2 ml pads of 5.7M CsCl (in 100 mM EDTA pH 7.6) in 9/16"×3½" polyallomar ultracentrifuge tubes. The resulting step gradient was centrifuged at 35,000 rpm for 15–20 hr at 10° C. using a Beckman SW41Ti rotor or equivalent. Following ultracentrifugation, the supernatant was carefully removed by aspiration and the tubes were inverted and allowed to drain well. With the tubes still inverted, the tops of the tubes were cut off using a razor blade and discarded, saving only the bottom 1.5 cm containing the RNA pellets. The sides were carefully wiped clean with a laboratory tissue wipe and the pellets were dissolved in 0.2 ml of TES buffer (10 mM TRIS-Cl pH 7.4, 5 mM EDTA, 1% SDS) and transferred to a 15 ml Corex® centrifuge tube. The bottom of each polyallomar tube was rinsed with a second 0.2 ml aliquot of TES and then the two aliquots were combined. The RNA was combined with an equal volume of chloroform:n-butanol (4:1 v/v) and vortexed briefly. The resulting emulsion was centrifuged at 8,000 g for 5 min. at 20° C. or at high speed in a clinical table-top centrifuge for 10 minutes. The aqueous layer was transferred to a fresh 15 ml Corex® centrifuge tube, the organic phase was back-extracted with an equal volume of TES, and the two aqueous layers were pooled. RNA was precipitated at −20° C. for at least 2 hr after adding a tenth volume of 3.0M sodium acetate pH 6.0 and two volumes of ethanol. The RNA was recovered by centrifugation at 10,000 g for 20 min. at 4° C. The supernatant layer was gently aspirated off and the RNA was dissolved in 0.5 ml of either sterile water or 1 mM EDTA, pH 7.6. A small aliquot was diluted 100 fold with water and the A260 of this dilution was measured to determine RNA concentration.

Isolation of poly(A)$^+$ RNA

Poly (A)$^+$ RNA was purified from 5 mg of total cellular RNA preparations by thermoelution from poly-U-Sephadex®. All buffers were sterilized by autoclaving prior to use. Total RNA was diluted to less than 500 μg/ml with low salt poly-U buffer (20 mM Tris-Cl, pH 8.0, 1 mM EDTA and 0.1% SDS). The RNA was denatured by heating at 65° C. for 5 minutes followed by rapid cooling on ice for 5 minutes. NaCl was added to a final concentration of 150 mM, and this solution was loaded onto a water jacketed column (Bio-Rad, 1414 Harbour Way South, Richmond, Calif. 94804, CAT #737–2231) containing 2 g of poly U-Sephadex (Bethesda Research Laboratories, CAT #5941SB) that had been equilibrated with high salt poly U buffer (20 mM Tris-Cl, pH 8.0, 1 mM EDTA, 0.1% SDS and 150 mM NaCl). The column was maintained at a temperature of 25°–30° C. with a circulating water bath. The column was then washed once with 6–7 ml of high salt poly-U buffer. The running temperature of the column was increased to 40° C. and it was washed again with 6–7 ml of high salt poly-U buffer. Seven ml of low salt poly-U buffer was then added to the column and the temperature was raised to 60° C. After waiting 5 minutes for the temperature of both the column and low salt poly-U buffer to equilibrate, poly (A)$^+$ RNA was eluted and collected in 0.5 ml fractions. Fractions containing RNA (determined by measuring the $A_{260}$ of a small aliqout from each fraction) were pooled and ethanol precipitated as described earlier. RNA was re-precipitated as above but with potassium acetate rather than sodium acetate, resuspended in water at a concentration of 1 mg/ml and stored at −80° C.

Construction of cDNA Libraries cDNA was synthesized from 5 μg of N-(aminocarbonyl)-2-chlorobenzenesulfonamide treated poly (A)$^+$ RNA using a cDNA synthesis kit (Amersham Corporation, CAT #RPN 1256). The manufacturer's recommended protocol was followed without modification. The mass of double-stranded (ds) cDNA synthesized was calculated from the amount of [α32P]dCTP incorporated during the first and second strand synthesis reactions. The average size of the cDNA synthesized was then estimated from its mobility during electrophoresis in alkaline agarose gels. The average number of 5' ends/ug of cDNA was then calculated. The double-stranded cDNA was ethanol precipitated and was recovered by centrifugation for 10 minutes at 4° C. The DNA pellet was briefly dried under vacuum and dissolved in $H_2O$. 250 uCi of [$^3$H] dCTP in 50% ethanol was added to a 1.5 ml microfuge tube and dried in vacuo. One microgram of ds cDNA in a volume of 7 μl was transferred into this tube, followed by 25 μl of 2× tailing buffer (2.5 mM β-mercaptoethanol, 100 mg/ml BSA, 3.5 mM $MnCl_2$ and 135 mM potassium cacodylate, pH 7.0). Ten units of terminal deoxynucleotidyl transferase was added and the tube was incubated at 30° C. for 21 minutes. The tailing reaction was stopped by addition of EDTA to a final concentration of 20 aM and the tube was placed on ice. The C-tailed reaction products were extracted once with an equal volume of phenol:chloroform (1:v/v) and purified by spun-column chromatography. Spun column chromatography was performed by plugging the bottom of a 1 ml disposable syringe with sterile glass wool and filling it with Sephadex® G-50 that was equilibrated in STE buffer (TE, pH 8.0 containing 100 mM NaCl). The syringe was inserted into a de-capped 1.5 ml microfuge tube placed in the bottom of 15 ml Corex® centrifuge tube. The column was centrifuged at 1600 g for 4 minutes in a bench top clinical centrifuge. Additional Sephadex® G-50 was added and the column was spun again. This process was repeated until a packed bed volume of 0.9 ml was obtained. Two rinses of the column were conducted with 0.1 ml of STE buffer and the syringe was centrifuged as above between each rinse. DNA samples were loaded onto the column in a volume of 0.1 ml in STE buffer and the column was centrifuged in a decapped microfuge tube as described above. The DNA was recovered by collecting the effluent in a microfuge tube and storing it at −20° C. The average number of dC residues added per 3' end of cDNA was then calculated from the % incorporation of the [$^3$H] dCTP into the cDNA.

Equilimolar amounts C-tailed ds cDNA and dG-tailed pBR322 vector DNA (New England Nuclear Research Products, 549 Albany St., Boston, Mass. 02118 CAT #NEE-118) were mixed together in 0.1M NaCl, 10 mM Tris-HCl, pH 7.8, and 1 mM EDTA in volume of less than 10 μl. The DNA in the mixture was annealed by first heating it to 70° C. for 10 minutes in a water bath. The bath was then turned off and the mixture was allowed to slowly cool to room temperature. The mixture was then moved tca cold room and slow-cooled to 4° C. Small aliquots of annealed DNA were used to transform competent *E. coli* HB101. Competent cells were prepared by diluting 0.1 ml of an overnight culture of HB101 grown in LB broth into 50 ml of the same media. This fresh culture was grown at 37° C. with shaking until it reached an A650 of 0.2–0.5. Cells were then harvested by centrifugation at 2500 g for 5 minutes at 4° C., resuspended in 25 ml of 0.25M $CaCl_2$ and kept on ice for 20 minutes. Cells were recovered by centrifugation as above, resuspeneded in 0.5 ml of 0.1M $CaCl_2$, stored on ice and used within 24 hours. One hundred microliter aliquots of these competent cells were placed into sterile 4 ml polyproplylene tubes, mixed with aliquots of the annealing reaction from above, and the transformation mixture was incubated on ice for 15 minutes. The cells were then heat shocked for 5 minutes in a 37° C. water bath without shaking. The cells were returned to the ice for 2 minutes before addition of 2 ml of LB medium. The cells were then grown for one hour at 37° C. with shaking and aliquots of the transformation mixture are plated on LB plates which contained 12.5 μg/ml tetracycline (tet). Plates were then incubated at 37° C. overnight.

Isolation of 2-1 cDNA clones

Antibiotic resistant colonies resulting from the transformation were picked and arrayed onto 150 mm LB agar plates containing 12.5 μg/ml tet. Colonies were grown up and transferred to 140 mm nitrocellulose filters by layering pre-wetted filters (accomplished by layering dry filters on fresh LB plates containing 12.5 μg/ml tet) onto each plate. The transferred colonies were grown up as above and these filters were referred to as the master filters of the cDNA library.

Two replica nitrocellulose filters were made of each master filter. To accomplish this, nitrocellulose filters were first prewetted as above. Individual wetted filters were then laid on top of a master filter and the pair of filters were placed between several sheets of dry 3MM paper This sandwich was placed between two glass plates that were then were pressed together to transfer bacteria from the master filter to the replica. The filters were then separated and the replica was place on a fresh LB/tet plate. This process was repeated until two replicas of each master filter had been made Master filters were returned to fresh plates and stored at 4° C.

Replica filters were grown at 37° C. until colonies reached 1–2 mm in diameter and then filters were transferred onto LB plates containing 200 μg/ml chloramphenicol. The plates were incubated overnight at 37° C. The next morning, bacteria on the filters were lysed and their DNA was fixed to the filters in situ. To lyse bacteria, filters were removed from the agar plates and placed colony side up for three minutes in glass tray containing 3 sheets of Whatman 3MM paper that had been saturated with 10% SDS. Filters were then transferred for 5 minutes to a tray containing 3 sheets of Whatman 3MM paper saturated with 0.5 N NaOH, 1.5M NaCl, followed by transfer to a tray containing 3MM paper saturated with 1M Tris-HCl pH 7.5, 1.5M NaCl for 6 minutes. The filters were air dried for one hour and baked at 70° C. for 2 hours in vacuo.

Replica copies of the cDNA library were differentially screened for clones representing mRNAs whose abundance rise following N-(amincarbonyl)-2-chlorobenzenesulfonamide treatment. To accomplish this, one replica of each master filter was hybridized with a $^{32}$P-labeled single-stranded cDNA probe made by reverse transcribing poly(A)⁺ RNA from untreated corn roots, while the other replica filter was hybridized with a $^{32}p$ single-stranded cDNA probe made by reverse transcribing poly (A)⁺ RNA from N-(aminocarbonyl)-2-chlorobenzenesulfonamide-treated corn roots. Probes were synthesized from 5 μg of each poly(A)⁺ RNA by performing first strand cDNA synthesis using the Amersham cDNA synthesis kit. First strand reactions were terminated by addition of EDTA to 20 mM, and then NaOH was added to a final concentration of 0.4M to hydrolyze RNA. After RNA hydrolysis had been carried out for 6 hours at 22° C., the pH of the cDNA solution was adjusted to neutrality with HCl and the first strand reactions were applied to a 1 cm× 10 cm Sephadex® G-100 column that was equilibrated with 10 mM Tris-HCl, pH 8.0, 20 mM NaCl, 0.2% SDS. Radioactive material eluting in the void volume was pooled and the DNA was ethanol precipitated. Labeled DNA was collected by centrifugation at 14,000 g for 20 minutes at 4° C. The pellet was dried in vacuo and the DNA was resuspended in a small volume TE pH 8 0. The radioactivity incorporated into the probe was determined by counting a 1 μl aliqout in a liquid scintillation counter using 5 ml of scintillation fluid.

Replica filters were divided into two sets of filters such that each set represented one copy of the cDNA library. Pairs of filters from each set were placed in heat-sealable bags with the colony sides facing outward. Each bag was filled with 70 ml of hybridization buffer, sealed, and incubated overnight at 65° C. in a water bath. Hybridization buffer consists of 6× SSC (1× SSC is 0.15M NaCl, 0.015M trisodium citrate, pH 7.0), 2× Denhardt's (Denhardt's is 0.02% bovine serum albumin (BSA), 0.02% polyvinyl pyrrolidine, 0.02% Ficoll Type 400 (MWr 400,000), 0.5% SDS, 50 mM sodium phosphate pH 6.8, 2 mM EDTA and 100 μg/ml denatured calf thymus DNA.

Screening of the library was accomplished by discarding the hybridization buffer in each bag and replacing it with 30 ml of hybridization buffer containing 5×10⁶ cpm/ml of probe made from poly(A)⁺ RNA purified from corn root tissue which had been treated with N-(aminocarbonyl)-2-chlorobenzenesulfonamide for six hours in the hydroponic system. The filters representing the second copy of the library was hybridized in the same manner with 5×10⁶ cpm/ml of probe made from poly(A)⁺ RNA isolated from roots of plants that had not been treated. The filters were hybridized at 65° C. for a minimum of 48 hours. Filters were then removed from the bags and washed twice for 15 minutes at room temperature with 2× SSC, 1 mM EDTA, 0.2% SDS and 1 mM sodium pyrophosphate, once at 65° C. with a 0.5× SSC and 0.1% SDS for one hour, and once for thirty minutes at 65° C. with 0.2× SSC and 0.1% SDS. Filters were air-dried briefly and exposed to Kodak XAR-5 film at −80° C. for approximately 36 hours using a single Du Pont Lightning Plus intensifying screen. Autoradiograms of the filters were developed using a Kodak automated film processor. Any colony displaying a stronger hybridization signal with the probe made using RNA from N-(aminocarbonyl)-2-chlorobenzenesulfonamide-treated plants than with the probe made using RNA from untreated RNA was deemed a positive clone in the differential screen and selected for further analysis.

One colony from the differential screen, designated 2-1, was chosen as a potential positive clone and was chosen for further analysis. Plasmid DNA was prepared from the 2-1 colony using a small scale plasmid DNA isolation procedure. This was accomplished by inoculating 5 ml of LB medium containing the appropriate antibiotic (tet) with the single bacterial colony. After overnight incubation at 37° C. with vigorous shaking, 1.5 ml of the culture was poured into a microcentrifuge tube. The tube was centrifuged for 20 seconds in a microcentrifuge and the medium was removed by aspiration leaving the bacterial pellet as dry as possible. An additional 1.5 ml of culture was added to the tube and the above steps were repeated. The pellet was resuspended in 100 μl of an ice-cold solution of GTE buffer (50 mM glucose, 10 mM EDTA, 25 mM TRIS-HCl, pH 8.0) with 4 mg/ml lysozyme (added to the solution just before use) with vortexing. After 5 minutes at room temperature, 200 ml of a freshly prepared solution of lysis buffer (0.2 N NaOH and 1% SDS) was added to the tube and the contents were mixed by inverting the tube rapidly two or three times. The tube was placed on ice for 5 minutes, followed by addition of 150 μl of an ice-cold solution of potassium acetate pH 4.8 (made by adding 11.5 ml of glacial acetic acid and 28.5 ml of $H_2O$ to 60 ml of 5M potassium acetate). The contents were mixed by inverting the tube sharply several times. After 5 minutes on ice, the tube was centrifuged for 5 minutes in a microcentrifuge at 4° C. The supernatant was transferred to a fresh tube and an equal volume of phenol:chloroform (1:1 v/v) was added with mixing. The resulting emulsion was centrifuged for 2 minutes in a microcentrifuge and the supernatant was transferred to a fresh tube. Two volumes of ethanol were added and the contents of the tube were mixed well. After 2 minutes at room temperature, DNA was collected by centrifugation for 5 minutes in a microcentrifuge. The supernatant was discarded and the tube was stood in an inverted position on a paper towel to allow all of the fluid to drain away. The pellet was washed with 250 μl of 70% ethanol and the tube was then recentrifuged. The supernatant was discarded and the pellet was dried briefly in vacuo. Crude plasmid DNA was dissolved in 50 μl of TE pH 8.0. The plasmid contained within clone In 2-1 was designated pIn 2-1.

An aliquot of the plasmid preparation was labelled by nick- translation using a commercial kit (Bethesda Research Laboratories, CAT#8160SB) following the manufacturer's suggested protocol. The labeled DNA was purified from the unincorporated nucleotides by spun column chromatagraphy.

An RNA slot blot procedure was used to confirm that the putative positive clone isolated during the screening of the cDNA library represented an mRNA that was strongly induced by N-(aminocarbonyl)-2-chlorobenzenesulfonamide. A nitrocellulose filter (Schlicher and Schull BA-85) was wetted by soaking it twice for 10 minutes in water, followed by a 10 minute soak in 1M ammonium acetate. The filter was then placed into a Slot Blot apparatus (Schleicher and Schuell, Inc., Keene, N.H. 03431, CAT #SRC072/0). Multiple 2.5 μg samples of total RNA from untreated corn roots, roots treated with 2-chlorobenzenesulfonamide, and roots treated with N-(aminocarbonyl)-2-chlorobenzene-sulfonamide were diluted to a final volume of 80 μl with sterile water. Forty pl of denaturation buffer (30% formaldehyde, 100 mM sodium phosphate pH 6.8) were added to each sample and all samples were then incubated at 65° C. for 20–30 minutes and quick-cooled in an ice slurry for 5 minutes. Thirty μl of 4M ammonium acetate were added to each sample and the 150 μl samples were added to slots in the blotting cell with the aid of a 10–15 mm Hg vacuum. The filter was removed from the blotting cell, air dried and baked for 2 hours at 70° C. in vacuo.

The filter was cut into six pieces such that each piece had one slot cox.raining RNA from each of the three treatments described above. One of the filter pieces was incubated with 10 ml of prehybridization buffer (50% deionized formamide, 5× SSC, 5× Denhardt's, 100 µg/ml denatured calf thymus DNA, 20 µg/ml homopoly(A), 40 mM sodium phosphate pH 6.8 and 0.5% BSA) in a heat-sealable bag for 6 hours at 42° C. with occasional mixing. The filter piece was then hybridized with nick-translated pIn 2-1. This was performed by discarding the prehybridization solution from the bag and replacing it with 2.5 ml of hybridization buffer (50% deionized formamide, 5× SSC, 100 µg/ml denatured calf thymus DNA, 20 µg/ml homopoly(A) and 40 mM sodium phosphate, pH 6.8) containing $1.25 \times 10^7$ cpm of nick translated 2-1 plasmid described above. Nick-translated plasmid was denatured by boiling for 10 minutes followed by quick-cooling on ice. The filter was then hybridized overnight at 42° C. with occasional mixing.

The filter was rems, red from the bag and washed twice at room temperature for 10–15 minutes on a rocking shaker with 2× SSC, 1 mM EDTA, 20 mM sodium phosphate pH 6.8, 1 mM sodium pyrophosphate and 0.5% SDS and twice for 30 minutes at 65° C. with 0.1× SSC and 0.5% SDS. The filter was briefly air-dried, wrapped in polyethylene food wrap and subjected to autoradiography overnight using Kodak XAR-5 film and a single Du Pont Lightning Plus intensifying screen.

The plasmid designated pIn 2-1 strongly hybridized to root RNA from N-(aminocarbonyl-2-chlorobenzenesulfonamide-treated plants, and hybridized extremely weakly, if at all, to RNA from both untreated plants and 2-chlorobenzenesulfonamide-treated plants. By these criteria, cDNA clone 2-1 was confirmed as representing an mRNA induced by N-(aminocarbonyl)-2-chlorobenzenesulfonamide.

Plasmid pIn 2-1 was used as a probe in a northern analysis to determine the size of its corresponding mRNA. Two and a half µg of poly(A)$^+$ RNA from both untreated and N-(aminocarbonyl)-2-chlorobenzenesulfonamide-treated corn roots and 2.5 µg of Brome mosaic virus RNA (used as RNA molecular weight markers) were each placed in separate 1.5 ml microfuge tubes, evaporated to dryness and taken up in 8 µl of Northern sample buffer (25% deionized formamide, 3% formaldehyde, 5 mM Na$_2$EDTA and 20 mM sodium phosphate pH 6.8). The RNA was incubated 15–20 minutes at 65° C., quick-cooled on ice, and 1 µl of northern loading buffer (5 mM sodium phosphate, pH 6.8, 50% glycerol and 0.2% bromophenol blue) was added to each tube. RNA samples were then loaded into 10 mm×1 mm slots of a 1.5% agarose gel prepared in 20 mM sodium phosphate pH 6.8, 3% formaldehyde, and the RNA was subjected to overnight electrophoresis at 36–48 volts at room temperature in 10 mM sodium phosphate, pH 6.8, 3% formaldehyde The lanes containing BMV molecular weight markers were cut from the gel with a razor blade and the remainder of the gel was blotted to a nylon membrane in a chemical fume hood essentially as described by Thomas, P. S., Proc. Natl. Acad. Sci. U.S.A., 77:520–5205 (1980). The agarose gel was inverted on a glass plate covered with two sheets of Whatman 3MM paper that had been saturated with 20× SSC. The glass plate was place over the top of a baking dish filled with 20× SSC such that the ends of the 3MM paper ext. ended over the edge of the glass plate and into 20× SSC in the dish. A sheet of Zeta-Probe nylon membrane (Bio-Rad Laboratories) was cut 0.5 cm larger than the gel, prewet in water, then soaked for several minutes in 20× SSC. The membrane was laid on top of the gel and covered with a sheet of Whatman 541 paper soaked in 20× SSC followed by and several sheets of 3MM paper soaked in 20× SSC. A 10 cm stack of paper towels was then placed on top of the 3MM sheets to draw buffer through the gel, and RNA in the gel was transferred to the membrane overnight at room temperature. The resulting RNA blot was then removed from the top of the gel after marking the positions of the sample wells of the gel relative to the membrane. The filter was air-dried for one hour and then baked for 2 hours at 70° C. in vacuo.

The RNA molecular weight markers were stained in 100 mM NaCl, 1 µg/ml of EtBr for 1–2 hours followed by destaining with shaking in 100 mM ammonium acetate, 10 mM β-mercaptoethanol for 2–3 hours. The positions of the RNA markers were recorded by photographing the gel on an ultraviolet transilluminator. The migration distances of each RNA molecular weight marker was plotted against the log of its molecular weight to establish a standard curve. This standard curve was used to estimate the size of the 2-1 mRNA by its position in the same agarose gel.

The RNA blot was prehybridized in Northern prehybridization buffer (50% deionized formamide, 5× SSC, 5× Denhardt's, 100 µg/ml boiled and sonicated calf thymus DNA, 20 µg/ml homopoly A, 40 mM sodium phosphate pH 6.8 and 0.5% BSA) using 200 µl of buffer per cm2 of blot in a heat-sealed bag. Prehybridization was carried out for 6 hours at 42° C. with occasional mixing. The plasmid pIn 2-1 was nick-translated using a nick-translation kit as described above to a specific activity of $5.9 \times 10^8$ cpm/µg of DNA. Prehybridization buffer was discarded and replaced with hybridization buffer (50% deionized formamide, 5× SSC, 100 µg/ml denatured calf thymus DNA, 20 µg/ml homopoly(A) and 40 mM sodium phosphate, pH 6.8) containing $2 \times 10^5$ cpm/ml of denatured, nick-translated pIn 2-1, using 100 µl of buffer/cm$^2$ of filter.

The blot was hybridized for 24 hours at 42° C. with occasional mixing then washed twice at room temperature for 10–15 minutes on a rocker with 2× SSC, 5 mM Na$_2$EDTA, 25 mM-sodium phosphate, pH 6.8, 1.5 mM sodium pyrophosphate and 0.5% SDS. This was followed by two washes for 30 minutes each with 0.1× SSC and 0.5% SDS at 64° C. The filter was air-dried, wrapped in polyethylene loud wrap and exposed overnight to Kodak XAR-5 film at −80° C. using a single Du Pont Lightning Plus intensifying screen.

The Northern blot results were consistent with those obtained in the slot blot experiment. No hybridization was seen with untreated corn root RNA, while a single intense hybridization signal to an 850–900 nucleotide (nt) mRNA was seen with N-(aminocarbonyl)-2-chlorobenzenesulfonamide-treated RNA.

The size of the pIn 2-1 cDNA insert was analyzed by digesting the plasmid to completion with Pst I and subjecting the digestion products to agarose gel electrophoresis. The results showed that pin 2-1 insert was a single 450 bp Pst I fragment. The pIn 2-1 insert not a full length copy of the message since Northern analysis indicated a 2-1 mRNA size of 850–900 nt. However, the pIn 2-1 insert was sufficiently large to use it as a probe for genomic clone isolations. A full-length cDNA clone was still needed to determine the boundaries of the structural and regulatory regions of the 2-1 gene(s).

A new cDNA library was made from RNA isolated from N-(aminocarbonyl)-2-chlorobenzenesulfonamide-treated corn roots using a procedure designed to maximize the probability of obtaining full length cDNA clones. First strand synthesis was performed in a 100 µl reaction containing 50 µg/ml of poly(A)$^+$ RNA, 50 mM Tris-HCl, pH 8.3 at 42° C., 45 mM KCl, 0.5 mM dATP, dGTP and dTTP, 0.2 mM dCTP, 5 mM DTT, 7.5 µg/ml oligo (dT)12–18, 400 units/ml placental ribonuclease inhibitor, 7.5 mM MgCl$_2$, 4 mM sodium pyrophosphate, 0.4 mCi/ml [α$^{32}$P] dCTP and 560 U/ml reverse transcriptase. The reaction was incubated at room temperature for 5 minutes and then transferred to 42° C. for 45 minutes. The single strand cDNA was extracted sequentially with equal volumes of phenol, phenol:chloroform (1:1 v/v) and chloroform followed by ethanol precipitation in the presence of ammonium acetate.

The second strand was synthesized from 1 μg of first strand cDNA in a reaction containing 20 mM Tris-HCl, pH 7.5, 5 mM MgCl$_2$, 10 mM (NH$_4$)$_2$SO$_4$, 100 mM KCl, 50 mg/ml BSA, 50 mM dNTPs, 0.1 mCi/ml [a32P]dCTP, 230 U/ml DNA polymerase I and 8.5 U/ml RNase H. The reaction mixture was incubated for one hour at 12° C. and one hour at 20° C. The products of the second strand reaction were size fractionated on a 1.0×15 cm Bio-Gel® A-50m (Bio-Rad Laboratories) column equilibrated and eluted with 0.3M sodium acetate in TE, pH 8.0. Fractions eluted from the column were collected aud small aliquots of every second fraction were analyzed for cDNA size distribution by electrophoresis in a 1.2% alkaline agarose gel. $^{32}$P end-labeled Hind III digestion fragments of pUC18, pBR322 and SV40 were run in the gel as size markers. After electrophoresis, the DNA was fixed in the gel by soaking it in 15% TCA for 10–15 minutes. Excess liquid was removed from the gel by blotting to a stack of stacking weighted paper towels placed over the gel for 1–2 hours and the gel was then wrapped in polyethylene wrap and exposed to x-ray film. Column fractions containing cDNA greater than 500 bp in length were pooled, ethanol precipitated twice, and dissolved in 8.5 μl of water.

Approximately 1–1.5 μg of cDNA was methylated at internal EcoRI sites by incubating it in 25 mM Tris-HCl, pH 7.5, 1 mM EDTA, 2.5 mM DTT, 10 μM S-adenosylmethionine with 20 U of Eco RI methylase per microgram of cDNA at 37° C. for 30 minutes. The methylase was inactivated by heating at 65° C. for 10 minutes and the DNA was extracted with phenol:chloroform (1:1) and precipitated with ethanol.

Eco RI linkers were ligated to the cDNA by incubation of 2 μg of ds cDNA with 7.5 μg of phosphorylated linkers in 66 mM Tris-HCl, pH 7.5, 5 mM MgCl$_2$, 5 mM DTT, 1 mM ATP and 20 units of T4 DNA ligase (New England Bioiabs, Inc., Beverly, Mass. 01915, CAT #202). The reaction was incubated overnight at 15° C. The products of the linker ligation reaction were digested to completion with 500 units of Eco RI for 4 hours at 37° C. The Eco RI digestion mixture was applied to a 1×10 cm Bio-Gel® A 50 m column and eluted with 0.3M sodium acetate in TE, pH 8.0 to separate the cDNA from excess linkers and size fractionate the cDNA. Fractions were analyzed by alkaline agarose gel electrophoresis as described above and fractions containing cDNA greater than 600 bp were pooled and ethanol precipitated. The cDNA was resuspended in 100 μl of TE pH 8.0. The mass of cDNA was estimated by counting an aliquot of the cDNA using the known specific activity of $^{32}$P dCTP used in the cDNA synthesis reactions. Aliquots of the cDNA were then ligated to Eco RI digested and dephosphorylated lambda λgt 11 arms (Stratagene, 11099 North Torrey Pines Rd., LaJolla, Calif. 92037, CAT #200211) using ligation conditions described above. The ligation products were packaged with Gigapack Plus extracts (Stratagene) following the manufacturer's recommended protocol. The titer of the resulting phage library was determined using *E. coli* Y1090 as a host.

Screening of λgt 11 Library

A 1.5 ml aliqout o#an exponentially growing culture of *E. coli* Y1090 grown in NZC broth were diluted with 0.6 ml of SM buffer (0.01% gelatin, 50 mM Tris-HCl pH 7.5, 5.8 g/l NaCl, 2 g/l MgSO$_4$) and 2.1 ml of 10 mM MgCl$_2$, 10 mM CaCl$_2$ and infected with 4×10$^5$ pfu of the phage cDNA library for 15 minutes at 37° C. Infected cultures were then mixed with 10 ml of NZC broth containing 1% agarose at 55° C. and spread on plates containing NZC broth +1.5% bacto-agar in 150 mm petri dishes. Plates were incubated at 37° C. overnight and then stored at 4° C. These plates were referred to as the master phage cDNA library.

Pre-cut 82 mm HAHY nitrocellulose filters (Millipore) were wetted in H$_2$O, soaked briefly in 1M NaCl and blotted dry on pacer towels. Multiple plate lifts were made by placing wetted nitrocellulose filters on top of each chilled master plate of the phage cDNA library for 30 to 90 seconds. Filters were keyed to the plate by asymmetrical stabbing a 20 ga syringe needle containing india ink through the filter and into the agar plate. The filters were then removed and phage DNA was fixed to the filters using the same procedure described above for lysis of bacterial colonies. The filters were then air-dried for 30–60 minutes and baked for 2 hours at 70° C. in vacuo. Pairs of filters were placed in heat-sealed bags with the plaque sides oriented outwards and prehybridized with 6× SSC, 25 mM sodium phosphate pH 6.8, 1 mM EDTA, 1% SDS and 100 μg/ml sheared and denatured calf thymus DNA for 6–7 hours at 65° C. with occasional mixing.

Plasmid pIn 2-1 was nick-translated as described above to a specific activity of 2.5×10$^8$ cpm/μg of DNA, and purifiec by spun-column chromatrography using Sepiaadex® G-50. Prehybridization buffer was removed from the bags containing the replicas of the phage library and replaced with 20 ml of the same buffer containing 1.5×10$^6$ cpm of denatured pIn 2-1 probe per ml of hybridization solution. Filters were hybridized at 65° C. overnight with occasional mixing. Filters were removed from the bags, washed twice at room temperature for 15 minutes with 2× SSC, 0.5% SDS, and twice at 65° C. for 30 minutes with 0.1× SSC, 0.1% SDS buffer. The filters were briefly air dried, wrapped in polyethylene wrap and exposed to Kodak X-OMAT XAR-5 film at −80° C. overnight using a single Du Pont Lightning Plus intensifying screen.

Plaques hybridizing with the pIn 2-1 probe were picked from the master plates. Stocks of these hybridizing phage were made by removing agarose plugs from the plates containing appropriate plaques, placing them in numbered 0.5 ml microfuge tubes containing 1 ml of SM buffer with 1 drop of chloroform and allowing the phage to diffuse out of the plugs overnight at 4° C. Plaque purification was performed on each phage by serially diluting the phage stocks, infecting 100 μl of an overnight culture *E. coli* Y1090 with 100 μl aliqouts of the dilutions and growing them on NZC plates as described above. Lifts of these plates were made and hybridized with a labeled $^{32}$P pIn 2-1 cDNA as previously described. Hybridizing plaques were repeatedly subjected to this procedure until all plaques on a given plate hybridized with the 2-1 cDNA probe.

Small scale phage DNA preparations of the λ2-1 cDNA clones were made using the procedure in Maniatis et al., Molecular Cloning: A Laboratory Manual, Cold Spring Harbor Laboratory, Cold Spring Harbor, N.Y., (1982). The phage DNAs were digested to completion with EcoRI and analyzed by electrophoresis in a 1% agarose gel. Results of this analysis showed one phage clone, designated 2–1.12, harbored a 900 bp insert. The insert containted a single internal Eco RI site that divided it into a 300 bp and a 600 bp fragment when digested with Eco RI. This insert was of sufficient size to be a full length copy of the 2-1 mRNA.

Restriction mapping of the pIn 2-1 and λ2-1.12 cDNAs insert showed that λ2-1.12 contained a complete copy of the pIn 2-1 cDNA and that all missing 2-1 RNA sequences were probably present in λ2-1.12.

The 600 bp Eco RI fragment from λ2-1.12 was subcloned into the plasmid vector pUC18. To accomplish this, pUC18 DNA was digested to completion with Eco RI. After digestion, a one-tenth volume of 1M Tris-HCl pH 8.4 was added directly to the tube. Calf intestinal alkaline phosphatase (CIAP) was then added using 0.5 units per microgram of DNA. The dephoSphorylation reaction was performed at 55° C. for 30 minutes. CIAP was inactivated by sequential extractions of the DNA with equal volumes of phenol, phenol:chloroform (1:1 v/v) and chloroform. The DNA was then precipitated with ethanol in the presence of 0.25M sodium acetate pH 6.0, collected by centrifugation and redissolved in TE, pH 8.0.

λ2-1.12 DNA was digested to completion with Eco RI, and equimolar aliquots of dephosphorylated, Eco RI digested pUC18 DNA and Eco RI digested λ2-1.12 DNA were ligated together overnight at 16° C. using ligation conditions described earlier. An aliquot of the ligation mixture was used to transform frozen competent *E. coli* HB101 cells (Bethesda Research Laboratories). Transformation of competent cells was accomplished by removing the cells from storage at −80° C. and thawing them on ice. The ligation mixture was diluted 5 fold with $H_2O$ and an aliquot of this dilution was mixed with 100 µl of competent cells. The mixture was incubated on ice for 30 minutes and then heat shocked for 45 seconds in a 42° C. water bath without shaking. The cells were returned to ice for 2 minutes and diluted with 0.9 ml of S.O.C. medium (2% Bacto-tryptone, 0.5% yeast extract, 10 mM NaCl, 2.5 mM KCl, 10 mM $MgCl_2$, 10 mM $MgSO_4$ and 20 mM glucose). The cells were then shaken at 225 rpm at 37° C. for 1 hour and aliquots of the transformation mixture were spread onto LB plates containing 50 µg/ml of ampicillin. Plates were then incubated at 37° C. overnight. Small scale plasmid preparations were performed on individual amp-resistant colonies and aliquots of the DNA were digested with EcoRI until a colony was found that contained the 600 bp EcoRI fragment from pIn 2-1.12 ligated into pUC18. This plasmid was called pIn2-1.12A.

DNA Sequence Analysis of 2-1 cDNA Clones

The nucleotide sequence of the 2-1 mRNA was determined by sequence analysis of pIn 2-1 and λ2-1.12A. The insert of pIn 2-1 was subcloned into the vector M13mp18 in order to perform dideoxy sequencing. For subcloning, an aliquot of pIn 2-1 was digested to completion with Pst I and the resulting 450 bp fragment was subcloned into the Pst I site of M13mp18 RF vector. An aliquot of the ligation mixture was used to transfect *E. coli* JM 101 and aliquots of the transfection reaction were plated on LB plates containing X-Gal and IPTG and grown overnight at 37° C. Individual white plaques were analyzed until a phage was found that contained the cDNA insert in the Pst I site of M13. A DNA sequencing template was prepared froln this phage by scooping a portion of a plaque out from the agar and using it to inoculate 3 ml of 2× YT media in a 15 ml falcon tube containing 200 µl of expotentially growing JM 101 cells. The culture was incubated at 37° C. with vigorous shaking for 5 hours. A 1 ml aliquot of the phage culture was removed and centrifuged in a 1.5 ml microfuge tube for 5–10 minutes at 4° C. One ml of phage supernatant was carefully pipetted off and placed into a fresh tube containing 200 µl of 20% PEG 8000, 2.5M NaCl. The tube was inverted several times, and then incubated at room temperature for 20–30 minutes. The phage were collected by centrifugation for 10 minutes in a microfuge at room temperature. The supernatant was carefully removed and the tube was recentrifuged to remove any remaining superantant from the tube walls. The phage were resuspended in 100 µl of 10 mM Tris-HCl, pH 7.6 and extracted with 50 µl of phenol:chloroform (1:1 v/v) by vortexing the tube. The tube was centrifuged for 5 minutes at room temperature and the upper aqueous phase was transferred to a new tube. Phage DNA was precipitated with 25 µl of 2M sodium acetate, pH 7.0 and 320 µl of ethanol at −70° C. for 10 minutes or overnight freezing at −20° C. The DNA, suitable for use as a sequencing template, was collected by centrifugation in a microfuge at 4° C. for 10–20 minutes and dissolved in TE pH 8.0.

This template DNA was sequenced using the dideoxy method of Sanger [Sanger, F. et al., Proc. Natl. Acad. Sci. U.S.A., 74:5463, 1977], using a dideoxy sequencing kit (Pharmacia Inc., 800 Centennial Avenue, Piscataway, N.J. 08854, CAT #27-1555-01) following the manufacturer's recommended procedures.

A portion of the 2-1 DNA insert in the M13 clone was deleted by cutking the RF DNA with Eco RI and religating the DNA back together. This removed approximately 170 bp from the cDNA insert adjacent to the sequencing primer in the vector. This subclone was sequenced as above using the universal primer to complete the sequencing of the pIn 2-1 cDNA clone.

The cDNA clone, 2-1.12A was sequenced to complete the sequence of the 2-1 mRNA. The pIn 2-1.12A sequence was determined by the method of Maxam and Gilbert (Maxam, A. M. and Gilbert, W., Methods in Enzymology, 65:499–512, 1980) with modifications described by Barker et al. (Barker et al., Plant Molecular Biology, 2:335–350, 1983). DNA sequence analysis confirmed the identity of pIn 2-1 and pIn 2-1.12 since 200 bp region common to both clones shared an identical nucleotide sequence.

Isolation of 2-1 Genomic Clone 21.14

Plant material used for DNA isolation was obtained from greenhouse grown plants of the inbred corn line Missouri 17 (Mo17). Leaf material from vegetative plants was halvested, deribbed, and frozen in liquid nitrogen. High molecular weight DNA was isolated from 30 g of leaf material as follows: frozen leaf material was placed in a coffee grinder along with a small amount of dry ice and ground to a fine powder. After the dry ice had sublimed, the frozen powder was transferred to a beaker and suspended in 100 ml of cold buffer A (100 mM Tris-HCl pH 9.0, 100 mM NaCl, 10 mM $MgCl_2$, 0.5M sucrose, 0.1% β-mercaptoethanol, 0.4% diethylthiocarbamic acid). Nuclei were pelleted from the slurry by centrifugation at 10,000 rpm for two minutes in a Sorvall GSA rotor. The supernatant was discarded and the pellet was resuspended in 3 ml of buffer A. The nuclei were lysed by resuspending them in 20 ml of lysis buffer (100 mM Tris-HCl pH 8.3, 100 mM NaCl, 50 mM $Na_2EDTA$, 1.5% SDS, 15% phenol) and incubating the mixture at 55° C. for 10 minutes with constant stirring. Ten ml of 5M potassium acetate was then added and the mixture was placed on ice for 10 minutes to precipitate SDS SDS-protein complexes and SDS-cell wall complexes. The precipitate was collected by centrifugation at 5000 rpm for 10 min. in a Sorvall table-top centrifuge. The supernatant was transferred to a new tube, and the solution was extracted with an equal volume of chloroform:isoamyl alcohol (24:1 v/v) after addition of 3 ml of 10M ammonium acetate. DNA was then precipitated by addition of an equal volume of isopropanol, collected by centrifugation and resuspended in 30 ml H$_2$O. Solid cesium chloride was added using 0.9 g for each ml of solution and ethidium bromide was added to 300 μg/ml. DNA was centrifuged at 45,000 rpm for 16 hours in a Beckman VTi50 rotor. Banded DNA was recovered from the gradient by side puncturing the centrifuge tubes with a 16 gauge needle and removing the band. The DNA was diluted to 30 ml with 1 g/ml CsCl (prepared by adding 100 g CsCl to 100 ml TE pH 8.0) and banded once again following the same procedure. Ethidium bromide was removed from the DNA by repeated extractions with sodium chloride-saturated, water-saturated isopropapol. The DNA was then precipitated with isopropanol. Mo17 genomic DNA was collected by centrifugation and resuspended in TE pH 8.0.

An Mo17 genomic library was constructed as follows: 100 micrograms of Mo17 DNA were digested with 24 units of restriction enzyme Sau 3A in Cutsall (100 mM potassium chloride, 20 mM Tris-HCl pH 7.5, 2 mM β-mercaptoethanol, 7 mM magnesium chloride). One fifth of the reaction was removed after 2, 4, 6, 8 and 10 minutes of digestion and the reaction was stopped by adding EDTA to 50 mM. The five time points were pooled, extracted with an equal volume of phenol: chloroform: isoamyl alcohol (25:24:1 v/v/v) and DNA in the pool was ethanol precipitated and collected by centrifugation. The DNA was dissolved in 0.1 ml H$_2$O and loaded on a 10–40% glycerol gradient (10–40% glycerol in 1M NaCl, 20 mM Tris-HCl pH 8.0, 1 mM EDTA). Centrifugation was performed at 40,000 rpm for 16 hours in a Beckman SW 41 rotor. Fractions (0.4 ml) were collected from the bottom of the polyallomer tube through a wide bore needle and aliqouts of the fractions were analyzed by electrophoresis in a 0.9% agarose gel. Fractions containing 12–20 kbp DNA fragments were pooled, extracted with an equal volume of phenol/chloroform (1:1 v/v), precipitated with ethanol and resuspended in TE pH 8.0. Four-tenths of a microgram of this size-fractionated DNA was ligated overnight to 1 microgram of Eco RI-Bam HI digested lambda EMBL 3 DNA (Stratagene) using 5 weiss units of DNA ligase (New England Biolabs) in ligase buffer (50 mM Tris-HCl pH 8.0, 10 mM dithiothreitol, 10 mM magnesium chloride, 1 mM ATP) at 15° C. for 24 hours. Ligated DNA was packaged using Gigapack Gold packaging extracts (Stratagene) following the manufacturer's recomended protocol.

A library of 500,000 phage was plated on 150 mm diameter LAM plates (10 g Bacto-Tryptone, 5 g yeast extract, 10 g NaCl, 2.5 g MgSO$_4$.7H$_2$O, 10 g agarose per liter, 80 ml per plate) at a density of about 25,000 plaques per plate. To do this, phage (in a volume of less than 200 μl) were added to 200 μl of 10 mM CaCl$_2$, 10 mM MgCl$_2$ and 200 μl of an overnight E. coli LE 392 culture grown in 2XYT (16 g Bacto-tryptone, 10 g yeast extract, 5 g NaCl 0.2% maltose, water to 1 liter) and phage were allowed to adsorb to host cells at 37° C. for 10–15 minutes. This culture was then added to 8 ml molten 0.8% top agarose (10 g Bacto tryptone, 2.5 g NaCl, 0.2 g MgCl$_2$, 8 g agarose, water to 1 liter) at 50° C. and poured onto LAM plates. After the top agarose hardened, plates were incubated at 37° C. overnight.

Phage lifts were performed the next morning by laying dry nitrocellulose filters (Millipore) on the surface of the plates for 5 minutes. Filters were then transferred to a piece of Whatman 3MM paper that was saturated with 0.5M NaOH, 1.5M NaCl. After 5 minutes the filters were transferred to a sheet of 3MM paper saturated with 0.5M Tris-HCl pH 7.5, 1.5M NaCl. After 5 minutes the filters were transferred to a piece of 3MM paper saturated with 2× SSC for 5–10 minutes. The filters were then baked at 80° C. for two hours in vacuo.

Filters were prehybridized at 42° C. for 4 hours in a 150 mm glass crystallizing dish using 150 ml of prehybridization buffer (50% deionized formamide, 5× SSC, 100 μg/ml denatured salmon sperm DNA, 0.05% SDS, 0.05M sodium phosphate pH, 0.1% Ficoll, 0.1% polyvinylpyrolidine, 0.1% BSA). One μg of plasmid pIn 2-1 was nick translated in 50 μl of 50 mM Tris-HCl pH 7.2, 10 mM MgSO$_4$, 0.1 mM DTT, 50 mg/ml BSA, 10 uCi 32P dATP (Amersham), 2 μg/ml DNase (Sigma DN-EP), 20 uM dATP, dTTP, dGTP, 5 units DNA polymerase I (BMB) at 15° C. for 1 hour. The reaction was stopped by adding 1 μl of 0.5M EDTA, and DNA was then precipitated by adding 50 μl of water, 30 μl of 10M ammonium acetate, 19 μg yeast tRNA carrier and 350 μl of ethanol. The DNA was collected by centrifugation, dissolved in 0.5 ml H$_2$O, and denatured by heating for 5 minutes in a boiling water bath followed by quick cooling on ice. Prehybridization solution was discarded and the filters were probed overnight at 42° C. with nick-translated pIn 2-1 with hybridization buffer (50% deionized formamide, 5× SSC, 100 μg/ml denatured salmon sperm DNA, 0.05% SDS, 0.02M sodium phosphate 0.2% Ficoll, 0.02% Bovine serum albumin, 10% dextran sulfate) using 5×10$^5$ cpm per ml of buffer. The next morning, filters were washed twice for 20 minutes in 1× SSC, 0.5% SDS at room temperature and three times for 20 minutes in 0.1× SSC, 0.5% SDS at 65° C. in a shaking water bath. The filters were blotted dry between two sheets of 3MM paper, wrapped in polyethylene food wrap, and exposed on Kodak XAR-5 film overnight at −80° C. using a single Du Pont Lighting Plus intensifying screen. Films were developed using a Kodak X-OMAT developer.

Positive plaques were picked by taking plugs from the agar plates with the thick end of a pasteur pipette and placing them in 0.5 ml of SM. Dilutions of the phage in each plug were used to infect E. coli LE 392 as before and plated on 80 mm diameter LAM plates using 3 ml top agarose, 100 μl 10 mM CaCl$_2$, 10 mM MgCl$_2$, and 100 μl of an overnight LE392 culture. Purification was performed on each phage plaque as described earlier. The phage lift-pick-plating cycle was carried out until pure plaques were obtained. Fifteen pure phage isolates, designated 21.1 to 21.15 were grown in liquid culture for isolation of DNA. Single pure plaques were removed from plates and eluted into 0.5 ml of SM. Fifty μl of these phage stocks were incubated with 50 μl of a two times concentrated overnight LE392 culture in 10 mM MgCl$_2$ at 37° C. for 15 minutes. The infected bacteria were then added to 20 ml of pre-warmed LB (10 g Bacto-Tryptone, 5 g Bacto yeast extract, 5 g NaCl, 1 g glucose, water to 1 liter) and shaken at 37° C. 180–200rpm. The cultures generally lysed after 4–7 hours. Chloroform was added to a concentration of 1%, and the lysates were shaken for an additional 10 minutes. Cellular debris was removed by centrifugation at 10,000 rpm for 10 minutes in a Sorvall SS 34 rotor. The supernatants were transferred to new tubes and DNAse I and RNAse A were added to 20 μg/ml and 10 μg/ml respectively. After a 15–30 minute incubation at 37° C., phage were precipitated by addition of a one fifth volume of 20% PEG 8000, 2.5M NaCl to the lysateo After 15 minutes at room temperature, the phage were collected by centrifugation at 15,000 rpm for 15 minutes at 4° C. in a Sorvall SS-34 rotor and resuspended in 0.5 ml of SM. Fifty μl of 0.5M EDTA, 70 μl of 10% SDS and 300 μl of phenol were added to phage suspensions to lyse them. The lysates were extracted with phenol:chloroform (1:1 v/v), and DNA in the aqueous phases was precipitated by adding one-tenth volume 3.0M sodium acetate and two-thirds volume isopropanol. DNA was collected by centrifugation and the pellet was washed with 70% ethanol, dried and resuspended in 50 µl $H_2O$.

Identification and Characterization of Genomic Clone 21.14

The fifteen genomic clones were first characterized by restriction mapping in an attempt to find regions in the clones corresponding to the 2-1 cDNA. Two µg of DNA was digested with several different restriction enzymes in ten µl of 1× cutsall (or 1.5 × cutsall for Sal I) and analyzed by electrophoresis using 1% agarose gels. Restriction maps generated for each of the clones failed to identify candidate genes for further analysis. Therefore, these genomic clones were mapped using a probe made by randomly primed cDNA synthesis using RNA from N-(aminocarbonyl)-2-chlorobenzenesulfonamide-treated corn roots as a template to identify regions in the various genomic clones that corresponded to the coding region of the genes. Phage DNA was digested with a variety of different restriction enzymes and the digestion products were separated by electrophoresis using 1% agarose gels. The DNA was transferred to Gene Screen Plus membranes (New England Nuclear) and hybridized with a randomly primed cDNA probe that was made as follows: 1 µg poly(A)$^+$ RNA from N-(aminocarbonyl)-2-chlorobenzenesulfonamide-treated corn roots was added to 30 µl of water and placed in a boiling water bath for 5 minutes. After cooling on ice, 10 µl of 10× first strand buffer (0.5M Tris-HCl pH 8.5, 0.4M KCl, 0.1M $MgCl_2$, 0.4 mM DTT,) 2.5 µl 2 mM dATP, 2.5 µl 2 mM dCTP, 5 µl 20 mM dGTP, 5 µl 20 mM dTTP, 1 µl RNAsin (Promega Biotech, Inc.), 20 µl random hexamer primers (16 µg/ul, Pharmacia, cat #272266-01 or P-L Bichemicals, cat #PLB9223), 10 µl α32P dATP (100 u Ci), 10 µl α32P dCTP (100 u Ci), and 20 units of reverse transcriptase were added. The reaction mixture was then incubated at 37° C. for one hour. The reaction was stopped by adding 10 µl 0.5M EDTA. RNA was hydrolyzed by adding 50 µl of 0.15M NaOH and heating the mixture for one hour at 65° C. Base was then neutralized by adding 25 µl of 2M Tris-HCl pH 8.0 and 50 µl 1M HCl. The DNA was precipitated with ammonium acetate and ethanol in the presence of carrier tRNA as described earlier. The randomly primed cDNA probe was then dissolved in 0.5 ml of $H_2O$. Hybridization and prehybridizations were carried out as described above for genomic library screening. Data from this restriction mapping analysis defined areas of each genomic clone that were homologous to pIn 2-1, but failed to identify any genomic clones corresponding to the In2-1 cDNA. Therefore, restriction fragments of the genomic clones that hybridized to the random cDNA probe were subcloned into either pUC19 or the vector Bluescript pBS(+), (Stratagene) for DNA sequence analysis.

Subcloning of genomic DNAs were performed by digesting 10 µg of phage DNA and a suitable vector (either pUC19 or pBS+) with the appropriate restriction enzymes. The DNAs were extracted with phenol/chloroform (1:1 v/v), precipitated with ethanol and resuspended in 10 µl of TE. Phage DNA was ligated to vector DNA in a final volume of 10 µl. After an overnight incubation at 15° C., the ligation products were used to transform competent JM83 cells. Colonies hasboring the desired plasmids were identified by performing small scale plasmid preparations and digesting aliquots of the resulting plasmids with diagnostic restriction enzymes.

The strategy used to sequence subcloned genomic fragments was to create a nested set of deletions for each subclone using Bal 31 nuclease (New England Biolabs). Plasmid DNA (20 µg) was linearized using an appropriate restriction enzyme and then extracted once with phenol:chloroform (1:1 v/v) and precipitated with ethanol. DNA was collected by centrifugation, washed once with 70% ethanol, dried, and resuspended in 100 µl of $H_2O$. Nuclease digestion was carried out in a total volume of 250 µl using 20 units Bal 31 under the assay conditions described by the manufacturer. Aliquets of 10 µl were removed at various times ranging up to 8 minutes and pooled into 5 groups. The reactions were stopped by adding the aliquots to a mixture of 150 µl $H_2O$, 5 µl carrier tRNA (5 mg/ml), 25 µl 0.2M EGTA, and 25 µl 3M sodium acetate. The 5 deletion pools were analyzed by gel electrophoresis to check for the proper degree of digestion. The pooled DNAs were then extracted with phenol:chloroform (1:1 v/v), ethanol precipitated and resuspended in 100 µl of $H_2O$. The 5' ends of the deletions were blunted by performing a fill-in reaction using Klenow Fragment of DNA polymerase I. One-tenth volume of 10× Klenow salts (0.5M Tris-HCl pH 7.2 or pH 7.5, 0.1M $MgSO_4$, 10 mM DTT), one twentieth volume of 5 mM deoxynucleotide triphosphates (all four dNTPs) and 1 unit of Klenow fragment of DNA polymerase I per µg of DNA was added and the fill-in reaction was incubated at room temperature for 30 minutes. DNA was then extracted with phenol:chloroform (1:1 v/v), precipitated with ethanol and resuspended in 100 µl of $H_2O$. Aliquots of the DNAs were then cut to completion with either Eco RI or Hind III to excise the deleted inserts. DNAs were extracted with phenol:chloroform (1:1 v/v), precipitated with ethanol, and resuspended at a concentration of 100 µg/ml in a final volume of 15–25 µl of $H_2O$. One-half microliter of DNA was ligated to 0.1 microgram of Sma I/Eco RI digested M13mp18 or 0.1 µg of Hind III/Sma I digested M13mP19 DNA in 20 µl of ligase buffer at 15° C. overnight. One third to one half of these ligations were used to transfect competent E. coli JM101 cells. Transfected cells were plated in 3 ml 0.8% top agarose containing 10 µl 0.1M IPTG, 100 µl 2% X-gal, and 100 µl of an overnight culture of JM101 cells (grown in 2× YT).

Phage lifts were next performed as described above. Lifts were probed with $^{32}$P-labelled gel purified-insert from the plasmid on which deletions were performed to detect plaques with Bal 31 deletions. Plaques hybridizing to the probe were picked and grown as follows: a positive plaque was stabbed with a sterile toothpick which was then put into 2 ml 2XYT containing 10 µl of a JM101 overnight culture. The culture was grown for 5 hours at 37° C. and small scale plasmid preparations were performed. One ml of overnight culture was poured into a microfuge tube and centrifuged for 20 seconds. The supernatant was poured off into a new tube and saved for later preparation of single-stranded DNA. The pelleted cells were resuspended in 0.35 ml of BPB (8% sucrose, 0.5% Triton X-100, 50 mM EDTA pH 8.0, 10 mM Tris-HCl pH 8.0). Twenty five µl of a freshly prepared lysozyme solution (10 mg/ml in BPB) was added and the tube was places in a boiling water bath for 40 seconds, followed immediately by centrifugation for 10 minutes at room temperature in a microcentrifuge. Chromosomal DNA as well as other debris formed a gelatinous pellet, and was removed with a sterile toothpick. Plasmid DNA was precipitated by addition of 30 µl 3M sodium acetate and 250 µl isopropanol. DNA was recovered by centrifugation, washed with 70% ethanol, dried and resuspended in 75 µl $H_2O$. Six µl aliquots were digested (in Cutsall) with appropriate enzymes that would excise the inserts. After analysis of these digestions by electrophoresis on 1% agarose gels, the subclones were ordered in decreasing order of size (increasing amount of Bal 3 deletion) and clones were chosen so that a series of progressive 100 bp deletions of the starting clone subjected to Bal 31 deletion was obtained.

Single stranded DNA for dideoxy chain-termination sequencing was isolated from the 1 ml of the supernatant saved at the start of the small scale plasmid preparation procedure. The supernatant was mixed with 150 µl 20% PEG 8000, 2.5M NaCl and phage were collected by centrifugation for 5 minutes in a microcentrifuge after 15 minutes at room temperature. All traces of supernatant were removed by aspiration, and the pellet was resuspended in 100 µl 0.3M sodium acetate, 1 mM EDTA. Phage were lysed by extraction with an equal volume of phenol:chloroform (1:1 v/v) and DNA was precipitated with ethanol. DNA was collected by centrifugation, washed with 70% ethanol, dried briefly and resuspended in 25 µl of $H_2O$.

Sequencing was performed using the M13 universal −10 17mer primer (New England Biolabs, Inc.) The annealing reaction was performed at 60°–65° C. for 1 hour using 3.5 µl template DNA, 2.5 µl annealing buffer (100 mM Tris-HCl pH 8.5, 50 mM $MgCl_2$), 1 µl universal sequencing primer (1 ng/ul) and 4 µl water. The annealed DNA was then placed on ice. The components of the sequencing reaction were: 1) Termination mixes containing dideoxy A,C,G, or T plus deoxy A,C,G, and T in appropriate ratios; 2) polymerase cocktail which contained 0.9 µl 0.1M Tris-HCl pH 8.3, 1 µl (10 u Ci) 35S dATP, 1 µl 0.1M dithiothreitol, 6.1 µl water, 0.25 µl Klenow (5 units/ul). Two µl of each component were mixed in a well of a microtiter dish—4 wells (A,C,G,T) for each annealing—and incubated at 37° C. for 20 minutes. At this time, 2 µl of chase solution (a solution containing 0.5 mM of all four dNTPs) was added to each well. After an additional 25 minutes of incubation, terminating dye (0.08% bromphenol blue, 0.08% xylene cyanol, 20 mM EDTA in deionized formamide) was added to the wells. The reactions were heated uncovered at 90° C. in an oven for 10 minutes, placed on ice, and subjected to electrophoresis in a 6% polyacrylamide gel in 1× TBE (0.089M Tris-borate, 0.089M boric acid, 0.002M EDTA) containing 8M urea at 1500 volts for approximately 2 hours. Urea was removed from the gel by soaking it in 10% methanol, 10% acetic acid for 15 minutes. The gel was then transferred to a sheet of Whatman 3MM paper and dried on a gel dryer with vacuum. The gel was autoradiographed with Kodak X-AR film overnight at room temperature with no intensifying screen. DNA sequences were read from the gel, entered into a computer and analyzed using the Cold Spring Harbor programs. The sequence of the promoter from the 21.14 gene extending 5' from the Nco I site that initiates protein synthesis is shown in FIG. 2. Sequence analysis also revealed that a 1.9 kbp Eco RI/Sal I subclone of genomic clone 21.14 contained sequences for the 3' half of 2-1 mRNA. This subclone was designated pJE482-62. Similarly, a 4.8 kbp Eco RI/Sal I subclone from 21.14 was shown to contain the coding sequences for the 5' half of the 2-1 mRNA. This clone was designated pJE 484-1. Complete sequence analysis revealed that genomic clone 21.14 contained a perfect copy of the 2-1 coding sequence distributed among 9 exons and eight introns. Therefore 21.14 was designated as a gene encoding the 2-1 mRNA.

Cloning and Mutagenesis of the Regulatory Regions of the 21.14

After identifying a genomic clone whose sequence agreed perfectly with that of the 2-1 cDNA clones, a search was begun for the regulatory regions of the gene. The first codon iniating protein synthesis in the message was identified in the 21.14 gene by its position and homology to the consensus sequence A..ATGG, as well as by comparison of the 21.14 genomic sequence to the open reading frame in the 2-1 cDNA sequence.

Construction of plasmids p484-1(Nco I) and p484-62 (Bgl II)

Site directed muratgenesis was performed on the regulatory regions of the 21.14 genomic clone so that the expression of a foreign coding sequence could easily be placed under the control of chemicals known to affect the expression of the 2-1 gene. An oligonucleotide of the sequence 5'-GAGCTGCGGTACCGGC-3' was designed to introduce an Nco I restriction site in pJE484-1 at the ATG codon corresponding to the start of the 2-1 protein coding region of the message. Another oligonucleotide, 5'-TGAGATCTGACAAA-3', was designed to introduce a Bgl II restriction site in pJE482-62 at the 3' end of the gene, 9 base pairs past the termination codon of the 2-1 protein. Both oligonucleotides were synthesized using an Applied Biosystems DNA synthesizer.

The plasmid pJE 484-1 was transformed into the dut⁻ ung⁻ E. coli. strain BW313 [disclosed in Proc. Natl. Aacd. Sci., U.S.A., Vol. 79, pp 488–492 (1982)]. Cultures were grown for the production of single-stranded DNA as described earlier in this Example. Colonies were picked with sterile toothpicks and used to inoculate two 5 ml tubes of 2XYT containing 100 µg/ml ampicillin and 5 µl of a M13K07 stock (a helper phage for packaging of single-stranded DNA; titer $10^{11}$ pfu/ml). The cultures were shaken at 37° C. and after two hours of growth, kanamycin was added to 50 µg/ml. The incubation was then continued at 37° C. overnight. The tubes were pooled and bacteria were removed by centrifugation at 8,000 rpm for 10 minutes in a Sorvall HB4 rotor at 4° C. Six ml of the supernatant were removed to a new tube and 1.5 ml 20% PEG, 2.5M NaCl added to it and mixed well. After 15 minutes at room temperature, phage particles were pelleted by centrifugation at 8,000 µm for 10 minutes in a Sorvall HB4 rotor. The pellet was resuspended in 0.4 ml 2XYT and transferred to a new microfuge tube. Phage particles were precipitated by adding 0.1 ml 20% PEG, 2.5M NaCl. After 5 minutes, phage were collected by centrifugation and all traces of supernatant were removed by aspiration. Phage particles were resuspended in 0.5 ml 0.3M sodium acetate, 1 mM EDTA, and extracted with phenol:chloroform (1:1 v/v). Phage DNA was then precipitated with ethanol, collected by centrifugation, washed once with 70% ethanol and resuspended in 50 µl of $H_2O$. The concentration of DNA was determined by measuring the absorbance of a 1 to 50 dilution of this solution. 0.5 pmole of this single-stranded DNA was annealed to 25 pmole of the oligonucleotide 5'-GAGCTGCGGTACCGGC-3' in 20 µl Fritz standard annealing buffer (8× annealing buffer is 1.5M KCl, 100 mM Tris-HCl pH 7.5) for 30 minutes at 55° C. 15 minutes at 37° C. and 15 minutes at room temperature. After annealing, 2.3 µl 10× fill-in buffer (0.625M KCl, 0.275M Tris-HCl pH 7.5, 0.15M $MgCl_2$, 20 mM DTT, 2 mM ATP, 1 mM of each dNTPs), 1 µl KlenoW (5 U/µl) and 1 µl of 0.6 U/µl DNA ligase were added. The tube was incubated overnight at room temperature. The next day, competent E. coli strain JM83 was transformed with the products of this ligation reaction (as described earlier) and plated on LB plates containing 100 µg/ml ampicillin. Small scale plasmid preparations were performed on the resulting colonies and the DNA was digested with Nco I until a transformant was found that contained a plasmid that was linearized by Nco I, indicating that the desired mutation had taken place. This new plasmid was designated pJE 484-1(Ncoi) (FIG. 3). In the same manner, the plasmid pJE 484-62 was mutagenized with the oligonucleotide 5'-TGAGATCTGACAAA-3' to create a new Bgl II site downstream of the translation stop site of the 2-1 protein. This new plasmid was designated pJE 484-62(Bgl II) (FIG. 3).

Identification of the Transcription Start Site of 21.14 Gene

Primer extension analysis was performed to determine the transcription start site of the 21.14 gene using a method based on the procedure of McKnight [McKnight S. L., Cell 31 355–366 1982]. A synthetic oligonucleotide, designated HH17, which is the reverse complement to bases 572 to 593 of the coding strand of the 21.14 gene (FIG. 1) was synthesized using an Applied Biosystems Model 380A DNA synthesizer. The HH17 oligonucleotide, 5'-CATGTCGTC-GAGATGGGACTGG-3', was end-labeled with $^{32}P$-gamma ATP (specific activity 3000 Ci/mole, NEN Research Products) as follows: 5 µl (8.34 pmoles) of $^{32}P$-gamma ATP was dried in a microfuge tube in vacuo. The pellet was dissolved in 2 µl of HH17 primer (5 pmole) and 2 µl of 2.5× kinase buffer (1× buffer is 50 mM Tris-HCl pH 9.5, 10 mM $MgCl_2$, 5 mM dithiothreitol, 1 mM spermidine, 0.1 mM EDTA). One µl of T4 polynucleotide kinase (5.3 U/µl, Pharmacia) was added, and the labeling was allowed to proceed at 37° C. for 15 minutes. The reaction was stopped by adding 75 µl TE (10 mM Tris-HCl pH 8, 1 mM EDTA), 54 µl 5M ammonium acetate, 20 µg yeast tRNA carrier and 350 µl ice-cold ethanol. The oligonucleotide was precipitated on dry ice for 30 minutes and recovered by centrifugation at 4° C. The pellet was dissolved in 90 µl of TE pH 8.0 and re-precipitated on dry-ice for 30 minutes after adding 10 µl 3M sodium acetate, pH 6 and 250 µl ice-cold ethanol. The oligonucleotide pellet was collected as before, rinsed with 95% cold ethanol and dried in vacuo. The pellet was dissolved in 50 µl of 10 mM Tris-HCl pH 8 at a final concentration of 0.1 pmole/µl and stored at 4oC.

Eight µg of total RNA isolated from the roots of Mo17 corn plants treated hydroponically for 6 hours with 200 mg/l N-(aminocarbonyl)-2-chlorobenzenesulfonamide was mixed with 2 µl (0.2 pmole) $^{32}P$-labeled HH17 primer, 2 µl of 5× annealing buffer (1.25M KCl, 10 mM Tris pH 7.9) and 1 µl of 30 mM vanadyl ribonucleoside complex (Bethesda Research Labs) at 0° C. Annealing was performed by heating the mixture at 65° C. for 3 minutes and cooling to 35° C. over a 2 hour period. Primmer extension was performed by adding 23 µl of PE mix (10 mM $MgCl_2$, 5 mM dithiothreitol, 20 mM Tris HCl pH 8.3, 0.33 mM of each dATP, dCTP, dGTP, dTTP, 100 µg/ml actinomycin-D), 0.5 µl of AMV reverse transcriptase (10 U/µl, Molecular Genetic Resources) to the tube followed by incubation at 37° C. for 45 minutes. Primer extension products were precipitated on dry ice for 20 minutes after adding 300 µl of ice-cold ethanol. The precipitate was collected by cenrifugation at 4° C., rinsed with 70% ice-cold ethanol and dried in vacuo.

The HH17 oligonucleotide was used as a primer for sequencing of plasmid pJE516 (described in Example 6). Four µg of pJE516 was denatured in 200 mM NaOH, 0.2 mM EDTA at room temperature for 5 minutes and base was neutralized with 2M ammonium acetate pH 5.4 at 0° C. The denatured DNA was precipitated on dry ice for 10 minutes after adding 2 volumes of ice-cold ethanol. The DNA was collected by centrifugation at 4° C. for 15 minutes, rinsed with 70% ethanol, dried in vacuo and dissolved in 10 µl of water. Seven µl of denatured pJE516 was sequenced with HH17 as the primer using a Sequenase® Kit (United States Biochemical Corporation) using the procedures recommended by the manufacturer.

The primer extensioDn products from above were dissolved in 3 µl of 0.1M NaOH, 1 mM EDTA for 30 minutes at room temperature. Six µl of gel loading buffer was then added and the solution was heated at 90° C. for 5 minutes. Primer extension products and primed pJE516 sequencing reactions were separated by electrophoresis on a 12% polyacrylamide gel in 1× TBE containing 7M urea. The gel was then dried and autoradiographed. Analysis of the primer extension products showed the presence of one major band whose length corresponded to a traDscription start site at base 532 of the 21.14 gene promoter fragment in FIG. 2 and two minor products corresponding to bases 533 and 536. The positions of these bases in FIG. 2 is indicated by arrows. Nucleotide 532 of 2-1 corn gene promoter designated 21.14 was therefore assigned as the major transcription start site.

EXAMPLE 2

Identification and Isolation of the Promoter and 3' Downstream Regions of the 2-2#4 Corn 2-2 Gene Isolation and Characterization of 2-2 cDNA clones Details of the techniques used to perform the procedures used in Example 2 are presented in Example 1. The cDNA library made using poly(A)$^+$ RNA from the roots of N-(aminocarbonyl)-2-chlorobenzenesulfonamide-treated Missouri 17 corn plants (described in Example 1) was analyzed for additional cDNA clones representing mRNAs induced by substituted benzenesulfonamides. The library was subjected to differential screening as before and a new colony displaying stronger hybridization with the cDNA probe made using RNA from roots treated with N-(aminocarbonyl)-2-chlorobenzenesulfonamide was identified. This colony was designated In 2-2.

A small scale plasmid preparation was performed on the plasmid contained in colony In 2-2. This plasmid was designated pIn 2-2. An aliquot of pIn 2-2 was nick translated as described earlier. A slot blot containing total RNA from N-(aminocarbonyl)-2-chlorobenzenesulfonamide-treated and untreated roots was prepared and probed with nick-translated pIn 2-2 as described for pIn 2-1 in Example 1. This analysis confirmed that pIn 2-2 contained a cDNA insert that hybridizes strongly to RNA from roots of plants treated with N-(aminocarbcayl)-2-chlorobenzenesulfonamide, but not to RNA from untreated roots.

The pIn 2-2 small scale plasmid preparation was digested to completion with Pst I and analyzed by agarose gel electrophoresis. The cDNA insert of the plasmid was excised by Pst I as a single 1200 bp fragment. Nick-translated pIn 2-2 was used to probe a Northern blot of RNA from both untreated and N-(aminocarbonyl)-2-chlorobenzenesulfonamide-treated roots. This probe hybridized to a single 1.35 knt mRNA that was present only in RNA from the roots of N-(aminocarbonyl)-2-chlorobenzenesulfonamide-treated plants. This indicated that the insert in pIn 2-2 was not a full length copy of the 2-2 mRNA.

A new plasmid cDNA library was made to isolate full length 2-2 cDNA clones. An aliqout of the ds cDNA used to make the λgt11 library described in Example 1 was ligated overnight into the vector pUC18 that had been cut to completion with Eco RI and dephosphorylated. Aliquots of the ligation reaction were used to transform competent *E. coli* DH5 (Bethesda Research Laboratories) using the protocol suggested by the manufacturer. A set of master filters of this library was made by arraying individual ampicillin resistant colonies onto nitrocellulose as described for the plasmid cDNA library in Example 1. Another set of master filters were prepared by transferring colonies directly to nitrocelluluse by laying a dry filter onto a plate that contained 150–250 transformed colonies per plate. The filter was then removed and placed colony side up on a fresh LB/amp plate. Three replica nitrocellulose filter copies of the library were prepared and the DNA in each colony was fixed to the filters as described previously. One set of replica filters was prehybridized and then hybridized with a mixed probe consisting of nick-translated plasmid DNAs from a number of sources including the plasmid pIn 2-2. Plasmid nick-translation, and filter prehybridization and hybridization were performed as described for the identification of specific cDNA clones from the λgt11 cDNA library in Example 1. A total of 1500 colonies were screened, and twelve of these colonies hybridized to the mixed cDNA probe.

These putative positive clones were characterized by performing small scale plasmid DNA preparations from each colony. Plasmids were digested to completion with Eco RI and the digestion products were separated by agarose gel electrophoresis. The DNA fragments in the gel were blotted to a Zeta Probe® membrane, and the blot was then hybridized with nick-translated pIn 2-2 to identify the 2-2 clones in the mixed population, as well as to obtain a size estimate for the insert sizes of any new 2-2 clones that were found. Five colonies hybridized to 2-2 probe, with one appearing to contain a full length 1.65 kbp insert. This clone was designated pIn 2-2-3.

Isolation of genomic clone 2-2#4

The library of Mo17 genomic DNA used to obtain genomic clones corresponding to the 2-1 cDNA was screened for 2-2 genomic clones as described in Example 1. Three 2-2 genomic clones were identified and plaque purified from this library. The three clones were mapped using a probe made by randomly primed cDNA synthesis using RNA from N-(amino carbonyl)-2-chlorobenzenesulfonamide-treated corn roots as described in Example 1. The result of this analysis indicated that the clone designated 2-2 #4 contained a region of homology to the randomly primed cDNA probe in the center of its insert, and was therefore chosen for further analysis.

DNA Sequence Analysis of ln2-2-3 and 2-2 #4 Clones

A plate stock of phage 2-2 #4 was prepared by diluting 100 μl of an overnight culture of LE392 with an equal volume of 10 mM $MgCl_2$, 10 mM $CaCl_2$. The diluted culture was incubated at 37° C. for 20 minutes with 40 μl of plaque purified 2-2 #4 phage. The culture was mixed with 3 ml of molten 55° C. top agarose (0.7% agarose in NZC broth), spread over the surface of a 100 mm NZC agar plate and grown at 37° C. for 8 hours. The surface of the plate was covered with 6 ml of SM and it was placed at 4° C. overnight on an orbital shaker at 50 rpm. The SM was removed from the plate, mixed with 50 μl of $CHCl_3$, and stored at 4° C. Serial dilutions of this stock were titered on *E. coli* LE 392 to determine phage liter.

A large scale preparation of genomic clone 2-2 #4 DNA was performed by diluting 3 ml of an overnight culture of *E. coli* LE392 grown in NZC medium with 3 ml of 10 mM $MgCl_2$, 10 mM $CaCl_2$ and inoculating the bacteria with $2\times10^6$ plaque forming units (pfu) of 2-2 #4. This culture was incubated at 37° C. for 15–20 minutes and then used to inoculate 500 ml of NZC at 37° C. The culture was grown at 37° C. with vigorous agitation until lysis occurred (approximately seven hours). The lysate was cooled to room temperature on ice, 1 mg each of DNASe I and RNAse A were added, and the culture was allowed to stand at room temperature for 30 minutes. Solid NaCl was added to 1M and the culture was placed on ice for 1 hour. Debris was removed from the lysate by centrifugation at 11,000 rpm in a Sorvall GSA rotor and polyethylene glycol (PEG) 8000 was added to a final concentration of 10% (w/v). After 2 hours at 4° C., phage were collected by centrifugation as above and resuspended in a total volume of 15 ml of SM. The phage were extracted with 15 ml of $CHCl_3$, centrifuged at 1600 g for 15 minutes in an HB-4 rotor and the upper phase containing the phage was stored at 4° C. overnight. Phage were purified by layering them on a step gradient consisting of 6 ml of 5M CsCl in TM (10 mM Tris-HCl pH 8.0, 10 mM $MgCl_2$) layered over 6 ml of 3M CsCl in TM. The gradient was centrifuged at 22,000 rpm in a Beckman SW28 rotor for 2 hours at 4° C. Phage banding at the 3M/6M CsCl interface were removed, mixed with an equal volume of saturated CsCl in TM and layered in the bottom of at, SW28 centrifuge tube. Phage were then sequentially overlaid with 3 ml of 6M CsCl in TM, 3 ml of 3M CsCl in TM and sufficient TM to fill the centrifuge tube. The gradient was centrifuged as before and phage were recovered in the same manner. Phage were dialyzed against three changes of 50 mM Tris-HCl, pH 8.0, 10 mM NaCl, 10 mM $MgCl_2$ for one one hour each and then transferred to a polypropylene tube. The volume was adjusted to 1.2 ml with dialysis buffer, and phage were lysed by addition of 172 μl $H_2O$, 37.5 μl 20% SDS, 60 μl 0.5M $Na_2EDTA$, pH 8.0 and 30 μl of 5 μg/ml proteinase K in water. After lysis for 1 hour at 55° C., phage DNA was extracted once with an equal volume of phenol, once with an equal volume of phenol:$CHCl_3$ (1:1 v/v), and once with an equal volume of $CHCl_3$. DNA was precipitated by adding 80 μl of 3M sodium acetate, pH 6.0 and 3.2 ml of ethanol and incubating the mixture for 5 minutes at room temperature. DNA was recovered by spooling it onto a pasteur pipet. Spooled DNA was rinsed in 70% ethanol and allowed to dissolve overnight by placing the pipet in 1 ml of TE, pH 8.0.

Fragments of genomic clone 2-2 #4, were subcloned by partially digested 35 μg of 2-2 #4 DNA with 80 units of Eco RI at 37° C. Time points of the digestion containing 8.5 μg of DNA were removed at times ranging from 7.5 to 45 minutes of digestion and Eco RI was inactivating by heating each time point to 70° C. for 10 minutes. Small aliquots of time points were analyzed by electrophoresis in a 0.8% agarose gel to determine the extent of digestion. Time points showing partial Eco RI digestion products were ligated overnight with pUC18 DNA that had been cut to completion with Eco RI and dephosphorylated. Ligation reactions were diluted with 4 volumes of water and aliquots of each diluted reaction were used to transform competent *E. coli* HB101. Aliquots of the transformation mixture were spread on LB plates containing ampicillin and plates were incubated overnight at 37° C. Plasmids from individual antibiotic resistant colonies were analyzed for inserts containing Eco RI fragments of phage 2-2 #4 DNA. Large scale plasmid preparations were done from subclones designated genomic 2-2 #2, 2-2#11, 2-2#17, and 2-2#23 whose inserts provide complete overlap of the region of the 2-2 #4 genomic clone that contained the 2-2 gene (FIG. 4A).

The sequences of the cDNA clone In 2-2-3 and relevant portions of plasmid genomic subclone #2, #11, #17 and #23 were determined by the method of Maxam and Gilbert (as described by Barker et al., *Plant Mol, Biol.*, 2, 335–350). The sequences of the genomic subclones were assembled to provide the complete nucleotide sequeDce of the 2-2 gene. Comparison of the nucleotide sequences of the 2-2-3 cDNA clone with the 2-2 #4 genomic sequence showed that 2-2 #4 contained a complete copy of the 2-2-3 cDNA clone dispersed among several exons.

The nucleotide sequence of the 5' untranslated and promoter regions of the 2-2 #4 gene is shown in FIG. 4B. The ATG functioning as the translation start codon for the 2-2 protein is contained within an natural Nco I site in the 2-2 #4 gene. Suitable promoter fragments useful for use in regulation the expression of recombinant DNA constructions can be removed from this subclone by cleavage of that Nco I site and removal of the promoter at any number of restriction sites 5' to that Nco I site such as at Xho I to yield a 1.9 kbp fragment. Later examples teach the use of such fragments.

A convenient Xho I site exists in genomic subclone 2-2 #11 nine nucleotides beyond the translation stop codon for the 2-2 protein (FIG. 4). Suitable downstream DNA fragments useful in regulation the expression of chimeric genes can be removed from this subclcne by cleavage of that Xho I site and removal of the downstream at any number of restriction sites 3' to that Xho I site such as Sal I to yield a 0.8 kbp fragment or Cla I to yield a 1.7 kbp fragment.

EXAMPLE 3

Identification and Isolation of the Promoter and 3' Downstream Regions of the 52.411 Corn 5-2 Gene Isolation and Characterization of 5-2 cDNA clones Details of the techniques used to perform Example 3 are presented in Example 1. The cDNA library made from poly (A)+ RNA from the roots of N-(aminocarbonyl)-2-chlorobenzenesulfonamide-treated Missouri 17 corn plants described in Example 1 was analyzed for additional cDNA clones representing N-(aminocarbonyl)-2-chlorobenzenesulfonamide-induced mRNAs. The differential screening method described in Example 1 was used to isolate a new colony that displayed stronger hybridization with the cDNA probe made using RNA from roots treated with N-(aminocarbonyl)-2-chlorobenzenesulfonamide. This colony was designated In 5-2.

A small scale plasmid preparation was performed on an overnight culture of In 5-2 and an aliquot of the plasmid, designated pIn 5-2, was nick-translated as described earlier. Slot blot analysis was performed as described in Example 1 using nick-translated In 5-2 plasmid. This analysis confirmed that pIn 5-2 contained a cDNA insert representing an mRNA that hybridizes strongly to RNA from N-(aminocarbonyl)-2-chlorobenzenesulfonamide-treated roots but not RNA from control roots. This plasmid was designated pIn 5-2.

An aliquot of the small scale plasmid preparation of pIn 5-2 was digested to completion with PSt I and analyzed by agarose gel electrophoresis. The cDNA insert of the plasmid was excised as a single 420 bp Pst I fragment. Plasmid pin 5-2 was nick-translated and used to probe a Northern blot of RNA from both untreated and N-(aminocarbonyl)-2-chlorobenzenesulfonamide-treated roots. The plasmid hybridized to a 2000 nt mRNA that was induced in root tissue by chemical treatment.

As the insert of pIn 5-2 was not a full length copy of the 5-2 mRNA, the λgt11 phage cDNA library made in Example 1 was screened for full length 5-2 cDNA clones. This was accomplished by probing the library with the purified cDNA insert from pIn 5-2 that had been nick-translated using the methods described in Example 1. Six different phage clones showed homology to the pIn 5-2 cDNA insert and were plaque purified. Small scale DNA preps were made from these phage and aliquots of these DNAs were digested to completion with Eco RI and analyzed by agarose gel electrophoresis. Three clones that contained insert similar in size to the 5-2 mRNA were subcloned into pUC18 by digestion of phage DNAs to completion with Eco RI and ligation of the resulting DNA into the Eco RI site of pUC18. One subclone, designated pIn 5-2.32, was chosen for further analysis.

Isolation of genomic clone 52.411

The library of Mo17 genomic DNA used to obtain genomic clones for the 2-1 message was screened with nick-translated pIn 5-2 as described in Example 1 to isolate genomic clones corresponding to the 5-2 message. Six 5-2 genomic clones were plaque purified from this library in this manner. These genomic clones were mapped by hybridization using a probe made from randomly primed cDNA synthesized using RNA from N-(aminocarbonyl)-2-chlorobenzenesulfonamide treated roots to identify regions of homology to the In 5-2 cDNA as described in Example 1. The results of this analysis indicated that all six clones appeared to contain the same regions of homology to the randomly primed cDNA probe. One clone, designated 52.411, was chosen for further analysis to determine its relationship to the In 5-2 cDNA.

Genomic clone 52.411 was digested to completion with Eco RI and Sma I and the resulting fragments were ligated into the vector pUC 19 that had been cut to completion with the seme two restriction endonucleases. Followinc transformation of *E. coli* with an aliquot of the ligation mixture, small scale plasmid preparations were performed on amp-resistant colonies that arose until a colony was found that contained a 12 kbp Eco RI/Sma I fragment ligated into pUC 19. This plasmid was designated pJE 490.

The plasmid pJE 490 was digested to completion with Eco RI and Sal I and the resulting fragments were ligated into the vector pUC 19 that had been cut to completion with the same two restriction endonucleases. Following transformation of *E. coli* with an aliquot of the ligation mixture, small scale plasmid preparations were performed on amp-resistant colonies that arose until a colony was found that contained a 4 kbp Eco RI/Sal I fragment ligated into pUC 19. This plasmid, called pJE 491, contains the 5' end of the 52.411 gene.

The plasmid pJE 490 was digested to completion with Sal I and the resulting fragments were ligated into the vector pUC 19 that had been cut to completion with the same restriction endonuclease. Following transformation of *E.* coli with an aliquot of the ligation mixture, small scale plasmid preparations were performed on amp-resistant colonies that arose until one was found that contained a 4.0 kbp Sal I fragment ligated into pUC 19. This plasmid, called pJE 493, contains the 3' end of the 52.411 gene.

DNA Sequence Analysis of In 5-2.32 and 52.411

The sequence of the cDNA clone pIn 5-2.32 was determined using both the dideoxy chain termination method and Maxam and Gilbert chemical sequencing. Maxam and Gilbert chemical sequencing was performed on pIn 5-2.32 as described in earlier examples. For dideoxy sequencing, the plasmid pIn 5-2.32 was digested with Eco RI and resulting DNA fragments were separated by agarose gel electrophoresis. The 2 kbp cDNA insert was purified from the gel and digested to completion with Sau 3A. The resulting DNA fragments were ligated into the Bam HI site of the RF form of the vector M13MP18. Aliquots of the transformation mixture were used to transfect E. coli JM 101. Aliquots of the transfection mixture were grown on 2XYT containing X-gal and IPTG. DNA was prepared from randomly chosen colorless plaques and sequenced by the dideoxy chain termination method using a Sequenase Kit® (U.S. Biochemicals) following the manufacturer's recommended protocols. The correct order of the Sau 3A fragments in pIn 5-2.32 was assigned by comparison of dideoxy sequence data from individual fragments with that derived for the cDNA by the Maxam and Gilbert method.

Regions of the genomic DNA inserts contained within the plasmi.ds pJE 491 and pJE 493 were sequenced by creating nested sets of deletions of each plasmid as described in Example 1. By comparison of the sequences derived from regions of pJE 491 to that derived from the In 5-2 cDNA clones, a 2.1 kbp Bam HI/Sal I genomic DNA fragment was identified containing 3.5 kbp of the 5-2 promoter as well as the start of the 5-2 structural gene (FIG. 3). This fragment was subcloned into the vector pBS(-). The resulting plasmid was designated pMC 3167.13. The sequence of the 5-2 gene upstream from the translation start of the 5-2 protein is shown in FIG. 5.

Figure 6:
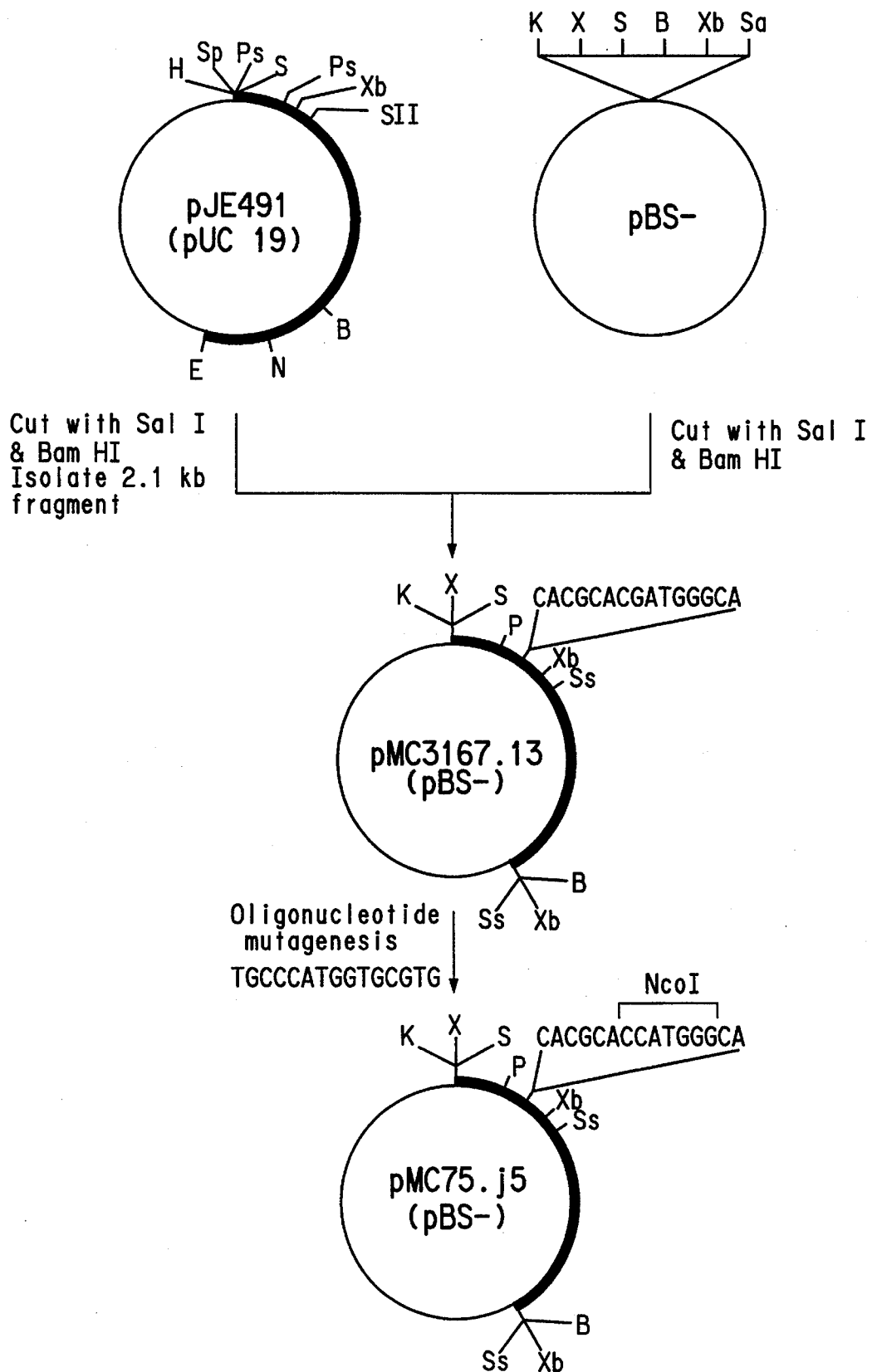
FIG. 6 depicts the creation of plasmid pMC75.j5 from the 5-2 corn gene.

Site directed mutagenesis was performed on the plasmid pMC 3167.13 to introduce a Nco I restriction site at the translation start of the 5-2 coding region. This was done so that the expression of a foreign coding sequence could easily be placed under the control of chemicals known to induce expression of the 5-2 gene. An oligonucleotide of the sequence 5'-TGCCCATGGTGCGTG-3' was designed to introduce the Nco I site at the ATG codon corresponding to the start of the coding regicn of the 5-2 protein. The methods used to perform the mutagenesis were described in Example 1. The resulting plasmid containing the mutagenized 5-2 promoter was designated pMC 75.j5, and is shown in FIG. 6.

EXAMPLE 4

Identification, Isolation and Modification of corn 218 gene Promoter

Isolation and Characterization of 218 cDNA clones

Details of the techniques used to perform the procedures used in this Example are presented in Example 1. Equimolar aliquots of the cDNA used to make the λgt11 phage cDNA library in Example 1 and pUC18 DNA that had been digested to completion with Eco RI and dephosphorylated were ligated together overnight. Aliquots of the ligation mixture were transformed into competent E. coli DH5 cells (BRL) and plated onto LB plates containing 50 ug/ml ampicillin. Antibiotic resistant colonies were arrayed onto nitrocellulose disks and analyzed for cDNA clones containing inserts representing mRNAs induced by substituted benzenesulfonamides as described in Example 1. A colony displaying stronger hybridization with the cDNA probe made from RNA of N-(aminocarbonyl)-2-chlorobenzenesulfonamide-treated corn roots was identified. This clone was designated In 218 and the plasmid contained within it was designated p218. Agarose gel electrophoresis of the Eco RI digestion products of p218 showed the plasmid contained a 900 bp insert. Hybridization of nick-translated p218 to size fractionated RNA isolated from N-(aminocarbonyl)-2-chlorobenzenesulfonamide-treated roots indicated that the cDNA was full length.

A library of Missouri 17 genomic DNA was made and screened for genomic sequences corresponding to the 218 cDNA clone using nick-translated p218 as described in Example 1 with the following changes: 1) genomic DNA was digested with Eco RI rather than Sau 3A and 2) Eco RI fragments of the appropriate size were cloned in the vector λDash that had been digested with Eco RI rather than using Bam HI XEMBL3. Eighteen genomic clones hybridizing to the 218 cDNA were identified and plaque purified from this library. The Eco RI inserts from members of each group were subcloned into the plasmid vector pBS(+) and the subcloned genomic DNA was digested with a variety of restriction enzymes. The digestion products were separated by agarose gel electrophoresis, blotted to nitrocellulose and probed with nick-translated pIn 2.8. Comparison of the restriction maps generated for the genomic subclones with that derived for the 218 cDNA indicated that one genomic subclone, designated pMC730, contained a 1.4 kbp Sac I/Xho I fragment that was very similar to and hybridized that hybridized with the 218 cDNA clone.

Plasmid pMC730 was digested to completion with Xho I and the the reaction mixture was diluted to 200 ul. After heating at 65° C. to inactivate XhoI, the diluted digest was ligated together to recirculate the plamid, and thus deleting a 6 kbp Xho I fragment from pMC730 that did not hybridize with the cDNA. This plasmid was designated pMC767. The plasmid pMC767 clone was sequenced 224 bases from the XhoI side and was found to compare well with the cDNA for 190 bases at which point an intron junction was encountered. To skip over this intron, pMC767 was digested to completion with Nco I and Xho I. The 5' overhanging ends were rendered blunt using T4 polymerase and the plasmid was recirculated as described above to create the plasmid pMC791 (FIG. 7).

From this plasmid a DNase I deletion series was generated for dideoxy sequencing. The entire Nco I to Eco RI region was sequenced (1710 bases) and compared with the cDNA (FIG. 8). The genomic sequence matched the cDNA sequence at its 5' end and extended over 1.5 kb beyond the 5' end of the cDNA (FIG. 7). The beginning of the 218 message was determined by using the genomic clone in a riboprobe protection experiment and the first ATG of the message was identified by searching downstream from this site, and is indicated at nucleotide 1516 by an arrow in FIG. 7. Computer analysis of the genomic sequence identified an Afl III site that contained this ATG (underlined in FIG. 7). Digestion with this enzyme produces a cohesive end containing the ATG start codon of the 218 gene product that is capable of ligating with any desired coding region. Thus a functional 1.4 kbp 218 promoter and 5 untranslated leader fragment may be obtained from pMC791 by partial Afl III digestion followed by complete digestion with SmaI to excise a 1.4 kbp promoter/untranslated leader fragment.

EXAMPLE 5

Identification, Isolation, and Modification of the Promoter and 3' Downstream Regions of the P6.1 Petunia Gene

Growth and Chemical Treatment of Plants

Petunia (Mitchell) seeds were germinated in soil and allowed to grow for one month under standard greenhouse conditions. Plants were transferred to a hydroponic growth apparatus in a greenhouse using foam plugs to support the plants. These plugs were then placed in holes in a wooden bDard and placed over a stainless steel sink containing 0.5× Hoagland's solution. The solution was aerated using standard aquarium pumps, and was changed weekly. After one month of hydroponic growth, plants were transferred to stainless steel trays containing either fresh 0.5 × Hoagland's or 0.5× Hoagland's containing 0.2 g per liter of N-(aminocarbonyl)-2-chlorobenzenesulfonamide. Root tissue was harvested after six hours of treatment.

Isolation of RNA

Root tissue was harvested by slicing roots off just below the foam plugs. Tissue (2–5 g) was wrapped in aluminum foil, quick frozen in liquid nitrogen and stored at −80° C. until used. Frozen tissue was transferred to a mortar precooled with liquid $N_2$ and ground to a fine powder with a chilled pestle. The powder was transferred to a 50 ml polyethylene centrifuge cubes containing 10 ml NTES (0.01M Tris-HCl pH 7.5, 0.1M NaCl, 1 mM EDTA, 1% SDS), 10 ml water-saturated phenol, and 10 ml chloroform: isoamyl alcohol (24:1 v/v). The emulsion was vigorously shaken for 15–30 minutes and then separated by centrifugation in 30 ml Corex® tubes at 5000 rpm for 10 minutes in a Sorvall HB-4 rotor. Nucleic acids were precipitated from the aqueous phase by the addition of 1 ml 3M sodium acetate, pH 6.0 and 25 ml ethanol. After 2 hours at −20° C., the precipitate was collected by centrifugation at 10,000 rpm for 20 minutes in a Sorvall SS34 rotor. Pellets were drained well and dissolved in 2 ml of $H_2O$. Two ml of 4M lithium acetate was added to selectively precipitate the RNA and the solution was held on ice for 3 hours. RNA was collected by centrifugation at 10,000 rpm in an SS-34 rotor for 20 minutes RNA was dissolved in 400 µl water, transferred to 1.5 ml microcentrifuge tubes and reprecipitated with ethanol for 2 hours at −20° C. RNA was collected by centrifugation in a microcentrifuge for 5 minutes and the final pellets were dissolved in 200 µl $H_2O$. RNA concentrations were dete#mined from the absorbance of the solutions at 260 nm. Yields of RNA from typical preparations were approximately 1 mg.

Isolation of Poly(A)+ RNA

Poly(A)+ RNA was purified from total RNA by oligo (dT) cellulose chromatography. 2.5 mg of RNA was diluted to 0.4 mg/ml (10 A260 per ml) in zero salt buffer (10 mM Tris-HCl pH 7.4, 0.5% SDS, 1 mM EDTA). The RNA was denatured at 65° C. for 5 minutes and then chilled on ice for 10 minutes. Sodium chloride was then added to bring the concentration to 0.4M. The RNA was applied to a plastic disposable column that was packed with 0.1 g oligo (dT) cellulose (Worthington) which has been equilibrated with high salt buffer (zero salt buffer containing 0.4M sodium chloride). RNA was passed over the column two or three times to-maximize binding of the poly(A)+ fraction. Following binding, the column was washed with 10 ml high salt buffer. Poly(A)+ was eluted with zero salt buffer in 6 one ml fractions. Absorbance of the fractions was measured at 260 nm and the fractions containing RNA were pooled. RNA was precipitated with ethanol and dissolved in 100 µl $H_2O$. Yields of poly(A)+ RNA were generally 0.5–1% of the total RNA applied to the column.

Construction of cDNA Library

Five µg of poly(A)+ RNA from N-(aminocarbonyl)-2-chlorobenzenesulfonamide-treated roots were ethanol precipitated, collected by centrifugation and dissolved in 10 µl of $H_2O$. The RNA was heated at 65° C. for 3 minutes and rapidly chilled on ice. First strand cDNA was prepared using a reaction mixture containing 10 µl RNA, 5 µl 10× first strand buffer (0.5M Tris-HCl pH 8.5, 0.4M KCl, 0.1M $MgCl_2$, 4 mM DTT), 5 µl of a nucleotide mixture containing each of the four dNTPs(ACGT) at 10 mM, 5 µl 100 µg/ml oligo $(dT)_{12-18}$, 5 µl $\alpha$-$^{32}$P dCTP, 2 µl placental rbonuclease inhibitor and 50 units of reverse transcriptase. The reaction was incubated at 42° C. for 1 hour. The mass of cDNA synthesized was calculated from the incorporation of $^{32}$P-dCTP into the synthesized DNA. The RNA:cDNA duplex was denatured by heating in a boiling water bath for 1.5 minutes, then quick chilled on ice. The following were then added to the 50 µl first strand reaction mixture: 50 µl 2× second strand buffer (100 mM HEPES pH 6.9, 100 mM KCl, 20 mM $MgCl_2$), 1 µl of a 10 mM dNTP mixture and 2 µl DNA polymerase 1 (50 U/µl). The reaction mix was incubated at 15° C. for 5 hours. At that time, 400 µl of S1 buffer (30 mM sodium acetate pH 4.4, 250 mM sodium chloride, 1 mM $ZnCl_2$) and 500 units of S1 nuclease were added. The incubation was continued for 1 hour at 37° C. The products of the S1 reaction were extracted with an equal volume of phenolchloroform (1:1 v/v) and precipitated with ethanol. The pellet was dissolved in 20 µl methylase buffer (50 mM Tris-HCl pH 7.5, 1 mM EDTA, 5 mM DTT) to which 2 µl 100 mM S-adenosylmethionine and 1 µl of Eco RI methylase (40 U/µl) were added. The methylation reaction was incubated at 37° C. for 15 minutes followed by 65° C. for 10 minutes. The ends of the cDNA were filled in by adding 2.5 µl 0.1M $MgCl_2$, 2.5 µl 0.2 mM d(ACGT)TP and 1 µl DNA polymerase 1 (5U/µl) to the tube and allowing the fill-in reaction to proceed for 20 minutes at room temperature. The cDNA was then extracted with phenol:chloroform (1:1 v/v) and ethanol precipitated. The pellet was dissolved in 32 µl $H_2O$, 10 µl phosphorylated Eco RI linkers (0.1 mg/ml), 5 µl 10× ligase buffer, and 3 µl of T4 DNA ligase (0.1 ml) (6 Weiss units/µl). The ligation reaction was then incubated at 15° C. for 16 hours. The DNA ligase was inactivsted by heating at 65° C. for 10 minutes and Eco RI linkers were digested for 2 hours at 37° C. by adding 40 µl $H_2O$, 10 µl 10× Eco RI buffer and 3 µl Eco RI (20 U/µl) to the DNA. The cDNA was then precipitated with ethanol, dissolved in 20 µl 1× TBE and subjected to electrophoresis in a 6% polyacrylamide gel. The gel was stained with ethidium bromide (1 µg/ml) to visualize the cDNA in the gel. A slice of the gel containing cDNA >0.5 kbp was cut out and DNA was recovered by electroelution of the cDNA into a dialysis bag. The electroeluted cDNA was extracted with phenol:chloroform (1:1 v/v), precipitated with ethanol, and dissolved in 20 µl $H_2O$. One µl of the cDNA was counted in a liquid scintillation spectrometer and the mass of cDNA was determined using the specific radioactivity of the $^{32}$P-dCTP used in the cDNA synthesis. One microgram of λgt10 arms that had been cut to completion with Eco RI and dephosphorylated was ligated to 30 ng of cDNA in a volume of 5 μl. The ligation mixture was then packaged using Gigapack extracts (Stratagene) as per manufacturer's instructions. Approximately 1 million recombinants were obtained from such a procedure.

Isolation of cDNA clone P6

Approximately 10,000 phage were plated out on 5 150 mM LB agar plates containing 10 mM $MgCl_2$ (2000 phage per plate) using the *E. coli* strain C600 as the host. Replica filters copies of the library were prepared from each plate as follows: Dry nitrocellulose filters were wetted by placing them onto the surfaces of agar plates containing the phage cDNA library. The filters were then transferred to a sheet of Whatman 3MM paper that had been saturated with 0.5M NaOH and 1.5M NaCl for 30 seconds to 1 minute. The filters were transferred to a sheet of Whatman 3MM that had been saturated with 1M Tris-HCl pH 7.0 and 1.5M NaCl for 5 minutes, rinsed in 2× SSC, air dried for 1 hour and baked in vacuo for 2 hours at 80° C. This process was repeated for each plate to make multiple filter copies of the library.

The replica filters of the cDNA library were screened for cDNA clones representing mRNAs induced by N-(aminocarbonyl)-2-chlorobenzenesulfonamide by the differential hybridization method described in Example 1. cDNA probes were prepared from poly(A)$^+$ RNA from both untreated and treated root tissue as described for first-strand cDNA synthesis in this example with the following modifications: One microgram of poly(A)$^+$ PNA, 2.5 μl of 1 mM dCTP and 10 μl $^{32}$P-dCTP (10 mCi/ml) were used in the reaction. Following probe synthesis, the RNA template was hydrolyzed by the addition of 25 μl 0.15M NaOH and incubating the cDNA at 65° C. for 1 hour. Base was neutralized by addition of 12.5 μl 2M Tris-HCl pH 8.0 and 25 μl 1N HCl. Single-stranded cDNA was separated from unincorporated label on a Sephadex® G50 column, equilibrated and run in 10 mM Tris-HCl pH 7.5, 1 mM EDTA. Fractions eluting in the void volume were pooled, ethanol precipitated and dissolved in $H_2O$.

Replica filters were prehybridized in a solution of 0.1% SDS, 4× SSC, 5× Denhardt's solution, 50 mM sodium phosphate pH 6.8 at 42° C. for 5 hours. The solution was replaced with hybridization buffer (prehybridization buffer containing 50% deionized formamide) containing 5×10$^5$ cpm/ml of probe using RNA from either untreated or N-(aminocarbonyl)-2-chlorobenzenesulfonamide-treated roots. Hybridizations were incubated for 24 hours at 42° C. The filters were then washed twice at room temperature for 1 hour with 2× SSC, 0.1% SDS. A final wash was conducted at 50° C. in 0.1× SSC, 0.1% SDS for one additional hour. Filters were exposed to X-ray film at −80° C. for 6G hours with one intensifying screen.

Plaques hybridizing more strongly with the probe derived from N-(aminocarbonyl)-2-chlorobenzenesulfonamide-treated roots were deemed positive clones in the differential screen. These plaques were removed from the plates with 100 μl capillary pipers and placed in 0.5 ml of SM. Plaque purification was performed on these phage as described in Example 1 by repeated differential screening using the hybridization procedure described above. One clone purified in this manner was designated P6.

A liquid lysate of P6 phage was prepared by absorbing 10% of the phage eluted from one plaque to 100 μl of an overnight culture of *E. coli* BNN102, and inoculating 30 ml NZCYM (per liter: 10 g NZ amine, 5 g yeast extract, 5 g NaCl, 1 g casamino acids, 2 g $MgSO_4$, pH 7.5) with the resulting infected culture. After 5 hours of growth at 37° C., complete lysis of the bacteria had occurred. The lysate was cleared by centrifugation at 10,000 rpm for 10 minutes in a Sorvall SS34 rotor, and the supernatant was transferred to a clean tube. RNAse A and DNAse I were added to 10 μg/ml and 20 μg/ml respectively and the lysate was incubated for 15 minutes at 37° C. One-fifth volume of 20% PEG 6000, 2.5M NaCl were added to the lysate and phage were allowed to precipitate for 15 minutes at room temperature. The phage were collected at 10,000 rpm for 10 minutes, and the pellet was drained well. Phage were resuspended in 0.5 ml 4% PEG 6000, 0.5M NaCl and transferred to a microfuge tube. The phage were extracted with 0.5 ml phenol:chloroform (1:1 v/v) and DNA was precipitated with 2 volumes of ethanol. DNA was collected by centrifugation and dissolved in 50 μl TE pH 8.0. Five μl of DNA were digested to completion with Eco R1 add resulting DNA fragments were analyzed by agarose gel electrophoresis. The results of this analysis showed that the P6 cDNA clone contained a single 700 bp insert.

The Eco R1 insert of P6 was subcloned from the phage vector λgt10 to the plasmid pUC119. Ten μg of P6 DNA was digested to completion with Eco RI and digestion products were subjected to electrophoresis on a 1% agarose gel. A piece of the gel containing the 700 bp Eco RI fragment was cut out and placed in a piece of dialysis tubing containing 0.5 ml 1× TAE (0.04M Tris-HCl pH 7.8, 2 mM EDTA). The DNA was electroeluted from the gel piece at 100 volts for 15 minutes. The buffer containing the DNA was removed from the bag, extracted with an equal volume of phenol:chloroform (1:1 v/v), and DNA was precipitated with ethanol in the presence of 0.3M sodium acetate. Ten μg of pUC119 was digested to completion with Eco R1, extracted with phenol:chloroform (1:1 v/v), and precipitated with ethanol. Equimolar amounts of vector and insert were ligated in a volume of 10 λl at 15° C. for 2 hours. An aliquot of the ligation mixture was used to transform competent *E. coli* JM83 cells. Aliquots of the transformation mixture were grown overnight at 37° C. on LB plates containing 75 μg/ml ampicillin that had been spread with X-Gal and IPTG. Small scale plamid preparations were performed on white colonies and aliquots of the DNAs were digested to completion with Eco R1 until one was found containing the desired 700 bp Eco RI fragment from P6 in pUC118. The resulting clone was designated P6.1.

Ten μg (2 mg/ml) of total RNA from control and N-(aminocarbonyl)-2-chlorobenzenesulfonamide-treated roots was denatured by adding 10 μl of deionized formamide, 3.5 μl formaldehyde, 4 μl 5× MEN buffer (40 mM MOPS pH 7.0, 10 mM sodium acetate, 1 mM EDTA) and incubating at 65° C. for 15 minutes. The RNA was subjected to electrophecesis in a 1.5% agarose gel containing formaldehyde and 1× MEN until the bromphenol blue had migrated to the bottom of the gel. RNA was stained in the presence of 10 mM sodium phosphate pH 6.8 and 1 μg/ml acridine orange for 30 minutes. The gel was then desrained in 10 mM sodium phosphate for 30 minutes, and the RNA was visualized on a UV transilluminator, photographed, and blotted to nitrocellulose (Millipore HAWP). To do this, Whatman 3MM paper was placed below the gel on a glass plate so that the ends of the paper extended into 20× SSC. A sheet of nitrocellulose which had been prewet with 2× SSC was placed on top of the gel followed by a layer of Whatman 3MM, then a stack of paper towels 10 cm high. A glass plate and weight were then placed on top of the stack. Following an overnight transfer, the filter was rinsed briefly in 2× SSC, air dried, and baked in vacuo for 2 hours at 80° C.

The filters were prehybridized for 5 hours in plastic dishes at 42° C. using the hybridization buffer described earlier. Plasmid p6.1 was nick-translated by combining 1 µg of DNA with 5 µl 10× buffer (0.5M Tris-HCl pH 8.0, 0.1M MgSO$_4$, 10 mM DTT and 0.5 mg/ml BSA), 5 µl 0.3 uM d(AGT)TP, 5 µl $^{32}$P-dCTP (Amersham, 10 mCi/ml, 400 Ci/mmole), 1 µl DNA polymerase 1 (5 U/µl, Boehringer-Mannheim), and 1 µl of 0.1 µg/ml DNAse 1 in a total volume of 50 µl. The mixture was incubated for 1.5 hours at 14° C., and the reaction was stopped by the addition of 5 µl of 0.25M EDTA. The reaction was then incubated for 5 minutes at 70° C., and labelled DNA was separated from unincorporated nucleotides by Sephadex® G-50 column chromatography. The prehybridization solution was removed from the bag and replaced with hybridization solution containing nick-translated plasmid P6.1 DNA at a concentration of 1×10$^6$ cpm/ml. Hybridization was carried out at 42° C. for 24 hours on shaking platform. Filters were washed twice with 2× SSC, 0.1% SDS at 42° C. followed by two washes in 0.1× SSC, 0.1%SDS at 60° C. The filter was wrapped in polyethylene food wrap and exposed to X-ray film at −80° C. for 16 hours with one intensifying screen.

The P6.1 probe hybridized to an 800 bp message in RNA from N-(aminocarbonly)-2-chlorobenzenesulfonamide-treated roots while no signal was observed in RNA from untreated plants. The insert size of the cDNA clone approximated the size of the hybridizing RNA, indicating that P6.1 was potentially a full-length cDNA clone.

Sequence Analysis of the cDNA clone P6.1

The nucleotide sequence of clone P6 was determined by sequencing a nested set of deletions mutants generated by digestion of the cDNA insert in P6.1 with Exo III nuclease. The Eco RI insert from cDNA clone P6.1 was subcloned into the Eco RI site of the vector Bluescript(−) (Stratagene). The resulting clone was designated P612. Ten µg of P612 DNA were digested with Kpn I (3' overhang which is resistant to Exo III digestion) and Xho I (5' overhang which is sensitive to Exo III). The DNA was extracted with phenol:chloroform (1:1 v/v), precipitated with ethanol then resuspended in 63.5µl of H$_2$O. Eight µl of 10× Exo III buffer (0.5M Tris-HCl pH 8.0, 50 mM MgCl$_2$, 100 mM β-mercaptoethanol) and 3 µl of Exo III (100 U/µl) were added and the mixture was incubated at 37° C. Aliquots of 2.5 µl were removed every 30 seconds for 15 minutes and added to 13.5 µl ice cold quenching buffer (100 mM sodium acetate pH 4.7, 600 mM NaCl, 20 mM zinc acetate). The aliquots were pooled into groups of five sequential time points and treated with 1 unit of S1 nuclease at room temperature for 30 minutes. Water (123 µl) was added to each pool, and 10 µl from each was analyzed by agarose gel electrophoresis. The remaining DNA was extracted with phenol:chloroform (1:1 v/v), precipitated with ethanol and resuspended in 20 µl of fill-in/ligation buffer (20 mM Tris-HCl pH 7.8, 25 mM NaCl, 10 mM MgCl$_2$, 20 mM DTT, 1 mM ATP, 0.1 mM dNTPs). Forty units of DNA ligase and 2 units of Klenow fragment were added and the mixture was incubated overnight at 15° C. Ten µl of the ligation mixture was used to transform competent E. coli host MV1193 cell and aliquots of the transformation mixture were spread onto L6 plates containing 75 µg/ml amp. Ten colonies froln each transformation were analyzed for insert size, and a series of clones were selected for sequenci.ng that represented deletions of the initial cDNA insert that were each progressively 150 base pairs longer. Single-stranded DNA from those clones were sequenced using the M13 reverse primer and the method of dideoxy chain termination described in Example 1.

Isolation of a genomic clone corresponding to P6 cDNA

Twenty grams of petunia leaf material was harvested, submerged in ice water and transferred to a chilled mortar. Twenty ml of Buffer A (10 mM Tricine pH 7.6, 1.4M sucrose, 5 mM MgCl$_2$, 5 mM β-mercaptoethanol) was added to the mortar and leaf tissue was ground to a fine pulp. The solution was diluted to 100 ml with Buffer A and filtered through four layers of cheesecloth. The filtrate was then passed through eight layers of cheesecloth and centrifuged at 2500 rpm for 10 minutes in a Sorvall GSA rotor. The pellet was resuspended in 100 ml Buffer A and centrifuged as before. The pellet was resuspended in 100 ml Buffer B (Buffer A containing 0.4% Triton X-100), held at 4° C. for 10 minutes, centrifuged as before. The resulting pellet was resuspended in 100 ml of Buffer B and the centrifugation was repeated at 2000 rpm for 10 minutes, yielding a crude nuclear pellet. This pellet was resuspended in 4 ml 50 mM Tris-HCl pH 8.0 and 20 mM EDTA to which 0.5 ml of 10% sarkosyl was added. The solution was incubated at 60° C. for 5 minutes, and then cooled to room temperature. One-tenth ml of a 5 mg/ml proteinase K solution was added and the incubation was continued at 37° C. for 4 hours with gentle shaking. The volume of the solution was measured and 1 g solid cesium chloride was added per 1.2 ml of solution. Ethidium bromide was added to 0.5 mg/ml and the density adjusted to 1.55 g/ml with CsCl. The DNA was banded by centrifugation at 40,000 rpm for 30 hr at 15° C. in a Beckman 70.1Ti rotor. The band was collected from the CsCl gradient by side puncturing of the centrifuge tube. Ethidium bromide was removed from the DNA by repeated extraction with isoamyl alcohol equilibrated with TE pH 8.0. The DNA was then dialyzed against 5 mM Tris-HCl pH 8.0, 0.25 mM EDTA for 2 days.

Conditions were established for partial digestion of petunia genomic DNA by performing pilot restriction digests. Ten µg of DNA was brought up to a volume of 150 µl with the appropriate restriction buffer. Thirty µl aliquots of the DNA was dispensed into a microcentrifuge tube labelled #1. Fifteen µl were dispensed into seven tubes labelled #2–8, and the remainder into tube #9. All tubes were chilled on ice. Sau 3A (4 units) was added to tube #1 and the contents of the tube were mixed well. Fifteen µl from tube #1 was added to tube #2. This twofold serial dilution was continued through to tube #8, and all tubes incubated at 37° C. for 1 hour. The restriction digestions were stopped by chilling the tubes to 0° C. and adding EDTA to 20 mM. The samples were subjected to electrophoresis through a 0.8% agarose gel at 1–2 V/cm. The enzyme concentration which yielded maximum intensity of fluorescence in the 15–20 kbp range was determined after ethidium bromide staining of the gel. Half of the enzyme/DNA ratio determined above was chosen for the preparative digestion of genomic DNA in order to maximize yield of DNA fragments in the 15–20 kbp size range. That enzyme concentration ranged between 0.06 and 0.25 units of Sau 3A per µg DNA.

Three hundred µg of DNA was divided into 3 tubes: ¼ in tube #1, ½ in tube #2 and ¼ in tube #3, and the concentration of DNA was adjusted to 67 µg/ml. Sau 3A was added to tube

2 at the final concentration which was thought to maximize for 15–20 kb molecules. Tube #1 contained one half that concentration while tube #3 contained twice as much Sau 3A. All reactions wE, re incubated at 37° C. for 1 hour. After stopping the digestion as above, aliquots from each of the digestions were analyzed by agarose gel electrophoresis and the appropriate digestions containing maximum amounts of 15–20 kbp fragments were pooled. The pooled sample was loaded onto a 10–40% sucrose gradient in 1M NaCl, 20 mM Tris-HCl pH 8 and 5 mM EDTA and centrifuged at 26,000 rpm for 24 hours at 20° C. in an Beckman SW41 rotor. Fractions of 0.5 ml were collected from the gradient and 15 µl of every third fraction were analyzed by agarose gel electrophoresis. Fractions containing 15–20 kbp DNA fragments were pooled and dialyzed against 4 liters TE for 16 hours at 4° C. After dialysis, the volume of DNA was reduced to 3–5 ml by repeated extraction with 2-butanol, followed by precipitation of the DNA with ethanol in the presence of 0.3M sodium acetate. The DNA was dissolved in TE at a concentration of 300–500 µg/ml.

Genomic DNA was ligated to Bam HI cut and dephosphorylated EMBL3 arms (Stratagene) according to the manufacturer's instructions using 2 fold molar excess of vector to insert. The ligation was packaged using Gigapack extracts (Stratagene). A library was plated by adsorbing 20,000 phage to 350 µl of an overnight culture of E. coli LE392 for 15 minutes at 37° C. A 7.5 ml aliquot of molten top agarose (LB plus 0.8% agarose at 50° C.) was added the bacteria and the culture was spread on 150 mm LB plates containing 10 mM $MgSO_4$. A total library of 260,000 phage was plated in this manner.

The genomic library was screened for P6 genomic clones using the cDNA insert from the P6.1 clone as a probe. To do this, the insert was cloned into the transcription vector BS(−) (Stratagene). Ten µg of P6.1 was digested to completion with Eco R1 and the resulting DNA fragments were separated by agarose gel electrophoresis. The cDNA insert fragment was electroeluted from the gel, extracted with an equal volume of phenol:chloroform (1:1 v/v) and precipitated with ethanol. Ten µg of vector pBS(−) DNA was digested to completion with Eco RI, with extracted phenol:chloroform (1:1 v/v) and precipitated with ethanol. Insert and vector were ligated together in a final volume of 10 µl for 2 hours at 15° C. and an aliquot of the ligation mixture was then used to transform competent E. coli JM83. The transformation mixture was plated out on LB plates containing 75 g/ml ampicillin which had been spread with X-gal and IPTG prior to plating of bacteria. Small scale plasmid preparations were performed on white colonies and DNAs were digested with Eco R1. A colony containing the desired P6 cDNA insert in the vector pBS(−) was identified and named P6.11.

P6.11 was linearized by digestion with Bam HI and $\alpha$-$^{32}$P UTP labelled RNA transcript was made from the plasmid using T3 polymerase following the manufacturer's protocols (Promega Biotech Inc.). Nitrocellulose replicas of the petunia genomic library were made and prehybridized for 3 hours as described earlier. The prehybridization solution was replaced with hybridization solution containing the p6.11 RNA probe at $2\times10^6$ cpm/ml. Hybridization was performed for 24 hours at 42° C. with gentle agitation. The filters were washed twice with 2× SSC, 0.1% SDS at 42° C., followed by two washes with 0.1× SSC, 0.1% SDS at 42° C. The filters were exposed to X-ray film at −80° C. for 24 hours using a single intensifying screen. Three phage displayed strong hybridization to the probe were plaque purified as described earlier and designated phage 1, 2 and 3.

Characterization of genomic clones

Phage were grown in liquid culture by inoculating 300 ml of NZCYM media with $10^{10}$ phage which had been previously adsorbed onto 1 ml of an overnight culture of E. coli LE392. The infected culture was grown at 37° C. with shaking until complete lysis of bacteria occurred (generally by 7 hours). Cellular debris was removed from the lysate by centrifugation, and the supernatant treated with 1 µg/ml of both DNAse and RNAse for 1 hour at room temperature. Solid sodium chloride was added to 1M, and PEG 6000 added to 10% (w/v). The phage were allowed to precipitate overnight at 4° C., and then collected by centrifugation in a Sorvall GSA rotor at 7000 rpm for 15 minutes. The phage pellets were resuspended in SM and 0.75 gram cesium chloride was added per ml SM. Gradients were centrifuged in a Beckman 70.1Ti rotor at 38,000 rpm for 24 hours at 15° C. Phage bands were collected from the sides of the tubes and dialyzed ocernight at 4° C. against 10 mM NaCl, 50 mM Tris-HCl pH 8, 10 mM $MgCl_2$. DNA was extracted from purified phage by adding sodium chloride to 20 mM, pronase to 0.5 mg/ml and SDS to 0.5% followed by incubation of the resulting solution at 37° C. for 1 hour. The sample was dialyzed against TE pH 8 and precipitated with ethanol. This yielded approximately 250 µg of phage DNA.

Phage DNAs were digested with Sal I to excise the insert DNA from vector. Agarose gel electrophoresis of digested DNA showed that phage 1, 2 and 3 contained inserts of 13, 14 and 10 kb respectively. By further restriction enzyme digestions and hybridizations to the cDNA clone P6.1, restriction maps were generated that indicated that the inserts of all three phage overlapped one another and were fragments of the same region of petunia DNA.

Two Eco R1 fragments of 0.6 kbp and 1.8 kbp from phage 1 and phage 3 were found to hybridize to cDNA P6.1 in mapping experiments described above. These fragments were separated by a 5 kbp non-hybridizing Eco RI fragments. This suggested either the presence of a large intron in the P6 gene or the existence of two genes homologous P6.1 on the same genomic DNA fragment. To address these possibilities, the two Eco R1 fragments were subcloned and sequenced. Ten µg of phage 1 DNA were digested to completion with Eco R1 and the products were separated by agarose gel electrophoresis. The 1.8 and 0.6 kbp fragments were electroeluted from the gel, extracted with phenol:chloroform (1:1 v/v) and precipitated with ethanol. Each fragment was ligated into Eco RI digested pUC119 DNA in a final volumes of 10 µl for 2 hours at 15° C. The ligations mixtures were used to transform competent E. coli JM83 cells. Aliquots of the transformation mixture were plated out on LB plates containing 75 g/ml ampicillin which had been spread with X-gal and IPTG prior to plating of bacteria. Small scale plasmid preparations were performed on white colonies and the resulting DNAs were digested with Eco R1. Subclones containing the desired 0.6 and 1.8 kbp fragments were chosen in both possible orientations to facilitate sequencing the ends of the fragments. These two orientations were identified by digesting subclones with Sal I for the 0.6 kbp fragment and Pvu II for 1.8 kbp fragment. The resulting plasmids were designated P619 and P620 (two orientations of the 0.6 kbp genomic fragment) and P621 and P622 (two orientations of the 1.8 kb genomic fragment).

Plasmid DNAs were sequenced by dideoxy chain termination method using $^{35}$S-dATP as described in earlier examples. Sequence analyses showed that the 1.8 kbp Eco RI genomic fragment contained a gene with perfect homology to the P6.1 cDNA while the 0.6 kbp genomic fragment contained a closely related gene. The homologous gene is the 1.8 kbp EcoR I fragment was designated gene P6.1.

Mapping the endpoints of Gene 1

A primer extension analysis was performed to determine the 5' end of the P6 RNA. An oligonucleotide complementary to the coding strand in the P6 gene from 12–33 bases downstream of the first in-frame ATG was synthesized using an Applied Biosystems DNA Synthesizer. The oligonucleotide, 5'-CCACTAAGACAATCTAAAGACC-3' was end-labelled with $^{32}$P by drying 50 uCi of $\alpha$-$^{32}$ATP in a microfuge tube using a Speedvac centrifuge. Two µl of olignucleotide (2.5 pmole/µl), 2 µl 5× kinase buffer (125 mM Tris-HCl pH 9.5, 25 mM MgCl$_2$, 12.5 mM DTT, 2.5 mM spermidine, 0.25 mM EDTA) and 1 µl T4 polynucleotide kinase (10 U/µl) were added and the tube was incubated at 37° C. for 15 minutes. Labelled olignucleotide was separated from unincorporated label by ethanol precipitation in the presence of ammonium acecate, followed by ethanol precipitation in the presence of sodium acetate. The pellet was dissolved in 50 µl of TE and 1 µl was counted by emmission of Cerenkov radiation. The incorporation of $^{32}$P bit this method was 3–8×10$^6$ counts per pmole of oligonucleotide. Ten µg of RNA from the roots of both untreated and N-(aminocarbonyl)-2-chlorobenzenesulfonamide-treated plants were annealed to 0.2 pmoles of oligonucleotide in a volume of 10 µl in 0.25M KCl, 2 mM Tris-HCl pH 7.9 and 0.3 mM vanadyl ribonucleoside complex (BRL) at 37° C., 45° C. and 55° C. for 3 hours. To the annealed RNA, 23.5 µl of primer extension mix (10 mM MgCl$_2$, 5 mM DTT, 20 mM Tris-HCl pH 8.3, 0.33 mM d(GATC) TP, 100 µg/ml actinomycin D) and 0.5 µl (10 units) avian reverse transcriptase (Life Sciences) were added and the mixture was incubated for 45 minutes at 37° C. The nucleic acids in the reaction were precipitated with ethanol and dried. The pellet was dissolved in 3 µl of 0.1M NaOH, 1 mM EDTA and the solution was left at room temperature for 30 minutes to hydrolyze the RNA template. Six µl termination dye (Example 1) was added and the sample was heated at 80° C. and quick-cooled. The primer extension products were separated on a 6% denaturing polyacrylamide sequencing gel. A 110 bp long primer extension product was observed, predicting an untranslated leader of 68 bp.

To determine the 5' endpoint of the P6.1 gene, two fragments of the gene were subcloned for RNAse protection analysis. Both fragments span the first in frame ATG downstream by 40 bases (to a Nhe I site) and upstream by either 130 (a DraI site) and 300 (a Spe I site) bases. Twenty µg of P622 DNA were digested with to completion with both Spe I and Nhe I. A separate aliquot of P622 was digested to completion with Dra I and Nhe I. The digestion products were separated by electrophoresis on a 5% acrylamide gel, and 340 bp Spe I/Nhe I and 170 bp Dra I/Nhe I DNA fragments were cut out of the gel and recovered by electroelution. The DNAs were extracted with phenol:chloroform (1:1 v/v) and precipitated with ethanol. These fragments were subcloned into the transcription vector Bluescript+ (BS+) (Stratagene). To accomplish this, 10 µg of BS+ was digested with Sma I and Xba I to subclone the Dra I/Nhe I fragment and Spe I and Xba I to subclone the Spe I/Nhe I fragment. BS(+) DNA was then extracted with phenol:chloroform (1:1 v/v) and precipitated with ethanol. Ligations were performed at room temperature for 2 hours in volumes of 10 µ. An aliquot of the ligation mixture was used to transform competent E. coli MV1193 using an X-gal selection. Small scale plasmid preparations were performed on a number of white colonies and the DNAs were digested with Eco R1 and Sac I. A colony containing a plasmid with the Dra I/Nhe I fragment in BS(+) was identified and designate P644. A colony containing a plasmid with the Spe I/Nhe I fragment in BS(+) was identified and designated P645.

RNA probes complementary to the coding strands in both P644 and P645 were synthesized in the following reaction: 50 uCi $^{32}$P-UTP, 2 µl 5× transcription buffer (200 mM Tris-HCl pH 7.5, 30 mM MgCl$_2$, 10 mM spermidine), 0.5 µl 0.2M DTT, and 0.5 µl of either T3 polymerase (plasmid P645) or T7 polymerase (plasmid P644). Incubation was carried out at 40° C. for 1 hour. The DNA template was hydrolyzed for 15 minutes at 37° C. by addition of 30 µl H$_2$O, 1 µl RNAsin, 2,5 µl vanadyl ribonucleoside complex, 6 µl 5× transcription buffer and 1 µl DNAse 1 (1 mg/ml) to the transcription reaction. The reaction was extracted with an equal volume of phenol:chloroform (1:1 v/v). The RNA was precipitated once with ethanol in the presence of ammonium acetate and once with ethanol in the presence of sodium acetate. The pellets were dissolved in 25 µl of TE. Ten µg of RNA from untreated and N-(aminocarbonyl)-2-chlorobenzenesulfonamide-treated plants were mixed with 1×10$^6$ cpm of each of the two probes in 30 ul of hybridization buffer (40 mM PIPES pH 6.7, 0.4M NaCl, 1 mM EDTA). The mixture was then overlayed with 30 µl of mineral oil and hybridizations were carried out at 45° C. for 16–24 hours. Single stranded RNA was selectively digested by adding 300 µl RNAse A and RNAse T1 to 40 µg/ml and 2 µg/ml respectively in 10 mM Tris-HCl pH 7.5, 5 mM EDTA, and 300 mM NaCl. Digestion was carried out at 30° C. for 1 hour and RNAses were inactivated by the addition of 20 µl 10% SDS and 50 µg of proteinase K followed by a 15 minute incubation at 37° C. The reaction mixture was extracted with phenol:chloroform (1:1 v/v) and the RNA hybrids were precipitated with 1 ml of ethanol after addition of 20 µg carrier of yeast tRNA. The pellets were dried and dissolved in formamide loading buffer. The samples were denatured at 90° C. for 3 minutes and analyzed on a denaturing acrylamide gel. Protected fragments of 110 bp were observed in induced but not control RNA using both probes. These results agree with the predicted transcriptional start site from the primer extension analysis. The sequence of the P6.1 gene 5' to its translation start site is shown in FIG. 8. The arrow indicates deduced transcription start site.

The 3' end of the gene was deduced from comparison of genomic and eDNA clone sequence data.

Construction of P614

A 4.5 kb Hind III/Sal I genomic fragment from phage 2 containing the P6.1 petunia gene was subcloned into pUC118. 20 µg of the genomic phage 2 was digested with Hind III and Sal I, and the products separated by agarose gel electrophoresis. The 4.5 kb band containing the gene was isolated by electroelution as described earlier. Ten µg of pUC118 was digested to completion with Hind III and Sal I and the vector was then purified from the polylinker fragment by chromatography on Sepharose® CL-2B (Pharmacia). Vector and insert were ligated together in a volume of 10 µl overnight at 15° C., and a portion of the ligation mixture was used transformed competent E. coli JM83. Aliquots of the transformation mixture were plated out on LB plates containing 75 g/ml ampicillin which had been spread with X-gal and IPTG prior to plating of bacteria. Small scale plasmid prearations were performed on white colonies and DNAs were digested with Hind III and Sal I until a colony was found that contained the 4.5 kb Hind III/Sal I genomic fragment containing the petunia P6.1 gene. This plasmid was designated P614.

Construction of P654

Figure 9:
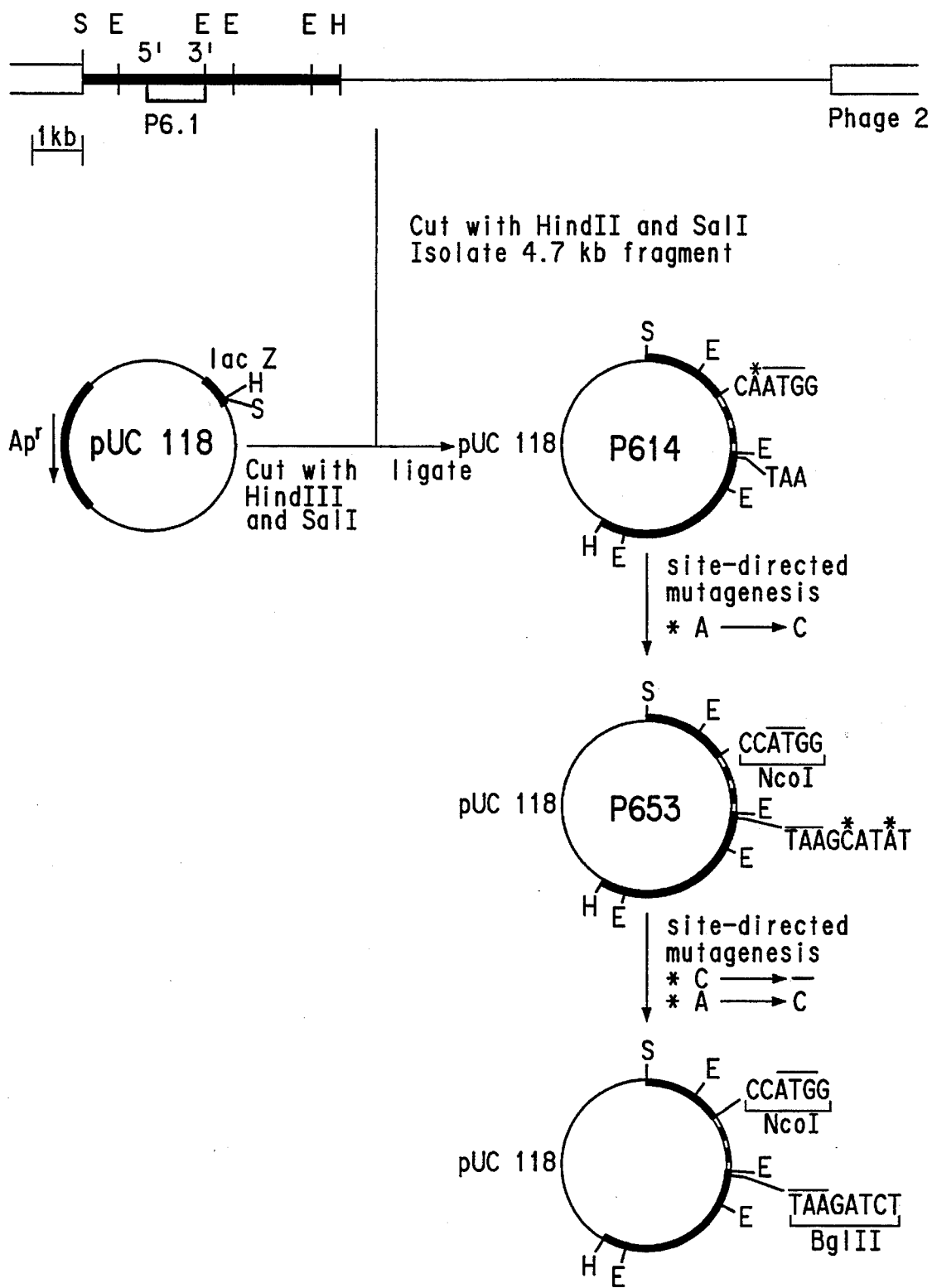
FIG. 9 depicts the creation of plasmid P614 and P654.

Convenient restriction sites were introduced into the P6.1 petunia gene at the translation start and stop sites of the F6.1 coding region to use the regulatory regions from the inducible petunia gene to test if they could be made generally useful for expressing foreign coding regions in transformed plants. Site-directed mutagenesis was performed on P614 to introduce an Nco I site was at the translation initiation ATG of the gene using the oligonucleotide 5-CGTTAGCCATG-GTTATGCTTA-3'. The methods used to accomplish this mutagenesis were described in Example 1. The plasmid resulting from the addition of an Nco I at the translation start site of the P6.1 gene fragment in P614 was designated P653. The plasmid P653 was further mutagenized using the oligonucleotide 5'-GCATATGCATAGATCTTATTGAATTCC-3' to introduce a Bgl II site at the translation stop codon of the P6.1 gene. The resulting final plasmid construction, containing a petunia P6.1 gene with Nco I and Bgl II sites bounding the coding region of the P6 protein coding region, was designated P654 (FIG. 9).

EXAMPLE 6

Isolation of the T2.1 Tobacco Gene

Isolation of cDNA T2

The procedures described for the isolation of the petunia cDNA clone P6.1 in Example 4 were repeated using *N. tabacum* (Petite Havana SRI) as the starting plant material. Differential screening of the resulting tobacco cDNA library prepared using poly(A)+ RNA from the roots of N-(aminocarbonyl)-2-chlorobenzenesulfonamide-treated tobacco plants identified a cDNA clone representing an N-(aminocarbonyl)-2-chlorobenzenesulfonamide-inducible mRNA species. This clone was designated T2.

The insert from T2 was subcloned into the vector pUC119 as a single Eco RI fragment using methods described in Example 4 for the sucloning of the insert of the P6 cDNA clone. The resulting plasmid containing the 1 kbp cDNA insert from cDNA clone T2 in the Eco RI site of pUC 119 was called T2.1 The same 1 kbp Eco RI cDNA fragment was also cloned into the Eco RI site of the vector pBS (−), with the resulting plasmid being designated T2.11.

A Northern blot of total RNA from the roots of untreated and N-(aminocarbonyl)-2-chlorobenzenesulfonamide-treated tobacco plants was probed with nick-translated T2.1 to determine the size of the corresponding T2 mRNA. The methods used for these procedures were described in Example 4. The T2.1 plasmid hybridized to an mRNA of 800 nt in RNA from the roots chemically treated plants, but not present in control plants. This indicated that cDNA T2 represented an N-(aminocarbonyl)-2-chlorobenzenesulfonamide-inducible mRNA species, and the insert in the cDNA clone was full-length. The fact that the RNA appeared smaller than the cDNA clone suggested that T2 may contain some artifactual sequence generated during its cloning.

The DNA sequence of T2 cDNA was determined by analyzing a set of deletions of T2 prepared as described previously. Examination of the sequence revealed that T2 contained a perfect inverted repeat from bases 11 to 164 and 518 to 671. Since the open reading frame begins past base 164, it was assumed that the first 164 bases were an artifact of cDNA synthesis and/or cloning that gave rise to a cDNA larger than its corresponding mRNA. The predicted peptide encoded by the T2 cDNA contains the same number of amino acids as the petunia gene P6 and is 95% similar at the amine acid level. It was therefore assumed that the T2 cDNA clone from tobacco represented a gene which is homologous to the petunia P6.1 gene.

Isolation of genomic clone T2.1

Figure 10:
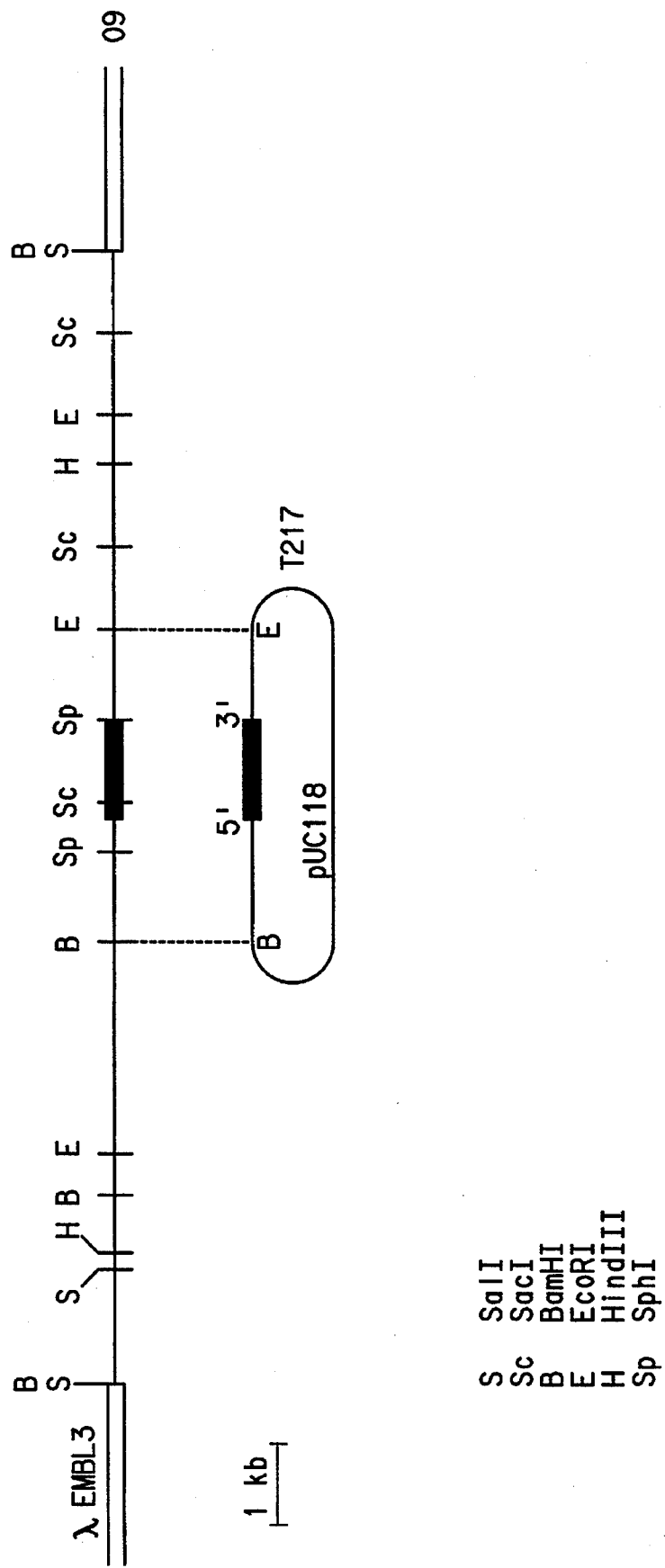
FIG. 10 depicts the creation of plasmid T217.

A genomic library was prepared from SRI tobacco as described in Example 4. A $^{32}$P-RNA probe was synthesized with T7 DNA polymerase using the cDNA insert of T2.11 as a template and and the resulting RNA transcript was used to screen the SRI genomic library as described earlier. From this screening, a plaque was identified with homology to the T2 cDNA. This phage was plaque purified and designated phage #9. DNA purified from phage #9 was digested with the restriction enzymes Eco RI, Bam HI, and Sal I and the resulting restriction fragments were separated by agarose gel electrophoresis and blotted to nitrocellulose. The blot was then prehybridized and hybridized with nick-translated T2.11. Results of this blotting experiment revealed that the cDNA probe hybridized to a unique 5.0 kbp Bam HI/Eco RI fragment. This Bam HI/Eco RI fragment, believed to contain a complete copy of the T2 gene, was then cloned into the vector pUC118 that had been digested to completion with Bam HI and Eco RI. The resulting plasmid was called T217 (FIG. 10). The gene contained within phase #9 was designated T2.1.

The 5' end of the T2.1 mRNA was mapped by primer extension analysis. The oligonucleotide used in this analysis was the same one chosen for analysis of the 5' end of the petunia P6.1 mRNA. This resulted in one mismatch relative to the tobacco gene positioned in the center of the oligonucleotide. Annealing of the primer was therefore performed at a lower temperature for the tobacco mRNA (25°, 30°, and 35° C.). Primer extension was then performed as described in Example 4. The primer extension product observed in this analysis was 110 bases long; exactly the length of the extension product observed using the petunia P6.1 mRNA as a template. This indicates that the 5' untranslated leader in the T2.1 mRNA was also 68 bp.

It is anticipated that those skilled in the art will be able to identify the promoter and downstream regulatory regions of the T2 gene by following methods and procedures described in Example 4. Later examples teach the use of such regulatory regions.

EXAMPLE 7

Construction of Recombinant Genes Whose Expression are Controlled by 2-1 Corn Promoter and 3' Downstream Region Construction of plasmids pJE 514 and pJE 516

Plasmids p484-1(Nco I) and p484-62 (Bgl II) from Example 1, which contained convenient restriction sites at the start and stop sites respectively of the 2-1 structural gene were used to create a new 2-1 gene from which the native coding sequence could be easily removed and replaced with foreign structural gene. Introduction of such a recombinant gene into transgenic plants should place expression of the foreign coding region under the control of substituted benzenesulfonamides.

To construct this new 2-1 gene, pJE 484-1 (Nco I) (FIG. 5) was digested to completion with Eco RI and Sma I, and 10 μg of digested DNA was subjected to electrophoresis on a 1% agarose gel overnight at 20V. The gel was stained with ethidium bromide and the DNA was visualized on a long wave UV transilluminator. A small trough was cut in the gel just ahead of the desired 7.5 kb insert fragment. The DNA was electroeluted into this trough at 300 V and buffer containing the DNA was transferred to a microcentrifuge tube. The purified DNA fragment was then extracted with an equal volume of phenol:chloroform (1:1 v/v), ethanol precipitated and resuspended in 10 μl of $H_2O$. The plasmid pJE 484-62(Bgl II) was digested with Eco RI and Nco I, and a 1.3 kb fragment was gel-purified in the manner described above. The 7.8 and 1.3 kbp DNA fragments were ligated together in 10 μl of 1× ligase buffer as described in earlier examples and the ligation products were used to transform competent *E. coli* JM83 cells. Small scale plasmid preparations were performed on transformed colonies and diagnostic restriction enzyme digestions were performed on 20 individual colonies until one was found that contained a copy of the 2-1 corn gene with the added Nco I and Bgl II site5 at its respective translation start and stop sites. This construction was designated pJE 514.

Figure 11:
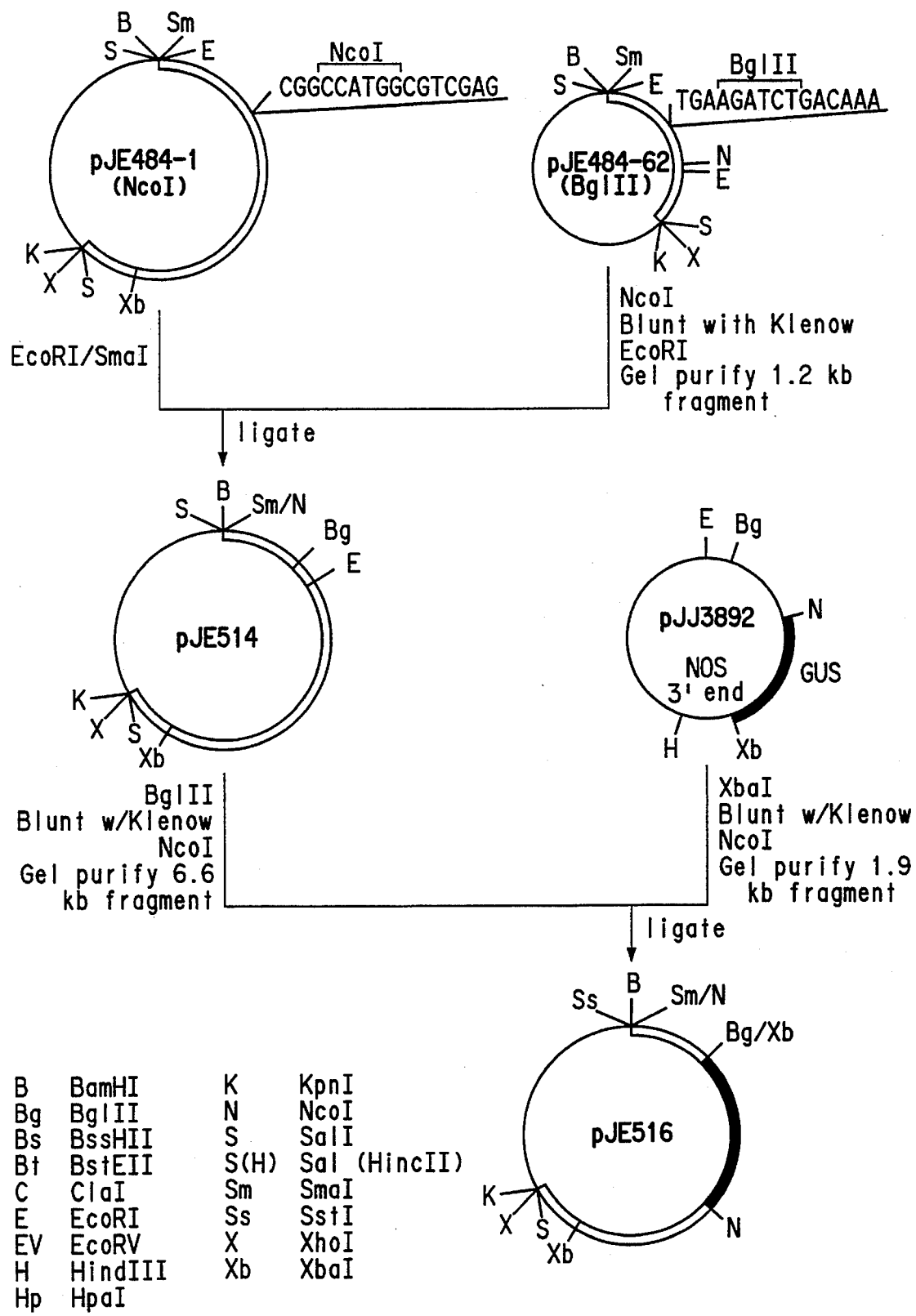
FIG. 11 depicts the creation of plasmid pJE516.

The coding sequence chosen to replace the 2-1 coding sequence of pJE 514 was β-glucuronidase (referred to as GUS) [Jefferson R., Proc. Natl. Acad. Sci. U.S.A. 83: 8447–8451, 1986). A GUS coding sequence was isolated from the plasmid pJJ 3892 as a 1.8 kbp Nco I/Xba I fragment. The identical 1.8 kbp Nco I/Xba I fragment is available in the plasmid pJJ 3431 (ATCC accessien number 67884, and described in Example 9), and thus pJJ 3431 can be substituted for pJj 3892 in this Example. To this end pJJ 3892 was digested to completion with Xba I and the resulting 5' overhangs were blunted using the Klenow fragment of DNA polymerase I as described in earlier examples. After extraction with phenol:chloroform (1:1 v/v) and ethanol precipitation, the DNA was digested to completion with Nco I and the resulting DNA fragments were separated by agarose gel electrophoresis. A 1.9 kbp DNA fragment corresponding to the GUS coding region was recovered from the gel and ligated with pJE 514 that had been digested to completion with Bgl II, blunt-ended with Klenow fragment of DNA polymerase I and then digested to completion with Nco I. An aliquot of this ligation mixture was used to transform *E. coli* HB101 and individual transformants were analyzed until one was found that contained the GUS coding sequence in place of the 2-1 structural gene. This plasmid was designated pJE 516 (FIG. 11).

Construction of plasmid pDuPE2

Plasmid pJE 516 was used as the starting material to produce a deletion series consisting of a GUS gene/2-1 3' downstream region fusion whose expression is regulated by progressively smaller 2-1 promoter fragments. The deletion series was generated by linearizing 40 μg of pJE 516 DNA with 25 units of Hpa I restriction endonuclease in 20 mM KCl, 10 mM Tris-HCl pH 7.4, 10 mM $MgCl_2$ and 1 mM DTT in a final volume of 100 μl. The reaction was incubated at 37° C. for 3 hours, and DNA was extracted with an equal volume of phenol:chloroform (1:1 v/v) and precipitated with ethanol. The linearized DNA was recovered by centrifugation and dried in vacuo.

The DNA pellet was resuspended in 180 μl of $H_2O$ and 30 μl of 10× Bal 31 buffer was added (final concentrations in the reaction were 20 mM Tris-HCl pH 8, 12 mM $MgCl_2$, 12 mM $CaCl_2$ and 300 mM NaCl). The Bal 31 digestion was carried out as recommended by the manufacturer (Bethesda Research Labs) using 2 units of Bal 31. This mixture was incubated at 30° C. for various time intervals (e.g. 0, 2.5 or 5 minutes), and the reaction in each aliquot was stopped by adding 50 μl of 100 mM EDTA, pH 7.6. The DNA was then extracted twice with 100 μl of phenol, twice with 100 μl of $CHCl_3$, then precipitated with 2.5 volumes of ethanol. Bal 31 digested DNA was recovered by centrifugation and dried in vacuo.

The dry DNA pellet was dissolved in 100 μl of Sal I buffer (150 mM NaCl 10 mM Tris-HCl pH 8, 10 mM $MgCl_2$ and 10 mM β-mercaptoethanol) and digested with 50 units of Sal I for 4 hour at 37° C. The reaction was extracted with phenol:chloroform (1:1 v/v) and ethanol precipitated as above. The ends of the DNA were rendered blunt using the Klenow fragment of DNA Polymerase I as follows: DNA was dissolved in 60 μl of 66 mM Tris-HCl pH 7.6, 6.6 mM $MgCl_2$, 52 mM NaCl, 1 mM β-mercaptoethanol, 0.5 mM dNTPs and 10 units of Klenow. The reaction was incubated at room temperature for 2 hours. The DNA was then fractionated by electrophoresis in a 0.7% low melting agarose gel. The gel was stained with 1 μg/ml ethidium bromide solution, and a gel piece containing the DNA fragment of the desired deletion length was excised from the gel under UV illumination. The gel piece was frozen at −80° C. for 20 minutes, thawed, crushed with a pipette tip, and centrifuged for 30 minutes in a microcentrifuge. The aqueous solution was transferred to a fresh tube, adjusted to a final concentration of 0.3M sodium acetate and 2.5 volumes of ethanol were added. The precipitated DNA was recovered by centrifugation, dissolved in 20 μl of water and was self-ligated (recyclization). Ligation reactions were performed in 50 mM Tris-Cl pH 7.8, 10 mM $MgCl_2$, 20 mM DTT and 1 mM ATP. The ligation reaction was carried out at room temperature for 8 hours, and diluted five fold with water prior to using it to transform of competent *E. coli* HB101 cells. Aliquots of the transformation mixture were spread on LB plates containing 50 μg/ml of amp and plates were incubated overnight at 37° C.

Individual amp resistant colonies were picked and grown up at 37° C. with vigorous shaking. in 2 ml of 2XTY containing 50 μg/ml amp. Small scale plasmid preparations were performed on the bacteria and aliquots of the DNAs were digested to completion with Nco I and Xho I. The resulting DNA fragments were analyzed by 1.5% agarose gelelectrophoresis to determine the size of the 2-1 promoter fragment remaining in each plasmid. Results from the analysis showed that one clone, designated pDuPE2 contained the GUS construction of PjE 516, operably linked to a 900 bp 2-1 promoter fragment (relative to the translation start site of the 2-1 gene).

Construction of plasmids pDuPI8 and pDuPI9

The Bal 31 digestion protocol used to create pDuPE2 was repeated using the plasmid pDuPE2 as the starting material to create progressively shorter 2-1 promoter fragments. DNA was first linearized with Xho I, followed by Bal 31 digestion at different time intervals (from 2–5 min). The Bal 31-digested DNA was extracted with phenol:chloroform (1:1 v/v), ethanol precipitated, and 5' ends of the DNA were filled-in using Klenow fragment. DNA was then further digested with Bam HI to excise the entire remaining 2-1/ GUS construction from the pBS(+) vector. The Bam HI digested DNA fragments were separated by electrophoresis in a 1% low-melting agarose gel and the DNA fragments containing the deleted constructs were extracted as described above and ligated into the Bam HI-Sma I sites of the vector pBluescript (S/K)+ vector (Stratagene). The ligation mixture was diluted four fold with with H₂O, and aliquots of the transformation reaction were spread onto LB plates containing 50 µg/ml amp and incubated overnight at 37° C. Small scale plasmid preparations were performed on amp-resistant colonies and DNAs were digested to completion with Nco I and Xho I. A series of clones containing 2-1 promoter fragments ranging in size from 500 to <100 bp was chosen from these colonies. The designated names of these constructions and the length of the 2-1 promoter fragment in each is shown in Table 1.

TABLE 1

| Construction Designation | Promoter Length (bp) |
| --- | --- |
| pDuPE2 | ~900 |
| pDuPI8 | 421 |
| pDuPI9 | 226 |

EXAMPLE 8

Construction of Recombinant Genes Whose Expression is Regulated by the 2-2 Corn Promoter and Various 3' Downstream Regions Construction of plasmid pHPH201(+)

Plasmid pRAJ275 (available from Clontech Laboratories, Inc. 4055 Fabian Way, Palo Alto, Calif. 94303) served as a source for an *E. coli* β-glucuronidase (GUS) gene in this construction. The GUS coding region in pRAJ275 has a unique Nco I site positioned at the initiator ATG codon of the protein coding sequence.

Genomic subclone 2-2#4-17 (Example 2) (320 µg) was partially digested with Nco I for 1 hour at 37° C. using 0.5 units of enzyme per microgram of plasmid DNA. The digestion was stopped by addition of Na₂EDTA to a final concentration of 20 mM and DNA was ethanol precipitated in the presence of 0.3M sodium acetate, pH 6.0. The partially digested plasmid was dissolved in 260 µl of TE, pH 8.0 and 40 µl of electrophoresis tracking dye. The DNA was loaded into 4 cm×1 cm×2 mm wells of a 2 mm thick 5% polyacrylamide gel in 1× TBE buffer and sujected to electrophoresis at 325 volts for 4 hours. A 1.68 kbp Nco I fragment was recovered from each lane of the gel as described earlier. One half of the purified Nco I fragment was ligated overnight in a total volume of 10 µl with 0.5 µg of pRAJ275 that had been cut to completion with Nco I and dephosphorylated. The ligation mixture was diluted to 50 µl with H₂O, and 3 µl of the dilution was used to transform 60 µl of competent *E. coli* HB101 cells. Aliquots of the transformation reaction were spread onto LB plates containing 50 µg/ml amp and plates were incubated overnight. Small scale plasmid preparations were performed on amp-resistant colonies until one was found that contained 1.68 kbp Nco I promoter fragment ligated into pRAJ275 such that it was operably linked to the 5' end of GUS gene. This plasmid was called pHPH201(+).

Construction of p2-2 Hind III 3' end

A construction containing the 3' end of the 2-2 gene that is generally useful in preparing recombinant genes whose expression is controlled by substituted benzenesulfonamides was prepared. Genomic subclone 2-2#4-11 (FIG. 4A) was digested to completion with Hind III. The 5' overhang was filled-in using the Klenow fragment of DNA polymerase I, and the DNA was extracted sequentially with a equal volumes of phenol:chloroform (1:1 v/v) and chloroform. The DNA was ethanol precipitated, collected by centrifugation and redissolved in TE pH 8.0. The vector pUC18 was cut to completion with Sac I and Kpn I and the resulting 3' overhangs were removed using the Klenow fragment of DNA polymerase I. The DNA was extracted with phenol:chloroform (1:1 v/v), precipitated with ethanol and redissolved in TE pH 8.0 as described above. The blunt-ended Hind III digestion products of genomic 2-2#11 (0.6 µg) were then ligated with 0.45 µg of the blunt-ended pUC 18 DNA overnight at 16° C. The ligation mixture was diluted to 50 µl with H₂O, and 1 µl of the dilution was used to transform 20 µl of competent *E. coli* HB101 cells. Aliquots of the transformation reaction were spread onto LB plates containing 50 µg/ml amp and plates were incubated overnight. Small scale plasmid preparations were performed on amp-resistant colonies and the resulting DNAs were digested with Eco RI and Bam HI until a colony was found that contained the 2.3 kbp Hind III fragment of genomic subclone 2-2#11 blunt-ended into the Kpn I/Sac I sites of pUC18. This plasmid construction was called p2-2 Hind III 3' end.

Construction of plasmid phPH102

Plasmids p2-2 Hind III 3' end and the vector pMSP'K (ATCC accession number 67723) were both digested to completion with Eco RI and Hind III. Following dephosphorylation of pMSP'K, 1.6 µg of vector was ligated overnight with 0.38 µg of Eco RI-Hind III digested p2-2 Hind III 3' in a final volume of 10 µl. The ligation was diluted to 50 µl with H₂O and 1 µl of the dilution was used to transform 60 µl of competent HB101 cells. Aliquots of the transformation mixture were spread onto LB plates containing 100 µg/ml of both spectinomycin and streptomycin (spec/strep) and plates were incubated overnight at 37° C. Small scale plasmid preparations were performed on spec/strep-resistant colonies and the resulting DNAs were digested with Eco RI and Hind III until one was found that contained the desired downstream sequences of the 2-2 gene on a 2.3 kbp Eco RI-Hind III fragment. The resulting plasmid was called pHPH102.

Construction of plasmid pHPH 220

The plasmid pHPH 102 was cut to completion with Xho I and the resulting 5' overhang was filled-in with Klenow fragment of DNA polymerase I. The blunt-ended DNA fragment was dephosphorylated as described in Example 1 and then cut to completion with Hind III. Plasmid pHPH201(+) was partially cleaved with Eco RI by digesting it with Eco RI at 37° C. for 90 minutes using 0.85 units of enzyme per microgram of DNA. Eco RI was inactivated by heating the digestion mixture to 70° C. for 10 minutes, and the resulting 5' overhang was filled-in with Klenow fragment as described above. This DNA was then digested to completion with Hind III and 2.1 µg of the resulting DNA was ligated overnight in a final volume of 15 µl with 0.8 µg of Hind III cut pHPH102 that had been blunt-ended at its unique Xho I site. The ligation mixture was diluted to 60 µl with H₂O and 1 µl was used to transform 80 µl of competent *E. coli* HB101 cells. Aliquots of the transformation mixture were spread onto LB plates containing 100 µg/ml of both spec/strep and plates were incubated overnight at 37° C.

Figure 12A:
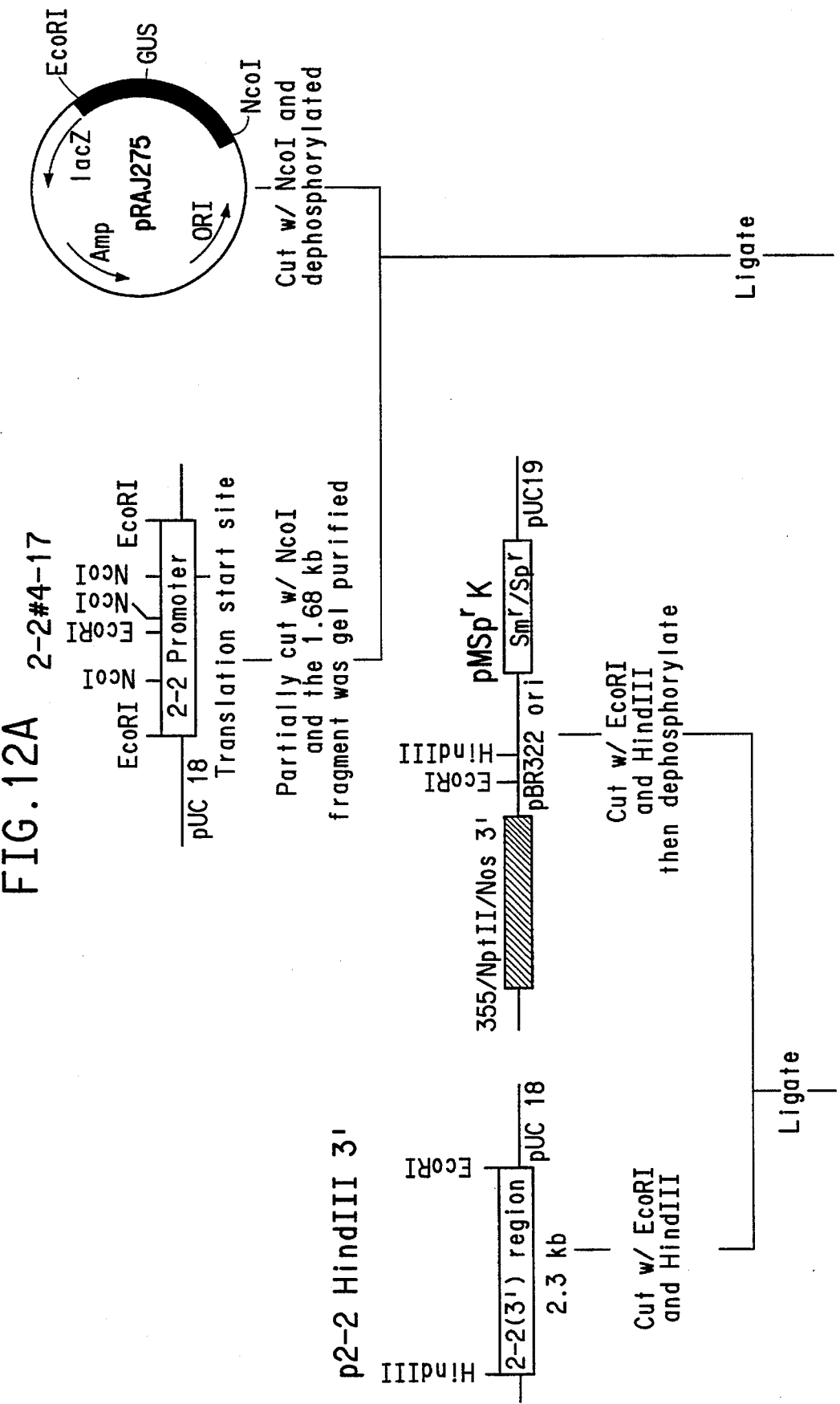
FIG. 12 depicts the creation of plasmid pHPH220.

Small scale plasmid preparations were performed on spec/strep-resistant colonies until one was found that contained the 3.6 kbp Hind III-Eco RI fragment from pHPH201(+) (consisting of the 1.7 kbp 2-2 promoter/GUS ceding region fusion) operably linked to the 2.3 kbp of downstream sequence originating from the 2-2 gene in the vector pMSP'K. This plasmid was called pHPH 220 (FIG. 12).

Construction of plasmid pIn 2-2(3.9)

Two and a half μg of DNA from genomic clone 2-2 #4 (Example 2) was digested to completion with Sal I. One μg of pUC18 DNA was also digested to completion with Sal I. The DNAs were extracted with equal volumes of phenol, phenol:chloroform (1:1 v/v) and chloroform. The DNA was then precipitated with ethanol in the presence of sodium acetate. A ligation reaction was carried-out overnight at 16 C with a 3:1 ratio of genomic 2-2#4 DNA to pUC18 in a volume of 10 μl. The ligation mixture was diluted 5 fold with water and an aliquot of the ligation mixture was used to transform competent E. coli DH5 α cells. Aliquots of the transformation reaction were plated on LB agar plates containing 50 μg/ml amp, 25 mM IPTG and 40 μg/ml X-Gal. Plasmid DNA from individual white colonies was prepared and digested to completion with Sal I. A clone was identified which contained the 3.9 kbp Sal I fragment from the 2-2#4 DNA which encompassed a region of the 2-2 gene extending from 3.6 kbp 5' from the translation start of the 2-2 protein to 180bp inside the coding region of the 2-2 protein. This plasmid was designated pIn 2-2(3.9).

Construction of pTDS130

Figure 13A:
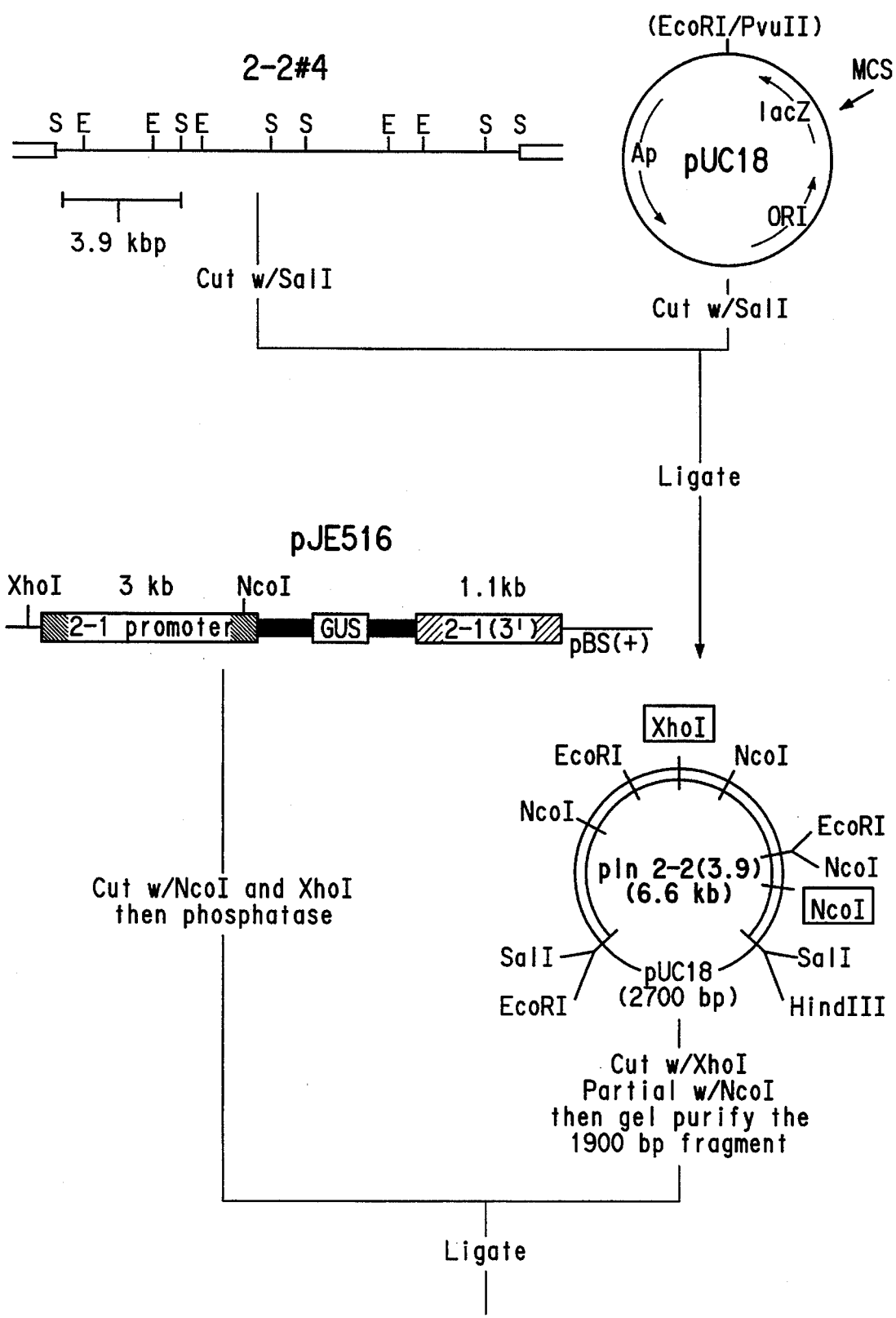
FIG. 13 depicts the creation of plasmids pTDS130 and pTDS133.

Twenty-five μg of pJE516 was digested to completion with Nco I and Xho I. The DNA fragments were dephosphorylated with 24 units of calf intestinal alkaline phosphatase for 40 minutes at 37° C. Fifty μg of plasmid pIn 2-2(3.9) DNA was cut to completion with Pvu I and dephosphorylated as described above, precipitated with ethanol in the presence of 0.3M sodium acetate and resuspended in TE pH 8.0. This DNA was then digested to completion with Xho I. Partial Nco I cleavage of the resulting pIn 2-2(3.9) DNA was performed by digesting the Xho I digested DNA sample with 1 unit of Nco I at 37° C. and removing ¼ of the digestion mixture at 15 minute intervals. The Nco I digestion was stopped in each time point by addition of EDTA to a final concentration of 40 mM. The DNAs were extracted sequentially with equal volumes of phenol, phenol:chloroform (1:1 v/v) and chloroform. DNA was precipitated with two volumes of ethanol, recovered by centrifugation and redissolved ill 10 μl Of TE, pH 8.0. Small aliquots of DNA from each digestion time were analyzed by agarose gel electrophoresis to find the digestion that contained the highest amount of the desired 1.9 kbp Xho I-Nco I promoter fragment. A total of 0.5 μg of partially digested DNA was ligated with 0.18 μg of pJE 516 DNA overnight at 16° C. The ligation reaction was heated at 70° C. for 10 minutes, diluted 5 fold with water, and 2 μl of the dilution was used to transform 100 μl of competent E. coli HB101. Aliquots of the transformation mixture were plated on LB agar plates containing 50 μg/ml amp and allowed to grow overnight at 37° C. Plasmid DNA prepared from amp-resistant colonies were analyzed by restriction endonuclease digestions until one was identified that contained the 1900 bp Xho I/Nco I promoter fragment of the 2-2 gene operably linked to the GUS/2-1 3' end downstream region fusion in the plasmid pJE516. This clone was designated pTDS130 (FIG. 13).

Construction of plasmid pTDS133

Plasmid pTDS130 was cut to completion with both Eco RI and Xho I and the enzymes were inactivated by heating the reaction at 40° C. for 20 minutes in the presence of 0.02% diethylpyrocarbonate (DEP). Excess DEP was destroyed by heating at 70° C. for 10 minutes, and 5' overhangs in the DNA were filled-in with the Klenow fragment of DNA polymerase I.

The DNA was extracted sequentially with equal volumes of phenol, phenol:chloroform (1:1 v/v) and chloroform followed by ethanol precipitation in the presence of sodium acetate. The DNA was then recirculized by subjecting it to overnight self-ligation. The ligation reaction was diluted five fold with water and 2 μl of the mixture was used to transform 100 μl of competent E. coli HB101. Aliquots of the transformation mixture were plated on LB agar plates containing 50 μg/ml Amp and allowed to grow overnight at 37° C. Small scale plasmid preparations were made from individual amp resistant colonies and analyzed by restriction endonuclease digestions until one was identified that contained the 465 bp Eco RI/Nco I promoter fragment of the 2-2 gene was operably linked to the GUS/2-1 fusion in the plasmid pTDS130. This plasmid was designated pTDS133 (FIG. 13).

Construction of plasmid pTDS134 and pTDS136

Figure 14:
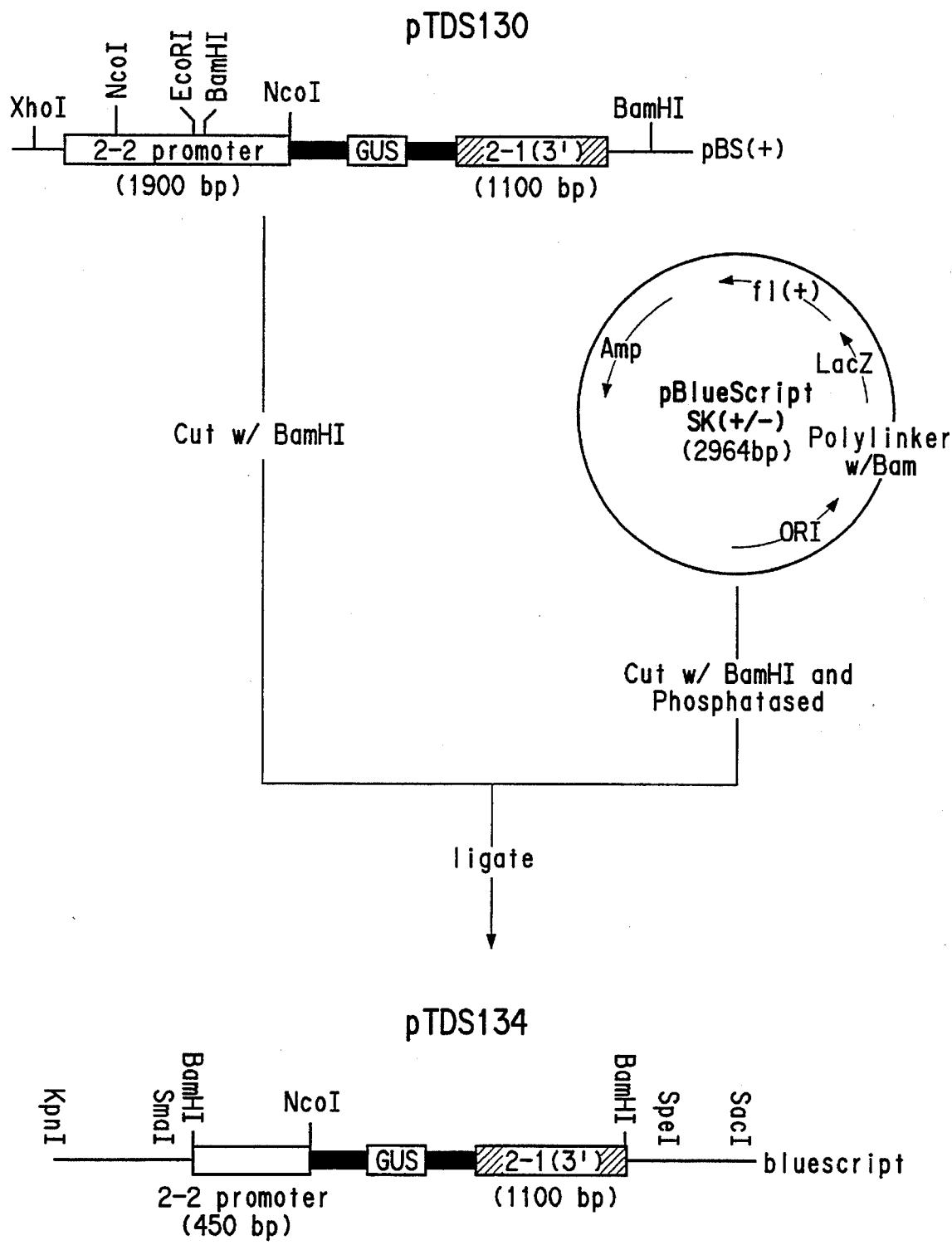
FIG. 14 depicts the creation of plasmid pTDS134.

Ten μg of pTDS133 DNA and 10 μg of the vector pBluescript SK(+) DNA were digested to completion with Bam HI. Vector DNA was dephosphorylated as described in earlier examples. Both DNAs were extracted with phenol:chloroform (1:1 v/v) and precipitated with ethanol. The digested pTDS133 and pBluescript SK(+) were ligated together at a 3:1 molar ratio (insert:vector) in a final volume of 10 μl overnight at 16° C. The ligation mix was diluted five fold with water and 2 μl of this dilution was used to transform 100 μl of competent E. coli HB101. Small scale plasmid preparations were made from individual amp resistant colonies and analyzed by restriction endonuclease digestions until one was identified that contained the 3.4 kbp Bam HI fragment from pTDS133 cloned into the Bam HI site of pBluescript S/K(+) in an orientation such that the 2-2 promoter was immediately adjacent to the Sma I site of the vector's polylinker. This plasmid construction was designated pTDS134 (FIG. 14). A second colony containing the same 3.4 kbp Bam HI fragment cloned in the opposite orientation such that the 2-2 promoter was immediately adjacent to the Spe I site of the vector's polylinker was also identified. This plasmid construction was designated pTDS136.

Construction of plasmid pTDS231

The plasmid pDH51 was disclosed by Maciej Pietrzak et al. and is described in Nucleic Acids Research, 14: 5857–5868 (1986).

Ten μg of pHPH201(+) DNA was digested to completion with both Eco RI and Pvu I for two hours at 37° C., and the resulting 5' overhangs were filled-in with Klenow fragment of DNA polymerase I. Ten μg of pDH51 DNA was digested to completion with Pst I and Nco I, and the resulting 5' and 3' overhangs were blunted with Klenow fragment of DNA polymerase I. The DNA samples were extracted sequentially with equal volumes of phenol, phenol:chloroform (1:1 v/v) and chloroform followed by ethanol precipitation. The blunt-ended pDH51 was then digested to completion with Bam HI and dephosphorylated. The pDH51 DNA (0.25 μg) was ligated overnight at 16° C. with 0.75 μg of digested pHPH201(+) DNA in a final volume of 10 μ. The ligation reaction was heated for 10 minutes at 70° C. and then diluted five fold with water. A 2 μl aliquot of the diluted ligation mixture was used to transform 100 μl of competent HB101 cells. Aliquots of the transformation mixture were plated on LB agar plates containing 50 μg/ml amp and allowed to grow overnight at 37° C. Small scale plasmid preparations were made from individual amp resistant colonies and analyzed by restriction endonuclease digestions until one was identified that contained a plasmid consisting of the 465 bp Eco RI/Nco I 2-2 promoter/GUS fusion from pHPH201(+) operably linked to the 3' end fragment derived from the CaMV 35S transcript in the plasmid pDH51. This clone was designated pTDS231 (FIG. 15).

Construction of 2-2 promoter deletions of pTDS130

Plasmid pTDS130 contains a unique Eco RI site that cleaves the 2-2 promoter 465 bp 5' to the ininiatior ATG codon of the 2-2 protein. This Eco RI site was cleaved to linearize pTDS 130 and provide a convenient starting point for the generation a of Bal 31 deletions of the promoter in this DNA construction. The procedure used to create the 2-2 promoter deletion series from this Eco RI site was described in Example 7. All deletions were subcloned into pBluescript (SK)+. A series of cDNA clones with shorter 2-2 promoter fragments regulating GUS expression (increasing Bal 31 digestion) was selected from the deletions series generated above. The plasmid constructions selected for analysis are shown in Table 2 with the length of the 2-2 promoter fragment remaining from the 5' end of the promoter to the translation start site in each construction. Promoter fragment lengths were determined by DNA sequence analysis of each construction.

TABLE 2

| Construction Name | Promoter Length (bp) |
|---|---|
| pTDS133 | 465 |
| pTDS134 | 450 |
| pDuPM17 | 248 |
| pDuPN27 | 208 |
| pDuPN4 | 150 |
| pDuPN7 | 130 |

The DNA sequence of the 2-2 promoter region with the locations of the start sites of each of the promoter fragments driving the expression of GUS in the various constructions is given in FIG. 14.

Construction of pDuPS22

A construction consisting of a recombinant gene encoding a sulfonylurea-resistant form of acetolactate synthase (ALS) under the transcriptional control of an inducible promoter fragment from the corn 2-2 gene was prepared. The details of the particular embodiment of such a construction presented here represents but one of any number of methods by which such a recombinant gene might be accomplished. It is expected that those skilled in the art will be able to make such recombinant gene using the sulfonylurea-resistant ALS gene contained in pAGS148 (ATCC accession number 67124) and any number of 2-2 promoter fragments whose use is taught in this work.

The construction pUC119/HRA was made using the plasmid pAGS148 as the starting material (ATCC accession number 67124, and described in detail in European patent application 0257993). pAGS148 was digested to completion with Eco RI and the 1.38 kbp Eco RI fragment containing the translation start site of the ALS protein, was subcloned into the Eco RI site of the vector pUC119. This construction was designated pUC119/AGS. The plasmid pUC119/AGS was digested to completion with Bbv I and the 5' overhangs of the resulting fragments were blunted with the Klenow fragment of DNA polymerase I. These blunted fragments were separated by agarose gel electrophoresis and the 1.2 kbp fragment was purified from the gel. Bam HI linkers (New England Biolabs, catalog #1017) were added to the fragment which was then subcloned into the Bam HI site of pUC119 to yield the plasmid pUC119/Bbv I.

The Plasmids pUC119/Bbv I and pAGS148 were digested to completion with Bst EII and Pst I and the resulting fragments were separated by gel electrophoresis. The 4.58 kb BstE II/Pst I fragment from pUC119/Bbv I and the 2.45 kb Bst EII/PstI fragment from pAGS148 were purified from the gels and ligated together to yield the plasmid pUC119/HRA.

Mutations were made in the tobacco SurA gene to change amino acid number 194 from proline to alanine and amino acid number 571 from tryptophan to leucine as described by Bedbrook et al. in European patent application 0257993. The 1.42 kbp Nco I/Bgl II fragment corresponding to nucleotides 533–1952 of the SurA gene was excised by restriction endonuclease digestion and used to replace the corresponding region in the pUC119/HRA to yield the plasmid pUCAD.

The plasmid pTDS130 was digested to completion with Nco I. The 5' overhangs of the Nco I sites were partially filled-in with the Klenow fragment of DNA polymerase I by using only dCTP and dGTP as nucleotides in the Klenow reaction. The remaining nucleotides of the overhangs that were not filled-in were removed by digestion with mung bean nuclease and the resulting blunted DNA fragments were separated by gel electrophoresis. A unique 450 bp DNA fragment was isolated from the gel and ligated together with equimolar amounts of pUCAD that had been digested to completion with Bam HI and rendered blunt-ended by digestion with mung bean nuclease. The resulting plasmid, containing an ALS gene encoding a sulfonylurea herbicide-resistant form of the enzyme under the transcriptional control of a 450 bp inducible 2-2 promoter fragment was designated pDUPS22.

EXAMPLE 9

Construction of Recombinant Genes whose Expression is Regulated by the 5-2 Corn Promoter Construction of pMC 710

Figure 17:
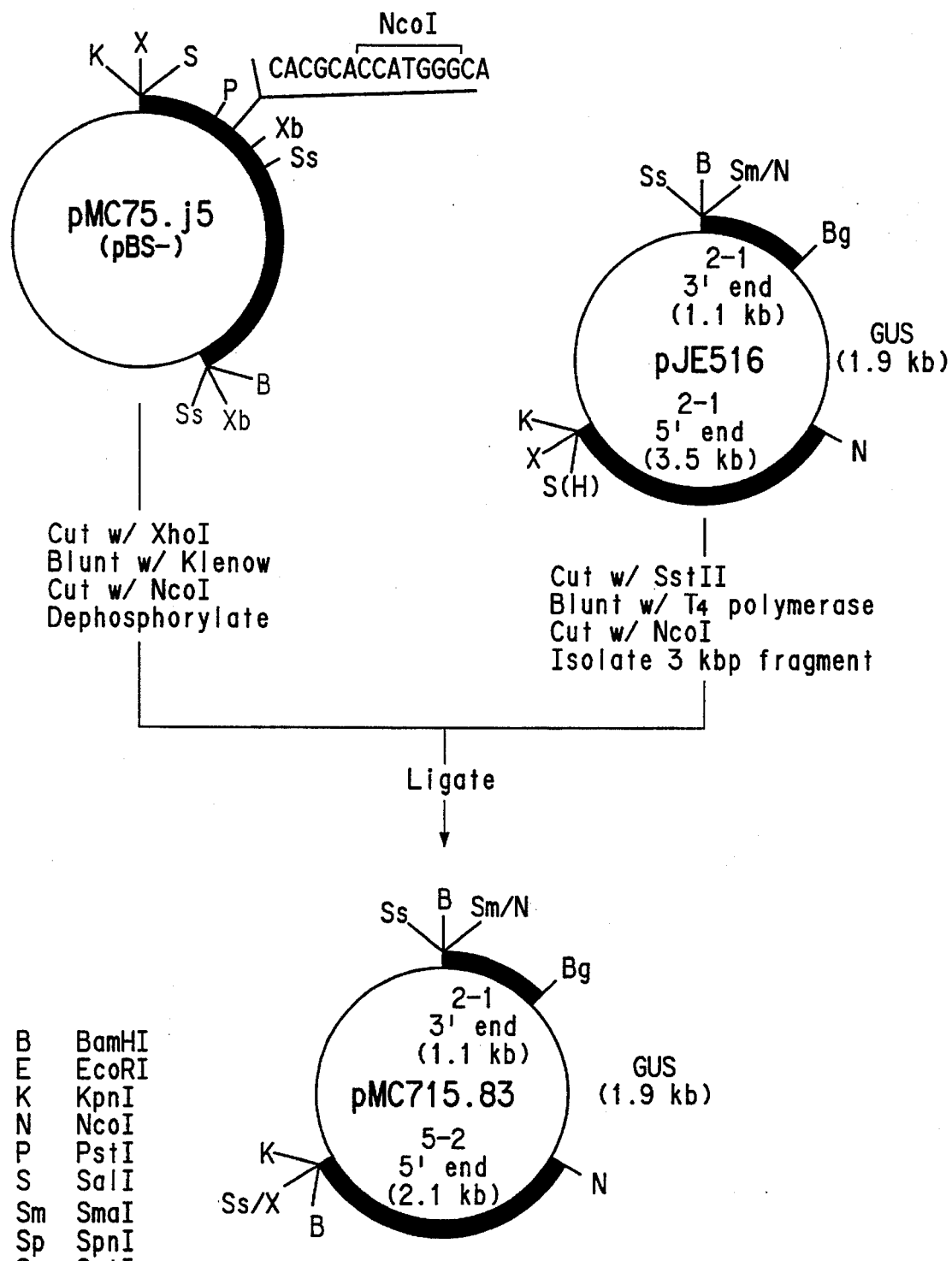
FIG. 17 depicts the creation of plasmid pMC715.83.

The 2-1 promoter fragment in the construction pJE 516 was removed and replaced with a 5-2 promoter. To this end, pJE 516 was digested to completion with Sst II and the resulting 3' overhang was removed using T4 DNA polymerase. This DNA was then digested to completion with Nco I and the DNA fragments were separated by agarose gel electrophoresis. The 3.8 kbp band corresponding to the GUS/2-1 3' end fusion from pJE516 was cut out of the gel and recovered as described earlier. The plasmid pMC 75.5 was digested to completion with Xho I and the resulting 5' overhang was filled-in using the Klenow fragment of DNA polymerase I. This DNA was then digested to completion with Nco I and dephosphorylated. The resulting DNA was ligated to the 3.0 kbp Nco I-blunt DNA fragment from pJE516. An aliquot of this ligation mixture was used to transform competent *E. coli* HB101 and individual transformants were analyzed until one was found that contained the 5-2 promoter operably linked to the GUS/2-1 3' end fusion in the vector pBS(−). This construction was designated pMC715.83 (FIG. 17).

EXAMPLE 10

Construction of a Chimeric Gene Whose Expression is Controlled by The 218 Corn Promoter The plasmid pMC791 (Example 4) was subjected to partial digestion with Afl III. The partially digested pMC791 was then digested to completion with Sma I. The digestion products were separated by gel electrophoresis and a 1.4 kbp Afl III/Sma I DNA fragment was isolated.

Figure 18A:
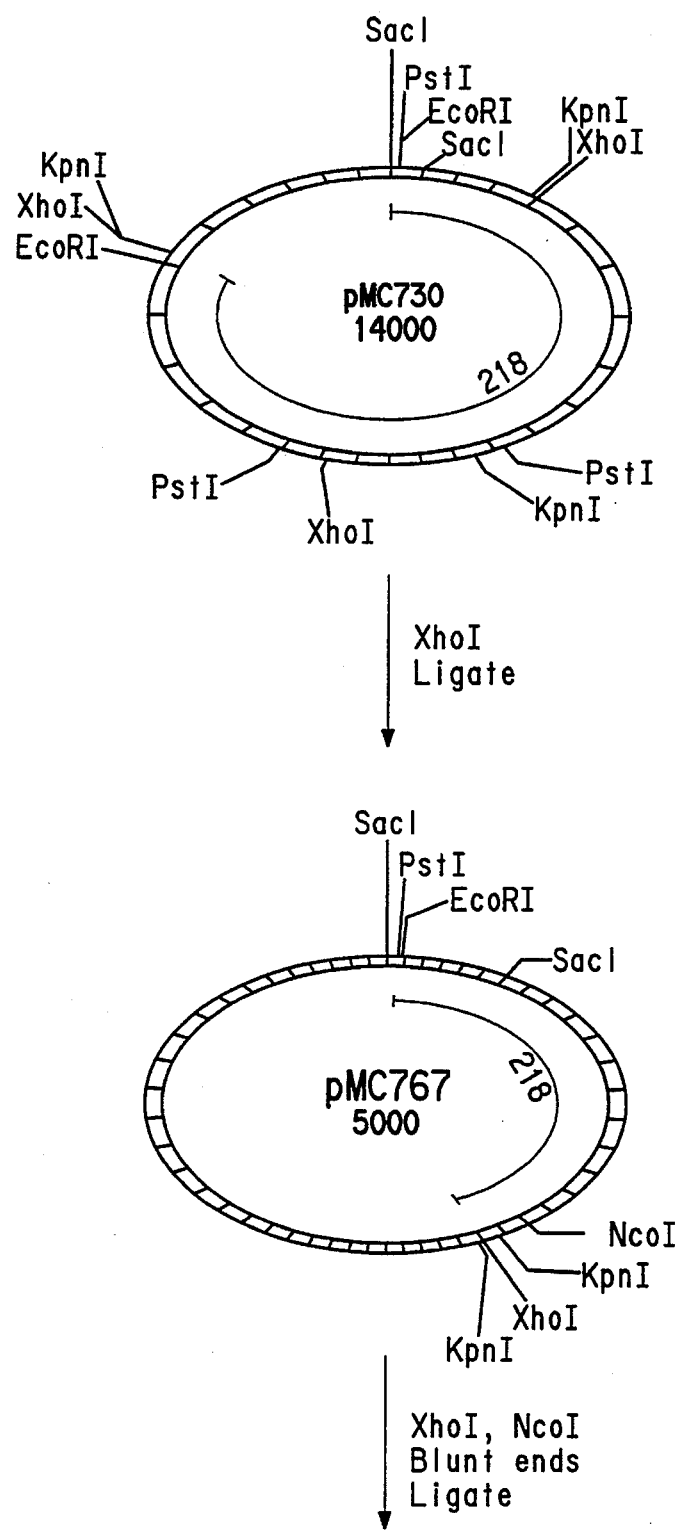
FIG. 18 depicts the creation of plasmid pMC7113.
Figure 18C:
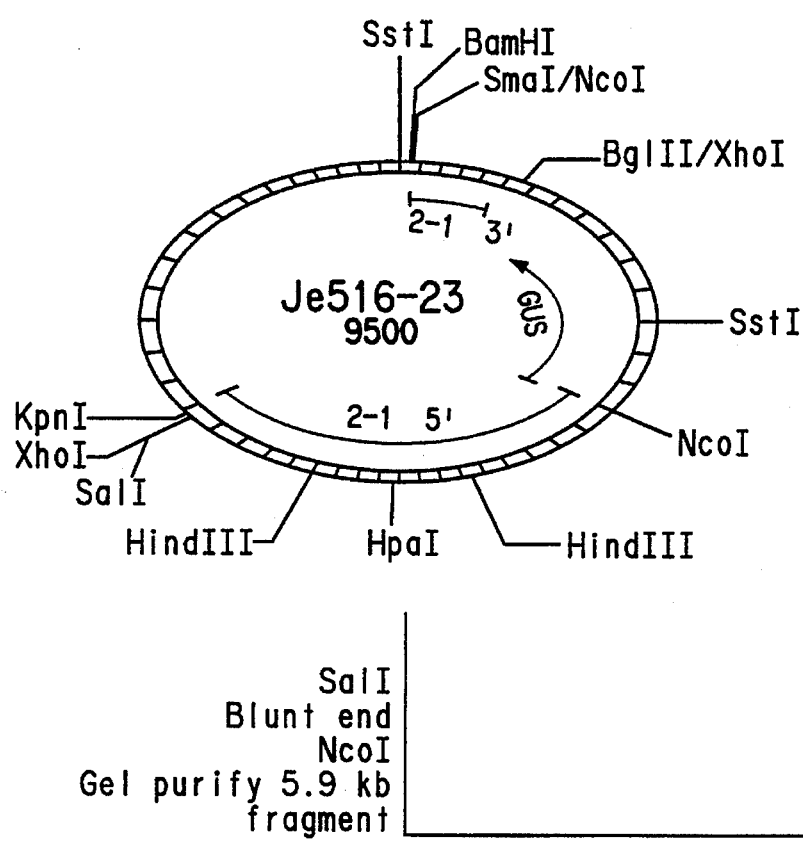

The plasmid pJE516 was digested to completion with Sal I and the resulting 5' overhang was filled in using $T_4$ DNA polymerase. The DNA was then digested to completion with Nco I, dephosporylated and ligated with an equimolar amount of the gel-purified 1.4 kbp Afl III/Sma I fragment from pMC791. An aliquot of the ligation mixture was used to transform competent *E. coli* HB101 cells. Aliquots of the transformation mixture were spread on LB agar plates containing ampicillin and the plates were incubated overnight at 37° C. Plasmid DNA prepared from amp-resistant colonies was analyzed by restriction endonuclease digestions until one was identified that contained the 1.4 kbp Sma I/Afl III promoter fragment of the 218 gene operably linked to the GUS/2-1-3' end fusion in pJE516. This plasmid was designated pMC7113 (FIG. 18).

EXAMPLE 11

Construction of Recombinant Genes Whose Expression are Regulated by Petunia P6.1 Gene Promoter Fragments and Various 3' Downstream Regions Construction of P655, P657, P658, and P660

Construction of P655

The reporter gene used for fusions was β-glucuronidase from *E. coli* as discussed in earlier examples. The source of this gene was the plasmid pJJ3431 (ATCC accession number 67884), which contains a GUS coding region fused to the 35S CaMV promoter region and the octopine synthase 3' end in pUC118. The regulatory regions from P6 gene were substituted into pJJ3431 in a stepwise fashion: first the 35S promoter was replaced with the P6 gene 1 promoter, then the octopine synthase (OCS) 3' end was replaced with the P6 gene 1 3' end.

Figure 19A:
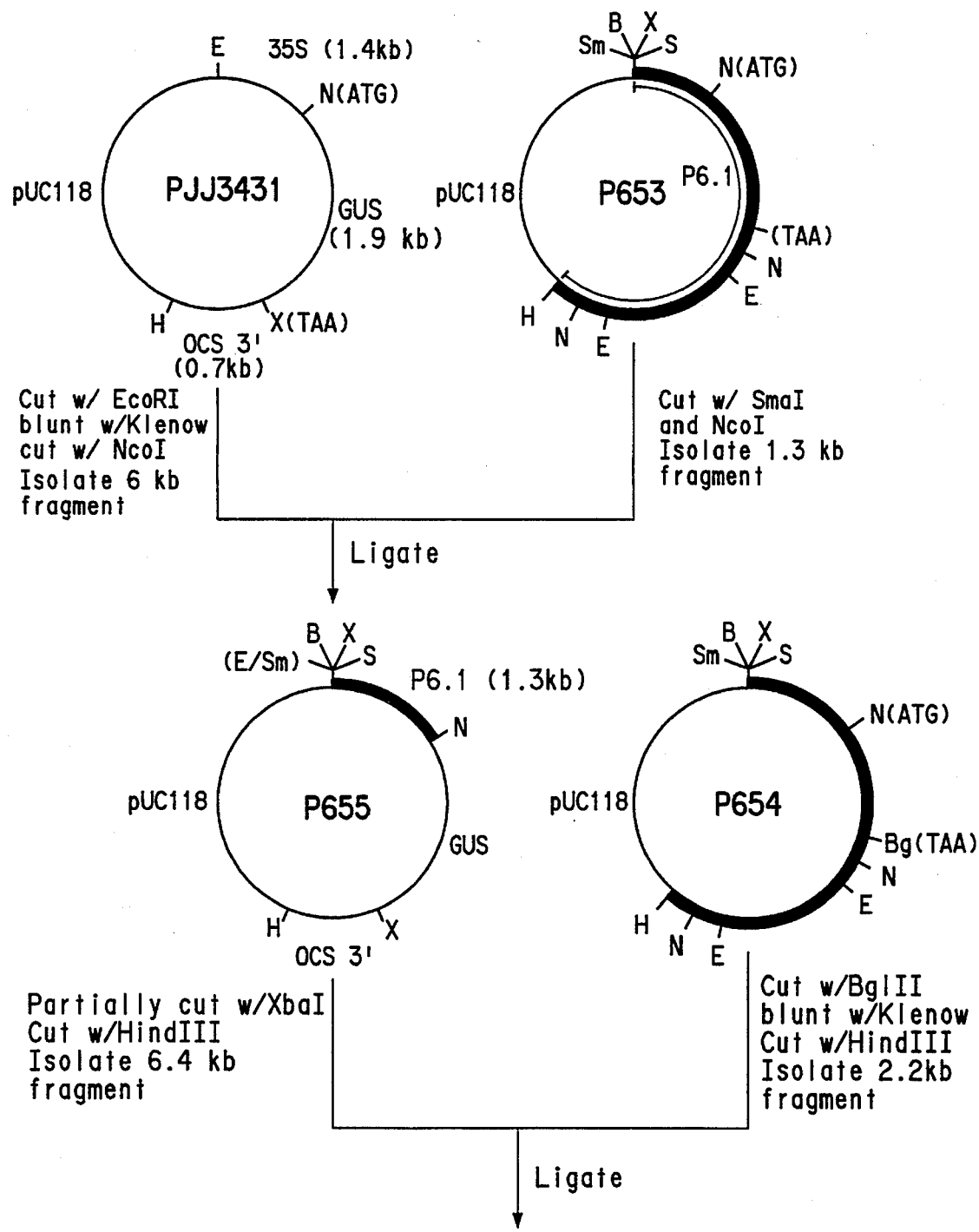
FIG. 19 depicts the creation of plasmids P655, P657 and P658.

The 35S promoter region was removed from pJJ3431 by digesting 10 μg of the plasmid with Eco RI and filling-in the resulting 5' overhang with Klenow fragment. After extraction with phenol:chloroform (1:1 v/v) and precipitation with ethanol, the DNA was restricted with Nco I and the products were separated by agarose gel electrophoresis. A 5.8 kbp DNA fragment corresponding to the GUS/OCS 3'end fusion in pUC118 was isolated by placing the gel slice containing this fragment in a dialysis bag with 500 μl of 1× TAE buffer and electroeluting the DNA from the agarose. The eluted DNA was extracted with phenol:chloroform (1:1 v/v) and precipitated with ethanol. The mutagenized petunia P6 gene 1 promoter region containing a unique Nco I site was purified by digesting 10 μg of the plasmid construction P653 (Example 4) to completion with Nco I and Sma I and gel purifying the 1.3 kbp P6 promoter fragment as previously described. Equimolar amounts of this 1.3 kbp promoter fragment and the GUS/OCS 3' end fragment were ligated overnight at 15° C. in a volume of 10 μl. The ligated DNA was used to transform competent *E. coli* JM83 and aliquots of the transformation mixture were plated on LB containing 75 μg/ml amp. Small scale plasmid DNA preparations from amp-resistant colonies were evaluated by digestion with Nco I and Bam HI until a colonoy containing a plasmid with the 1.3 kbp P6 gene 1 mutagenized promoter fragment operably linked to the GUS/OCS fusion of pJJ 3431 was found. This plasmid was designated P655 (FIG. 19).

Construction of P657

In the construction P655, the petunia P6/GUS fusion was operably linked to an OCS 3' end at an Xba I site. In order to replace the OCS 3' end fragment in P655 with the mutagenized P6 gene 3' end in P654, it was necessary to first partially digest P655 with Xba I as there was an Xba I site in the polylinker region of P655 in addition to the site of the OCS 3' end fusion. Due to a relatively inactive lot of Xba I, it was possible to generate partially cut molecules by digesting 10 μg of P655 DNA with 30 units of enzyme for 1 hour. After checking for partial digestion by agarose gel electrophoresis, the 5' overhang of the Xba I site was filled in with Klenow fragment of DNA polymerase I. The DNA was extracted with phenol:chloroform (1:1 v/v), ethanol precipitated, redissolved and digested to completion with Hind III. The products of this digestion were separated by agarose gel electrophoresis and the desired DNA fragment corresponding to P655 without the OCS 3' end was purified from the gel.

The 3' end of the P6.1 gene was isolated by digesting the plasmid P664 to completion with Bgl II and filling-in the resulting 5' overhang with Klenow fragment. The DNA was extracted with phenol:chloroform (1:1 v/v), precipitated with ethanol, redissolved, and digested to completion with Hind III. The resulting products were separated by agarose gel electrophoresis, and the 2.2 kbp fragment containing the P6.1 gene 3' end was excised from the gel and purified as described earlier.

The 2.2 kbp P6 3' end fragment was ligated with the purified Xba I fragment of P655 from above overnight at 15° C. in a final volume of 10 μl. An aliquot of the ligation reaction was used to transform competent *E. coli* JM83 cells. Small scale plasmid preparations from individual ampicillin resistant colonies were analyzed by digestion with Hind III and Bam HI until one was found that contained the P6.1 3' end operably linked to the P6.1 promoter/GUS fusion. This plasmid was designated P657 (FIG. 19).

Construction of P658

In order to map potential regulatory regions in the promoter of P6.1, a 1 kb deletion was made in the promoter fragment of the P657 construction, leaving a 300 bp P6.1 promoter fragment operably linked to a GUS/P6.1 3'downstream fragment. Ten μg of P657 was digested to completion with Xba I and Spe I. The resulting 5' overhangs were filled-in with Klenow fragment and the products were separated by agarose gel electrophoresis. The 7.6 kb fragment (P657 with 1 kb of the 5' end of the promoter deleted) was recovered from the gel by electroelution, extracted with phenol:chloroform (1:1 v/v) and precipitated with ethanol. The DNA was ligated back to itself overnight at 15° C. in a 10 μl ligation reaction. An aliquot of the ligation mixture was used to transform competent *E. coli* JM82. Plasmid DNA from individual amp resistant colonies was digested with Hind III and Bam HI until a colony containing the desired plasmid was found. This colony, containing a GUS/ OCS 3' end fusion operably linked to a 300 bp P6.1 promoter fragment was designated P658 (FIG. 19).

Construction of P660

A construction consisting of a GUS/OCS 3' downstream region fusion operably linked to a 600 bp P6.1 promoter fragment was prepared. A convenient Eco RI site 600 bp upstream of the initiating codon ATG was used to generate the 600 bp promoter fragment. However, since 2 Eco RI sites are found in the 3' downstream region of the P6.1 gene, a promoter deletion was made in the plasmid P655 and the OCS 3' end was replaced with the 3' downstream region from the P6.1 gene.

Figure 20A:
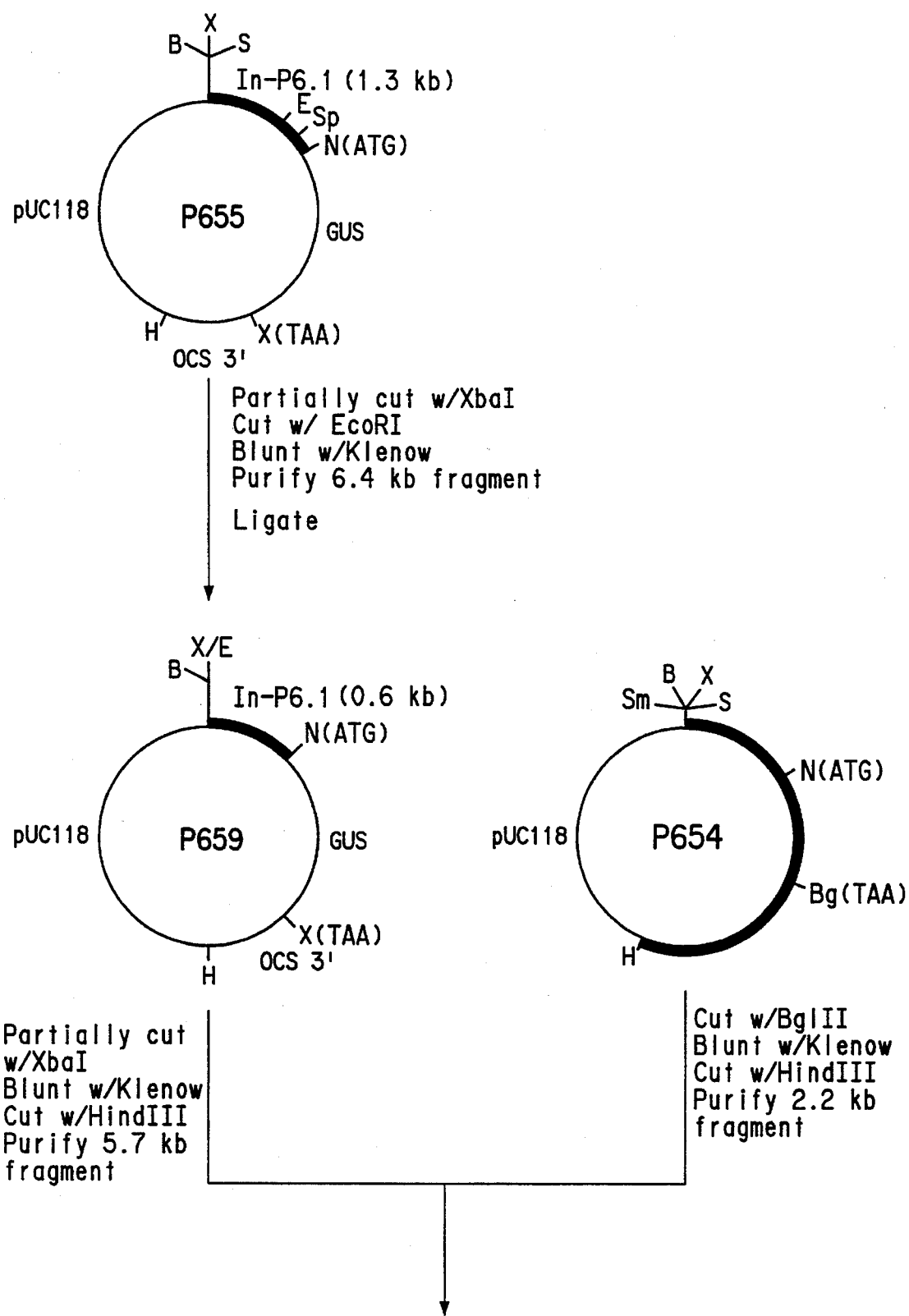
FIG. 20 depicts the creation of plasmid P660.

Ten μg of P655 was partially digested with Xba I, extracted with phenol:chloroform (1:1 v/v) and precipitated with ethanol. The DNA was then digested to completion with Eco RI and the products separated by agarose gel electrophoresis. The 6.4 kbp DNA fragment corresponding to P655 lacking 700 bp from the 5' end of the P6.1 promoter was purified, and the 5' overhangs were filled-in with Klenow fragment. The DNA was extracted with phenol:chloroform (1:1 v/v) and precipitated with ethanol. The 6.4 kbp fragment was ligated to itself overnight at 15° C. in a volume of 10 μl. An aliquot of the ligation mixture was used to transform competent *E. coli* JM83 cells. Plasmid DNA from individual amp resistant colonies was digested with Hind III and Bam HI until a colony containing the desired 3.2 kb Hind III/Bam HI fragment was found, diagnostic of the presence of a 600 bp promoter fragment in the construction. This plasmid was designated P659 (FIG. 20).

To replace the OCS 3' end of P659 with the 3' end of the P6.1 gene, 10 μg of P659 DNA was first partially digested with Xba I. The 5' overhang was filled-in with Klenow fragment, and the blunt-ended DNA was extracted with phenol:chloroform (1:1 v/v) and precipitated with ethanol. The DNA was then digested to completion with Hind III and the resulting DNA fragments were separated by agarose gel electrophoresis. The 5.7 kb fragment corresponding to P659 without the OCS 3' end was electroeluted from the gel, extracted with an equal volume of phenol:chloroform (1:1 v/v) and ethanol precipitated. This fragment was ligated overnight at 15° C. in a volume of 10:1 to the same Bgl II-blunt/Hind III fragment of P654 used in the construction of P657. An aliquot of the ligation mixture was used to transform competent *E. coli* JM83. Plasmid DNA from individual ampicillin resistant colonies was digested with Bam HI and Hind III until one was found that contained a 4.7 kbp Bam HI/Hind III fragment. This construction, consisting of GUS operably linked to a 600 bp P6.1 promoter fragment and a 1.3 kbp P6.1 3' downstream region fragment, was designated P660 (FIG. 20).

EXAMPLE 12

Construction of Recombinant Genes Under Transcriptional Control of Chimeric Promoters Containing An Inducible Regulatory Element From the Corn 2-2 Promoter Oligonucleotides were synthesized using an Applied Biosystems Model 380A DNA synthesizer. All oligonucleotides were purified using Applied Biosystems Oligonucleotide Purification Cartridges (cat. #400771) using the protocol supplied by the manufacturer.

Construction of pHPH401 and pHPH401 dcm

Complementary oligonucleotides 32 and 33, of the sequences:

```
32 5'-AATTCGTTAACCGCACCCTCCTTCCCGTCGTTTCCCATCTCTTCCTC
    CTTTAGA-3'

33 5'-GGAGGAAGAGATGGGAAACGACGGGAAGGAGGGTGCGGTTAACG-3'
``` and complementary oligonucleotides 34 and 35 of the sequences:

```
34 5'-GCTACCACTATATAAATCAGGGCTCATTTTCTCGCTCCTCACAGGC
    CTGGTAC-3'

35 5'-CAGGCCTGTGAGGAGCGAGAAAATGAGCCCTGATTTATATAGTGGT
    AGCTCTAAA-3'
``` phosphorylated by incubation of 10 ug of each oligo with 25–50 units of $T_4$ polynucleotide kinase in 50 ul of 50 mM Tris-HCl pH 7.5, 10 mM $MgCl_2$, 10 mM DTT for 20 min at 37° C. An additional 25 ul of 50 Tris-HCl pH 7.5, 10 mM MgCl2, 10 mM DTT containing 12.5–25 units of polynucleotide kinase were added and the incubation was continued for 20 min at 37° C. Kinase reactions were heated to 70° C. for 10 minutes and then cooled on ice. Phosphorylated oligos 32, 33, 34 and 35 were mixed at a final concentration of 13 ug/ml each in water and 1 ul of this mixture was ligated overnight at 15° C. with 1.5 ug of the plasmid vector pBluescript S/K(+) was digested to completion with Eco RI and Kpn I and dephosphorylated using calf intestinal alkaline phosphatase. The ligation mixture was diluted to 60 ul with $H_2O$, and 2 ul of the dilution was used to transform 60 ul of competent HB101 cells. Aliquots of the transformation reaction were spread onto LB plates with 50 ug/ml amp and plates were incubated overnight at 37° C. Small scale plasmid preparations were performed on amp-resistant colonies and colonies found to contain 100 bp Eco RI/Kpn I insets by restriction digestion were sequenced using the M13 universal primer. One colony containing oligonucleotides 32–35 cloned into the Eco RI/Kpn site of pBluescript S/K(+) was designated pHPH401.

The plasmid pHPH401 was transferred to the dcm-*E. coli* strain NS2616. Any commonly available dcm-*E. coli* strain can be used for this purpose. Competent NS2216 cells were made by inoculating a 50 ml of LB broth with 100 ul of an overnight culture of NS2216 (grown in LB) and incubating this new culture at 37° C. with shaking until the $A_{650}$ reached 0.25. The culture was chilled to 0° C. on ice. Bacteria were harvested by centrifugation at 1500× g for 10 minutes, resuspended in 25 ml of 100 mM $CaCl_2$ and incubated on ice for 30 min. The bacteria were recentrifuged as above and resuspended in 0.5 ml of 100 mM $CaCl_2$. After 4 hours on ice, 100 ul of competent cells were removed, 4 ng of pHPH401 was added, and the cells were incubated on ice for 30 minutes. The cells were then heat shocked for 5 minutes in a 37° C. water bath without shaking. The cells were returned to the ice for 2 minutes before addition of 2 ml of LB medium. Cells were incubated at 37° C. for 1 hour and aliquots of the transformation mixture were plated on LB agar plates containing 50 ug/ml amp and allowed to grow overnight at 37° C. Small scale plasmid preparations from individual amp resistant colonies were analyzed by restriction endonuclease digestions until one was identified that contained pHPH401. The strain was designated HPH401 dcm- and the dcm- plasmid in this strain was designated pHPH401 dcm-.

Construction of pHPH410

Complementary oligonucleotides 36 and 37 of the sequences:

```
36  5'-CTCATCAGCACCCCGGCAGTGCCACCCCGACTCCCTGCACCTGCCAT
    GGCTGTGGCTCGAGGTAC-3'

37  5'-CTCGAGCCACAGCCATGGCAGGTGCAGGGAGTCGGGGTGGCACTGCC
    GGGGTGCTGATGAG-3'
``` were phosphorylated as above and diluted to 33 ng/ul of each oligo in $H_2O$. One ul of this dilution was ligated overnight with 1.4 ug Kpn I and Stu I digested and dephosphorylated pHPH401 dcm- in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations were prepared from individual amp resistant colonies and colonies found to contain 160 bp Eco RI/Kpn I insets by restriction digestion were sequenced using the M13 universal primer. One colony containing oligonucleotides 36 and 37 cloned into the Kpn I/Stu I sites of pHPH401 dcm- was designated pHPH410.

Construction of the 443 Promoter in pHPH443

Complementary oligonucleotides 44 and 45 of the sequences:

```
44  5'-AATTCTACGTACCATATAGTAAGACTTTGTATATAAGACGTCACC
    TCTTACGTGCATGGTTATATGCGACATGTGCAGTGACGTT-3'

45  5'-AACGTCACTGCACATGTCGCATATAACCATGCACGTAAGAGGTGA
    CGTCTTATATACAAAGTCTTACTATATGGTACGTAG-3'
``` were phosphorylated as above and diluted to 13.3 ng/ul of each oligo in $H_2O$. One ul of this dilution was ligated overnight with 1.5 ug Hpa I and Eco RI digested and dephosphorylated pHPH410 in a volume of 15 ul. The ligation reaction was diluted to 60 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations were prepared from individual amp resistant colonies add colonies found to contain 240 bp Pst I/Kpn I insets by restriction digestion were sequenced using the M13 universal primer. One colony containing oligonucleotides 44 and 45 ligated into the Eco RI/Hpa I Fires of the plasmid pHPH410 was designated pHPH443. The sequence of the insert containing in the plasmid pHPH443 is shown in FIG. 21. This DNA fragment represents a chimeric promoter consisting of a 77 bp chemically inducible element from the maize 2-2 promoter (nucleotides 9–86 of FIG. 21) operably linked to the −1 to −94 of the alcohol dehydrogenase 1-1S allele [Dennis et al. (1984) Nucleic Acid Res. 12: 3983–4000] (nucleotides 87–180 of FIG. 21) and using a 5' untranslated region from the corn 2-2 gene (nucleotides 181–225 of FIG. 21). The arrow and underlining in the figure denote the transcription and translation start sites, respectively, of the promoter.

Construction of pHPH412

Complementary oligonucleotides 46 and 47 of the sequences:

```
46  5'-CTCATCTCGCTTTGGATCGATTGGTTTCGTAACTGGTGAAGGACTGA
    GGCCTAACGGTAC-3'

47  5'-CGTTAGGCCTCAGTCCTTCACCAGTTACGAAACCAATCGATCCAAAG
    CGAGATGAG-3'
``` were phosphorylated as above and diluted to 13.3 ng/ul of each oligo in $H_2O$. One ul of this dilution was ligated overnight with 1.4 ug Kpn I and Stu I digested and dephosphorylated pHPH401 dcm- in a volume of 15 ul. The ligation reaction was diluted to 60 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations were prepared from individual amp resistant colonies and colonies found to contain 240 bp Kpn I/Pst I I inserts by restriction digestion were sequenced using the M13 universal primer. One colony containing oligonucleotides 45 and 46 cloned into the Kpn I/Stu I sites of the plasmid pHPH401 dcm- was designated pHPH411.

Complementary oligonucleotides 48 and 49 of the sequences:

48 5'-GTCTCGGAGTGGATGATTTGGGATTCTGTTCGAAGATTTGCGGAGG
GGGGCCATGGCGACGGTAC-3'

49 5'-CGTCGCCATGGCCCCCCTCCGCAAATCTTCGAACAGAATCCCAAAT
CATCCACTCCGAGAC-3' were phosphorylated as above and diluted to 20 ng/ul of each oligo in H$_2$O. One ul of this dilution was ligated for 4 hours with 1.4 ug Kpn I and Stu I digested and dephosphorylated pHPH411 in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations prepared from individual amp resistant colonies were sequenced using the M13 universal primer. One colony containing oligonucleotides 48 and 49 ligated into the Kpn I/Stu I sites of pHPH411 was designated pHPH412.

Construction of pHPH460

Complementary oligonucleotides 62 and 63 of the sequences:

62 5'-GTACGTACCATATAGTAAGACTTTGTATATAAGACGTCACCTCTTA
CGTGCATGGTTAACA-3'

63 5'-AGCTTGTTAACCATGCACGTAAGAGGTGACGTCTTATATACAAAGT
CTTACTATATGGTACGTACTGCA-3' were phosphorylated as above and mixed together at 10 ng/ul of each oligo in H$_2$O. One ul of this dilution was ligated for 6 hours with 1 ug Psi I and Hind III digested and dephosphorylated pBluescript S/K(+) in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 Ug/ml amp and allowed to grow overnight at 37° C. Small scale plasmid preparations made from individual amp resistant colonies were sequenced using the M13 universal primer until a colony containing oligonucleotides 62 and 63 cloned into the Psi I/Hind III sites of pBluescript S/K(+) was found. This plasmid was designated pHPH460.

Construction of pHPH461

Complementary oligonucleotides 75 and 76 of the sequences:

75 5'-ATATGCGACATGTGCAGTGACGTTATCAGATATAGCTCACCCTATAT
ATATAGCTCTGTCCGGTGTCGAC-3'

76 5'-TCGAGTCGACACCGGACAGAGCTATATATATAGGGTGAGCTATATCT
GATAACGTCACTGCACATGTCGCATAT-3' were phosphorylated as above and mixed together at 12.5 ng/ul of each oligo in H$_2$O. One ul of this dilution was ligated for 6 hours with 1 ug Hpa I and Xho I digested and dephosphorylated pHPH460 in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations made from individual amp, resistant colonies were sequenced using the M13 universal primer. One colony containing oligonucleotides 75 and 76 cloned into the Hpa I/Xho I sites of pHPH460 was designated pHPH461.

Construction of pHPH462

Complementary oligonucleotides 77 and 78 of the sequences:

77 5'-AAGTGACAATCACCATTCATCTCGCTTTGGATCGATTGGTTTCGTAA
CTGGTGAAGGACTGAGGCCTAACGGTAC-3'

78 5'-CGTTAGGCCTCAGTCCTTCACCAGTTACGAAACCAATCGATCCAAAC
GAGATGAATGGTGATTGTCACT-3' were phosphorylated as above and mixed together at 10 ng/ul of each oligo in H$_2$O. One ul of this dilution was ligated for 6 hours with 1 ug Kpn I and Hinc II digested and dephosphorylated pHPH461 in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations made from individual amp resistant colonies were sequenced using the M13 universal primer. One colony containing oligonucleotides 77 and 78 cloned into the Kpn I/Hinc II sites was designated pHPH462.

Construction of pHPH463 and pHPH463dam

Phosphorylated, complimentary oligonucleotides 48 and 49, described above, were mixed together at 25 ng/ul of each oligo in H₂O. One ul of this dilution was ligated for 6 hours with 1 ug Stu I and Kpn I digested and dephosphorylated pHPH462 in a volume of 10 ul. The ligation reaction was diluted to 50 ul with water and 2 ul aliquot of the diluted ligation mixture was used to transform 40 ul of competent HB101 cells. Aliquots of the transformation mixture were spread on LB agar plates containing 50 ug/ml amp and allowed to grow overnight at 37° C. Small scale plasmid preparations made from individual amp resistant colonies were sequenced using the M13 universal primer. One colony containing oligonucleotides 48 and 49 cloned into the Stu I/Kpn I sites of pHPH462 was designated pHPH463. The sequence of the insert contained in the plasmid pHPH463 is shown in FIG. 22. This DNA fragment represents a chimeric promoter consisting of the −1 to −136 region of the 2-2 promoter (nucleotides 7-146 of FIG. 22) operably linked to the 5' untranslated leader from the maize alcohol dehydrogenase 1-1S allele [Dennis et al. (1984) Nucleic Acids Res. 12:3983–4000] (nucleotides 147–247 of FIG. 22) and modified to incorporate an Nco I site at the translation state coden. The arrow and underlining in the figure denote the transcription and translation start sites, respectively, of the promoter.

The plasmid pHPH463 was transformed into the dam- E. coli strain CHS26 using the procedure described above for the transformation of pHPH401 into the dcm- E. coli strain NS2216, The plasmid pHPH463 in E. coli CHS26 was designated pHPH463dam-,

Construction of pHPH467

Complementary oligonucleotides 88 and 89 of the sequences:

88 5'-GTTAACAAGGATCGGCGCGCCACGCCGAGCTCGCCGCTATATTTATA
   TTTGCTCAATGGACAGGCATGGGGCTATCTCGCTTTGGAT-3'

89 5'-CGATCCAAAGCGAGATAGCCCCATGCCTGTCCATTGAGCAAATATA
   AATATAGCGGCGAGCTCGGCGTGGCGCGCCGATCCTTGTTAACTGCA-3' were prepared and phosphorylated by incubation of 5 ug of each oligo with 25–50 units of T₄ polynucleotide kinase in 50 ul of 50 mM Tris-HCl pH 7.5, 10 mM MgCl₂, 10 mM DTT for 1 hour at 37° C. Kinase reactions were heated to 70° C. for 10 minutes and then cooled on ice. Oligonucleotides were mixed together at 35 ng/ul of each oligo in H₂O. One ul of this dilution was ligated for 4 hours with 1 ug of Pst I and Cla I digested and dephosphorylated pHPH463dam- in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations made from individual amp resistant colonies were sequenced using oligonucleotide 49 as a primer. One colony containing oligos 88 and 89 cloned into the Pst I/Cla I sites of pHPH463dam- was designated pHP467.

Construction of pHPH500

Five ug of complementary oligonucleotides 92 and 93 of the sequences:

92 5'-GTACCATATGTAAGACTTTGTATATAAGACGTCACCTCTTACGTG
   CATGGTTATATGCGACATGTGCAGTGACGTTAAC-3'

93 5'-GTTAACGTCACTGCACATGTCGCATATAACCATGCACGTAAGAGG
   TGACGTCTTATATACAAAGTCTTACATATGGTAC-3' that together constitute the inducible element from the 2-2 promoter were phosphorylated as described above for oligos 88 and 89. Oligonucleotides were mixed together at 20 ng/ul of each oligo in H₂O. One ul of this dilution was ligated for 4 hours with 1 ug of Sma I digested and dephosphorylated pBluescript S/K(+) in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations made from individual amp resistant colonies were sequenced using the M13 universal primer. One colony containing oligos 92 and 93 cloned into the Sma I site of pBluescript S/K(+) in an orientation such that the 5' side of the inducible element was 3' to the Bam HI site of the vector polylinker was designated pHPH500.

Construction of pHPH478

The plasmid pHPH500 was digested to completion with Bam HI and Hpa I. The digestion products were separated by polyacrylamide gel electrophoresis and the 85 bp fragment corresponding to the inducible element of the 2-2 promoter was recovered as described above. This fragment was ligated overnight with 1 ug of Bam HI and Hpa I digested and dephosphorylated pHPH467 in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations made from individual amp resistant colonies were analyzed by restriction endonuclease digestion until a plasmid containing the Bam HI/Hpa I fragment of pHPH500 cloned into the Bam HI/Hpa I sites of pHPH467 was identified. This plasmid was designated pHPH478. The sequence of the insert contained in the plasmid pHPH478 is shown in FIG. 23. This DNA fragment represents a chimeric promoter consisting of a 76 bp chemically inducible element derived from the maize 2-2 promoter (nucleotides 9–85 of FIG. 23) operably linked to the −1 to −94 region of the phytochrome type 3 promoter (Hershey et al. (1987) Gene 61: 339–348] (nucleotides 86–155 of FIG. 23) and using a 5' untranslated region from the maize alcohol dehydrogenase 1-1S allele [Dennis et al. (1984) Nucleic Acids Res. 12: 3983–4000] (nucleotides 156–256 of FIG. 23) and modified to incorporate an Nco I site at the translation start codon. The arrow and underlining in the figure denote the transcription and translation start sites, respectively, of the promoter.

Construction of pHPH443GUS, pHPH410GUS, pHPH412GUS, pHPH463GUS and pHPH478GUS

Sixty micrograms of the plasmid pHPH443 were digested to completion with Xba I and Nco I. The resulting DNA fragments were separated by electrophoresis overnight at 180 V in a single 1 cm wide lane of a 2 mm thick, 7.5% polyacrylamide gel made in TBE and containing 25% glycerol. DNA fragments were visualized under UV light after staining the gel in 0.5 ug/ml ethidium bromide in H$_2$O for 20 minutes. The 230 bp DNA fragment corresponding to the insert of pHPH443 was excised from the gel with a scalpel, placed in a 1.5 ml microcentrifuge tube, crushed with a spatula and suspended in gel elution buffer. The tube was then shaken vigorously overnight at 37° C. Gel fragments were removed from the resulting slurry by filtration through glass wool and DNA in the filtrate was precipitated on dry ice after adding 1 ml of ethanol. DNA was recovered by centrifugation and resuspended by vigorous vortexing in 0.3 ml of TE pH 8.0. The suspension was centrifuged and the supernatant was transferred to a new tube, made 0.3M in sodium acetate and precipitated on dry ice as described above. DNA was collected by centrifugation, and the pellet was dissolved in 20 ul of TE pH 7.5 after being dried in vacuo. A 0.5 ul aliquot of pHPH443 insert DNA were ligated to 1 ug Xba I and Nco I digested and dephosphorylated pTD136 (Example 8) in a volume of 10 ul. The ligation reaction was diluted he 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations were performed on amp-resistant colonies and the resulting DNAs were digested with Xba I and Nco I until a colony was found that contained the 230 bp Xba I/Nco I fragment from pHPH443 in pTD136. This plasmid, consisting of the promoter fragment of pHPH443 operably linked to the GUS/2-1 3' end construction in pTDS136 was called pHPH443GUS.

Similarly, the Xba I/Nco I promoter fragments of pHPH410, pHPH412, pHPH463 and pHPH478 were cloned into the Xba I/Nco I sites of pTDS136 to create the plasmids pHPH410GUS, pHPH412GUS, pHPH463GUS and pHPH478GUS, respectively.

Construction of pHPH420GUS

Thirty micrograms of the plasmid pHPH412 were digested to completion with Hpa I and Nco I. The resulting DNA fragments were separated by electrophoresis overnight at 250 V in a single 1 cm wide lane of a 2 mm thick 7.5% polyacrylamide gel made in TBE and containing 25% glycerol. DNA fragments were visualized under UV light after staining the gel in 0.5 ug/ml ethidium bromide in H$_2$O for 20 minutes. The 200 bp DNA fragment corresponding to the insert of pHPH412 was recovered from the gel as described above and dissolved in 20 ul of TE pH 8.0. The concentration of the pHPH412 insert was determined by its absorbance at 260 nm and 40 ng of pHPH412 insert DNA were ligated to 1 ug Hpa I and Nco I digested and dephosphorylated pHPH443GUS in a volume of 10 ul. The ligation reaction was diluted to 50 ul with water and 2 ul aliquot of the diluted ligation mixture was used to transform 40 ul of competent HB101 cells. Aliquots of the transformation mixture were plated on LB agar plates containing 50 ug/ml amp and allowed to grow overnight at 37° C. Small scale plasmid preparations were performed on amp-resistant colonies and the resulting DNAs were digested with Xba I and Nco I until a colony was found that contained the 200 bp Hpa I/Nco I promoter fragment from pHPH412 in pHPH443 GUS. This plasmid construction was called pHPH420GUS. The sequence of the insert contained in the plasmid pHPH420 is shown in FIG. 24. This DNA fragment represents a chimeric promoter consisting of a 77 bp chemically inducible element derived from the maize 2-2 promoter (nucleotides 9–86 of FIG. 24) operably linked to the −94 to +101 region of the maize alcohol dehydrogenase 1-1S allele [Dennis et al. (1984) Nucleic Acids Res. 12: 3983–4000] (nucleotides 87–281 of FIG. 24) and modified to incorporate an Nco I site at the translation start codon. The arrow and underlining in the figure denote the transcription and translation start sites, respectively, of the promoter.

EXAMPLE 13

Construction of Recombinant Promoters Containing Various Modifications of the 2-2 Inducible Element Construction of plasmids pΔ1-pΔ70

Individual oligonucleotides incorporating various base changes at one or more positions in their sequences were prepared using an Applied Biosystems Model 380A DNA synthesizer by using mixtures of nucleoside phosphoramidites at specific cycles in the synthesis, In a similar manner, populations of complementary oligonucleotides to those made above were prepared by incorporating mixture of nucleoside phosphoramidites at appropriate synthesis cycles so as to complement the possible base heterogeneities in the first strand.

The complementary pairs of oligos-:

103  5'-CACCTCTTACGTGCATGGTTANATGNNACATNTGCAGTGANGTT-3'

104  5'-AACNTCACTGCANATGTNNCATNTAACCATGCACGTAAGAGGTGA
CGT-3'

105  5'-CACCTCTTACGTGCATGGTTATATGCGACATGTGNAGTPACGTT 106  5'-AACGTRACTNCACATGTCGCATATAACCATGCACGTAAGAGGTG
ACGT-3'

-continued 107 5'-CACCTCTTACGTGCATGGTTATATGCGACARGTGCPPRGACGTT 108 5'-AACGTCPRRGCACPTGTCGCATATAACCATGCACGTAAGAGGTG ACGT-3'

109 5'-CACCTCTTACGTGCATGGTTATATGCGPRPTGTGCAGTGACGTT 110 5'-AACGTCACTGCACARPRCGCATATAACCATGCACGTAAGAGGTG ACGT-3'

111 5'-CACCTCTTACGTGCATGGTTATATGCGACATGRPCAGTGPCGTT 112 5'-AACGRCACTGRPCATGTCGCATATAACCATGCACGTAAGAGGTG ACGT-3'

115 5'-CACCTCTTACGTGCATGGTTPTPRPCGACATGTGCAGTGACGTT 116 5'-AACGTCACTGCACATGTCGRPRARAACCATGCACGTAAGAGGTG ACGT-3'

117 5'-CACCTCTTACGTGRARGPTRATATGCGACATGTGCAGTGACGTT 118 5'-AACGTCACTGCACATGTCGCATATPARCPTPCACGTAAGAGGTG ACGT-3' where
N=A,C,G,T
P=A,G
R=C,T were phosphorylated as described in Example 12 and each pair was ligated in equimolar ratios with pHPH443GUS that had been digested to completion with both Hpa I and Aat II and dephosphorylated. The ligation reactions were diluted to 50 ul with water and 2 ul aliquot of the diluted ligation mixtures were used to transform 40 ul of competent HB101 cells. Aliquots of the transformation mixtures were plated on LB agar plates containing 50 ug/ml amp and allowed to grow overnight at 37° C. Small scale plasmid preparations

N=A,C,G,T
P=A,G
R=C,T were phoshphorylated as described in Example 12 and ligated in equimolar ratios with pHPH443 GUS that had been digested with both Xba I and Aat II and dephosphorylated. The ligation reactions were transformed into HB101 cells and plasmids in which base changes had been introduced in the region of pHPH443GUS corresponding to the 77 bp inducible element from the 2-2 promoter were selected as described above. Table 3 lists the plasmids that were found to contain base changes in the 77 bp inducible element from the 2-2 promoter listed below and the positions of those changes.

```
    GTACCATATAGTAAGACTTTGTATATAAGACGTCACCTCTTACGTGCATGGTTATATGCG
1   ----------+---------+---------+---------+---------+---------+ 60
    CATGGTATATCATTCTGAAACATATATTCTGCAGTGGAGAATGCACGTACCAATATACGC

ACATGTGCAGTGACGTT
61  ---------+------- 77
    TGTACACGTCACTGCAA
``` were performed on amp-resistant colonies and the resulting DNAs were sequenced using either oligo 35 (Example 12) or oligo HH114 primer (HH114 sequence: 5'-GGAGGAA-GAGATGGGAAACGACGGG-3'). Plasmids in which base changes had been introduced in the region of PHPH443GUS corresponding to the 77 bp inducible element from the 2-2 promoter were selected. Table 3 lists the plasmids that contained single base changes in time region of interest.

Similarly, the complementary pairs of oligonucleotides-:

121 5'-CTAGTGAATTCGTACCATATAGRAAGPCRRTGTATATAAGACGT-3'

122 5'-CTTATATACAPPGRCTTPCTATATGGTACGAATTCA-3'

123 5'-CTAGTGAATTCGTACCATATAGTAAGACTTRPRATPTAAGACGT-3'

124 5'-CTTARATPRPAAGTCTTACTATATGGTACGAATTCA-3'

125 5'-CTAGTGAATTCGTACCATATAGTAAGACTTTGTPRATPPGACGT-3'

126 5'-CRRATRPACAAAGTCTTACTATATGGTACGAATTCA-3'

127 5'-CTAGTGAATTCGTACCATARAPTPAPACTTTGTATATAAGACGT-3'

128 5'-CTTATATACAAAGTRTRARTPTATGGTACGAATTCA-3' where:

TABLE 3

| Plasmid pΔ # | Nucleotide change From | Nucleotide change To | Position |
|---|---|---|---|
| 0 | No changes | | |
| 1 | G | C | 70 |
| 2 | T | C | 64 |
|   | G | C | 70 |
|   | T | A | 71 |
| 3 | A | G | 69 |
| 4 | A | G | 69 |
|   | G | A | 70 |
|   | T | C | 71 |
| 5 | T | C | 64 |
|   | A | G | 69 |
|   | T | C | 71 |
| 6 | T | C | 64 |
| 7 | T | A | 55 |
|   | C | T | 59 |
|   | G | A | 60 |
|   | G | A | 65 |
|   | C | A | 74 |
| 8 | T | T | 55 |
|   | G | T | 60 |
|   | C | A | 74 |
| 9 | C | T | 74 |
| 10 | T | G | 55 |
|   | C | A | 59 |
|   | C | G | 74 |
| 11 | C | G | 59 |
|   | G | T | 60 |
|   | G | T | 74 |
| 12 | C | G | 59 |
|   | G | A | 65 |
| 13 | T | A | 55 |
|   | C | G | 59 |
|   | G | A | 65 |
|   | C | T | 74 |
| 14 | T | C | 55 |
|   | C | T | 59 |
|   | G | T | 65 |
| 15 | C | A | 68 |
|   | G | A | 72 |
| 16 | C | T | 68 |
|   | G | A | 72 |
| 17 | C | G | 68 |
|   | G | A | 72 |
| 18 | C | G | 68 |
| 19 | C | T | 68 |
| 20 | A | G | 61 |
|   | C | T | 62 |
|   | A | G | 63 |
| 21 | A | G | 61 |
| 22 | C | T | 62 |
| 23 | A | G | 61 |
|   | A | G | 63 |
| 24 | A | G | 63 |
| 25 | C | G | 62 |
|   | A | T | 63 |
| 26 | G | A | 67 |
| 27 | T | C | 66 |
|   | G | A | 67 |
| 28 | T | C | 66 |
|   | G | A | 67 |
|   | A | G | 73 |
| 29 | A | G | 73 |
| 31 | T | C | 66 |
|   | A | G | 73 |
| 32 | A | G | 67 |
|   | A | G | 73 |
| 33 | T | C | 66 |
| 34 | A | G | 54 |
|   | T | C | 57 |
| 35 | A | G | 16 |
|   | T | C | 18 |
| 36 | A | G | 16 |
| 37 | T | G | 19 |
| 38 | T | C | 18 |
| 39 | T | C | 18 |
|   | T | T | 19 |
| 40 | T | C | 12 |
| 41 | G | A | 21 |
|   | T | C | 22 |
|   | A | G | 25 |
| 42 | G | A | 21 |
| 43 | T | C | 20 |
|   | G | A | 21 |
| 44 | T | C | 20 |
| 45 | T | C | 12 |
|   | A | G | 16 |
|   | T | C | 18 |
| 46 | T | C | 22 |
| 47 | A | G | 25 |
| 48 | G | T | 21 |
|   | T | C | 22 |
| 49 | T | C | 20 |
|   | T | C | 22 |
|   | A | G | 25 |
| 50 | T | C | 20 |
|   | G | A | 21 |
|   | T | C | 22 |
| 51 | A | T | 56 |
|   | T | C | 57 |
| 52 | G | A | 58 |
| 53 | A | G | 56 |
| 54 | A | G | 54 |
| 55 | A | G | 54 |
|   | A | G | 56 |
| 56 | T | C | 12 |
| 57 | G | C | 25 |
| 58 | T | C | 24 |
| 59 | A | G | 23 |
|   | T | C | 24 |
| 60 | A | G | 23 |
|   | A | G | 28 |
| 61 | A | G | 23 |
| 62 | A | G | 27 |
|   | A | G | 28 |
| 63 | T | C | 9 |
| 64 | G | A | 11 |
| 65 | G | A | 11 |
|   | G | A | 15 |
| 66 | T | C | 9 |
|   | G | A | 11 |
| 67 | A | G | 13 |
| 68 | G | A | 11 |
|   | A | G | 13 |
| 69 | G | A | 15 |
| 70 | C | T | 47 |

EXAMPLE 14

The Use of N-(aminocarbonyl)-2-chlorobenzene-sulfonamide to Induce the Expression of Recombinant GUS/2-1 Corn Gene Constructions in Transformed Rice Protoplasts Transformation of Rice Protoplasts Rice suspension cultures, initiated from anther-derived callus, were maintained by weekly subculture at a 1:4 dilution ratio with fresh liquid N6 medium as described by Chu et al. [Sci Sinica 18:659–668 (1975)] containing 2 mg/ml 2,4-dichlorophenoxyacetic acid and 3% w/v) sucrose, pH 6.0. Protoplasts were isolated from suspensions of rice cells 4–6 days after subculture by overnight incubation (16–18 hrs) in 4 ml of enzyme solution (2% (w/v) cellulose "Onozuka" RS and 0.5% (w/v) Macerozyme (both from Yakult Honsha, Nishinomiya, Japan), 13% (w/v) mannitol, pH 5.6) per gram of cells and agitation of the mixture on a rotary shaker at 30 rpm at 25 C. Released protoplasts were filtered through a 60 mm mesh size nylon screen, transferred to 50 ml Pyrex® test tubes and washed twice by centrifugation at 80 g for 10 minutes in Kren's F solution (140 mM NaCl, 3.6 mM KCl, 0.75 mM.$Na_2HPO_4 7H_2O$, 5 mM glucose, 125 mM $CaCl_2$, pH 7.0). Protoplasts were purified by resuspending the pellet in N6 medium with 17% (w/v) sucrose, centrifuging at 80 g for 20 minutes and collecting the floating layer. Cell counts were made with a Fuchs-Rosenthal hemocytometer.

Protoplasts were transformed as follows: Multiple aliquots of the protoplasts (5–10×10$^6$ cells) were centrifuged gently (80 g) for 4 minutes in sterile tubes. The supernatant was discarded and the cells were resuspended in 1 ml of Kern's F, pH 5.8 buffer. Ten µg of transforming DNA in less than 15 µl of TE pH 8.0 were added per million protoplasts. The tubes were shaken gently to disperse the cells in the DNA solution, and 0.6 ml of a solution containing 40% PEG (Polysciences Inc., Warrington Pa. 18976, CAT #1102) and 3 mM $CaCl_2$ was added. The resulting protoplast cell suspension was mixed gently and incubated at room temperature for 20 minutes. A volume of 13–15 mls of Kren's F, pH 7.0 solution was then added to dilute out PEG.

N-(aminocarbonyl)-2-Chlorobenzenesulfonamide Induction of Transformed Rice

The transformed protoplasts were collected by centrifugation at 80 g for 4 minutes. The supernatant was discarded and the protoplasts were resuspended in 2.0 ml of Kren's F, pH 5.8. The protoplast sample was divided into two 1 ml aliquots. One ml of protoplast medium was added to one aliquot of the protoplasts, while 1 ml of the protoplast medium containing 100 µg/ml N-(aminocarbonyl)-2-chlorobenzenesulfonamide was added to the other aliquot. Protoplasts were then incubated at 25° C. in the dark for 16 hours.

The inducibility of the recombinant GUS genes whose expression were controlled by 2-1 corn gene promoter and downstream sequences were determined by measuring the level of the β-glucuronidase enzyme activity in protoplasts cultured in the presence and absence of N-(aminocarbonyl)-2-chlorobenzenesulfonamide. GUS activity was assayed by harvesting protoplasts in a clinical centrifuge at 80 g for 5 minutes, and resuspending them in 1.0 ml 1× GUS lysis buffer (50 mM sodium phosphate pH 7.0, 10 mM β-mercaptoethanol, 10 mM EDTA, 0.1% Triton X-100, 0.1% N-lauroylsarcosine). The suspension containing the lysed protoplasts was vortexed and spun at top speed in a table top clinical centrifuge for 5 minutes. Eighteen µl of the supernatant was transferred to a tube containing 782 µl of water for determination of protein content in the protoplast lysate. Protein content in the diluted lysate was determined using the Bio-Rad Protein Assay kit (Bio-Rad Laboratories, Richmond, Calif. 94804) following the manufacturer's recommendations for the microassay procedure. A protein concentration curve was prepared using bovine serum albumin as a standard. The protein content, so determined, was multiplied by a factor of 7.2 to give the protein content in 130 µl of extract (the amount of extract present in a single time point of the assay-see below). Of the remaining supernatant, 585 µl was transferred to a fresh tube.

The substrate for the GUS assay was 4-methyl-umbelliferyl-β-D-glucuronide (4-MUG) and was obtained from Sigma Chemical Co., St. Louis Mo. 63178 (CAT #9130). 4-MUG was prepared as a 10 mM stock in 1× GUS buffer. Sixty-five µl of a pre-warmed (37° C.) 10 mM 4-MUG stock was added to the pre-warmed 585 µl protoplast extract, and a 100 µl aliquot of the resulting mixture was transferred to a well of a 24-well microtiter dish containing 0.9 ml of 0.2M $Na_2CO_3$. Similar aliquots are removed at 1 hour, 2 hour, and 3 hours. The 4-MU flourescence of individual samples, from each time point was determined quantitatively using an excitation wavelength of 365 nm and measuring flourescence at an emission wavelength of 455 nm. A standard curve of 4-MU flourescence was also prepared by measuring the flourescence of 100 nM and 1 uM 4-MU (Sigma Chemical Co., CAT #1508). GUS activity in the transient assay was expressed as picomoles of 4-MU produced per µg protein per hour.

The results of transient assays of the type described above are summarized in Table 4 for the plasmid constructions pJE 516, pDuPE2, pDuPI8, pDuPI9, pDuPI6 and pDupI13. Plasmid pBM117 was also run in each assay as a control for constitutive GUS expression. The plasmid consists of a GUS coding region under the control of CaMV 35S promoter and 3' downstream regions. GUS activity resulting from transcription driven by the 2-1 promoter and downstream regions (pJE516) was consistently highly induced by addition of 100 µg/ml of N-(aminocarbonyl)-2-chlorobenzenesulfonamide to the protoplast medium.

TABLE 4

| Sample | Promoter Size (in bp) | GUS ACTIVITY (FU/µg-min.) Uninduced* | INDUCED* | Fold Induction |
| --- | --- | --- | --- | --- |
| NO DNA | N/A | ND | 45.5 | 0 x |
| pBM117 | N/A | 241.1 | 604.3 | 2.6 x |
| pJE516 | ~3000 | 569.4 | 4314.0 | 7.6 x |
| pDuPE2 | ~900 | 227.3 | 1793.0 | 7.9 x |
| pDuPI8 | 421 | 121.1 | 714.1 | 5.9 x |
| pDuPI9 | 226 | 106.6 | 96.9 | 0 x |

*Induction in table was accomplished by the addition of 100 µg/ml of N-(aminocarbonyl)-2-chlorobenzenesulfonamide to transformed protoplasts.

EXAMPLE 15

The Use of
N-(aminocarbonyl)-2-chlorobenzenesulfonamide to
Induce Expression of Recombinant 2-2 Corn
Promoter/GUS Gene Constructions in Transformed
Rice Protoplasts Rice suspension cultures, initiated from anther-derived callus, were utilized as the source of protoplasts for the transient transformation and expression assays. The method for isolation, transformation and chemical treatment of protoplasts, as well as GUS assays were described in Example 14. Protoplasts were transformed with pBM117, and the 2-2 promoter/GUS fusions described below.

The induction of pTDS130, pTDS133, pTDS134, pDuPM17, pDuPN27, pDuPN4 and pDuPN7 recombinant DNA constructions (all described in Example 7) by N-(aminocarbonyl)-2-chlorobenzenesulfonamide in transformed protoplasts were analyzed by the transient expression assay method of Example 14. The N-(aminocarbonyl)-2-chlorobenzenesulfonamide inducibility of GUS expression in protoplasts transformed with these constructions is presented in Table 5. The results show that the chemical strongly induces expression of all constructions with 2-2 promoter fragments that are longer than 208 bp. A rapid loss of chemical inducible GUS activity occurs when the size of the 2-2 promoter fragment is less than 208 bp 5' to the translation stark site in the promoter. This indicates that there is a DNA element in the 2-2 promoter contained, at least in part, between nucleotides −210 and −130 bp of 5' of the translation start site of the C-US gene that appears necessary for induction of 2-2 promoter activity by N-(aminocarbonyl)-2-chlorobenzenesulfonamide.

TABLE 5

| Sample | Promoter Size (in bp) | GUS ACTIVITY (FU/µg-min) Uninduced* | GUS ACTIVITY (FU/µg-min) Induced* | Fold Induction |
|---|---|---|---|---|
| NO DNA | N/A | ND | 0.45 | 0.0 x |
| pBM117 | N/A | 1.68 | 7.47 | 4.5 x |
| pTDS130 | −1900 | 1.38 | 88.72 | 64.1 x |
| pTDS133 | 465 | 1.52 | 102.72 | 67.7 x |
| pTDS134 | 450 | 1.65 | 78.27 | 47.4 x |
| pDuPM17 | 248 | 1.25 | 75.92 | 60.5 x |
| pDuPN27 | 208 | 1.43 | 118.69 | 82.8 x |
| pDuPN4 | 150 | 0.83 | 24.3 | 29.0 x |
| pDuPN7 | 130 | 0.54 | 1.52 | 2.8 x |

*Induction in Table 5 was accomplished by the addition of 100 µg/ml of N-(aminocarbonyl)-2-chlorobenzenesulfonamide to transformed protoplasts.

EXAMPLE 16

The Use of
N-(aminocarbonyl)-2-chlorobenzenesulfonamide to
Induce Expression of Recombinant 5-2 Corn
Promoter/GUS Gene Constructions in Transformed
Rice Protoplasts Rice suspension cultures, initiated from anther-derived callus, were utilized as the source of protoplasts for the transient transformation and expression assays. The method for isolation and transformation of protoplasts, and the GUS assays were described in Example 14. Protoplasts were transformed with pBM117 and the 5-2 promoter/GUS fusions described below.

The response of pMC 715.53 was analyzed by transient expression assay in rice protoplasts. No induction of GUS expression was observed in transformed protoplasts treated with N-(aminocarbonyl)-2-chlorobenzenesulfonamide. Since the in vivo induction in the 5-2 gene is the weakest of all corn genes tested, it may be possible that its inducibility cannot be measured in a transient assay.

EXAMPLE 17

The Use of
N-(aminocarbonyl)-2-chlorobenzenesulfonamide to
Induce A Chimeric 218 Corn Promoter/GUS Fusion
in Transformed Rice Protoplasts Rice suspension cultures, initiated from anther-derived callus, were utilized as the source of protoplasts for the transient transformation and expression assays. The method for isolation, transformation and chemical treatment of protoplasts, as well as GUS assays are described in Example 14.

The induction of GUS activity in response to treatment of rice protoplasts transformed with pTDS130 (Example 8) and pMC7113 with 100 mg/l of N-(aminocarbonyl)-2-chlorobenzenesulfonamide was analyzed by transient expression. The results are presented in Table 6.

TABLE 6

| Construction | GUS ACTIVITY* UNINDUCED | GUS ACTIVITY* INDUCED | FOLD INDUCTION |
|---|---|---|---|
| No DNA | 3 | 3 | 0 |
| pHPH130 | 17.3 | 546 | 31.5 |
| pMC7113 | 78.4 | 952 | 12.1 |

*GUS activity expressed as flourescence units/hr/106 protoplasts

The results in Table 6 show that GUS activity resulting from transcription of a GUS gene under the control of the 218 promoter was consistently highly induced by addition of 100 ug/ml of N-(aminocarbonyl)-2-chlorobenzenesulfonamide to the protoplast medium.

EXAMPLE 18

The Use of
N-(aminocarbonyl)-2-chlorobenzenesulfonamide to
Induce Expression of Recombinant P6 Petunia
Promoter/GUS Gene Constructions in Transformed
Rice Protoplasts Rice suspension cultures, initiated from anther-derived callus, were utilized as the source of protoplasts for the transient transformation and expression assays. The method for isolation and transformation of protoplasts, and the GUS assays were described in Example 14. Protoplasts were transformed with pBM117 and various P6.1 promoter/GUS fusions described below.

The responses of P655, P657, P658, and P660 were analyzed by transient expression assay in rice protoplasts. The degree of induction of GUS expression in transformed protoplasts in response to N-(aminocarbonyl)-2-chlorobenzenesulfonamide treatment is presented in Table 7. GUS activity resulting from transcription driven by the P6 promoter and various 3' downstream regions was consistently induced by addition of 100 µg/ml of N-(aminocarbonyl)-2-chlorobenzenesulfonamide to the protoplast medium.

In addition, all DNA sequences required for this induction appear to reside in the P6.1 promoter, since substitution of a 3' end from a non-inducible gene (the OCS gene) had no effect on the induction of the P6.1 promoter/GUS construction.

TABLE 7

| Sample | P6 Promoter Size (in bp) | GUS ACTIVITY (FU/µg-min) Uninduced* | INDUCED* | Fold Induction |
|---|---|---|---|---|
| NO DNA | N/A | ND | 27.0 | 0.0 x |
| pBM117 | N/A | 174.8 | 325.7 | 1.9 x |
| P655 | 1300 | 61.8 | 317.6 | 5.1 x |
| P657 | 1300 | 66.6 | 488.1 | 7.3 x |
| P658 | 300 | 64.5 | 404.3 | 6.3 x |
| P660 | 600 | 112.8 | 510.9 | 4.5 x |

*Induction in Table 7 was accomplished by the addition of 100 ug/ml of N-(aminocarbonyl)-2-chlorobenzenesulfonamide to transformed protoplast.
ND = not determined

EXAMPLE 19

The Use of
N-(aminocarbonyl)-2-chlorobenzenesulfonamide to
Induce Recombinant Genes Under Transcriptional
Control of Chimeric Promoters Containing An
Inducible Element From the Corn 2-2 Promoter in
Transformed Rice Protoplasts Rice suspension cultures, initiated from anther-derived callus, were utilized as the source of protoplasts for the transient transformation and expression assays. The method for isolation, transformation and chemical treatment of protoplasts, as well as GUS assays were described in Example 14.

The induction of GUS activity in response to treatment of rice protoplasts transformed with pTDS130, pHPH410GUS, pHPH412GUS, pHPH420GUS, pHPH443GUS, pHPH463GUS and pHPH478GUS with N-(aminocarbonyl)-2-chlorobenzenesulfonamide was analyzed by transient expression. The results are presented in Table 8.

TABLE 8

| CON-STRUCTION | GUS ACTIVITY* | | FOLD INDUCTION |
|---|---|---|---|
| | UNINDUCED | INDUCED | |
| No DNA | 10 | 8 | 0 |
| pTDS130 | 124.4 | 849.2 | 6.8 |
| pHPH410GUS | 17 | 14 | .8 |
| pHPH412GUS | 21.5 | 26.6 | 1.2 |
| pHPH420GUS | 317.5 | 1674.5 | 5.3 |
| pHPH443GUS | 55.0 | 590.6 | 10.7 |
| pHPH463GUS | 90.7 | 781.3 | 8.6 |
| pHPH478GUS | 13 | 160.7 | 12.4 |

*GUS activity expressed as flourescence units/hr/$10^6$ protoplasts

These results demonstrate that addition of the 77 bp element derived from the corn 2-2 promoter to the promoters regions of non-inducible GUS genes causes these gene to display induciblity when assayed in transformed rice protoplasts treated with 100 ug/ml of N-(aminocarbonyl)-2-chlorobenzenesulfonamide.

EXAMPLE 20

The Use of
N-(aminocarbonyl)-2-chlorobenzenesulfonamide to
Induce Recombinant Genes under the
Transcriptional Control of Recombinant Promoters
Containing Various Modifications of the 77 bp 2-2
Inducible Element in Transformed Rice Protoplasts Rice suspension cultures, initiated from anther-derived callus, were utilized as the source of protoplasts for the transient transformation and expression assays. The method for isolation, transformation and chemical treatment of protoplasts, as well as GUS assays were described in Example 14.

The induction of GUS activity in response to N-(aminocarbonyl)-2-chlorobenzenesulfonamide treatment of rice protoplasts transformed with pΔ0- pΔ70 was analyzed by transient expression. The degree of induction of GUS expression in transformed protoplasts in response to N-(aminocarbonyl)-chlorobenzenesulfonamide treatment is presented in Table 9.

TABLE 9

| pΔ PROMOTER | GUS ACTIVITY UNINDUCED* | GUS ACTIVITY INDUCED* | FOLD INDUCTION |
|---|---|---|---|
| No DNA | 10 | 8 | 0 |
| pHPH443 | 89 | 954 | 10.7 |
| pΔ0 | 115 | 1100 | 9.5 |
| 1 | 86 | 1001 | 11.6 |
| 2 | 25.5 | 72 | 2.8 |
| 3 | 29.5 | 495 | 16.8 |
| 4 | 22 | 70.5 | 3.2 |
| 5 | 39 | 111.5 | 2.9 |
| 6 | 20 | 106 | 5.3 |
| 7 | 20 | 37.5 | 1.9 |
| 8 | 15 | 31.5 | 2.1 |
| 9 | 75 | 1465 | 19.5 |
| 10 | 20 | 95 | 4.75 |
| 11 | 26 | 133.5 | 5.1 |
| 12 | 127 | 1467 | 11.6 |
| 13 | 33 | 301.5 | 9.1 |
| 14 | 317 | 2280 | 7.2 |
| 15 | 18 | 32 | 1.8 |
| 16 | 10 | 24.5 | 2.4 |
| 17 | 8.5 | 23.5 | 2.8 |
| 18 | 19 | 161 | 8 |
| 19 | 32 | 223 | 7 |
| 20 | 64 | 543.5 | 8.5 |
| 21 | 54 | 802 | 14.9 |
| 22 | 21.5 | 137.5 | 6.4 |
| 23 | 107 | 1417 | 13.2 |
| 24 | 747 | 2925 | 3.9 |
| 25 | 47 | 725 | 15.4 |
| 26 | 16.5 | 61 | 3.7 |
| 27 | 11.5 | 61 | 5.3 |
| 28 | 13.5 | 14 | 1 |
| 29 | 44 | 491 | 11.2 |
| 30 | 19.5 | 103.5 | 5.3 |
| 31 | 41.5 | 182 | 4.4 |
| 32 | 27.5 | 125 | 4.5 |
| 33 | 98.5 | 1249.5 | 12.7 |
| 34 | 214.5 | 2256 | 10.5 |
| 35 | 69.5 | 774 | 11.1 |
| 36 | 94.5 | 1019.5 | 10.8 |
| 37 | 120.5 | 1073 | 8.9 |
| 38 | 117.5 | 1790 | 15.2 |
| 39 | 96.5 | 925 | 9.6 |
| 40 | 112.5 | 1501.5 | 13.3 |
| 41 | 97 | 1085 | 11.2 |
| 42 | 43.5 | 602.5 | 13.9 |
| 43 | 27.5 | 298 | 10.8 |
| 44 | 41.5 | 298 | 7.2 |
| 45 | 80 | 994.5 | 12.4 |
| 46 | 42.5 | 484.5 | 11.4 |
| 47 | 36 | 328.5 | 9.1 |
| 48 | 40.5 | 379.5 | 9.4 |
| 49 | 26 | 166 | 6.4 |
| 50 | 44.5 | 349.5 | 7.9 |
| 51 | 57.5 | 483.5 | 8.4 |
| 52 | 46 | 328 | 7.1 |
| 53 | 49 | 469.5 | 9.6 |
| 54 | 52 | 518 | 10 |
| 55 | 58.5 | 471.5 | 8.1 |
| 56 | 31 | 239.5 | 7.7 |
| 57 | 29 | 245 | 8.4 |
| 58 | 32 | 288.5 | 9.0 |
| 59 | 38.5 | 209.5 | 5.4 |
| 60 | 31.5 | 199 | 6.3 |
| 62 | 23 | 178 | 7.7 |
| 63 | 29 | 268 | 9.2 |
| 64 | 35 | 196.5 | 5.6 |
| 65 | 20.5 | 219.5 | 10.7 |
| 66 | 26 | 291.5 | 11.2 |
| 67 | 156.5 | 1256.5 | 8.0 |
| 68 | 132.5 | 1045 | 7.9 |
| 69 | 138.5 | 1101.5 | 7.9 |
| 70 | 397.5 | 1726 | 4.3 |

*GUS activity expressed as flourescence units/hr/10⁶ protoplasts.

The results show that, with the exception of the pΔ28 construction, all 70 modification of the 77 bp element from the 2-2 promoter are able to impart chemical inducibility to heterologous promoters. It is not known why the pΔ28 construction was not able to respond to treatment with N-(aminocarbonyl)-2-chlorobenzene sulfonamide.

EXAMPLE 21

Figure 25:
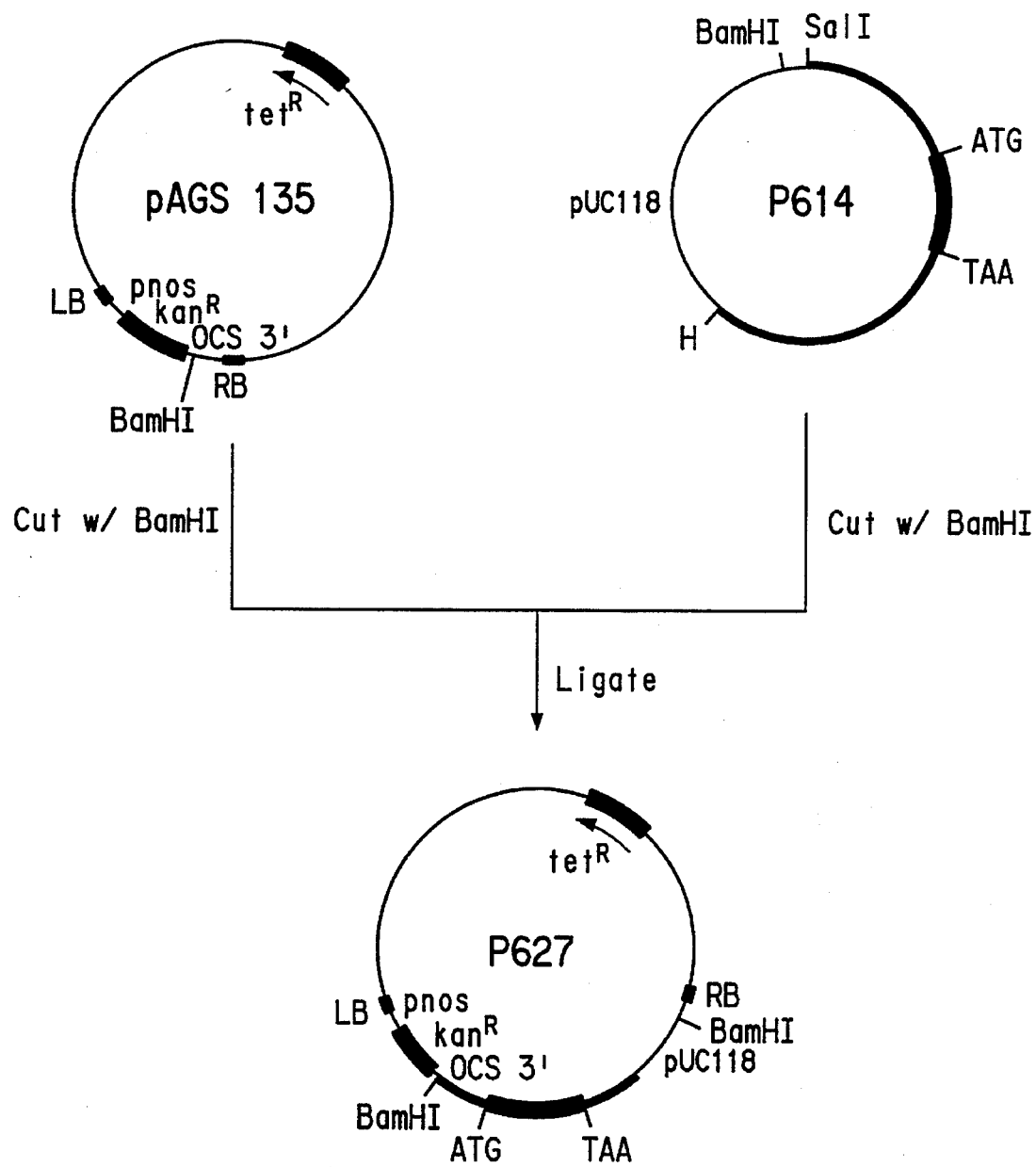
FIG. 25 depicts the creation of plasmid P627.

The Use of
N-(aminocarbonyl)-2-chlorobenzenesulfonamide to
Induce Expression of the Petunia gene P6.1 in
Transgenic Tobacco The 5' and 3' end mapping data in Example 5 showed that the P614 construction contained a 1.3 kb promoter fragment and a 2.2 kb downstream fragment of the petunia P6 gene. The P614 construction was transformed into tobacco to determine both if this petunia DNA fragment included all the elements necessary for chemical induction, and if this petunia gene could be both expressed and chemically induced in a heterologous plant species. Plasmid P614 was linearized with Bam HI site and ligated into the Bam HI site of the binary vector pAGS135. The binary vector pAGS135 used in this example is but one of a large number of binary vectors available that could be used for this purpose. pAGS135 is a cosmid binary vector whose replicon is derived from the broad host range plasmid pRK2 and contains left and right borders fragment from the octopine Ti plasmids pTiA6 and pTiAch5, respectively [van den Elzen et al., Plant Mol. Biol., 5: 149–154 (1985)]. The border fragments delimit the segment of DNA which becomes incorporated into the host plant genome during the process of Agrobacterium-mediated transformation. A chimeric marker gene (consisting of a neomycinphosphotransferase (NPTII) coding region linked to the nopaline synthase promoter and the octopine synthase 3' end) which specifies kanamycin resistance in plant cells is positioned between the left and right border fragments. A unique Bam HI site downstream of the NPTII gene served as a convenient cloning site. The plasmid pAGS135 differs from the plasmid pAGS112 [disclosed in van den Elzen et al., Plant Mol. Bio., 5:149–154 (1985)] in that the Xho I in pAGS112 downstream from the right border has been deleted by digestion of pAGS112 with Xho I and re-circularizing the plasmid by self-ligation after blunting the Xho I 5' overhangs. An aliquot of the ligation mixture was used to transformed E. coli HB101, and transformants were grown on LB containing ampicillin (75 μg/ml) and tetracycline (1 μg/ml). Small scale plasmid preparations were made from antibiotic resistant colonies and digested with to completion with Bam HI to identify the colonies with the desired construction. The orientation of the plasmid P614 in the binary vector (determined by Hind III digests) was such that transcription would proceed towards the right T-DNA border, with puC118 sequences between the end of the petunia gene and the right T-DNA border. This plasmid DNA construction was called P627 (FIG. 25).

Transformation of Tobacco with the Petunia P6.1 Gene

The plasmid P627 was moved into *Agrobacterium tumefaciens* (AL4404/pAL4404) by a triparental mating. Agrobacteria were grown to stationary phase in minimal A medium, while P627 and pRK 2013 (necessary for mobilization of plasmid) were grown for a few hours to logarithmic growth in LB broth. Equal volumes (0.5 ml) of the three strains were concentrated and plated on one LB plate and allowed to grow overnight at 28° C. A loopfull of cells was scraped off the plate and resuspended in 3 ml of 10 mm $MgSO_4$. Serial ten fold dilutions of these cells (in 10 mM $MgSO_4$) were plated on LB containing rifampicin (100 µg/ml) and tetracycline (1 µg/ml) and incubated for 3 days at 28° C. Antibiotic resistant colonies were streaked onto minimal A plates containing 1 µg/ml tetracycline and incubated for 3 days at 28° C.

Tobacco (SR1) was used as the recipient for transformation. In vitro grown leaf material was sliced into strips using a scalpel. The strips were dipped into *Agrobacterium tumefaciens* containing the construct P627 (bacterial concentration was 0.2 $A_{550}$). Leaf pieces were placed on media containing MS major salts, MS minor salts, B5 vitamins, MS iron, 3% sucrose, 0.1 µg/l NAA, 1.0% BA, 0.7% TC agar, pH 5.8 and incubated for 2–3 days under growlights. Leaf material was removed and washed by placing in liquid culture medium containing 500 µg/l cefotaxime and rotating gently for 3–4 hours. The leaf pieces were then placed on medium containing 100 µg/l carbinicillin and 300 mg/l kanamycin and transferred every 2 weeks. Shoots appeared after 2–8 weeks and were transferred to rooting medium (0.5× MS major salts, MS minor salts, iron, 1% sucrose, 0.8% agar, and 2 µM indolebutyric acid). Eight independent transformed plants were regenerated. Plants were transferred to the greenhouse and grown hydroponically in the apparatus described in Example 4 when they became 2–3 inches tall. Two plants that had been regenerated from cell culture, but not transformed were also transferred and included as controls.

Expression of the P6.1 Gene in Transgenic Tobacco

Figure 26:
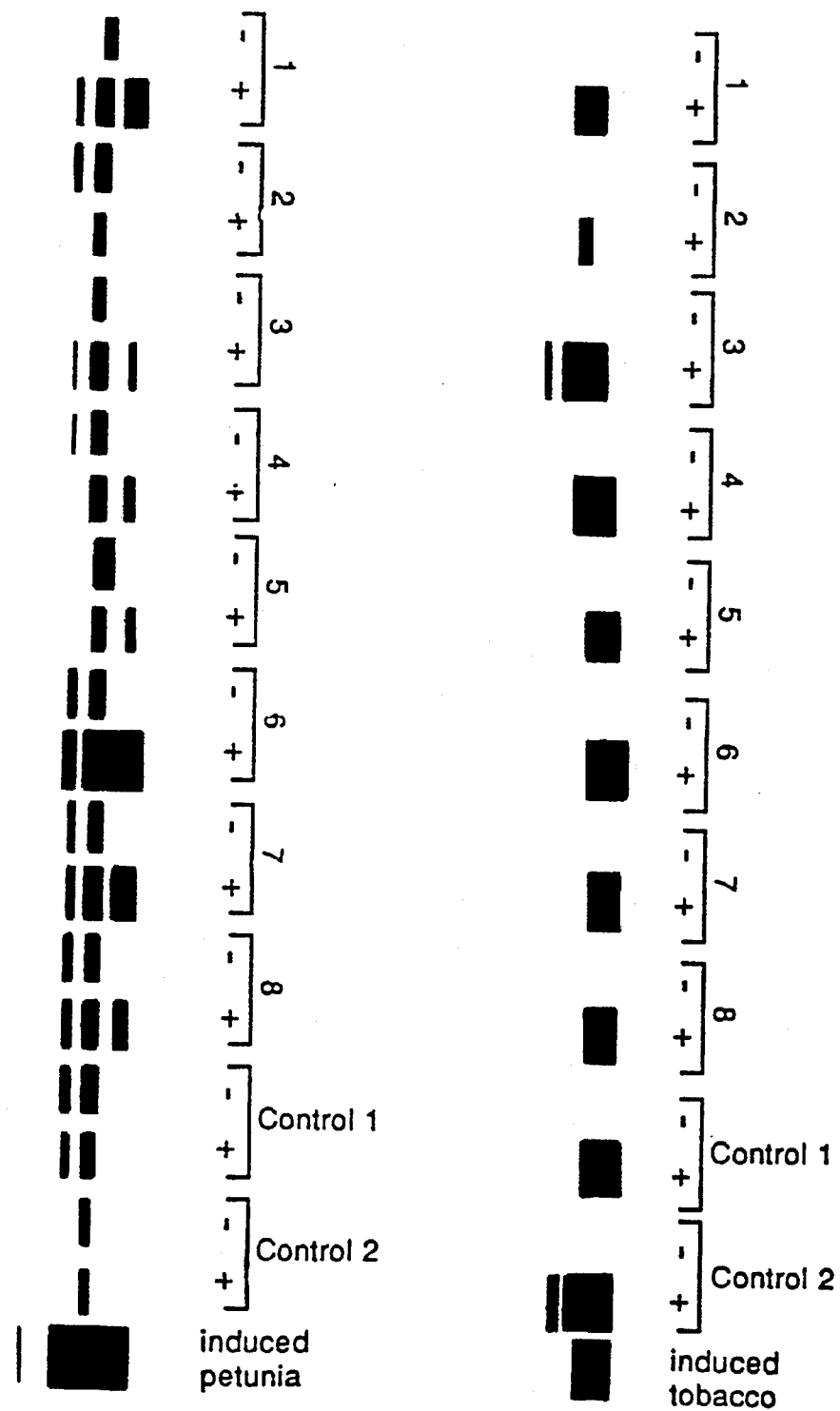
FIG. 26 shows the results of RNAse protection analysis that demonstrates N-(aminocarbonyl)-2-chlorobenzenesulfonamide induction of the P6.1 gene in transgenic tobacco.
Figure 27A:
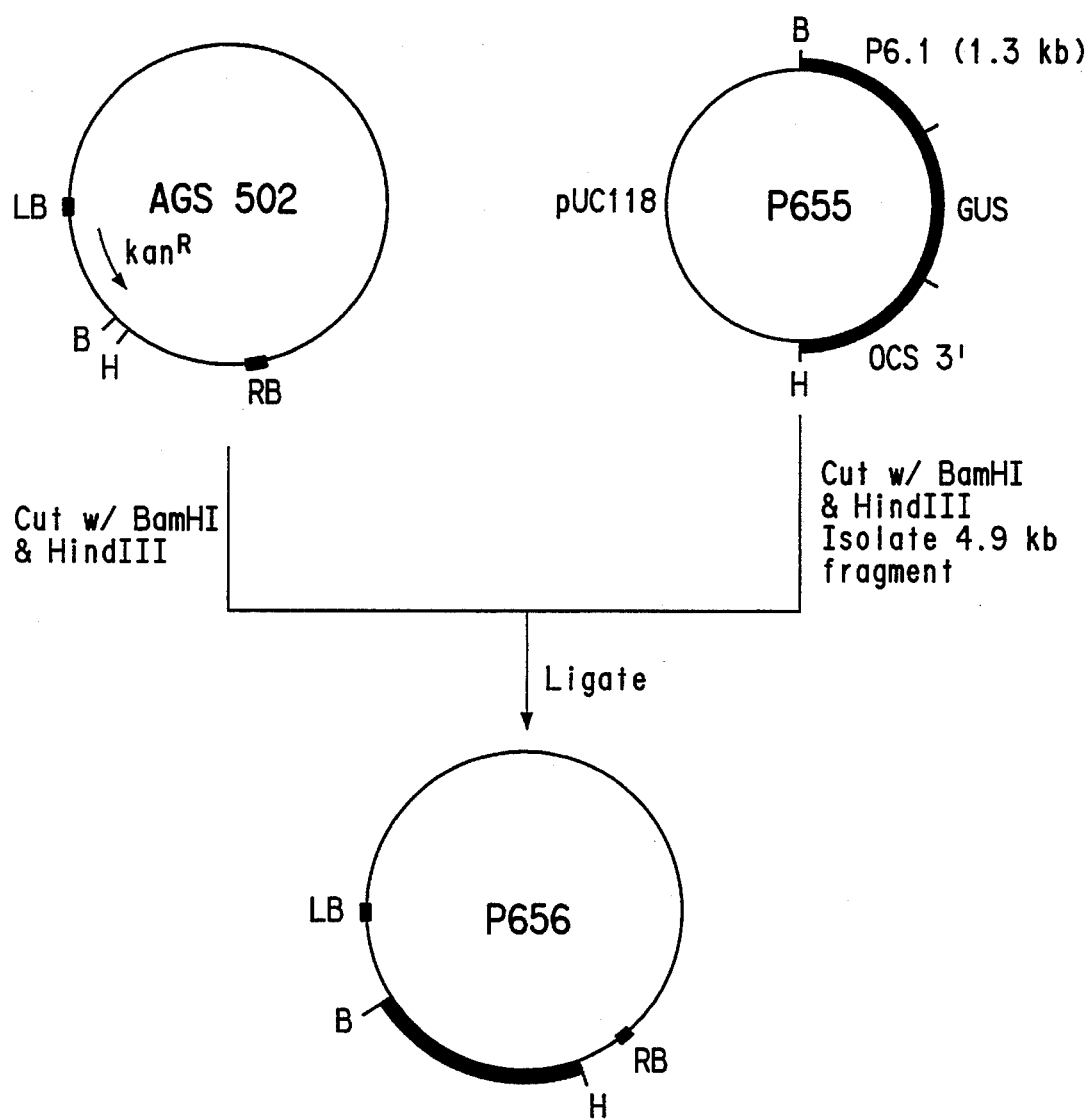
FIG. 27 depicts the creation of plasmids P656, P661, P662 and P663.
Figure 27B:
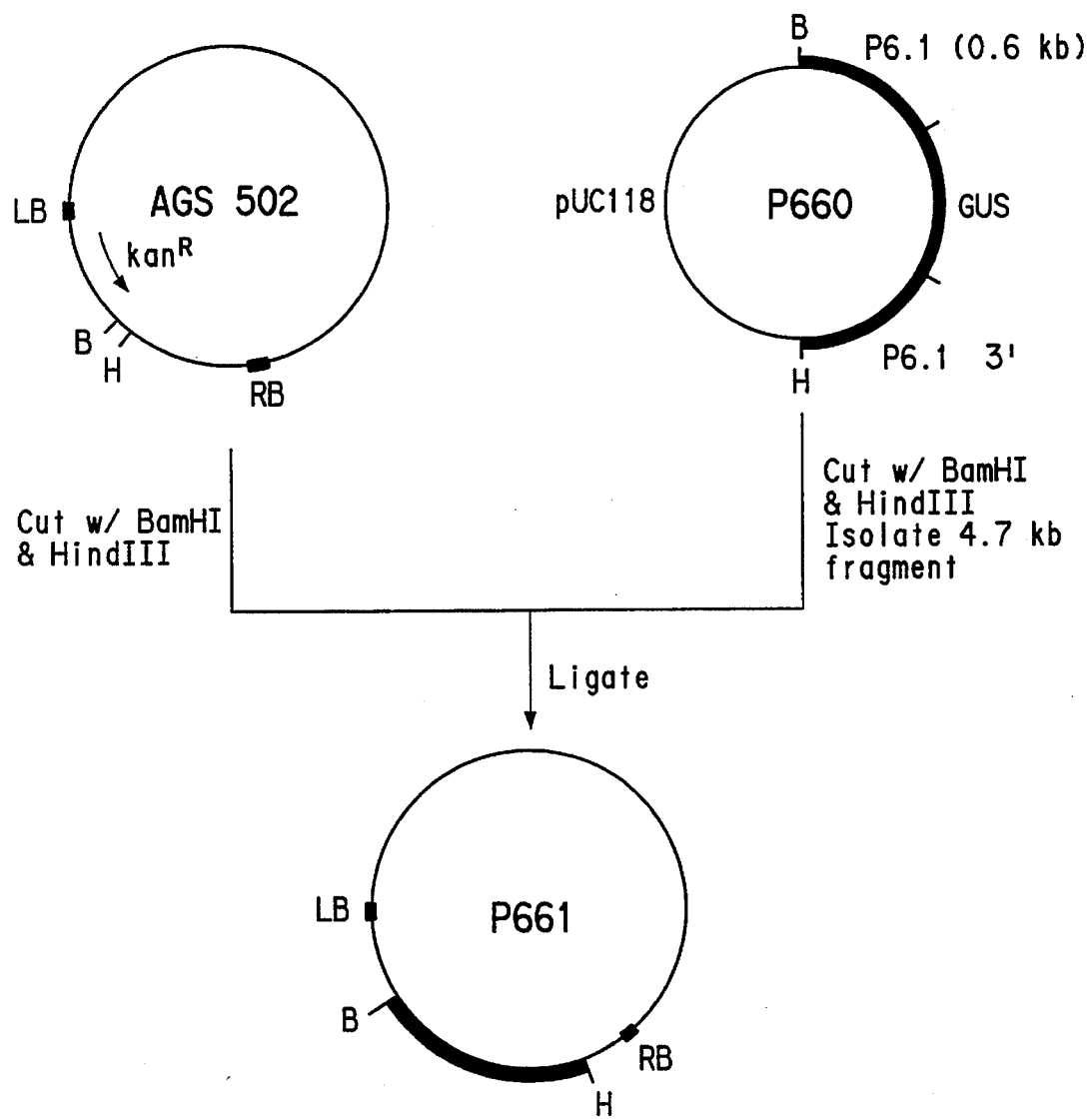
Figure 27C:
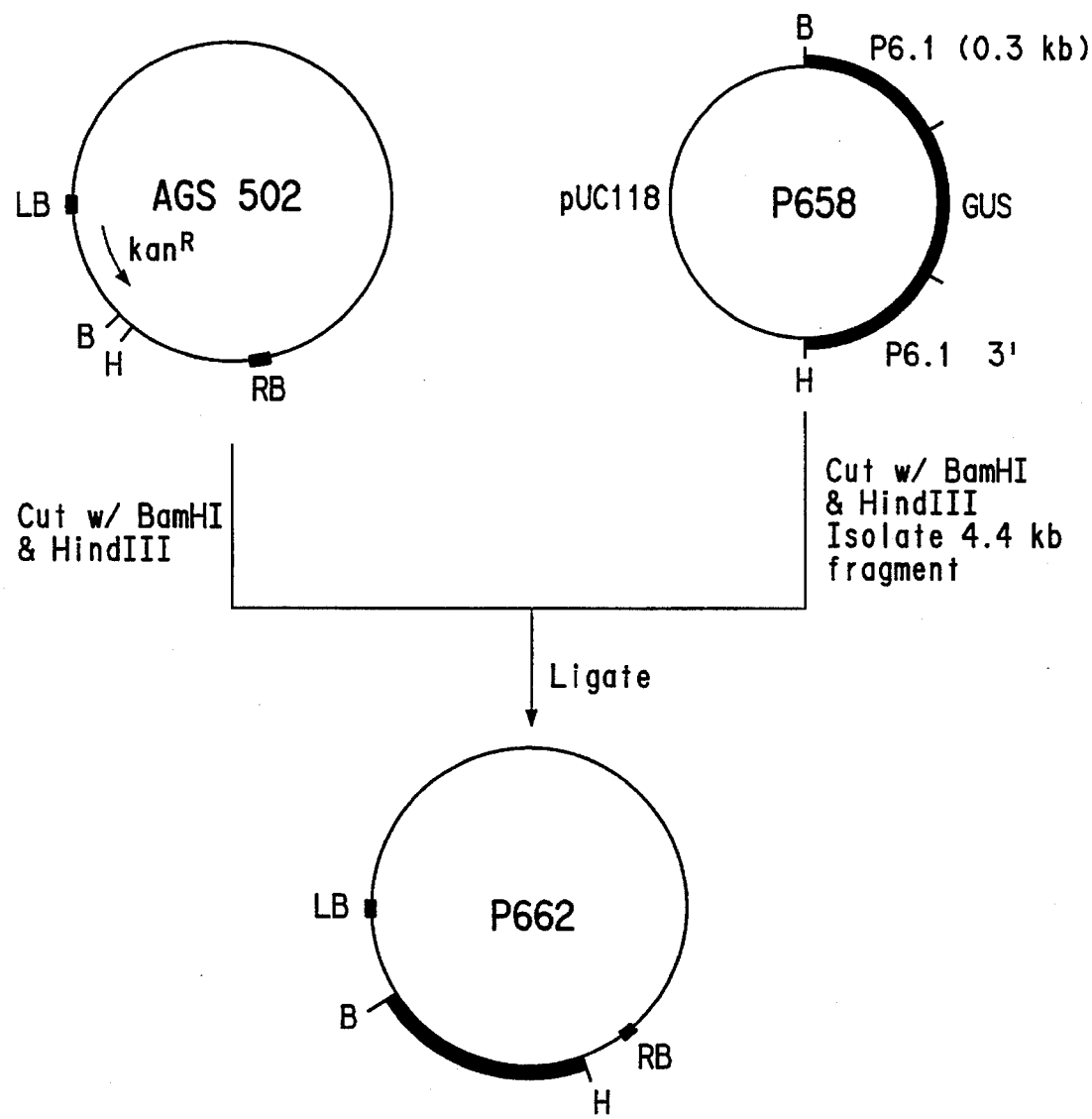
Figure 27D:
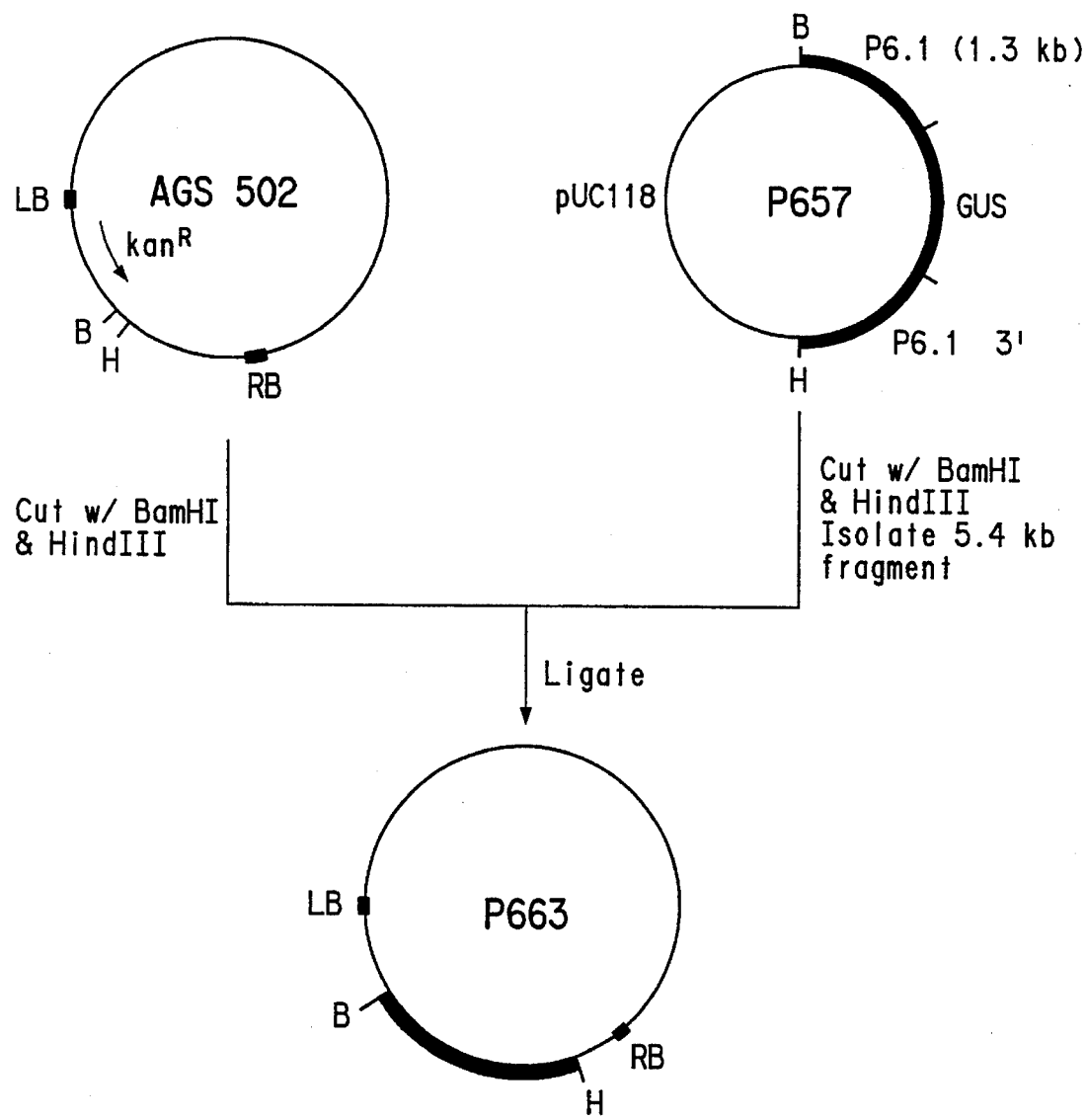

Three weeks following the transfer of transformed and control plants to hydroponics, half the exposed roots extending through the foam plug from each of the plants were harvested and frozen in liquid $N_2$. The plants were then treated hydroponically with 200 mg/l N-(aminocarbonyl)-2-chlorobenzenesulfonamide as described in Example 4. After six hours of chemical treatment, the remainder of the exposed roots were harvested and frozen as above. The plants, in their foam plugs, were transferred to soil in shaded pots in the greenhouse for 2–3 days to let roots still in the foam to grow out. Plants were then transferred to the light and grown to maturity. RNA was prepared from root tissue as described earlier. RNAse protection analysis was then performed as described in Example 4 to determine the inducibility of the transforming P6 petunia gene as well as the endogenous T2 gene in transformed plants. The probe used for this analysis was prepared by digesting the plasmid P611 to completion with Pvu II and synthesizing an RNA probe complementary to the coding strand of the P6.1 mRNA using T3 RNA polymerase. The Pvu II site occurs 150 bp from the 3' end of the Eco RI fragment in P611 and therefore should generate a protected fragment of 150 bp if the introduced petunia gene is expressed in tobacco. All eight transformants demonstrated inducible expression of the transferred gene in their roots (FIG. 26). These results demonstrated that the 4.5 kbp petunia genomic DNA fragment contained all the elements required for induction of the gene by N-(aminocarbonyl)-2-chlorobenzenesulfonamide, and that this inducibility could be transferred to another species.

Expression of the P6.1 Gene in Transgenic Tobacco Callus

The inducibility of the P6.1 gene was also examined in callus tissue derived from transformed tobacco plants. It was felt that if the expression of chemically inducible genes were responsive to chemical stimulation in callus, then testing and selection for callus to be regenerated to whole plants could be accelerated. To this end, leaf tissue from one of the P6.1 tobacco transformants was placed on media that supports callus induction (MS media containing 0.1 µg/l napthalene acetic acid and 0.3 µg/l kinetin). After five weeks, 1–1.5 cm calli had developed. These calli were transferred to liquid media (MS media containing 0.1 µg/l napthalene acetic acid and 0.1 µg/l benzyladenine) and shaken at 28° C. overnight. The next day, pieces of the callus were transferred to MS media, or MS media containing 100 mg/l N-(aminocarbonyl)-2-chlorobenzenesulfonamide and shaken at 28° C. Samples of callus tissue were removed from the flasks at 6 and 20 hours and frozen in liquid $N_2$. RNA was prepared from callus tissue using the procedure described in Example 4. The inducibility of both the introduced petunia P6 gene and the endogenous tobacco T2.1 gene by N-(aminocarbonyl)-2-chlorobenzanesulfonamide treatment was evaluated using the RNAse protection analysis as described above. Both the endogenous tobacco gene and the transforming petunia gene were barely detectable in untreated callus tissue, while strong expression of both genes was observed in N-(aminocarbonyl)-2-chlorobenzenesulfonamide-treated callus. The levels of expression observed for both genes approximated that seen for their expression in the root tissue of intact, chemically treated tobacco plants. It was therefore concluded that the inducibility of foreign genes whose expression is regulated by promoters responsive to substituted benzenesulfonamides is assayable at the level of transformed callus tissue.

EXAMPLE 22

The Use of N-(aminocarbonyl)-2-chlorobenzenesulfonamide to Induce Expression of Recombinant Petunia gene P6.1 promoter/GUS fusions in Trangenic Tobacco Plants Construction of P655

The plasmid P655 was digested to completion with Hind III and Bam HI and the resulting DNA fragments were separated by agarose gel electrophoresis. The 3.9 kbp DNA fragment, containing a recombinant gene consisting of a GUS coding region operably linked to a 1.3 kbp P6.1 promoter fragment and an OCS 3' downstream region, was excised from the gel and recovered by electroelution as described earlier. The DNA was then extracted with an equal volume of phenol:chloroform (1:1 v/v) and ethanol precipitated. The binary vector pAGS502 was digested to completion with Hind III and Bam HI, extracted with an equal volume of phenol:chloroform (1:1 v/v) and ethanol precipitated. Equimolar amounts of vector and the gel purified 3.9 kbp insert were ligated in 10 µl for 4 hours at 15° C. An aliqout of the ligation mixture was used to transform *E. coli* HB101 and aliquots of the resulting transformed cells were plated on LB plates containing 10 µg/ml tetracycline. Small scale plasmid preparations were prepared from tetracycline-resistant colonies and subjected to digestion with Hind III and Bam HI until a colony was found that contained the desired 3.9 kbp DNA fragment in the binary vector pAGS 502. The binary vector pAGS502 used in this example is but one of a large number of binary vectors are available and could be used for this purpose. To make pAGS502, the Eco RI-Hind fragment of pAGS111 [van den Elzen et al., Plant Mol. Biol., 5: 149–154 (1985)] (consisting of a NOS/NPTII/OCS 3' end gene between the left and right T-DNA borders) was rendered blunt and cloned into the blunted Eco RI site of the wide host range plasmid pRK290 [disclosed in Ditta et al., Proc. Natl. Acad. Sci. U.S.A., 77: 7347–7351 (1980)]. The Xho I site downstream from the right border was deleted by digestion with Xho I and re-circularizing the plasmid by self-ligation after blunting the Xho I 5' overhangs. The polylinker sequence 5'-GGATCCTCTAGAAAGCTTC-GAACTCGAGGAATTCGTT-3' was then inserted between the Bam HI-Hpa I sites within the T-DNA borders to create pAGS502. This plasmid construction was designated P656 (FIG. 27).

Construction of P661

The methods used to create the plasmid construction P656 were repeated using the plasmid constructions P658 and pAGS 502 as starting materials. A 4.7 kbp DNA fragment, consisting of a GUS structural gene operably linked to a 600 bp P6.1 promoter fragment and a 2.2 kbp P6.1 3' end fragment, results from digestion of P660 with Hind III and Bam HI. This 4.7 kbp DNA fragment was subcloned into Bam HI/Hind III digested pAGS502 as described above and the resulting plasmid construction was designated P661 (FIG. 27).

Construction of P662

The methods used to create the plasmid construction P656 were repeated using the plasmid construction P658 as the starting material. A 4.4 kbp DNA fragment, consisting of a GUS structural gene operably linked to a 300 bp P6.1 promoter fragment and a 2.2 kbp P6.1 3' end fragment, results from digestion of p658 with Hind III and Dam HI. This 4.4 kbp DNA fragment was subcloned into Bam HI/Hind III digested pAGS502 as described above and the resulting plasmid construction was designated P662 (FIG. 27).

Construction of P663

The methods used to create the plasmid construction P656 were repeated using the plasmid construction P657 and pAGS 502 as the starting materials. A 5.4 kbp DNA fragment, consisting of a GUS structural gene operably linked to a 1.3 kbp P6.1 promoter fragment and a 2.2 kbp P6.1 3' end fragment, results from digestion of P658 with Hind III and Bam HI. This 5.4 kbp DNA fragment was subcloned into Bam HI/Hind III digested pAGS 502 as described above and the resulting plasmid construction was designated P663 (FIG. 27).

Transformation of Tobacco with P661, P662, and P663

The plasmids P656, P662,and P663 were moved into *Agrobacterium tumefasciens* (AL4404/pAL4404) using the triparental mating procedure and tobacco (SR1) leaf pieces were transformed with each of the four chimeric GUS/P6.1 fusions using the procedures described in Example 21.

Induction of GUS Activity by N-(aminocarbonyl)-2-chlorobenzenesulfonamide

A number of regenerated plants that had been transformed with the P661, P662, or P663 constructions were transferred to the hydroponic system described in Example 5. Root tissue was harvested from these hydroponically-grown plants and treated with N-(aminocarbonyl)-2-chlorobenzenesulfonamide as described in Example 14. The root material was then used to make crude protein extracts which were tested for GUS activity. The plants were then transferred to soil in pots and grown to maturity in a greenhouse as described earlier.

Roots were homogenized in ice cold GUS assay buffer (50 mM sodium phosphate pH 7.0, 10 mM DTT, 0.1% Triton X-100, 1 mM EDTA using a Dounce type homogenizer. Cellular debris was then removed by centrifugation. Fluorometric GUS assays were performed using a Perkin-Elmer Fluorescence Spectrophotometer (650-40) set for an excitation wavelength of 365 nm and an emission wavelength of 455 nm. A standard fluorescense vs. MU concentration curve was prepared by diluting 50 µl of various concentrations of MU into 950 µl 0.2M $Na_2CO_3$ and measuring the fluorescence.

GUS activity in root extracts of transformed plants was assayed by adding 15 µl of the substrate (1 mM 4-methyl umbilliferyl glucuronide in assay buffer) to 1 ml of crude root extract and incubating at 37° C. Fluorescence measurements were taken at of 0, 15 and 30 minute time points by adding a measured amount (1 to 50 µl) of the GUS reaction to 1 ml 0.2M $Na_2CO_3$ and measuring the fluorescence of the MU generated in the GUS reaction. Protein concentrations in the crude root extracts were determined by Bradford protein assays. From 10 to 20 µl of root extract were; added to 1 ml of Bradford Assay Stain (10 µg/ml Coomassie Brilliant Blue G in 8.5% phosphoric acid) and the absorbance of the samples was measured at 595 nm. A protein concentration vs. absorbance curve was prepared using BSA as a protein standard. GUS activity in each root extract was standardized to protein concentration and expressed as GUS activity per microgram protein.

The results of one such analysis are shown in Table 10. A number of plants transformed with the P661, P662, and P663 constructions show induction of GUS activity following treatment with N-(aminocarbonyl)-2-chlorobenzenesulfonamide. The variability seen in the expression of the chimeric GUS gene is commonly seen when testing primary transformants for the expression of a transforming gene.

TABLE 10

N-(aminocarbonyl)-2-chlorobenzenesulfonamide Inducible GUS Expression in Tobacco Plants Transformed with Petunia P6 Promotor/Gus Constructions

| Plant # | Promoter Size (in bp) | GUS ACTIVITY (FU/µg-min) | | Fold Induction |
|---|---|---|---|---|
| | | Uninduced | Induced | |
| P663/1 | 1300 | 7.4 | 13.6 | 1.8 |
| P663/10 | 1300 | 3.1 | 8.9 | 2.9 |
| P663/11 | 1300 | 6.7 | 21.0 | 3.1 |
| P663/17 | 1300 | 8.5 | 44.9 | 5.3 |
| P663/36 | 1300 | 31.5 | 31.2 | 1.0 |
| P663/81 | 600 | 45.8 | 102.1 | 2.2 |
| P661/105 | 600 | 4.3 | 7.0 | 1.6 |
| P662/44 | 300 | 2.2 | 7.8 | 3.5 |
| P662/55 | 300 | 25.8 | 76.6 | 3.0 |
| P662/65 | 300 | 2.9 | 5.1 | 1.7 |

EXAMPLE 23

The Use of
N-(aminocarbonyl)-2-chlorobenzenesulfonamide to
Induce Expression of Recombinant Corn 2-1
Promoter/GUS Gene Constructions in Trangenic
Tobacco

Construction of pJE518 and pJE519

Figure 28A:
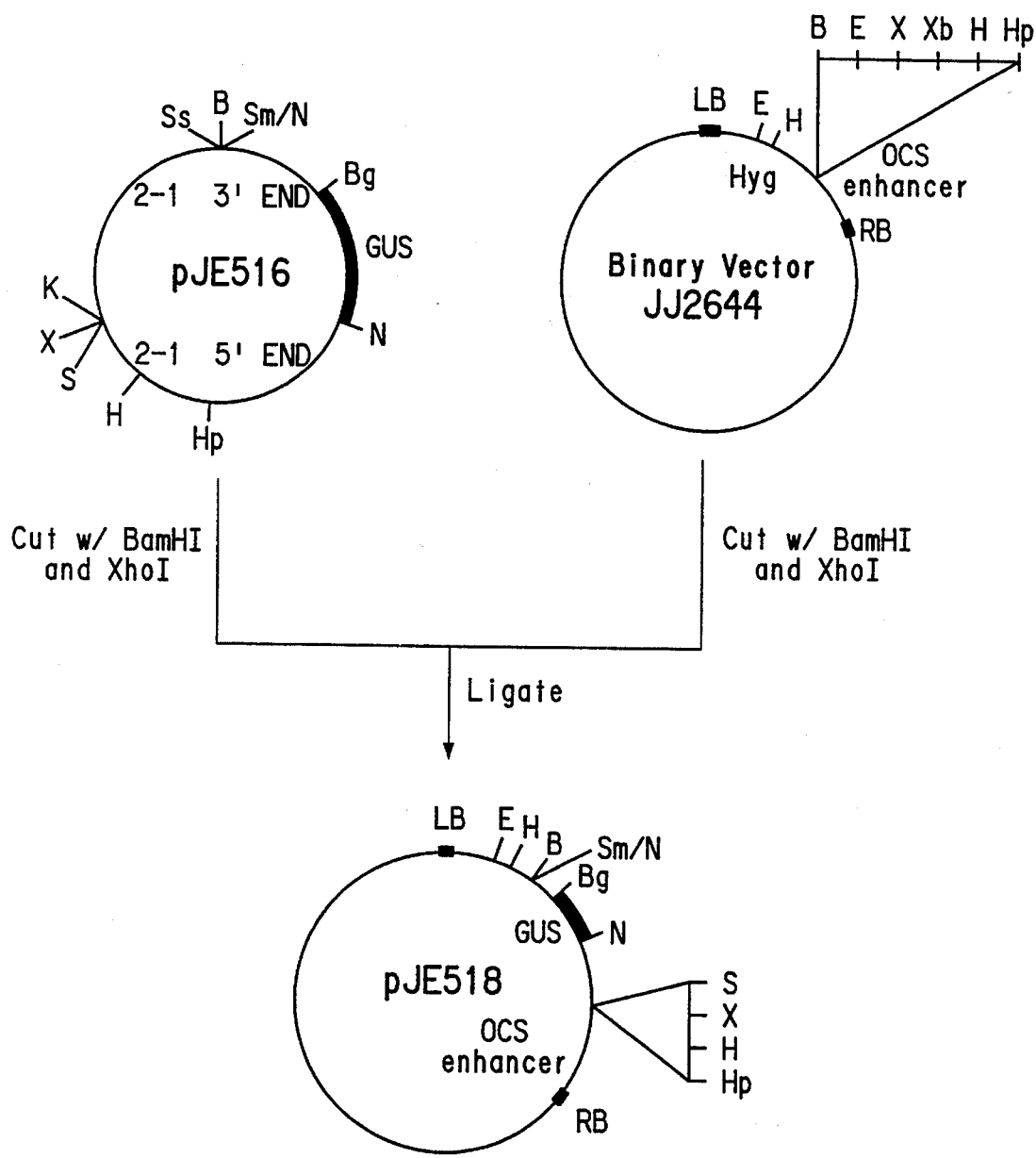
FIG. 28 depicts the creation of plasmid pJE518 and pJE519.

The recombinant 2-1/GUS gene contained in plasmid pJE516 was stably introduced into tobacco by Agrobacterium mediated transformation. The plasmid pJE516 was digested to completion with Bam HI and Xho I and the resulting 6.0 kbp DNA fragment consisting of a 3 kbp 2-1 promoter fragment/GUS/1.1 kbp of 2-1 gene 3' downstream fragment was gel purified. This purified 6 kb Bam HI/Xho I fragment from pJE516 was then ligated into the Bam HI/Xho I site of the binary vector pJJ 2644. The binary vector pJJ2644 is but one of a large number of binary vectors that are available and may be used ill this example. It was derived from the broad host range vector pRK2 and contains a hygromycin resistance gene (HYG) under control of the Agrobacterium 1',2' promoter and nopaline synthase 3' end between the left and right T-DNA borders. The HYG gene specifies hygromycin resistance in transformed plants. A polylinker sequence was inserted downstream from the HYG gene to provide a set of unique restriction site for cloning. The Xho I site downstream of the T-DNA right border was removed as described earlier for the vector pAGS502. The resulting plasmid was designated pJE518 (FIG. 28).

The plasmid pJE 516 was also digested to completion with Bam HI and Hpa I. This excised a 4.5 kbp DNA fragment from the vector consisting of a 1.5 kb 2-1 promoter fragment/GUS/1.1 kbp of 2-1 gene 3' downstream fragment fusion, This fragment was gel purified and ligated into the Bam HI/Hpa I site of pJJ 2644 to create the plasmid pJE519 (FIG. 28). These two plasmid construction were used to transform tobacco (Petite Havanna).

Transformation of Tobacco

The constructs in pJE518 and pJE519 were mobilized from *E. coli* HB101 into *Agrobacterium tumefaciens* in order to perform tobacco transformation. Fresh cultures of Agrobacterium AL4404 harboring plasmid pAL4404 were grown in Minimal A media (10.5 g $K_2PO_4$, 4.5 g $KH_2PO_4$, µg $(NH_4)_2SO_4$, 0.5 g $NaCitrate.2H_2O$, 1 ml 1M $MgSO_4.7H_2O$, 10 ml 20% glucose, water to 1 l). *E. coli* HB101 harboring plasmid pRK 2013, and *E. coli* HB101 strains harboring the plasmids to be mobilized (pJE518 and pJE519) were grown overnight in L broth. Equal numbers of each type of cells were mixed together, plated on LB plates, are allowed to grow at 28° C. overnight. A loop full of the resulting bacteria was suspended in 10 mm $MgSO_4$, plated at $10^0$, $10^{-2}$ and $10^{-4}$ dilutions on LB plates with 100 µg/ml rifampicin, 1 µg/ml tetracycline and allowed to grow at 28° C. for 2–3 days. Single colonies growing on these plates were streaked on minimal A plates (minimal A media plus 1% agar) containing 1 µg/ml tetracycline. Overnight liquid cultures were grown from these streaked colonies in minimal A at 28° C.

Leaves were taken from 3–4 inch tall tobacco plants (Petit Havana) that had been grown in Magenta boxes and cut crosswise into approximately 5 mm wide strips using a surgical scalpel. The strips were then dipped briefly into the agrobacterium overnight culture and placed on bacterial cocultivation plates. Bacterial cocultivation plates contain MS salts (1.9 g/l $KNO_3$, 1.65 g/l $NH_4NO_3$, 0.44 g/l $CaCl_2.2H_2O$, 0.37 g/l $MgSO_4.7H_2O$, 0.17 g/l $KH_2PO_4$, 10.3 mg/l $ZnSO_4.7H_2O$, 16.9 mg/l $MnSO_4.H_2O$, 6.2 mg/l $H_3BO_3$, 0.84 mg/l KI, 0.2 5 mg/l $Na_2MoO_4.2H_2O$, 0.025 µg/l $CuSO_4.5H_2O$, 0.025 mg/l $COCl_2.6H_2O$, 37.2 µg/l $Na_2EDTA.2H_2O$, 27.8 µg/l $FeSO_4.7H_2O$), B5 vitamins (1 µg/l nicotinic acid, 10 µg/l thiamine HCl, 1 µg/l pyridoxine HCl, 100 µg/l myo-inositol), 0.59 g/l MES, 30 g/l sucrose, 8 g/l agar, 0.1 µg/l napthaleneacetic acid, and 1 µg/l benzyladenine.

After incubation at 27° C. with 16 hour days/8 hour nights for three days, bacteria were washed from the leaves by shaking them for 3 hours with liquid MS (same media as used in bacterial co-cultivation plates, but without agar) containing 500 µg/l cefotaxime. The leaf pieces were then placed on MS medium containing 100 µg/l vancomycin and 30 µg/l hygromycin and incubated at 27° C. and incubated under the same conditions described above. Shoots began to appear after about one month. These shoots were transferred to MS media containing 1 µM indolebutyric acid and 30 µg/l hygromycin when they were about 1 cm tall. Plantlets were moved to Magenta boxes (containing the same media), and allowed to grow to 2–3 inches tall before being moved to hydroponics.

Induction of GUS Activity by N-(aminocarbonyl)-2-chlorobenzenesulfonamide

Seven plants transformed with the pJE518 construction and five plants transformed with the pJE519 construction were transferred to the hydroponic system described in Example 4. These transformants were grown hydroponically until they had developed sufficient root mass to allow removal of small samples without destroying the plants. At this point approximately one-third of the root material from each plant was harvested and frozen in liquid nitrogen. The plants were then moved to trays containing 0.5× Hoagland's solution with 200 mg/l N-(aminocarbonyl)-2-chlorobenzenesulfonamide. After 6 hours of incubation in the presence of the chemical, another one-third of the root material was harvested from each plant. Root material was used to make crude protein extracts which were tested for GUS activity. Plants were then transferred to soil in pots and grown to maturity in a greenhouse.

Root material was homogenized in ice cold GUS assay buffer (50 mM sodium phosphate pH 7.0, 10 mM DTT, 0.1% Triton X-100, 1 mM EDTA using a Polytron (Brinkmann Instruments) GUS activity in roots was then measured after 0, 1, 2, and 4 hours as described in Example 15.

The results of this analysis are shown in Table 11. A number of plants transformed with the pJE 518 and the pJE519 construction show up to a 13 fold induction of GUS activity following treatment with N-(aminocarbonyl)-2-chlorobenzenesulfonamide. The variability seen in the expression of the recombinant 2-1 promoter/GUS construction is commonly seen when testing primary transformants for the expression of a transforming gene. The plants showing the highest level of responsiveness to chemical treatment were both self-fertilized and backcrossed to Petite Havana tobacco. Seeds resulting from backcrosses of a number of these plants were germinated and grown in Magenta boxes with a hygromycin selection. After a root structure formed on each plant, root pieces of each were excised and incubated overnight on rooting media with or without N-(aminocarbonyl)-2-chlorobenzenesulfonamide. GUS assays were performed on extracts of these roots on the following day. The results of this assay are given in Table 12. Roots from the progeny of the backcrosses show N-(aminocarbonyl)-2-chlorobenzenesulfonamide inducible GUS activity, with two plants transformed with the pJE519 construction showing a ten-fold induction. Additional progeny of these crosses will be tested for the inducibility of the recombinant GUS gene in response to the both hydroponic and foliar application of N-(aminocarbonyl)-2-chlorobenzenesulfonamide.

TABLE 11

N-(aminocarbonyl)-2-chlorobenzenesulfonamide Inducible GUS Expression in Tobacco Plants Transformed with 2-1 Promoter/ Gus Constructions

| Plant # | GUS ACTIVITY (FU/µg-min) | | Fold Induction |
|---|---|---|---|
| | Uninduced* | Induced* | |
| A. Transgenic plants containing pJE518 construction | | | |
| 518-1 | 1.0 | 1.9 | 1.9 |
| 518-2 | 1.2 | 1.8 | 1.5 |
| 518-3 | 0.67 | 8.9 | 13.0 |
| 518-4 | 2.9 | 5.5 | 1.9 |
| 518-5 | 0.72 | 0.24 | 0.33 |
| 518-6 | 0.74 | 2.4 | 3.2 |
| 518-7 | 0.67 | 5.0 | 7.5 |
| B. Transgenic plants containing pJE519 construction | | | |
| 519-1 | 0.75 | 1.8 | 2.4 |
| 519-2 | 0.70 | 1.1 | 1.5 |
| 519-3 | 0.41 | 1.3 | 3.2 |
| 519-4 | 1.56 | 7.2 | 4.6 |
| 519-5 | 0.39 | 3.9 | 10.0 |

*Induction in Table 7 was accomplished by hydroponic treatment transformed plants with 200 mg/l of N-(aminocarbonyl)-2-chlorobenzenesulfonamide

TABLE 12

GUS Assays for Backcross Progeny
GUS Activity (FU/mg-min)

| Plant | Cross | −Inducer | +Inducer | Fold Induction | Fold Induction of Parent |
|---|---|---|---|---|---|
| 801-3 | 518.2 × Petite Havana | 1.04 | 4.4 | 4.2 | 1.5 |
| 801-4 | 518.2 × Petite Havana | 1.03 | 5.3 | 5.1 | 1.5 |
| 802-5 | 5.8.6 × Petite Havana | 1.39 | 7.9 | 5.7 | 3.2 |
| 802-6 | 5.8.6 × Petite Havana | 1.46 | 4.8 | 3.3 | 3.2 |
| 803-5 | 519.3 × Petite Havana | 0.20 | 2.0 | 10 | 3.2 |
| 803-6 | 519.3 × Petite Havana | 0.16 | 1.5 | 9.4 | 3.2 |

EXAMPLE 24

The Use of N-(aminocarbonyl)-2-chlorobenzenesulfonamide to Induce Expression of Recombinant Genes Under the Control of the Corn 2-2 Promoter in Transgenic Tobacco Construction of pJE573. pJE578-1 and pJE578-8

The chimeric 2-2/GUS gene contained in plasmid pTDS130 was stably introduced into tobacco by agrobacterium mediated transformation. The plasmid pTDS130 was digested to completion with Xba I and the resulting 4.3 kbp DNA fragment consisting of a 1.2 kbp 2-2 promoter fragment/GUS/1.1 kbp of 2-1 gene 3' downstream fragment was gel purified. This purified 4.5 kbp Xba I fragment from pJE516 was then ligated into the binary vector pAGS502 to yield the plasmid pJE573.

The plasmid pTDS130 was also digested to completion with Bam HI and the 3.4 kbp DNA fragment consisting of a 0.45 kbp 2-1 promoter fragment/GUS/1.1 kbp of 2-1 gene 3' downstream fragment from pJE516 was then ligated into the binary vector pAGS502 to yield the plasmids pJE578-1 and pJE578-8. These two plasmids represent each of the two possible orientations of the 2-2 recombinant constructions in the binary vector.

Construction of pDuPU3

The chimeric 2-2/HRA gene contained in plasmid pDuPS22 was digested with Kpn I and Sal I and the resulting 4.3 kbp DNA fragment consisting of a 0.45 kbp 2-2 promoter fragment/HRA/1.1 kbp of 2-1 gene 3' downstream fragment was gel purified. This purified fragment from pDuPS22 pDuPS22 was then ligated into the binary vector pZS96 to yield the plasmid pDuPU3.

Transformation of Plants

Mobilization of the constructs in pJE573, pJE578-1 and pJE578-8 from E. coli (strain HB101) into Agrobacterium tumefaciens, transformation of SR1 tobacco leaf disks, and regeneration of plants were performed as described in Example 23.

The recombinant ALS gene in pDuPU3 was mobilized from E. coli HB101 into Agrobacterium tumefaciens strain LBA4404 by a triparental mating. E. coli HB101 containing the plasmid pRK2013 was used as a helper for plasmid mobilization matings. Bacterial strains HB101 containing pDUPU3, HB101 with pRK2013, and LBA4404 were grown overnight in 5 ml of LB broth with appropriate selective antibiotics. Bacteria were harvested by centrifugation at 4000× g for 10 minutes at 22° C. and resuspended in 5 ml LB broth. Matings were performed by mixing 100 ul of each culture in a 1.5 ml microfuge tube and pipetting aliquots of the mixture onto sterile Millipore type HA nitrocellulose disks. Disks were placed on 6–8 sheets of sterile Whatman #1 filter paper to remove excess liquid from cultures and then transferred to LB agar in 100 mm petri dishes. After incubation for approximately 16 hours at 30° C., bacteria were washed from the nitrocellulose discs into sterile 4 ml polypropylene culture tube using 1 ml of 10 mM $MgSO_4$. The bacteria were serially diluted and various dilutions were plated onto LB agar plates containing 100 ug/ml each of rifampacin and ampicillin and incubated at 30° C. Small scale plasmid preparations made from resistant colonies were analyzed for the presence of the desired insert DNA by Southern blot analysis of Ti plasmids.

Transformation of Plants

Constructions were introduced into the planks via *Agrobacterium tumefaciens* infection of tobacco leaf disks. Standard aseptic techniques for the manipulation of sterile media and axenic plant/bacterial cultures were followed, including the use of a laminar flow rood for all transfers. Potted tobacco plants for leak disk infections were grown in a growth chamber maintained for a 12 hour, 24° C. day, 12 hour, 20° C. night cycle, at 80% relative humidity, under mixed cool white fluorescent and incandescent lights. Tobacco leaf disk infections were carried out essentially by the method of Horsch et al. (Horsch, R. B., Fry, J. E., Hoffman, N. L., Eichholtz, D., Rogers, S. G., and Fraley, R. T. (1985) Science 227, 1229–1231).

Young 4–6 inch partially expanded leaves were harvested with a scalpel from 4–6 week old plants. The leaves were surface sterilized for 30 minutes by submerging them in approximately 500 ml of a 10% Clorox, 0.1% SDS solution and then rinsing 3 times with sterile deionized water. Leaf disks were then prepared using a sterile paper 6 mm punch and they were inoculated by submerging them for several minutes in 20 ml of a 1:10 dilution of an overnight LB broth culture of Agrobacteria carrying the plasmid of interest. After inoculation, leaf disks were placed in petri dishes containing CN agar medium (MS salts (Gibco) 30 gm sucrose, 8 gm agar, 0.1 ml of 1 mg/ml NAA, and 1 ml of 1 mg/ml BAP per liter, pH 5.8). The plates were sealed with parafilm and incubated under mixed fluorescent and "Gro and Sho" plant lights (General Electric) for 2–3 days in a culture room maintained at approximately 25° C.

Leaf disks were transferred to fresh CN medium containing 500 mg/L cefotaxime and 100 mg/L kanamycin. The disks were incubated under the growth conditions described above for 3 weeks and then transferred to fresh media of the same composition. Approximately 1–2 weeks later shoots which developed on kanamycin-selected explants were excised with a sterile scalpel and planted in A medium (MS salts (Gibco), 10 gm sucrose, and 8 gm agar per liter) containing 100 mg/L kanamycin. Shoots which rooted were transferred to soil and grown in a growth chamber as described above.

Induction of GUS Activity In Plant Transformed with B-glucoronidase Gene Constructions Plants transformed with the JE573, pJE578-1 and pJE578-8 constructions were grown hydroponically, treated with 200 mg/l N-(aminocarbonyl)-2-chlorobenzene and assayed for the induction of GUS activity as described in Example 23.

The results of this analysis are shown in Table 13. A number of plants transformed with the JE573, pJE578-1 and pJE578-8 constructions display the induction of GUS activity following treatment with N-(aminocarbonyl)-2-chlorobenzenesulfonamide. The variability seen in the expression of the chimeric GUS gene is commonly seen when testing primary transformants for the expression of a transforming gene. The plants showing the highest level of response to chemical treatment have been selfed, and progeny of these selfs will be tested for stability of the gene and the inducibility of the chimeric GUS gene in response to the foliar application of inducing compounds.

TABLE 13

| Plant I.D. | GUS Specific Activity (Fu/µg protein/min) | Fold Induction | X Progeny Segregation Kan-R/Kan-S | # of loci |
|---|---|---|---|---|
| CONSTRUCT 573 | | | | |
| −inducer | | | | |
| 4 | 0.54 | 1.12 | 2.1 | 90/11 | 2 |
| 5 | 1.25 | 3.62 | 2.9 | 39/16 | 1 |
| 6 | 0.50 | 3.06 | 6.1 | 102/4 | 3 |
| 8 | 0.45 | 1.76 | 4.0 | 38/13 | 1 |
| 9 | 0.016 | 0.128 | 8.0 | 0/50 | 0* |
| 10 | 3.73 | 5.34 | 1.4 | 100/18 | 2 |
| 11 | 0.42 | 1.40 | 3.3 | 36/3 | 2 |
| 12 | 0.35 | 1.54 | 4.4 | 63/6 | 2 |
| CONSTRUCT 578-1 | | | | |
| +inducer | | | | |
| 13 | 0.006 | 0.003 | 1 | 41/22 | 1 |
| 14 | 0.003 | 0.003 | 1 | NA | NA |
| 19 | 0.094 | 0.128 | 1.4 | 118/4 | >2 |
| 27 | 0.062 | 0.127 | 2 | 45/19 | 1 |
| 32 | 0.272 | 1.445 | 5.3 | 53/24 | 1 |
| 35 | 0.004 | 0.002 | 1 | NA | NA |
| 37 | 0.018 | 0.145 | 8.3 | 52/16 | 1 |
| CONSTRUCT 578-8 | | | | |
| +inducer | | | | |
| 6A | 1.86 | 6.19 | 3.3 | 46/14 | 1 |
| 6B | 1.18 | 2.73 | 2.3 | 80/35 | 1 |
| 7 | 0.79 | 1.80 | 2.3 | 125/0 | >2 |
| 9 | 1.45 | 4.20 | 2.9 | NA | NA |
| 10 | 4.83 | 6.25 | 1.3 | 121/8 | 2 |

Induction of Herbicide-Resistant ALS in Plants Transformed With pDuPS22

Plants transformed with the pDuPS22 construction were grown in soil for three weeks and two upper leaves were harvested from each plant. One leaf was placed into a beaker containing 0.5× Hoagland's solution such that the bottom 2 cm of the cut end of the leaf was submerged in liquid. The second leaf was placed in a beaker containing 0.5× Hoagland's containing 200 mg/l N-(aminocarbonyl)-2 chlorobenzenesulfonamide. Leaves were then incubated in the growth chamber for 16–24 hours and divided in half. One half was analyzed for the expression of ALS mRNA, while the other was analyzed for the expression of sensitive and herbicide resistant ALS enzyme levels.

The expression of stable cytoplasmic mRNA transcribed from the wild type and transforming ALS genes in transformed plants were measured by RNAse protection analysis. In this manner, expression of the pDuPS22 construction was distinguished from the wild type ALS genes by virtue of the fact that the pDUPS22 transcript has a 2-2 untranslated leader that is divergent from the untranslated leader of the native ALS genes. To this end, the Eco RI/Nco I fragment of the tobacco SurB ALS gene that spans the region from 133 bp 5' to the SurB translation start site to 348 bp beyond the SurB translation start was cloned in to the vector pTS64 to create the plasmid designated pTSNTC (the isolation of the wild type SurB gene is taught in European Patent application number 0257993, and a herbicide-resistant SurB gene is available from ATCC as accession number 67124 and may be substituted for the wild-type SurB gene to obtain the same result.) The plasmid pTS64 was prepared by digesting the plasmid pSP64 (Promega Biotech, Inc.) to completion with Bam HI and ligating the vector with synthetic double stranded oligonucleotide of the sequence

```
5'-GATCTATCGATCCATGGTCTAGAAAA-3'
   3'-ATACGTAGGTACCAGATCTTTT-5'.
```

The ligation mixture was then heated to 65° C. for 10 min. and digested to completion with Xba I. The digestion mixture was heated to 65° C. for 10 min. again and subjected to ligation with T4 DNA ligase overnight. Following transformation of the ligation mixture into competent *E. coli* DH5, a colony was identified that contained desired sequence

```
5'-GATCTATCGATCCATGGT-3'
   3'-ATACGTAGGTACCAGATC-5'
``` encoding a Cla I site and an Nco I site inserted into the pSP64 polylinker.

A 520 b $^{32}$P-labelled antisense ALS RNA probe was prepared from Eco RI linearized pTSNTC using SP6 polymerase in the presence of $\alpha$-$^{32}$P dCTP with a kit by following the manufacturer's recommended protocol. Hybridization of wild type ALS mRNA to this 520 b $^{32}$P-labelled antisense RNA should protect 410 b of the probe, while hybridization to the pDUPS22 transcript should protect only 348 bp of the probe corresponding to the region 3' to the translation start site of the pDuPS22 mRNA.

RNAse protection assays were carried out using the protocol of Zinn et al. (Zinn et al. Cell (1983) 34, 865–879). Labelled antisense strand RNA was annealed to total PNA from either wild type tobacco plants or to 10 µg of total RNA from plants transformed with the pDuPS22 construction. The sizes of the labelled RNA fragments remaining after digestion with RNAse T1 and RNAse A were determined by electrophoresis using 6% denaturing polyacrylamide gels. Results of such analyses showed that N-(aminocarbonyl)-2 chlorobenzenesulfonamide treatment of plants transformed with the pDuPS22 2-2 promoter/HRA recombinant gene resulted in the induction of high levels of stable cytoplasmic HRA mRNA.

As a preliminary test of the inducibility of the sulfonylurea-resistant ALS gene, several small leaves were excised from each of sixteen kanamycin-resistant shoots, sliced into 2–3 mm pieces, and placed on callus induction medium that consisted of MS salts, 100 mg/L i-inositol, 0.4 mg/L thiamine, 3% sucrose, 1 mg/L NAA, 0.2 mg/L BAP, 0.8% agar, 500 mg/L cefotaxime, pH 5.8 containing either 10 ppb chlorsulfuron, 10 ppb chlorsulfuron+100 ppm D5293, N-(aminocarbonyl)-2-chlorobenzenesulfonamide 100 ppm D5293, or no selective agent. Callus formation was scored as plus or minus after three weeks of growth. Results are summarized below:

| | |
|---|---|
| No Selection | 16/16 formed callus |
| 10 ppb Chlorsulfuron | 12/16 formed callus |
| 10 ppb Chlorsulfuron + 100 ppm D5293 | 0/16 formed callus |
| 100 ppm D5293 | 0/16 formed callus |

Protein extracts were prepared from leaves of a number of kanamycin resistant planks that were treated with N-(aminocarbonyl)-2 chlorobenzenesulfonamide and assayed for ALS enzyme activity as described by Chaleff and Mauvais [Chaleff R. C. and Mauvais C. J. (1984) Acetolactate synthase is the site of action of two sulfonylurea herbicides in higher plants. Science 224:1443–1445]. The reaction product, acetoin, was quantified by measuring optical density at 530 nm [Westerfield WW (1945) A colorometric determination of blood acetoin. J. Biol. Chem. 161:495–502]. For each extract, replicate enzyme assays were performed reactions either with no herbicide or 100 ppb chlorsulfuron. The average ALS activity in the presence of chlorsulfuron, expressed as a percentage of the total average ALS activity measured in the absence of herbicide, is presented in Table 14.

These results show that two of the seven plants showed increases in the level of chlorsulfuron-resistant ALS following chemical treatment. It should be noted that there is a well documented biological mechanism that keeps the ALS specific activity fixed in tobacco. Therefore, even though all plants tested showed induction of herbicide-resistant ALS mRNA, the inability to increase the total ALS activity in leaves is to be expected. Those plants showing near 100% resistant ALS activity when uninduced represent plants where sufficient expression of the resistant ALS gene was obtained in the absence of chemical treatment to yield significant amounts of resistant enzyme. The level of gene expression in untreated plants transformed with genes driven by the 2-2 promoter is a position effect, and is seen to vary dramatically from undetectable to very high level, both with 2-2/ALS and 2-2/GUS gene constructions. It is expected that a number of plants with no uninduced ALS activity will be found when a larger population of 2-2/ALS transformants is studied.

TABLE 14

| Plant | OD 530 -- No Herbicide | OD530 -- 100 ppb Chlorsulfuron | % Uninhibited Activity |
|---|---|---|---|
| Untransformed | | | |
| Untreated | 0.204 | 0.010 | 5 |
| Treated with D5293 | 0.267 | 0.034 | 13 |
| Transformant #44B | | | |
| Untreated | 0.333 | 0.306 | 92 |
| Treated with D5293 | 0.385 | 0.365 | 95 |
| Transformant #53A | | | |
| Untreated | 0.244 | 0.251 | 103 |
| Treated with D5293 | 0.331 | 0.312 | 94 |
| Transformant #61A | | | |
| Untreated | 0.376 | 0.347 | 92 |
| Treated with D5293 | 0.912 | 0.901 | 99 |
| Transformant #63A | | | |
| Untreated | 0.457 | 0.178 | 39 |
| Treated with D5293 | 0.835 | 0.732 | 88 |
| Transformant #74C | | | |
| Untreated | 0.859 | 0.822 | 96 |
| Treated with D5293 | 0.400 | 0.408 | 102 |
| Transformant #79A | | | |
| Untreated | 0.492 | 0.309 | 63 |
| Treated with D5293 | 0.366 | 0.325 | 89 |

TABLE 14-continued

| Plant | OD 530 -- No Herbicide | OD530 -- 100 ppb Chlorsulfuron | % Uninhibited Activity |
|---|---|---|---|
| Transformant #93A | | | |
| Untreated | 0.324 | 0.313 | 97 |
| Treated with D5293 | 0.989 | 1.003 | 101 |

EXAMPLE 25

The Use of N-(aminocarbonyl)-2-chlorobenzenesulfonamide to Induce Expression of a Recombinant 2-1 Promoter/GUS Construction in Transgenic Brassica Standard aseptic techniques for the manipulation of sterile media and axenic plant/bacterial cultures were followed, including the use of a laminar flow hood for all transfers.

Seeds of *Brassica napus* cv. Westar were sterilized by soaking in 70% ethanol for three minutes followed by a 20 min treatment in 20% v/v bleach (sodium hypochlorite). The seeds were rinsed in sterile distilled water three times and planted at a density of nine seeds per Magenta box on seed germination media (Germination media: MS (Murashige and Skoog) salts, 1% sucrose, 3 mM MES buffer, and 0.8% Hazleton TC agar). Seeds were germinated at 24° C. using a 16 h light/8 h dark photoperiod with a light intensity of 4000 lux. After five days, the hypocotyls from the germinated seedlings were excised and cut into sections ranging in length from 0.5 to 1.0 cm.

Single colonies from freshly streaked plates of *A. tumefaciens* strain LBA4404 containing pJE519 (Example 23) were grown overnight in minimal A medium (10.5 g/l $K_2HPO_4$, 4.5 g/l $KH_2PO_4$, 1.0 g/l $(NH)_2SO_4$, 0.5 g/l Na citrate $2H_2O$, to 990 ml; autoclave and add sterile solutions are added; 1 ml of 1M $MgSO_4$, 10 ml of 20% glucose. The host strain LBA4404 is rifampicin resistant and the introduced binary plasmid specifies bacterial tetracycline resistance.

The agrobacterium suspensions were diluted in hormone-free plant media (MS salts, Gamborg's B5 vitamins, 3% sucrose, 3 mM MES buffer, pH 5.8) to a concentration of $2.8 \times 10^8$ cfu/ml using the optical density of the culture at 550 to estimate the bacterial concentration.

The hypocotyl sections were individually dipped in the agrobacterium suspension and then placed onto sterile Whatman #1 filter paper which had been placed on top of callus regeneration media (MS salts, B5 vitamins, 3% sucrose, 3 mM MES buffer, 0.2 mg/l 2,4-D, 3 mg/l kinetin, 0.8% Hazleton TC agar). The hypocotyl sections were then cocultivated with Agrogribacterium for two flays using the same temperature and light conditions used for the seed germination. No feeder layers were used. The cocultivation was terminated by transferring the hypocotyl sections to petri plates with liquid callusing medium with 500 mg/l cefotaxime and 200 mg/l vancomycin and gently swirling the plates for about five hours.

The hypocotyl sections were transferred to solid callusing medium with 500 mg/l cefotaxime but no selective antibiotics for four days to ensure that the agrobacteria were killed and that the transformed cells could recover from the agrobacterium infection before selection was applied. On the fourth day, the hypocotyl sections were transferred to callusing media with 500 mg/l carbenicillin (Geopen) and 20 mg/l hygromycin B as the selective antibiotic. The light and temperature regime was the same as that used for seed germination. After 24 days on selection, green transformed calli could be seen growing from 60% of the cut ends of the hypocotyl sections. The negative controls for the transformation, consisting of hypocotyl sections not exposed to Agrobacterium, showed no green callus growth on media with selective antibiotic.

After 30 days, the calli were large enough (1 to 3 mm) to be excised from the hypocotyl sections. The excised hypocotyls were transferred to regeneration medium IT-15 (MS salts, B5 vitamins, 3% sucrose, 3 mM MES buffer, 2.5 mM IBA, 15 mM Dropp (thidiazeron), 0.2% Gel-rite, pH 5.8; supplemented with 500 mg/l Geopen, 20 mg/l hygromycin B). This medium supports healthy callus growth and rapid regeneration of shoots from non-selected hypocotyl sections. The transformed calli are currently being tested on this media for rapid organogenesis.

Plants will be regenerated from calli when their diameters have reached at least 0.5 cm by transferring them to KR medium containing 500 mg/l Geopen and 20 mg/l hygromycin. KR medium consists of K3 major salts (35 mM $KNO_3$, 1 mM $(NH_4)_2SO_4$, 1 mM $MgSO_4$, 1.5 mM $KH_2PO_4$, 3.1 mM $NH_4HO_3$, $CaCl_2$ added to 6.3 mM after autoclaving MS micronutrients, B5 vitamins, 1% sucrose, 0.025% xylose, 3 mM MES buffer, 0.1 mg/l IAA, 2 mg/l zeatin, 0.25% low EEO agarose, pH 5.7). At two week intervals, the outer layers of the calli will be trimmed off with a scalpel and they will be transferred to fresh media. When shoots have regenerated from the calli, they will be cut away from the callus and transferred to Magenta boxes containing rooting medium (0.5× MS salts, MS micronutrients B5 vitamins, 1% sucrose, 3 mM MES buffer, 0.8% TC agar, pH 5.8) containing 500 mg/l Geopen. If shoots become vitrified, the lids of the boxes will be raised slightly and the opening sealed with Micropore tape to allow ethylene to escape.

The regenerated transformants will be transferred to hydroponics, grown, and treated with N-(aminocarbonyl)-2-chlorobenzenesulfonamide as described in Example 23. It is expected that Brassica plants transformed with the pJE519 construction will show the induction of both GUS mRNA and GUS enzyme activity upon chemical treatment.

EXAMPLE 26

Induction of the 2-1, 2-2, and 5-2 corn genes in vivo by Various Chemical Compounds The ability at various substituted benzenesulfonamides and related compound to induce the expression of the 2-1, 2-2, and 5-2 genes of Missouri 17 corn was evaluated. Corn seeds were germinated and grown hydroponically in 2 liter beakers as described in Example 1. On the tenth day, plants were transferred into fresh 0.5× Hoagland's solution containing the chemical to be tested. Root tissue was harvested from the plants after six hours of chemical treatment, quick-frozen by immersion in liquid $N_2$, and stored at $-80°$ C. until analyzed.

Slot Blot Analysis of RNA from Chemically Treated Corn Plants

Details of the RNA isolation and slot blot analysis procedures are presented in Example 1. Total RNA was prepared from the root tissue of plants that had been treated with various chemicals using the previously described guanidine thiocyanate procedure. Replicate blots, each consisting of 2 μg of total RNA from tissues treated with each of the chemicals shown in tables 8 and 9, were prepared on nitrocellulose membranes using a Minifold II® Slot-blotter (Schleicher & Schuell) following the manufacturer's recommeneded procedure. Replicate blots were prehybridized and hybridized with cDNA probes made by nick translation of the purified cDNA inserts from plasmid pIn 2-1, pIn 2-2-3, and pIn 5-2. Slot blots were washed as described in Example 1 and exposed to Kodak X-OMAT XAR-5 film for 24 hours at −80° C. using a single Du Pont Lightning Plus intensifying screen. Film was developed using a Kodak X-OMAT film processor. The abililty of a chemical to induce the mRNA encoded by the three inducible genes was evaluated in one of two ways. Qualitative evaluation was performed by direct visual comparison of the autoradiographic signal intensities on the films for the hybridization of each probe to the different RNA samples. Quantitative evaluation was performed by cutting each slot containing hybridized RNA from the blot, immersing it in 2 ml of Du Pont ECONOFLUOR® scintillation cocktail and counting the radioactivity in each slot in a scintillation counter. The net amount of radioactivity hybridizing to N-(aminocarbonyl)-2-chlorobenzenesulfonamide-treated RNA after subtraction of radioactivity hybridizing to untreated RNA is presented in Table 15.

TABLE 15

| Compound* | In 2-1 | In 2-2 | In 5-2 |
|---|---|---|---|
| 1 | 204 | 332 | 47 |
| 2 | 111 | 270 | 58 |
| 3 | 70 | 260 | 61 |
| 4 | 295 | 237 | 76 |
| 5 | 296 | 136 | 59 |
| 6 | 244 | 135 | 53 |
| 7 | 251 | 129 | 72 |
| 8 | 173 | 124 | 47 |
| 9 | 53 | 110 | 33 |
| 10 | 203 | 94 | 63 |
| 11 | 102 | 70 | 36 |
| 12 | 49 | 8 | 14 |
| 13 | 60 | 1 | 55 |

*The names of the compounds tested for induction of the 2-1, 2-2 and 5-2 promoters in corn roots are listed below. All compounds were used at a concentration of 200 mg/l.
1. diethyl [[2-[(butylaminocarbonyl)aminosulfonyl]phenyl]]-phosphonate
2. N'-[2-(n-butylaminocarbonyl)]-6-chloro-N,N-dimethyl-1,2-benzene-disulfonamide
3. N-isopropylcarbamoylbenzenesulfonamide
4. 2-chloro-N-(methylaminocarbonyl)benzenesulfonamide
5. N-(aminocarbonyl)-2-chlorobenzenesulfonamide
6. 1-cyclohexyl-3-methylsulfonylurea
7. 1-butyl-3-methylsulfonylurea
8. 2-chloro-N-[[3-(2-ethoxyethoxy)propyl]aminocarbonyl]-benzenesulfonamide
9. 2,3-dichloro-N-[(cyclopropylamino)carbonyl]benzene-sulfonamide
10. methyl 2-[(aminocarbonyl)aminosulfonyl]benzoate
11. N-(aminocarbonyl)-2,3-dichlorobenzensulfonamide
12. 2,3-dichloro-N-[(cyclopentylamino)carbonyl]-benzenesulfonamide
13. N-(aminocarbonyl)-4-(1,1-dimethylethyl)-2-nitrobenzene-sulfonamide The responsiveness of the 2-1, 2-2 and 5-2 genes of Missouri 17 corn to hydroponic application of plant hormones and various chemical compounds associated with plant stress was examined. In addition, the responsiveness of the corn genes to stress stimuli was also examined. The results are summarized in Table 16.

TABLE 16

|  | In2-1 | In2-2 | In5-2 |
|---|---|---|---|
| PLANT HORMONES |  |  |  |
| Abscisic acid (100 ppm) | + | − | − |
| 6-Benzyladenine (benzyl amino purine) (100 ppm) | ++ | − | − |
| 2,4-dichlorophenoxyacetic acid (100 ppm) | +++ | + | − |
| Gibberellic acid (100 ppm) | − | − | − |
| Indole acetic acid (100 ppm) | +++ | + | n/a |
| Indole butyric acid (100 ppm) | ++ | + | n/a |
| Naphthaleneacetic acid (100 ppm) | + | − | − |
| p-chlorophenoxyacetic acid (100 ppm) | ++ | ++ | + |
| STRESS STIMULATION |  |  |  |
| Acetylsalicylic acid (200 ppm) | ++ | ++ | ++ |
| NaCl (100 mm) | − | − | − |
| Proline (20 mm) | − | − | − |
| Salicylic acid (200 ppm) | + | + | + |
| Salicylamide (200 ppm) | ++ | − | − |
| Urea (100 mm) | − | − | − |

A maximum induction level is represented by "++++". This was correlated to the level of induction routinely observed with 100 ppm N-Aminocarbonyl-2-chlorobenzenesulfonamide as the inducing compound.

EXAMPLE 27

Response of a Recombinant Gene Whose Expression is Controlled by a 2-2 corn promoter to substituted benzenesulfonamides and Structurally Related Compounds in Transformed Rice Protoplasts The ability of various substituted benzenesulfonamides and related compounds to induce the expression of recombinant genes consisting of a GUS coding region driven by regulatory sequence derived from the 2-2 corn gene was evaluated in transformed rice protoplasts. Details concerning establishing rice suspension cultures, isolation and transformation of protoplasts, and the assay of GUS activity were described in Example 14.

Rice protoplasts were transformed with the recombinant DNA construction pTDS133 and then treated with different compounds at a concentration of 100 μg/l as described in Example 10. Table 17 summarizes the results of two such analyses. A number of substituted benzenesulfonamides tested demonstrated the ability to induce GUS activity in transformed protoplasts, with N'-[2-(n-butylaminocarbonyl)]-6-chloro-N,N-dimethyl-1,2--benzenedisulfonamide being most active.

In this example, the ability of the various substituted benzenesulfonamides to induce the expression of a recombinant 2-2 promoter/GUS construction in transformed rice protoplasts is shown to correlate with the ability of the same compounds to induce the expression of the endogenous 2-1 and 2-2 genes in hydroponically grown Missouri 17 corn (Example 17). This indicates that the rice protoplast transient assay system is a valuable predictive method for determining the ability of a chemical to induce genes whose expression is regulated by promoters that are inducible by substituted bezenesulfonamides and related compounds in whole plants.

TABLE 17

| COMPOUND | Assay 1 | Assay 2 | Assay 3 | AVE. INDUCTION |
|---|---|---|---|---|
| 1 | 0 | 0 | | 0 |
| 2 | 1 | 1 | | 1 |
| 3 | 7.67 | N/A | | 7.67 |
| 4 | 29.8 | N/A | | 29.8 |
| 5 | 8.7 | 6.8 | 43 | 7.75 |
| 6 | N/A | 4 | | 4 |
| 7 | 8.9 | 5.4 | | 7.15 |
| 8 | 27 | 14.5 | | 20.75 |
| 9 | 7.4 | 11.2 | | 9.3 |
| 10 | N/A | 1.6 | | 1.6 |
| 11 | N/A | 3.6 | | 3.6 |
| 12 | N/A | N/A | 17 | 17 |
| 13 | N/A | N/A | 16 | 16 |
| 14 | N/A | N/A | 27.3 | 27.3 |
| 15 | N/A | N/A | 24.1 | 24 |
| 16 | N/A | N/A | 30.2 | 30 |
| 17 | N/A | N/A | 16.6 | 16.6 |
| 18 | N/A | N/A | 1.6 | 1.6 |
| 19 | N/A | N/A | 5.2 | 5.2 |
| 20 | N/A | N/A | 38.6 | 38.6 |
| 21 | N/A | N/A | 24.2 | 24.2 |

The chemical names of the compounds tested for induction of the 2-2 promoter/GUS fusion are listed below:

1. NO DNA 2. 35S-GUS control 3. methyl 2-[(aminocarbonyl)aminosulfonyl]benzoate

4. N'-butylaminocarbonyl-6-chloro-N,N-dimethyl-1,2-benzenedisulfonamide

5. N-(aminocarbonyl)-2-chlorobenzenesulfonamide

6. N-(aminocarbonyl)-4-(1,1-Dimethylethyl)-2-nitrobenzenesulfonamide

7. N-(aminocarbonyl)-2,3-dichlorobenzenesulfonamide 8. 2,3-dichloro-N-[(cyclopentylamino)carbonyl]benzenesulfonamide 9. 2-chloro-N-(methylaminocarbonyl)benzenesulfonamide 10. α-[(1,3-dioxolan-2-yl-methoxy)-imino]-benzeneacetonitrile 11. phenylmethyl 2-chloro-4-(trifluoromethyl)-5-thiazolecarboxylate 12. methyl 3-[(butylaminocarbonyl)-aminosulfonyl]-2-thiophenecarboxylate 13. methyl 2-[[(butylamino)aminosulfonyl]-6-chlorobenzoate 14. methyl 3-[(butylaminocarbonyl)aminosulfonyl]-2-furancarboxylate 15. N-[(butylamino)carbonyl]-3-methyl-2-propylsulfonyl-benzenesulfonamide 16. N'-[(butylamino)carbonyl]-N-methyl-N-(1,1,2,2-tetrafluoroethyl)-1,2-benzenedisulfonamide 17. 2-methoxy-6-methyl-N-(methylaminocarbonyl)benzenesulfonamide 18. N,N-dimethyl-2-[(aminocarbonyl)aminosulfonyl]-3-pyridine carboxamide 19. N-(butylaminocarbonyl)-4-chloro-3-pyridinesulfonamide 20. N-(propylaminocarbonyl)-2-pyridinesulfonamide 21. 2,6-dichloro-N-[(1,1-dimethyl)aminocarbonyl]-3-pyridinesulfonamide

EXAMPLE 28

Induction of the Petunia P6 Gene and the Tobacco T2 Gene by Salicylic Acid

Petunia and tobacco plants were grown as described in Example 5 and treated hydroponically with either 200 mg/l of N-(aminocarbonyl)-2-chlorobenzenesulfonamide or 100 mg/l of salicylic acid for 2, 4, 6 and 22 hours. Total RNA was isolated from the roots of treated plants and analyzed for the expression of PG mRNA by RNAse protection as described in Example 4. P6 RNA was detectable by 2 hours following N-(aminocarbonyl)-2-chlorobenzenesulfonamide treatment and reached maximum levels by 6 hours. However, maximal levels of P6 RNA were seen by 2 hours following salicylic acid treatment, and this level declined to that seen in untreated plants by 6 hr. This result may suggest a different mode of action for the chemicals.

UTILITY

The promoters shown in FIGS. 2, 4, 5 and 7 are useful for regulating the expression of structural genes operably linked to plant promoters derived from the genes in response to the external application of compounds of the Formulae I–IX. Regulation of genes is achieved by application of the compounds of formulae I–IX to transgenic plants containing chimetic genes consisting of structural genes encoding a gene product to be regulated operably linked to promoters described in figures XX-YY and their derivatives.

A number of methods are available for application of the inducing compounds described herein. The inducer may be applied directly to the crop seed. The seeds may be uniformly coated with the inducer according to standard seed treating procedures prior to planting. Alternatively, the inducer may be applied over the exposed seeds in open furrows at planting, just prior to covering the seed with soil (in-the-furrow treatment). The inducer may be applied post-emergence at the specific time that expression of the desired gene(s) is appropriate. Post emergent application may be directed so that the inducer is primarily applied to the crop. The amount of inducer will vary depending on the specific inducer and the method of application used. The crop species and cultural practices may also have an effect.

It is expected that regulating the temporal expression of genes responsible for a number of plank traits will be agronomically beneficial in transgenic plants. Examples of traits include herbicide resistance where limiting a plant's resistance to a class of herbicide(s) by controlling the expression of a gene conferring herbicide resistance would be beneficial. In this manner, unwanted volunteer plants germinating in the field as a result of seed lost during the harvest could be easily eliminated if the inducing gene were left unactivated. Examples of such herbicide resistance genes include resistant forms of the acetolactate synthase gene (sulfonylurea herbicide resistance), the 5-enolpyruvylshikimate-3-phosphate synthase gene (glyphosata resistance), and the BAR gene (encoding Basta resistance).

Controlling the expression of genes conferring pathogen and insect resistance would also be of agronomic benefit. By limiting the expression of these resistance genes to the times in the pest's life cycle when infestation occurs, one would limit the rate of appearance of resistance to the gene product in the pest population by limiting the expression of the resistance genes to short periods of time. Restricting the expression of resistance genes to relatively short times during the growth cycle of the plant may well minimize any yield penalty associated with constitutive expression of the desired gene. Examples of such genes include any of genes encoding *Bacillus thurengensis* insecticidal endotoxins, chitinase genes, protease inhibitor genes, genes encoding nematode resistance and so on. In addition by using recombinant, chemically inducible promoters one may be able to express a pest toxin in only affected tissues and prevent their expression in portion(s) of the plant to be used as foodstuffs.

Chemically regulating the expression of genes involved in pytohormone biosynthesis in transgenic plants may have agricultural benefit. For example, chemical induction of 1-amino-cyclopropane-1-carboxylic acid synthase genes just prior to harvest may accelerate fruit ripening as a harvest aid by providing a burst of ethylene synthesis immediately prior to harvest. Similarly, regulating the expression of other genes involved in the biosynthesis of other phytohormones such as cytokinins, auxins, gibberellins, and abscisic acid to control hormone levels in field grown plants may prove to have great agricultural utility.

There would be substantial agronomic benefit in regulating the expression of a great number of plant traits if one knew which gene(s) encode the protein(s) responsible for these traits. As these genes and their products are discovered, regulating their expression by external chemical control may well have agronomic value. In this manner, yield penalties associated with constitutive expression of a trait that may be needed for a relatively short period of time, can be minimized. Examples of such genes and traits are drought resistance genes, salt tolerance genes, pathogen resistance genes, and so on.

By expressing genes for degradative enzymes in specific plants tissues just prior to harvest, one may be able to reduce the processing costs associate with converting raw plant materials to useable forms. Examples include the expression α-amylase in rice seeds just prior to harvest to reduce processing costs for the brewing industry, increasing the yield of sucrose in sugarbeets by expression of just prior to harvest, improving the nutritional quality of soybeans by reducing raffinose and raffinosaccharides in by expression of high levels of α-galactosidase in seeds just prior to harvest, expression of ligninase in plant tissues used by the pulp and paper industries.

What is claimed is:

1. A nucleic acid promoter fragment from the 5' flanking promoter region of a plant gene inducible by compounds of formula I–IX, wherein I–IX are defined as the following:

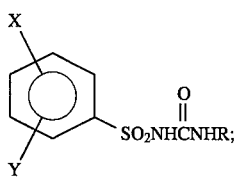   I

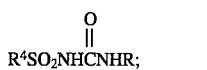   II

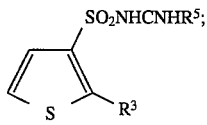   III

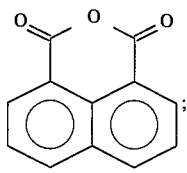   IV

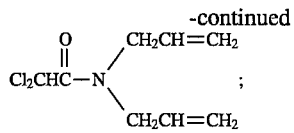   V

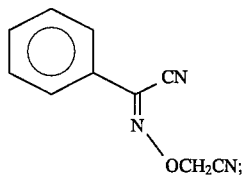   VI

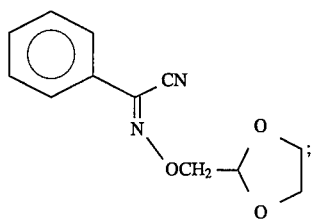   VII

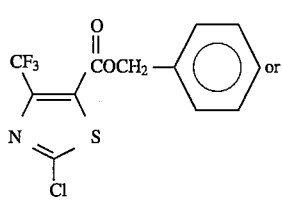   VIII

-continued

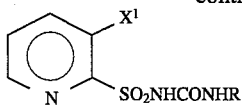

IX wherein
X is H, F, Cl, Br CF$_3$, or C$_1$–C$_2$ alkyl;
X$^1$ is H, F, Cl, C$_1$–C$_2$ alkyl, SO$_2$NR$^1$R$^2$ or CO$_2$R$^1$;
Y is H, Cl or SO$_2$NR$^1$R$^2$, CO$_2$R$^1$, NO$_2$, (P(O)(OR$^1$)$_2$;
R is H, C$_1$–C$_6$ alkyl, C$_3$–C$_6$ cycloalkyl, benzyl or C$_2$–C$_4$ haloalkyl or C$_2$–C$_4$ substituted with C$_1$–C$_2$ alkoxy or C$_1$–C$_2$ alkylthio;
R$^1$ is C$_1$–C$_3$ alkyl;
R$^2$ is C$_1$–C$_3$ alkyl;
R$^3$ is CO$_2$R$_2$;
R$^4$ is C$_1$–C$_6$ alkyl or C$_3$–C$_6$ cycloalkyl;
R$^5$ is C$_1$–C$_3$ alkoxy or NR$^6$R$^7$;
R$^6$ is H, OCH$_3$, C$_1$–C$_4$ alkyl, C$_3$–C$_6$ cycloalkyl, C$_1$–C$_4$ alkyl substituted with C$_1$–C$_2$ alkoxy or ethoxyethoxy; and
R$^7$ is H or C$_1$–C$_2$ alkyl;
and agriculturally suitable salts thereof; which when denatured, immobilized to a solid support membrane and hybridized to the promoter region from the gene encoding the cDNA clone 5-2 deposited with the American Type Culture Collection (ATCC) and given the ATCC accession number 67804, and washed at 65° C. with an aqueous solution of 0.1× SSC and 0.1% SDS shows a detectable autoradiographic signal after 24 hours of exposure of the solid support to X-ray film of 24 hours at −80° C.

2. A nucleic acid promoter fragment of claim 1 comprising a nucleotide sequence from the 5' flanking promoter region of a plant gene corresponding to cDNA clone 5-2 deposited with the American Type Culture Collection (ATCC) and given the ATCC accession number 67804, such that exposure of plants transformed with said promoter fragment to a compound of Formula I–IX causes increased expression of a DNA sequence coding for a selected gene product operably linked 3' to said promoter fragment.

3. A nucleic acid promoter fragment of claim 2 wherein said compound of formulae I–IX is a compound selected from the group consisting of 2-chloro-N-(methylaminocarbonyl)benzenesulfonamide, 1-(n-butyl)-3-methylsulfonylurea, methyl 2-[(aminocarbonyl)aminosulfonyl]benzoate, N-isopropylcarbamoylbenzenesulfonamide, N-(aminocarbonyl)-2-chlorobenzenesulfonamide and N'-[2-(n-butylaminocarbonyl)]-6-chloro-N,N-dimethyl-1,2-benzenedisulfonamide.

4. A nucleic acid promoter fragment of claim 3 wherein said compound of Formula I–IX is 2-chloro-N-(methylaminocarbonyl)benzenesulfonamide.

5. A nucleic acid promoter fragment of claim 1 comprising the nucleotide sequence of 889 base pairs running in the 5' to 3' direction from base pair position 1 to base pair position 889 as shown in FIG. 5.

6. A recombinant DNA construct, capable of transforming a plant, comprising a nucleic acid promoter fragment of any one of claims 1–4 or 5, a DNA sequence coding for a selected gene product operably linked to said promoter fragment, and a suitable 3' downstream region such that the exposure of said transformed plant to a compound of Formula I–IX, wherein I–IX are defined as the following:

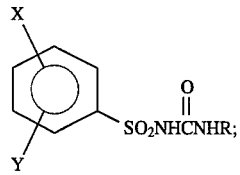

I

II

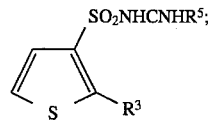

III

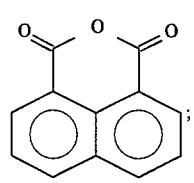

IV

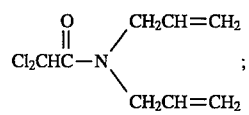

V

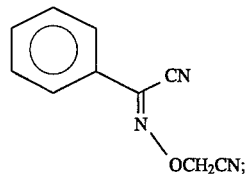

VI

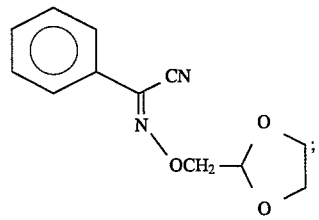

VII

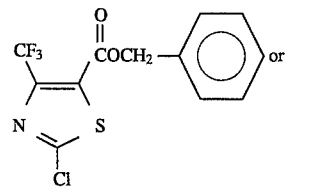

VIII

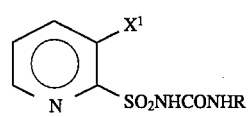

IX wherein
X is H, F, Cl, Br CF$_3$, or C$_1$–C$_2$ alkyl;
X$^1$ is H, F, Cl, C$_1$–C$_2$ alkyl, SO$_2$NR$^1$R$^2$ or CO$_2$R$^1$;
Y is H, Cl or SO$_2$NR$^1$R$^2$, CO$_2$R$^1$, NO$_2$, P(O)(OR$^1$)$_2$;
R is H, C$_1$–C$_6$ alkyl, C$_3$–C$_6$ cycloalkyl, benzyl or C$_2$–C$_4$ haloalkyl or C$_2$–C$_4$ substituted with C$_1$–C$_2$ alkoxy or C$_1$–C$_2$ alkylthio;
R$^1$ is C$_1$–C$_3$ alkyl;
R$^2$ is C$_1$–C$_3$ alkyl;
R$^3$ is CO$_2$R$_2$;
R$^4$ is C$_1$–C$_6$ alkyl or C$_3$–C$_6$ cycloalkyl;

$R^5$ is $C_1$–$C_3$ alkoxy or $NR^6R^7$;

$R^6$ is H, $OCH_3$, $C_1$–$C_4$ alkyl, $C_3$–$C_6$ cycloalkyl, $C_1$–$C_4$ alkyl substituted with $C_1$–$C_2$ alkoxy or ethoxyethoxy; and $R^7$ is H or $C_1$–$C_2$ alkyl;

and agriculturally suitable salts thereof; causes increased expression of said DNA sequence for a selected gene product.

7. A transgenic plant containing a nucleic acid promoter fragment selected from the group consisting of:

(a) A nucleic acid promoter fragment from the 5' flanking promoter region of a corn gene inducible by compounds of formulae I–IX which when denatured, immobilized on a solid support and hybridized to the promoter region from the gene encoding the cDNA clone 2-1 deposited with the American Type Culture Collection (ATCC) and given the ATCC accession number 67805, and washed at 42° C. with an aqueous solution of 0.1× SSC and 0.1% SDS shows a detectable autoradiographic signal after 24 hours of exposure of the solid support to X-ray film of 24 hours at −80° C.;

(b) a nucleic acid promoter fragment from the 5' flanking promoter region of a corn gene inducible by compounds of formulae I–IX which was denatured, immobilized on a solid support membrane and hybridized to the promoter region from the gene encoding the cDNA clone 2-2 deposited with the American Type Culture Collection (ATCC) and given the ATCC accession number 67803 and washed at 42° C. with an aqueous solution of 0.1× SSC and 0.1% SDS shows a detectable autoradiographic signal after 24 hours of exposure of the solid support to X-ray film of 24 hours at −80° C.;

(c) a nucleic acid promoter fragment comprising a nucleotide sequence from the 5' flanking promoter region of a petunia gene inducible by compounds of formulae I–IX which when denatured, immobilized on a solid support membrane and hybridized to the promoter region from the gene encoding the cDNA clone P6.1 deposited with the American Type Culture Collection (ATCC) and given the ATCC accession number 67823 and washed at 42° C. with an aqueous solution of 0.1× SSC and 0.1% SDS shows a detectable autoradiographic signal after 24 hours of exposure of the solid support to X-ray film of 24 hours at −80° C.;

(d) a nucleic acid promoter fragment comprising a nucleotide sequence from the 5' flanking promoter region of a tobacco gene inducible by compounds of formula I–IX which when denatured, immobilized on a solid support membrane and hybridized to the promoter region from the gene encoding the cDNA clone T2.1 deposited with the American Type Culture Collection (ATCC) and given the ATCC accession number 67822, and washed at 42° C. with an aqueous solution of 0.1× SSC and 0.1% SDS shows a detectable autoradiographic signal after 24 hours of exposure of the solid support to X-ray film of 24 hours at −80° C.;

(e) a nucleic acid promoter fragment nucleotide sequence from the 5' flanking promoter region of a corn gene inducible by compounds of formulae I–IX which when denatured, immobilized on a solid support membrane and hybridized to the promoter region from the gene encoding the cDNA clone 218 deposited with the American Type Culture Collection (ATCC) and given the ATCC accession number 68262, and washed at 42° C. with an aqueous solution of 0.1× SSC and 0.1% SDS shows a detectable autoradiographic signal after 24 hours of exposure of the solid support to X-ray film of 24 hours at −80° C.;

(f) a nucleic acid promoter fragment from the 5' flanking promoter region of a plant gene inducible by compounds of formula I–IX which when denatured, immobilized to a solid support membrane and hybridized to the promoter region from the gene encoding the cDNA clone 5-2 deposited with the American Type Culture Collection (ATCC) and given the ATCC accession number 67804, and washed at 65° C. with an aqueous solution of 0.1× SSC and 0.1% SDS shows a detectable autoradiographic signal after 24 hours of exposure of the solid support to X-ray film of 24 hours at −80° C.;

(g) a nucleic acid promoter fragment from the 5' flanking promoter region of a plant gene inducible by compounds of formulae I–IX which was denatured, immobilized to a solid support membrane and hybridized to the promoter region from the gene encoding the cDNA clone T2.1 deposited with the American Type Culture Collection (ATCC) and given the ATCC accession number 67822, and washed at 65° C. with an aqueous solution of 0.1× SSC and 0.1% SDS shows a detectable autoradiographic signal after 24 hours of exposure of the solid support to X-ray film of 24 hours at −80° C.;

(h) a nucleic acid promoter fragment as is (g) wherein said compound of formulae I–IX is a compound selected from the group consisting of 2-chloro-N-(methylaminocarbonyl)benzenesulfonamide, 1-(n-butyl)-3-methylsulfonylurea, methyl 2-[(aminocarbonyl)aminosulfonyl]benzoate, N-isopropylcarbamoylbenzenesulfonamide, N-(aminocarbonyl)-2-chlorobenzenesulfonamide and N'-[2-(n-butylaminocarbonyl)]-6-chloro-N,N-dimethyl-1,2-benzenedisulfonamide;

(i) a nucleic acid promoter fragment as in (h) wherein said compound of Formula I–IX is 2-chloro-N-(methylaminocarbonyl)benzenesulfonamide; and (j) a nucleic acid promoter fragment as in (f) comprising the nucleotide sequence of 889 base pairs running in the 5' to 3' direction from base pair position 1 to base pair position 889 as shown in FIG. 5 from a gene substantially homologous to cDNA clone 5-2;

such that exposure of said transgenic plant to a compound of Formula I–IX wherein I–IX are defined as follows:

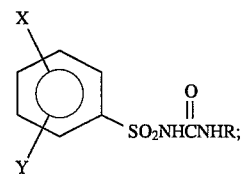

I

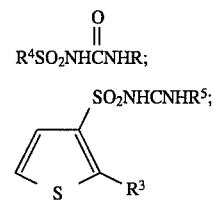

II

III

121
-continued

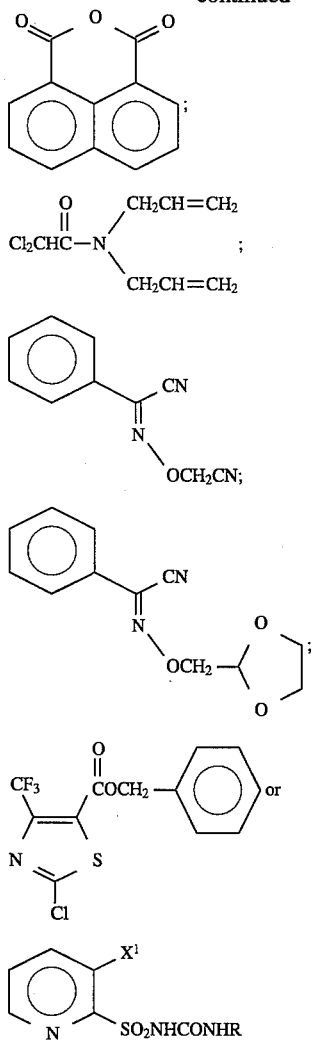

wherein

X is H, F, Cl, Br CF$_3$, or C$_1$–C$_2$ alkyl;

122

$X^1$ is H, F, Cl, C$_1$–C$_2$ alkyl, SO$_2$NR$^1$R$^2$ or CO$_2$R$^1$;

Y is H, Cl or SO$_2$NR$^1$R$^2$, CO$_2$R$^1$, NO$_2$, P(O)(OR$^1$)$_2$;

R is H, C$_1$–C$_6$ alkyl, C$_3$–C$_6$ cycloalkyl, benzyl or C$_2$–C$_4$ haloalkyl or C$_2$–C$_4$ substituted with C$_1$–C$_2$ alkoxy or C$_1$–C$_2$ alkylthio;

R$^1$ is C$_1$–C$_3$ alkyl;

R$^2$ is C$_1$–C$_3$ alkyl;

R$^3$ is CO$_2$R$_2$;

R$^4$ is C$_1$–C$_6$ alkyl or C$_3$–C$_6$ cycloalkyl;

R$^5$ is C$_1$–C$_3$ alkoxy or NR$^6$ R$^7$;

R$^6$ is H, OCH$_3$, C$_1$–C$_4$ alkyl, C$_3$–C$_6$ cycloalkyl, C$_1$–C$_4$ alkyl substituted with C$_1$–C$_2$ alkoxy or ethoxyethoxy; and R$^7$ is H or C$_1$–C$_2$ alkyl;

and agriculturally suitable salts thereof; causes increased expression of a DNA sequence coding for a selected gene product operably linked 3' to said promoter fragment.

8. A transgenic plant of claim 7 wherein said plant is a monocotyledonous plant selected from the group consisting of corn, oats, millet, wheat, rice, barley, sorghum, emaranth, onion, asparagus and sugar cane.

9. A transgenic plant of claim 8 wherein said plant is a monocotyledonous plant selected from the group consisting of corn and rice.

10. A transgenic plant of claim 7 wherein said plant is a dicotyledonous plant selected from the group consisting of alfalfa, soybean, petunia, cotton, sugarbeet, sunflower, carrot, celery, cabbage, cucumber, pepper, canola, tomato, potato, lentil, flax, broccoli, tobacco, bean, lettuce, oilseed rape, cauliflower, spinach, brussel sprout, artichoke, pea, okra, squash, kale, collard greens, tea, coffee, geranium, carnation, orchid, rose, impatiens, petunia, begonia, fuscia, marigold, chrysanthemum, gladiola, astromeria, salvia, veronica, daisey, and iris.

11. Seed obtained by growing a transgenic plant of claim 7.

12. A recombinant DNA construct of claim 6 wherein said DNA sequence for a selected gene product is selected from the group consisting of the sequence for β-glucuronidase and acetolactate synthase.

* * * * *